United States Patent
Boatman et al.

(10) Patent No.: US 7,241,792 B2
(45) Date of Patent: Jul. 10, 2007

(54) FUSED PYRAZOLE DERIVATIVES AND METHODS OF TREATMENT OF METABOLIC-RELATED DISORDERS THEREOF

(75) Inventors: P. Douglas Boatman, San Diego, CA (US); Thomas O. Schrader, San Diego, CA (US); Graeme Semple, San Diego, CA (US); Philip J. Skinner, San Diego, CA (US); Jae-Kyu Jung, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 7 days.

(21) Appl. No.: 11/315,753

(22) Filed: Dec. 22, 2005

(65) Prior Publication Data

US 2006/0205955 A1 Sep. 14, 2006

Related U.S. Application Data

(60) Provisional application No. 60/638,668, filed on Dec. 23, 2004, provisional application No. 60/676,521, filed on Apr. 29, 2005.

(51) Int. Cl.
*A61K 31/407* (2006.01)
*C07D 231/54* (2006.01)
(52) U.S. Cl. .................................. 514/405; 548/359.1
(58) Field of Classification Search ............. 548/359.1; 514/405
See application file for complete search history.

(56) References Cited

U.S. PATENT DOCUMENTS

2006/0167270 A1* 7/2006 Semple et al. ............ 548/364.1

FOREIGN PATENT DOCUMENTS

| DE | 10148617 A1 | 4/2003 |
|---|---|---|
| EP | 0529854 A2 | 3/1993 |
| EP | 1305286 B1 | 12/2004 |
| WO | WO 0166520 A1 | 9/2001 |
| WO | WO 0179169 A2 | 10/2001 |
| WO | WO 02094830 A2 | 11/2002 |
| WO | WO 03002582 A1 | 1/2003 |
| WO | WO 03022814 A1 | 3/2003 |
| WO | WO 03062200 A2 | 7/2003 |
| WO | WO 03078409 A1 | 9/2003 |
| WO | 2004032928 A1 | 4/2004 |
| WO | 2004033431 A2 | 4/2004 |
| WO | 2004103370 A1 | 12/2004 |
| WO | WO 2005011677 A1 | 2/2005 |
| WO | WO 2005016867 A2 | 2/2005 |
| WO | WO 2005016870 A1 | 2/2005 |
| WO | WO 2005044816 A1 | 5/2005 |
| WO | WO 2005077950 A2 | 8/2005 |

OTHER PUBLICATIONS

Alterman, M. et al., "Fast microwave-assisted preparation of aryl and vinyl nitriles and the corresponding tetrazoles from organohalides", J. Org. Chem. 65:7984-89 (2000)(supporting information attached).
Bays, H. et al., "Pharmacotherapy for Dyslipidaemia—Current therapies and future agents", Expert Opinion on Pharmacotherapy, Ashley, London, GB, vol. 4(11):1901-38 (2003).
Cahn, R.S. et al., "Specification of molecular chirality", Angew. Chem. Internat. Edit. 5(4):385-415 (1966).
Chang, A. Y. et al., "Ciglitazone, a new hypoglycemic agent", Diabetes 32:830-38 (1983).
Clayton, S. et al., "A total synthesis of (±)-epibatidine", Tetrahedron Letters 34(46):7493-6 (1993).
Cohen, T. et al., "Synthetically useful β-lithioalkoxides from reductive lithiation of epoxides by aromatic radical anions", J. Org. Chem. 55:1528-36 (1990).
Coleman, D.L., "Fat(fat) and Tubby (tub): Two autosomal recessive mutations causing obesity syndromes in the mouse", Journal of Heredity 81:424-7 (1990).
Coleman, Douglas L., "Diabetes-obesity syndromes in mice", Diabetes 31:1-6 (1982).

(Continued)

Primary Examiner—Joseph K. McKane
Assistant Examiner—Michael P. Barker
(74) Attorney, Agent, or Firm—Lyle W. Spruce

(57) ABSTRACT

The present invention relates to certain fused pyrazole derivatives of Formula (Ia), and pharmaceutically acceptable salts thereof, which exhibit useful pharmacological properties, for example, as agonists for the RUP25 receptor.

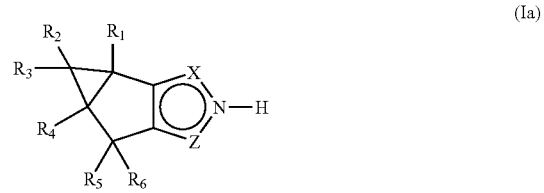

(Ia)

Also provided by the present invention are pharmaceutical compositions containing compounds of the invention, and methods of using the compounds and compositions of the invention in the treatment of metabolic-related disorders, including dyslipidemia, atherosclerosis, coronary heart disease, insulin resistance, type 2 diabetes, Syndrome-X and the like. In addition, the present invention also provides for the use of the compounds of the invention in combination with other active agents such as those belonging to the class of α-glucosidase inhibitors, aldose reductase inhibitors, biguanides, HMG-CoA reductase inhibitors, squalene synthesis inhibitors, fibrates, LDL catabolism enhancers, angiotensin converting enzyme (ACE) inhibitors, insulin secretion enhancers, DP receptor antagonists, and the like.

62 Claims, No Drawings

OTHER PUBLICATIONS

Collier, T. L. et al., "Radiosynthesis and in-vivo evaluation of the psuedopeptide s-opioid antagonist", J. Labelled Cpd. Radiopharm. 42(1):S264-6 (1999).
Cornhill, J. Frederick et al., "Topographic study of sudanophilic lesions in cholesterol-fed minipigs by image analysis", Arteriosclerosis Thrombosis, and Vascular Biology 5(5):415-426 (1985).
Corsaro, A. et al., "Steric course of some cyclopropanation reactions of L-threo-hex-4-enopyranosides", Tetrahedron Letters 60:3787-95 (2004).
Delporte, Marie-Laure et al., "Pre- and post-translational negative effect of β-adrenoceptor agonists on adiponectin secretion: in vitro and in vivo studies", Biochem. J. 367:677-85 (2002).
Effenberger, F. et al., "Regioselective halo- and carbodesilylation of (trimethylsilyl)-1- methylpyrazoles", J. Org. Chem. 49:4687-95 (1984).
Eriksson et al., "Increased incidence of congenital malformations in the offspring of diabetic rats and their prevention by maternal insulin therapy", Diabetes 31:1-6 (1982).
Flechtner-Mors, M. et al., "Effects of acipimox on the lipolysis rate in subcutaneous adipose tissue of obese subjects", Diabetes Metab Res Rev 17:387-90 (2001).
Friedman, J. et al., "Tackling a weighty problem", Cell 69:217-20 (1992).
Gerrity, R. et al., "Diabetes-induced accelerated atherosclerosis in swine", Diabetes 50:1654-65 (2001).
Guyton, John R., "Effect of Niacin on Atherosclerotic Cardiovascular Disease", Am J Cardiol, 82:18U-23U (1998).
Haddach, A. et al., "An efficient method for the N-debenzylation of aromatic heterocycles", Tetrahedron Letters 43:399-402 (2002).
Hodgson, D. et al., "Intramolecular cyclopropanation of unsaturated terminal epoxides", J. Am. Chem. Soc. 126:8664-5 (2004).
Hodgson, D., "Intramolecular cyclopropanation of unsaturated terminal epoxides", JACS 126:8664-5 (2004)(supporting information attached).
Hodson, et al., J. Am. Chem. Soc. 126:8664 (2004).
Holland, G. et al., "Heterocyclic tetrazoles, a new class of lipolysis inhibitors", J. Med. Chem. 10:149-54 (1967).
Horinoshi, H. et al., "Troglitazone (CS-045), a new antidiabetic drug", Ann. Rep. Sankyo Res. Lab. 46:1-57 (1994).
Katritzky, A. et al., "Alpha-lithiation of N-alkyl groups in pyrazoles", Tetrahedron Letters 39:2023-9 (1983).
Koranyi, L. et al., "Glucose transporter levels in spontaneously obese (db/db) insulin-resistant mice", J. Clin. Invest. 85:962-7 (1990).
Krynitsky, J. et al., "2-ethylhexanonitrile", Org. Synth. Coll. vol. 4 p. 436 (1963); vol. 32 p. 65 (1952).
Latli, B. et al., "Novel and potent 6-chloro-3-pyridinyl ligands for the α4β2 neuronal nicotinic acetylcholine receptor", J. Med. Chem. 42:2227-34 (1999).
Latli, B. et al., "Supporting information for "Novel and potent 6-chloro-3-pyridinyl ligands for the α4β2 neuronal nicotinic acetylcholine receptor, J. Med. Chem. pp. 2227(1999).
Le Bas, M-D et al., "Radioiodinated analogs of EP 00652218 for the exploration of the tachykinin nk1 receptor by spect", J. Labelled Cpd. Radiopharm. 44(1):S280-2 (2001).
Lorenzen, A. et al., "Characterization of a g protein-coupled receptor for nicotinic acid", Mol. Pharmacol. 59(2):349-57 (2001).
Lorenzen, A. et al., "G protein-coupled receptor for nicotinic acid in mouse macrophages", Biochem. Pharm. 64:645-48 (2002).
Mariano, P. et al., "Mechanistic aspcts of gas-phase photodecarbonylation reactions of bicycle[3.1.0]hexanones", J. Org. Chem. 45:1753-62 (1980).

Matsuda, M. et al., "Role of adiponectin in preventing vascular stenosis", J. Biol. Chem. 277(40):37487-91 (2002).
Miller, R.D. et al., "Deoxygenation of sulfoxides promoted by electrophilic silicon reagents: preparation of aryl-substituted sulfonium salts", J. Org. Chem. 53:5571-3 (1988).
Movassaghi, M. et al., "A direct method for the conversion of terminal epoxides into γ-butanolides", J. Am. Chem. Soc. 124(11):2456-7 (2002).
Newman-Evans, R. et al., "The influence of intramolecular dynamics on branching ratios in thermal rearrangements", J. Org. Chem. 55:695-711 (1990).
Nishimura, J. et al., "A novel synthesis of methylcyclopropanes", Tetrahedron Letters 25:2647-59 (1969).
Olivo, H. et al., "Synthetic studies on the trans-Chlorocyclopropane dienyne side chain of Callipeltoside-A", Org. Lett. 2(25):4055-8 (2000)(supporting information attached).
Prelog, V. et al., "Basic principles of the CIP-system and proposals for a revision", Angew. Chem. Int. Ed. Engl. 21:567-83 (1982).
Royo, T. et al., "Effect of gemfibrozil on peripheral atherosclerosis and platelet activation in a pig model of hyperlipidemia", European Jour. Of Clinical Invest. 30:843-52 (2000).
Schaus, S. et al., "Highly selective hydrolytic kinetic resolution of terminal epoxides catalyzed by chiral (salen)cobalt(III)-complexes. Practical synthesis of enantioenriched terminal epoxides and 1,2-Diols", JACS 124:1307 (2002)(supporting information attached).
Shafrir, E., "Diabetes mellitus theory and practice", Diabetes pp. 299-340 (1990).
Smith, A. et al, Total synthesis of the neotropical poison-frog alkaloid (-)-205B, Org. Lett. 7(15):3247-50 (2005)(supporting information attached).
Soga, T. et al., "Molecular identification of nicotinic acid receptor", Biochem. And biophys. Res. Comm. 303:364-69 (2003).
Surrey, A., "Malononitrile", Org. Synth. Coll. vol. 3 p. 535 (1955); vol. 25, p. 65 (1945).
Taber, D. et al., "Synthesis of the eight enantiomerically pure diastereomers of the 12-F2-Isoprostanes", J. Am. Chem. Soc. 124:13121-6 (2002)(supporting information attached).
Truett, G. et al., "Rat obesity gene fatty (fa) maps to chromosome 5: evidence for homology with the mouse gene diabetes (db)", Proc. Natl. Acad. Sci. 88:7806-9 (1991).
Tunaru, S. et al., "PUMA-G and HM74 are receptors for nicotinic acid and mediate its anti-lipolytic effect", Nature Medicine 3:1-4 (2003).
Turner, S. et al., "Enantiospecific synthesis of annulated nicotine analogues from D- and L-glutamic acid Pyridotropanes", J. Org. Chem. 65:861-70 (2000).
Van Herk, T. et al., "Pyrazole derivatives as partial agonists for the nicotinic acid receptor", J. Med. Chem. 46:3945-51 (2003).
Wise, A. et al., "Molecular identification of high and low affinity receptors for nicotinic acid", Journ. Biol. Chem. 278(11):9869-74 (2003).
Yagi, H. et al., "Removal of benzyl-type protecting groups frompeptides by catalytic transfer hydrogenation with formic acid", J. Org. Chem. 44(19):3442-4 (1979).
Zhang, R. et al., "Cyclopropanation reactions of pyroglutamic acid-derived synthons with akylidene transfer reagents", J. Org. Chem. 64:547-55 (1999)(supporting information attached).
Zhu, Gui-dong et al., "Synthesis and mode of action of 125I- and 3H-labeled thieno[2,3-c]pyridine antagonists of cell adhesion molecule expression", J. Org. Chem. 67:943-8 (2002).
International Search Report for PCT/US2005/046599, 2006.

* cited by examiner

FUSED PYRAZOLE DERIVATIVES AND METHODS OF TREATMENT OF METABOLIC-RELATED DISORDERS THEREOF

CROSS REFERENCE TO RELATED APPLICATIONS

This application claims priority to U.S. Ser. No. 60/638,668, filed Dec. 23, 2004, and U.S. Ser. No. 60/676,521, filed Apr. 29, 2005, both incorporated by reference in their entirety.

FIELD OF THE INVENTION

The present invention relates to certain fused pyrazole derivatives, and pharmaceutically acceptable salts thereof, which exhibit useful pharmacological properties, for example as agonists for the nicotinic acid receptor, RUP25. Also provided by the present invention are pharmaceutical compositions containing one or more compounds of the invention, and methods of using the compounds and compositions of the invention in the treatment of metabolic-related disorders, including dyslipidemia, atherosclerosis, coronary heart disease, insulin resistance, type 2 diabetes, Syndrome-X and the like. In addition, the present invention also provides for the use of the compounds of the invention in combination with other active agents such as those belonging to the class of α-glucosidase inhibitors, aldose reductase inhibitors, biguanides, HMG-CoA reductase inhibitors, squalene synthesis inhibitors, fibrates, LDL catabolism enhancers, angiotensin converting enzyme (ACE) inhibitors, insulin secretion enhancers, thiazolidinedione, DP receptor antagonists and the like.

BACKGROUND OF THE INVENTION

Compounds of the Invention as Antilipolytic Agents

Atherosclerosis and stroke are the numbers one and number three leading causes of death of both men and women in the United States. Type 2 diabetes is a public health problem that is serious, widespread and increasing. Elevated levels of low density lipoprotein (LDL) cholesterol or low levels of high density lipoprotein (HDL) cholesterol are, independently, risk factors for atherosclerosis and associated cardiovascular pathologies. In addition, high levels of plasma free fatty acids are associated with insulin resistance and type 2 diabetes. One strategy for decreasing LDL-cholesterol, increasing HDL-cholesterol, and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

It is also worth noting in passing that an increase in cellular levels of cAMP down-regulates the secretion of adiponectin from adipocytes [Delporte, M L et al. *Biochem J* (2002) July]. Reduced levels of plasma adiponectin have been associated with metabolic-related disorders, including atherosclerosis, coronary heart disease, insulin resistance and type 2 diabetes [Matsuda, M et al. *J Biol Chem* (2002) July and reviewed therein].

Nicotinic acid (niacin, pyridine-3-carboxylic acid) is a water-soluble vitamin required by the human body for health, growth and reproduction; a part of the Vitamin B complex. Nicotinic acid is also one of the oldest used drugs for the treatment of dyslipidemia. It is a valuable drug in that it favorably affects virtually all of the lipid parameters listed above [Goodman and Gilman's Pharmacological Basis of Therapeutics, editors Harmon J G and Limbird L E, Chapter 36, Mahley R W and Bersot T P (2001) pages 971–1002]. The benefits of nicotinic acid in the treatment or prevention of atherosclerotic cardiovascular disease have been documented in six major clinical trials [Guyton J R (1998) *Am J Cardiol* 82:18U–23U]. Nicotinic acid and related derivatives, such as, acipimox have recently been discussed [Lorenzen, A et al (2001) *Molecular Pharmacology* 59:349–357]. Structure and synthesis of additional analogs or derivatives of nicotinic acid are discussed throughout the Merck Index, An Encyclopedia of Chemicals, Drugs, and Biologicals, Tenth Edition (1983), which is incorporated herein by reference in its entirety.

Nicotinic acid inhibits the production and release of free fatty acids from adipose tissue, likely via an inhibition of adenylyl cyclase, a decrease in intracellular cAMP levels, and a concomitant decrease in hormone sensitive lipase activity. Agonists that down-regulate hormone sensitive lipase activity leading to a decrease in plasma free fatty acid levels are likely to have therapeutic value. The consequence of decreasing plasma free fatty acids is two-fold. First, it will ultimately lower LDL-cholesterol and raise HDL-cholesterol levels, independent risk factors, thereby reducing the risk of mortality due to cardiovascular incidence subsequent to atheroma formation. Second, it will provide an increase in insulin sensitivity in individuals with insulin resistance or type 2 diabetes. Unfortunately, the use of nicotinic acid as a therapeutic is partially limited by a number of associated, adverse side-effects. These include flushing, free fatty acid rebound, and liver toxicity.

The rational development of novel, nicotinic acid receptor agonists that have fewer side-effects will be valuable, but to date this has been hindered by the inability to molecularly identify the nicotinic acid receptor. Furthermore, other receptors of the same class may exist on the surface of adipocytes and similarly decrease hormone sensitive lipase activity through a reduction in the level of intracellular cAMP but without the elicitation of adverse effects such as flushing, thereby representing promising novel therapeutic targets. Recent work suggests that nicotinic acid probably acts through a specific GPCR [Lorenzen A, et al. (2001) *Molecular Pharmacology* 59:349–357 and reviewed therein]. Further work has suggested that the effects of nicotinic acid on macrophages, spleen and probably adipocytes are mediated via this specific GPCR [Lorenzen A, et al. (2002) *Biochemical Pharmacology* 64:645–648 and reviewed therein].

SUMMARY OF THE INVENTION

The present invention is drawn to compounds which bind to and activate the RUP25 receptor, and uses thereof. The term RUP25 receptor as used herein includes the human sequences found in GeneBank Accession No. NM_177551 for the nucleotide, GenBank Accession No. NP_808219 for the polypeptide, and naturally-occurring allelic variants, mammalian orthologs, and recombinant mutants thereof.

One aspect of the present invention pertains to certain fused pyrazole derivatives as represented by Formula (Ia):

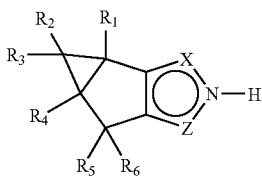

(Ia)

or a pharmaceutically acceptable salt, hydrate or solvate thereof, wherein:

X is N and Z is $CR_7$, or X is $CR_7$ and Z is N;

$R_1$ and $R_4$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-4}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol;

$R_2$ and $R_3$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, arylsulfinyl, arylsulfonyl, arylthio, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ dialkylcarboxamide, $C_{1-6}$ dialkylthiocarboxamide, $C_{1-6}$-dialkylamido, $C_{1-6}$-dialkylthioamido, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, heterocyclic-oxy, heterocyclic-sulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid and thiol; wherein said $C_{1-6}$ alkyl is optionally substituted with substituents selected from the group consisting of $C_{1-6}$ acyl, $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, nitro, phenoxy and phenyl; or $R_2$ and $R_3$ together with the carbon to which they are both bonded form a $C_{3-6}$ cycloalkyl;

$R_5$ and $R_6$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol; and $R_7$ is carbo-$C_{1-6}$-alkoxy, carboxy or tetrazol-5-yl.

In some embodiments, $R_1$ and $R_4$ are cis to each other.

Another aspect of the present invention pertains to pharmaceutical compositions comprising a compound of the present invention in combination with a pharmaceutical acceptable carrier.

Another aspect of the present invention pertains to pharmaceutical compositions as described herein further comprising one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer, thiazolidinedione and DP receptor antagonist.

Another aspect of the present invention pertains to methods of treatment of a metabolic-related disorder comprising administering to an individual in need of such treatment a therapeutically-effective amount of a compound of the present invention or a pharmaceutical composition thereof.

Another aspect of the present invention pertains to methods of reducing VLDL or LDL levels in an individual comprising administering to said individual in need of such treatment a therapeutically-effective amount of a compound of the present invention or a pharmaceutical composition thereof.

Another aspect of the present invention pertains to methods of reducing serum triglyceride levels in an individual comprising administering to said individual in need of such treatment a therapeutically-effective amount of a compound of the present invention or a pharmaceutical composition thereof.

Another aspect of the present invention pertains to methods of reducing serum Lp(a) levels in an individual comprising administering to said individual in need of such treatment a therapeutically-effective amount of a compound of the present invention or a pharmaceutical composition thereof.

Another aspect of the present invention pertains to methods of treatment of a metabolic-related disorder comprising administering to an individual in need of such treatment a therapeutically-effective amount of a compound of the present invention and a DP receptor antagonist.

Another aspect of the present invention pertains to methods of modulating a RUP25 receptor comprising contacting the receptor with a compound of the present invention.

Another aspect of the present invention pertains to methods of modulating a RUP25 receptor for the treatment of a metabolic-related disorder in an individual in need of such modulation comprising contacting said receptor with a therapeutically-effective amount of a compound of the present invention.

Another aspect of the present invention pertains to compounds wherein the compound is an agonist.

Another aspect of the present invention pertains to compounds wherein the compound is a partial agonist.

Another aspect of the present invention pertains to methods of treating atherosclerosis in a human patient in need of such treatment comprising administering to the patient a compound of the present invention in an amount that is effective to treat atherosclerosis.

Another aspect of the present invention pertains to methods of treating dyslipidemia in a human patient in need of such treatment comprising administering to the patient a compound of the present invention in an amount that is effective to treat dyslipidemia.

Another aspect of the present invention pertains to methods of raising HDL in an individual comprising administering to the individual a therapeutically-effective amount of a compound of the present invention.

Another aspect of the present invention pertains to compounds of the present invention for use in a method of treatment of the human or animal body by therapy.

Another aspect of the present invention pertains to compounds of the present invention for use in a method of treatment of a metabolic-related disorder of the human or animal body by therapy.

Another aspect of the present invention pertains to the use of compounds of the present invention for the manufacture of a medicament for use in the treatment of a metabolic-related disorder.

In some embodiments of the present invention, the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

Some embodiments of the present invention pertain to methods wherein the individual is a mammal.

Some embodiments of the present invention pertain to methods wherein the mammal is a human.

Another aspect of the present invention pertains to methods of producing a pharmaceutical composition comprising admixing at least one compound of the present invention and a pharmaceutically acceptable carrier or excipient.

The inventions described in this application were made by Arena Pharmaceuticals, Inc as a result of activities undertaken within the scope of an Oct. 21, 2002 joint research agreement between Merck & Co, Inc. and Arena Pharmaceuticals, Inc.

These and other aspects of the invention disclosed herein will be set forth in greater detail as the patent disclosure proceeds.

DETAILED DESCRIPTION OF THE INVENTION

The scientific literature has adopted a number of terms, for consistency and clarity, the following definitions will be used throughout this patent document.

AGONISTS shall mean moieties that interact and activate the receptor, such as the RUP25 receptor and initiates a physiological or pharmacological response characteristic of that receptor. For example, when moieties activate the intracellular response upon binding to the receptor, or enhance GTP binding to membranes.

ATHEROSCLEROSIS is intended herein to encompass disorders of large and medium-sized arteries that result in the progressive accumulation within the intima of smooth muscle cells and lipids.

Chemical Group, Moiety or Radical:

The term "$C_{1-6}$ acyl" denotes a $C_{1-6}$ alkyl radical bonded to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-6}$ acyloxy" denotes an acyl radical bonded to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{2-6}$ alkenyl" denotes a radical containing 2 to 6 carbons wherein at least one carbon-carbon double bond is present, some embodiments are 2 to 4 carbons, and some embodiments have 2 carbons. Both E and Z isomers are embraced by the term "alkenyl." Furthermore, the term "alkenyl" includes di-enes. Accordingly, if more than one double bond is present, then the bonds may be all E or Z or a mixtures of E and Z. Examples of an alkenyl include vinyl, propenyl, allyl, isopropenyl, 2-methyl-propenyl1-methyl-propenyl, but-1-enyl, but-2-enyl, but-3-enyl, buta-1,3-dienyl, and the like.

The term "$C_{1-6}$ alkoxy" denotes an alkyl radical, as defined herein, bonded directly to an oxygen atom. Examples include methoxy, ethoxy, n-propoxy, iso-propoxy, n-butoxy, t-butoxy, iso-butoxy, sec-butoxy and the like.

The term "$C_{1-6}$ alkyl" denotes a straight or branched carbon radical containing the number of carbons as indicated, for examples, in some embodiments, alkyl is a "$C_{1-4}$ alkyl" and the group contains 1 to 4 carbons. In some embodiments alkyl contains 1 to 13 carbons, some embodiments contain 1 to 2 carbons, some embodiments contain 1 carbon. Examples of an alkyl include, but not limited to, methyl, ethyl, n-propyl, iso-propyl, n-butyl, iso-butyl, t-butyl, sec-butyl, and the like.

The term "$C_{1-6}$ alkylcarboxamide" denotes a single $C_{1-6}$ alkyl group bonded to the nitrogen of an amide group, wherein alkyl has the same definition as found herein. The $C_{1-6}$ alkylcarboxamide may be represented by the following:

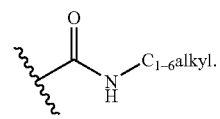

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-6}$ alkylsulfinyl" denotes a $C_{1-6}$ alkyl radical bonded to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-6}$ alkylsulfonamide" refers to the group

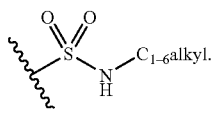

wherein $C_{1-6}$ alkyl has the same definition as described herein.

The term "$C_{1-6}$ alkylsulfonyl" denotes a $C_{1-6}$ alkyl radical bonded to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical bonded to a sulfide group of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-6}$ alkylthiocarboxamide" denotes a single $C_{1-6}$ alkyl group bonded to the nitrogen of a thioamide group, wherein alkyl has the same definition as found herein. The $C_{1-6}$ alkylthiocarboxamide may be represented by the following:

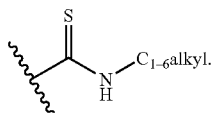

Examples include, but not limited to, N-methylthiocarboxamide, N-ethylthiocarboxamide, N-n-propylthiocarboxamide, N-iso-propylthiocarboxamide, N-n-butylthiocarboxamide, N-sec-butylthiocarboxamide, N-iso-butylthiocarboxamide, N-t-butylthiocarboxamide and the like.

The term "$C_{1-6}$ alkylthioureyl" denotes the group of the formula: —NC(S)N— wherein one are both of the nitrogens are substituted with the same or different $C_{1-6}$ alkyl groups and alkyl has the same definition as described herein. Examples of an alkylthioureyl include, but not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-6}$ alkylureyl" denotes the group of the formula: —NC(O)N— wherein one are both of the nitrogens are substituted with the same or different $C_{1-6}$ alkyl group wherein alkyl has the same definition as described herein. Examples of an alkylureyl include, but not limited to, CH$_3$NHC(O)NH—, NH$_2$C(O)NCH$_3$—, (CH$_3$)$_2$N(O)NH—, (CH$_3$)$_2$N(O)NH—, (CH$_3$)$_2$N(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments are 2 to 3 carbons, and some embodiments have 2 carbons. Examples of an alkynyl include, but not limited to, ethynyl, prop-1-ynyl, 3-prop-2-ynyl, but-1-ynyl, 1-methyl-prop-2-ynyl, buta-1,3-diynyl, and the like. The term "alkynyl" includes di-ynes.

The term "amino" denotes the group —NH$_2$.

The term "$C_{1-6}$ alkylamido" denotes a $C_{1-6}$ acyl group, as defined herein, bonded to an NH group. The $C_{1-6}$ alkylamido group may be represented by the following formula:

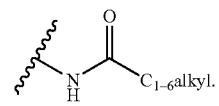

Examples of an alkylamido group include, but not limited to, —NHCOMe, —NHCOEt, and the like.

The term "amino-$C_{1-6}$-alkylsulfonyl" denotes an alkylsulfonyl group, as defined herein, bonded to an NH group. The amino-$C_{1-6}$-alkylsulfonyl group may be represented by the following formula:

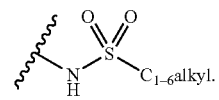

Examples of an amino-$C_{1-6}$-alkylsulfonyl group include, but not limited to, —NHSO$_2$Me, —NHSO$_2$Et, —NHSO$_2$propyl, and the like.

The term "$C_{1-6}$ alkylthioamido" denotes a $C_{1-6}$ thioacyl group, as defined herein, bonded to an NH group. The $C_{1-6}$ alkylthioamido group may be represented by the following formula:

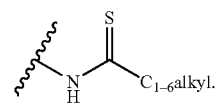

Examples of an alkylthioamido group include, but not limited to, —NHCSMe, —NHCSEt, and the like.

The term "$C_{1-6}$ alkylamino" denotes one alkyl radical bonded to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylsulfinyl" denotes an aryl group bonded to a sulfoxide radical of the formula: —S(O)— wherein the aryl radical has the same definition as described herein.

The term "arylsulfonyl" denotes an aryl group bonded to a sulfonyl radical of the formula: —S(O)$_2$— wherein the aryl radical has the same definition as described herein.

The term "arylthio" denotes an aryl group bonded to a thio radical of the formula: —S— wherein the aryl radical has the same definition as described herein.

The term "carbamimidoyl" refers to a group of the following chemical formula:

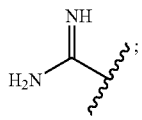

and in some embodiments, one or both hydrogens are replaced with another group. For example, one hydrogen can be replaced with a hydroxyl group to give a N-hydroxycarbamimidoyl group, or one hydrogen can be replaced with an alkyl group to give N-methylcarbamimidoyl, N-ethylcarbamimidoyl, N-propylcarbamimidoyl, N-butylcarbamimidoyl, and the like.

The term "carbo-$C_{1-6}$-alkoxy" denotes a $C_{1-6}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "$C_{3-7}$ cycloalkyl" denotes a saturated ring radical containing 3 to 6 carbons; some embodiments contain 3 to 5 carbons; some embodiments contain 3 to 4 carbons. Examples include, cyclopropyl, cyclobutyl, cyclopentyl, cyclohexyl.

The term "$C_{3-7}$ cycloalkyloxy" denotes a cycloalkyl radical, as defined herein, bonded directly to an oxygen atom. Examples include cyclopropyloxy, cyclobutyloxy, cyclopentoxy, and the like.

The term "$C_{2-8}$ dialkylamino" denotes an amino substituted with two of the same or different alkyl radicals wherein alkyl radical has the same definition as described herein. A $C_{2-8}$ dialkylamino may be represented by the following groups:

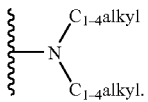

Some embodiments include $C_{2-6}$ dialkylamino, such as —N($C_{1-3}$ alkyl)$_2$. Examples of dialkylamino include, but not limited to, dimethylamino, methylethylamino, diethylamino, methylpropylamino, methylisopropylamino, and the like.

The term "$C_{1-6}$ dialkylamido" denotes two alkyl radicals, that are the same or different, bonded to an amido group, wherein alkyl has the same definition as described herein. A $C_{1-6}$ dialkylamido may be represented by the following group:

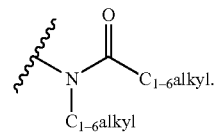

wherein $C_{1-6}$ has the same definition as described herein. Examples of a dialkylamido include, but not limited to, —N($CH_3$)$COCH_3$, —N($CH_3$)$COCH_2CH_3$, and the like.

The term "$C_{1-6}$ dialkylthioamido" denotes two alkyl radicals, that are the same or different, bonded to a thioamido group, wherein alkyl has the same definition as described herein. A $C_{1-6}$ dialkylthioamido may be represented by the following group:

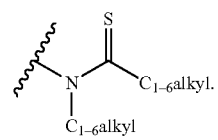

wherein $C_{1-6}$ has the same definition as described herein. Examples of a dialkylthioamido include, but not limited to, —N($CH_3$)$CSCH_3$, —N($CH_3$)$CSCH_2CH_3$, and the like.

The term "$C_{1-6}$ dialkylcarboxamide" denotes two alkyl radicals, that are the same or different, bonded to an amide group, wherein alkyl has the same definition as described herein. A $C_{1-6}$ dialkylcarboxamido may be represented by the following group:

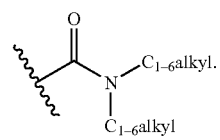

wherein $C_{1-6}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "$C_{1-6}$ dialkylthiocarboxamide" denotes two alkyl radicals, that are the same or different, bonded to a thioamide group, wherein alkyl has the same definition as described herein. A $C_{1-6}$ dialkylthiocarboxamido may be represented by the following group:

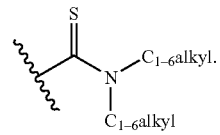

Examples of a dialkylthiocarboxamide include, but not limited to, N,N-dimethylthiocarboxamide, N-methyl-N-ethylthiocarboxamide and the like.

The term "C$_{1-6}$ haloalkoxy" denotes a haloalkyl, as defined herein, which is directly bonded to an oxygen atom. Examples include, but not limited to, difluoromethoxy, trifluoromethoxy, 2,2,2-trifluoroethoxy, pentafluoroethoxy and the like.

The term "C$_{1-6}$ haloalkyl" denotes an alkyl group wherein the alkyl is substituted with halogen ranging from one to fully substituted, wherein a fully substituted haloalkyl can be represented by the formula C$_h$L$_{2h+1}$ wherein L is a halogen and "h" represents the number of carbon atoms; when more than one halogen is present then the halogens may be the same or different and selected from the group consisting of F, Cl, Br and I; it is understood that the terms "alkyl" and "halogen" have the same definition as found herein. In some embodiments, haloalkyl is a "C$_{1-4}$ haloalkyl" and the group contains 1 to 4 carbons, some embodiments contain 1 to 3 carbons, some embodiments contain 1 to 2 carbons, some embodiments contain 1 carbon. In some embodiments, haloalkyl contains 5 halogens. In some embodiments, haloalkyl contains 4 halogens. In some embodiments, haloalkyl contains 3 halogens. In some embodiments, the halogen is F. When the haloalkyl is fully substituted with halogen atoms, this group is referred herein as a perhaloalkyl, one example, is an alkyl fully substituted with fluorine atoms and is referred to herein as a "perfluoroalkyl." In some embodiments, examples of a haloalkyl include, but not limited to, difluoromethyl, fluoromethyl, 2,2,2-trifluoro-ethyl, 2,2-difluoro-ethyl, 2-fluoro-ethyl, 1,2,2-trifluoro-ethyl, 1,2-difluoro-ethyl, 1,1-difluoro-ethyl, 1,1,2-trifluoro-ethyl, 3,3,3-trifluoro-propyl, 2,2-difluoro-propyl, 3,3-difluoro-propyl, 3-fluoro-propyl, 2,3,3-trifluoro-propyl, 2,3-Difluoro-propyl, 2,2,3,3,3-pentafluoro-propyl, 2,2,3,3-tetrafluoro-propyl, 2,2,3-trifluoro-propyl, 1,2,3,3-tetrafluoro-propyl, 1,2,3-trifluoro-propyl, 3,3-difluoro-propyl, 1,2,2,3-tetrafluoro-propyl, 4,4-difluoro-butyl, 3,3-difluoro-butyl, 4,4,4-trifluoro-butyl, 3,3-difluoro-butyl, and the like. In some embodiments, examples of a perfluoroalkyl include, but not limited to, trifluoromethyl, pentafluoroethyl, heptafluoropropyl, 1,2,2,2-tetrafluoro-1-trifluoromethyl-ethyl, and the like.

The term "C$_{1-6}$ haloalkylsulfinyl" denotes a haloalkyl radical bonded to a sulfoxide group of the formula: —S(O)— wherein the haloalkyl radical has the same definition as described herein.

The term "C$_{1-6}$ haloalkylsulfonyl" denotes a haloalkyl radical bonded to a sulfone group of the formula: —S(O)$_2$— wherein haloalkyl has the same definition as described herein.

The term "C$_{1-6}$ haloalkylthio" denotes a haloalkyl radical directly bonded to a sulfur atom wherein the haloalkyl has the same meaning as described herein.

The term "halogen" or "halo" denotes to a fluoro, chloro, bromo or iodo group.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, C$_{1-4}$ acyl or C$_{1-4}$ alkyl. Examples of heteroaryl groups include, but not limited to, pyridyl, benzofuranyl, pyrazinyl, pyridazinyl, pyrimidinyl, triazinyl, quinolinyl, benzoxazolyl, benzothiazolyl, 1H-benzimidazolyl, isoquinolinyl, quinazolinyl, quinoxalinyl and the like. In some embodiments, the heteroaryl atom is O, S, NH, examples include, but not limited to, pyrrolyl, indolyl, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, C$_{1-4}$ acyl or C$_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "heteroarylcarbonyl" denotes a heteroaryl group, as defined herein, that is directly bonded to the carbon of a carbonyl group (i.e., C=O). Examples of heteroarylcarbonyl groups include, but not limited to, pyridyl-carbonyl, benzofuranyl-carbonyl, pyrazinyl-carbonyl, pyridazinyl-carbonyl, pyrimidinyl-carbonyl, triazinyl-carbonyl, quinolinyl-carbonyl, benzoxazolyl-carbonyl, benzothiazolyl-carbonyl, 1H-benzimidazolyl-carbonyl, isoquinolinyl-carbonyl, quinazolinyl-carbonyl, quinoxalinyl-carbonyl, pyrrole-carbonyl, indolyl-carbonyl, and the like.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

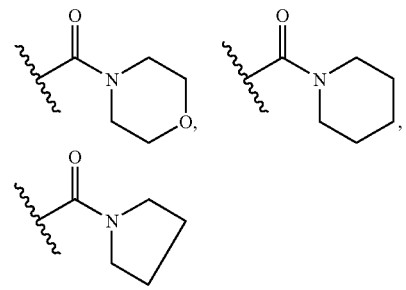

and the like.

The term "heterocyclic-oxy" refers to a heterocyclic group, as defined herein, that is directly bonded to an oxygen atom. Examples include the following:

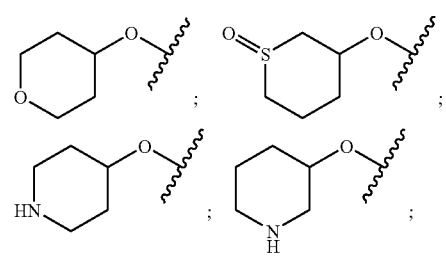

-continued

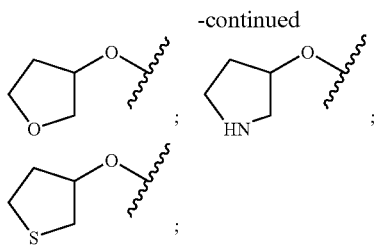

and the like.

The term "heterocyclicsulfonyl" denotes a heterocyclic group, as defined herein, with a ring nitrogen where the ring nitrogen is bonded directly to an $SO_2$ group forming an sulfonamide. Examples include, but not limited to,

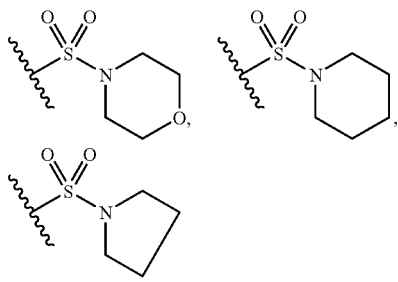

and the like.

The term "hydroxyl" denotes the group —OH.

The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

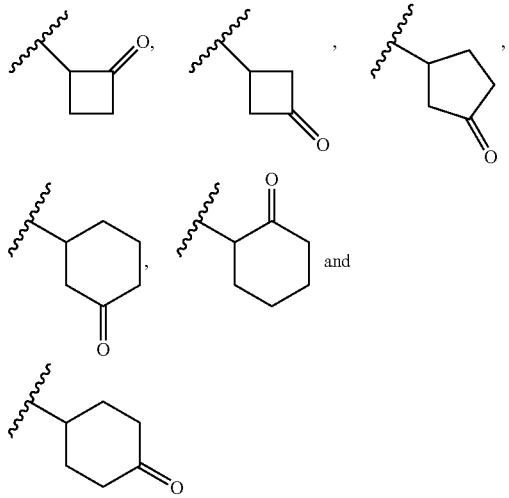

The term "nitro" denotes the group —$NO_2$.
The term "phenoxy" refers to the group $C_6H_5O$—.
The term "phenyl" refers to the group $C_6H_5$—.
The term "sulfonamide" refers to the group —$SO_2NH_2$.

The term "sulfonic acid" refers to the group —$SO_3H$.
The term "thiol" denotes the group —SH.
The term "$C_{1-6}$ thioacyl" denotes a $C_{1-6}$ alkyl radical bonded to a thiocarbonyl wherein the definition of alkyl has the same definition as described herein; some examples include but not limited to, —$CSCH_3$, —$CSCH_2CH_3$, —$CSCH_2CH_2CH_3$, and the like.

The term COMPOSITION shall mean a material comprising at least two compounds or two components; for example, and without limitation, a Pharmaceutical Composition is a Composition comprising a compound of the present invention and a pharmaceutically acceptable carrier.

The term COMPOUND EFFICACY shall mean a measurement of the ability of a compound to inhibit or stimulate receptor functionality, as opposed to receptor binding affinity.

The term CONSTITUTIVELY ACTIVATED RECEPTOR shall mean a receptor subject to constitutive receptor activation.

The term CONSTITUTIVE RECEPTOR ACTIVATION shall mean stabilization of a receptor in the active state by means other than binding of the receptor with its endogenous ligand or a chemical equivalent thereof.

The terms CONTACT or CONTACTING shall mean bringing the indicated moieties together, whether in an in vitro system or an in vivo system. Thus, "contacting" a RUP25 receptor with a compound of the invention includes the administration of a compound of the present invention to an individual, for example a human, having a RUP25 receptor, as well as, for example, introducing a compound of the invention into a sample containing a cellular or more purified preparation containing a RUP25 receptor.

CORONARY HEART DISEASE is intended herein to encompass disorders comprising a narrowing of the small blood vessels that supply blood and oxygen to the heart. Coronary heart disease usually results from the build up of fatty material and plaque. As the coronary arteries narrow, the flow of blood to the heart can slow or stop. Coronary heart disease can cause chest pain (stable angina), shortness of breath, heart attack, or other symptoms.

DECREASE is used to refer to a reduction in a measurable quantity and is used synonymously with the terms "reduce", "diminish", "lower", and "lessen".

DIABETES as used herein is intended to encompass the usual diagnosis of DIABETES made from any of the methods including, but not limited to, the following list: symptoms of diabetes (e.g., polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

The phrase DISORDERS OF LIPID METABOLISM is intended herein to include, but not be limited to, dyslipidemia.

The term DYSLIPIDEMIA is intended herein to encompass disorders comprising any one of elevated level of plasma free fatty acids, elevated level of plasma cholesterol, elevated level of LDL-cholesterol, reduced level of HDL-cholesterol, and elevated level of plasma triglycerides.

The phrase IN NEED OF TREATMENT, as used herein, refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, that includes the knowledge that the individual is ill, or will be ill, as the result of a disease, condition or disorder that is treatable by the compounds of the invention. Further, the phrase "in need of treatment" also refers to the "prophylaxis" of an individual which is the judgment made by the caregiver that the individual will become ill. In this context, the compounds of the invention are used in a protective or preventive manner. Accordingly, "in need of treatment" refers to the judgment of the caregiver that the individual is already ill or will become ill and the compounds of the present invention can be used to alleviate, inhibit, ameliorate or prevent the disease, condition or disorder.

The term INDIVIDUAL as used herein refers to any animal, including mammals, for example, mice, rats, other rodents, rabbits, dogs, cats, swine, cattle, sheep, horses, or primates, and in one embodiment, humans.

The terms INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

The term INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. In some embodiments, the baseline intracellular response is inhibited in the presence of the inverse agonist by at least 30%, in other embodiments, by at least 50%, and in still other embodiments, by at least 75%, as compared with the baseline response in the absence of the inverse agonist.

The term LIGAND shall mean an endogenous, naturally occurring molecule specific for an endogenous, naturally occurring receptor.

The phrase METABOLIC-RELATED DISORDERS is intended herein to include, but not be limited to, dyslipidemia, atherosclerosis, coronary heart disease, insulin resistance, obesity, impaired glucose tolerance, atheromatous disease, hypertension, stroke, Syndrome X, heart disease and type 2 diabetes.

As used herein, the terms MODULATE or MODULATING shall mean to refer to an increase or decrease in the amount, quality, response or effect of a particular activity, function or molecule.

As used herein, a term "PARTIAL AGONIST" is a moiety that activates an intracellular response when it binds to a receptor (for example, a RUP25 receptor) but to a lesser degree/extent compared to a full agonist. The term partial agonist is a relative term since a partial agonist generates a partial response compared to that of a full agonist. It is understood that since new compounds are being discovered over time a compound once described as a full agonist can later change to a partial agonist based on a discovery of new full agonist.

The term PHARMACEUTICAL COMPOSITION shall mean a composition for preventing, treating or controlling a disease state or condition comprising at least one active compound, for example, a compound of the present invention including pharmaceutically acceptable salts, pharmaceutically acceptable solvates and/or hydrates thereof, and at least one pharmaceutically acceptable carrier.

The term PHARMACEUTICALLY ACCEPTABLE CARRIER or EXCIPIENT shall mean any substantially inert substance used as a diluent or vehicle for a compound of the present invention.

The phrase THERAPEUTICALLY-EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Invention

One aspect of the present invention pertains to certain fused pyrazole derivatives as represented by Formula (Ia):

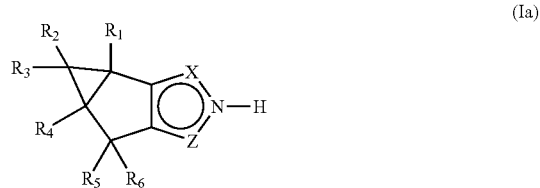

(Ia)

or a pharmaceutically acceptable salt, hydrate or solvate thereof; wherein X, Z, $R_1$, $R_2$, $R_3$, $R_4$, $R_5$ and $R_6$ have the same definitions as described herein, supra and infra.

One aspect of the present invention pertains to certain fused pyrazole derivatives as represented by Formula (Ia), or a pharmaceutically acceptable salt, hydrate or solvate thereof, wherein:

X is N and Z is $CR_7$, or X is $CR_7$ and Z is N;

$R_1$ and $R_4$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$alkylthioamido, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$-haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol;

$R_2$ and $R_3$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, arylsulfinyl, arylsulfonyl, arylthio, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ dialkylcarboxamide, $C_{1-6}$ dialkylthiocarboxamide, $C_{1-6}$-dialkylamido, $C_{1-6}$-dialkylthioamido, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, heterocyclic-oxy, heterocyclic-sulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid and thiol; wherein said $C_{1-6}$ alkyl is optionally substituted with substituents selected from the group consisting of $C_{1-6}$ acyl, $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$-haloalkylthio, hydroxyl, nitro, phenoxy and phenyl;

$R_5$ and $R_6$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol; and $R_7$ is carbo-$C_{1-6}$-alkoxy, carboxy or tetrazol-5-yl.

It is understood that the present invention embraces each compound and generic formulae, infra and supra, wherein $R_1$ and $R_4$ groups are cis with respect to each other.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituents or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, and the like. In some embodiments, the term "substituted" refers to 1, 2, 3, 4, 5 or 6 substituents. In some embodiments, the term "substituted" refers to 1, 2, 3, 4 or 5 substituents. In some embodiments, the term "substituted" refers to 1, 2, 3 or 4 substituents. In some embodiments, the term "substituted" refers to 1, 2 or 3 substituents. In some embodiments, the term "substituted" refers to 1 or 2 substituents. In some embodiments, the term "substituted" refers to 1 substituent.

It is understood and appreciated that compounds of Formula (Ia) may have one or more chiral centers, and therefore can exist as enantiomers and/or diastereomers. The invention is understood to extend to and embrace all such enantiomers, diastereomers and mixtures thereof, including but not limited to racemates. Accordingly, one embodiment of the present invention pertains to compounds of Formula (Ia) and formulae used throughout this disclosure that are R enantiomers. Further, one embodiment of the present invention pertains to compounds of Formula (Ia) and formulae used throughout this disclosure that are S enantiomers. In another embodiment, compounds of the present invention have two stereochemical centers and both are R. In another embodiment, compounds of the present invention have two stereochemical centers and both are S. In another embodiment, compounds of the present invention have three stereochemical centers wherein all are R. In another embodiment, compounds of the present invention have three stereochemical centers wherein two are R and the third is S. In another embodiment, compounds of the present invention have three stereochemical centers wherein two are S and the third is R. It is understood that compounds of Formula (Ia) and formulae used throughout this disclosure are intended to represent all individual enantiomers and mixtures thereof, unless stated or shown otherwise.

Compounds of the present invention may exist in various tautomeric forms. For example, it is well appreciated to those skilled in the art that tetrazoles can exist in at least two tautomeric forms and although in certain Formulae described herein represents one form it is understood that all tautomeric forms are embraced by the present invention; by way of illustration, when X is N and Z is $CR_7$ wherein $R_7$ is tetrazol-5-yl then two possible tautomers for the tetrazole ring are shown below:

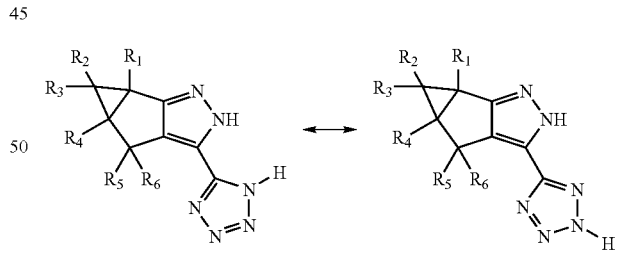

Likewise, it is understood that when X is $CR_7$, wherein $R_7$ is tetrazol-5-yl, and Z is N that tautomers can also exist for the tetrazole ring.

In addition, it is well appreciated to those skilled in the art that pyrazole heterocycles can also exist in at least two tautomeric forms and although the Formulae described herein represents one form it is understood that all tautomeric forms are embraced by the present invention. By way of illustration, two possible tautomers for the pyrazole ring (when X is N and Z is $CR_7$) are shown below:

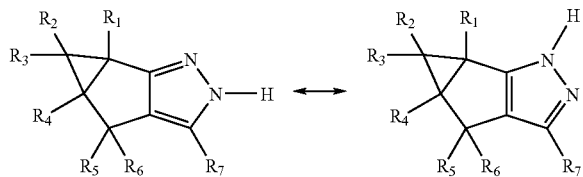

Similarly, tautomers can exist for when X is $CR_7$ and Z is N. Further, it is understood that when $R_7$ is a tetrazol-5-yl ring then tautomers can exist for both the pyrazole ring and also the tetrazole ring in combination. It is understood that all tautomers that can exist for the compounds disclosed herein are within the scope of the invention.

It is further understood that tautomeric forms can also have corresponding nomenclature for each tautomer. Therefore, the present invention includes all tautomers and the various nomenclature designations for all tautomers.

Some embodiments of the present invention pertain to compounds wherein X is N; Z is $CR_7$; and $R_7$ is carbo-$C_{1-6}$-alkoxy or carboxy.

Some embodiments of the present invention pertain to compounds wherein X is N; Z is $CR_7$; and $R_7$ is carboxy. Some embodiments can be represented by Formula (Ic) as illustrated below:

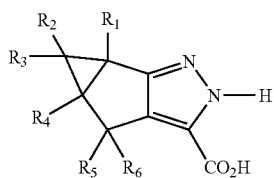

(Ic)

wherein each variable in Formula (Ic) has the same meaning as described herein, supra and infra.

Some embodiments of the present invention pertain to compounds wherein X is N; Z is $CR_7$; and $R_7$ is tetrazol-5-yl. Some embodiments can be represented by Formula (Ie) as illustrated below:

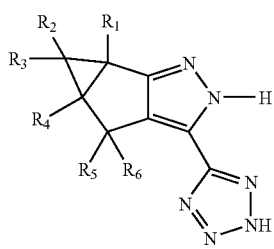

(Ie)

wherein each variable in Formula (Ie) has the same meaning as described herein, supra and infra.

Some embodiments of the present invention pertain to compounds wherein X is $CR_7$; $R_7$ is carbo-$C_{1-6}$alkoxy or carboxy; and Z is N.

Some embodiments of the present invention pertain to compounds wherein X is $CR_7$; $R_7$ is carboxy; and Z is N. Some embodiments can be represented by Formula (Ig) as illustrated below:

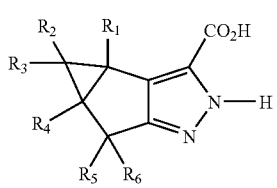

(Ig)

wherein each variable in Formula (Ig) has the same meaning as described herein, supra and infra.

Some embodiments of the present invention pertain to compounds wherein X is $CR_7$; $R_7$ is tetrazol-5-yl; and Z is N. Some embodiments can be represented by Formula (Ii) as illustrated below:

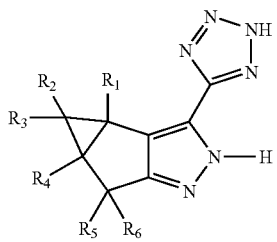

(Ii)

wherein each variable in Formula (Ii) has the same meaning as described herein, supra and infra.

Some embodiments of the present invention pertain to compounds wherein $R_1$ is H or halogen.

Some embodiments of the present invention pertain to compounds wherein $R_1$ is H.

Some embodiments of the present invention pertain to compounds wherein $R_4$ is H or halogen.

Some embodiments of the present invention pertain to compounds wherein $R_4$ is H.

Some embodiments of the present invention pertain to compounds wherein $R_1$ and $R_4$ are both H.

Some embodiments of the present invention pertain to compounds represented by Formula (Ik) as illustrated below:

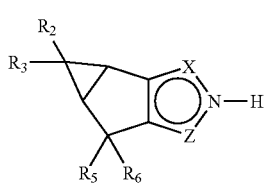

(Ik)

wherein each variable in Formula (Ik) has the same meaning as described herein, supra and infra.

Some embodiments of the present invention pertain to compounds wherein $R_5$ is H or halogen.

Some embodiments of the present invention pertain to compounds wherein $R_5$ is H.

Some embodiments of the present invention pertain to compounds wherein $R_6$ is H or halogen.

Some embodiments of the present invention pertain to compounds wherein $R_6$ is H.

Some embodiments of the present invention pertain to compounds wherein $R_5$ and $R_6$ are both H.

Some embodiments of the present invention pertain to compounds represented by Formula (Im) as illustrated below:

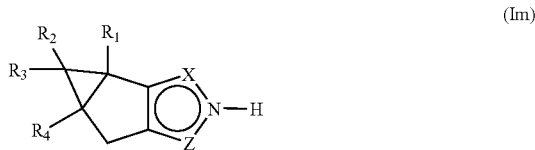

(Im)

wherein each variable in Formula (Im) has the same meaning as described herein, supra and infra.

Some embodiments of the present invention pertain to compounds wherein $R_1$, $R_4$, $R_5$ and $R_6$ are each H. Some embodiments can be represented by Formula (Io) as illustrated below:

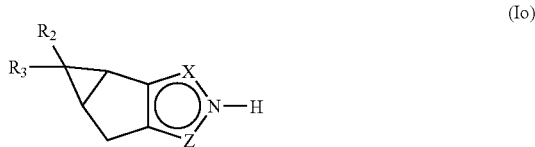

(Io)

wherein each variable in Formula (Io) has the same meaning as described herein, supra and infra.

Some embodiments of the present invention pertain to compounds wherein $R_2$ and $R_3$ are each selected independently from the group consisting of H, $C_{1-6}$ alkyl and halogen; wherein said $C_{1-6}$ alkyl is optionally substituted with substituents selected from the group consisting of $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, phenoxy and phenyl.

Some embodiments of the present invention pertain to compounds wherein $R_2$ and $R_3$ together with the carbon to which they are both bonded form a $C_{3-6}$ cycloalkyl.

Some embodiments of the present invention pertain to compounds wherein $R_2$ is H or $C_{1-6}$ alkyl; and $R_3$ is H, $C_{1-6}$ alkyl and halogen; wherein said $C_{-4}$ alkyl is optionally substituted with substituents selected from the group consisting of $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, phenoxy and phenyl.

Some embodiments of the present invention pertain to compounds wherein $R_2$ is H or $C_{1-6}$ alkyl; and $R_3$ is H, $C_{2-6}$ alkenyl, $C_{1-6}$ alkyl, $C_{3-7}$ cycloalkyl, halogen or phenyl; wherein said $C_{1-6}$ alkyl is optionally substituted with substituents selected from the group consisting of $C_{1-6}$ alkoxy, $C_{1-6}$ alkylthio, hydroxyl, phenoxy and phenyl; or $R_2$ and $R_3$ together with the carbon to which they are both bonded form a cyclopropyl, cyclopentyl or cyclohexyl group.

Some embodiments of the present invention pertain to compounds wherein $R_2$ is H or $CH_3$; and $R_3$ is H, methyl, ethyl, n-propyl, isopropyl, isobutyl, n-butyl, n-pentyl, vinyl, hydroxymethyl, methoxymethyl, benzyl, phenyl, phenoxymethyl, methylsulfanylmethyl, ethoxymethyl, cyclopropyl, 1-but-2-enyl, or allyl; or $R_2$ and $R_3$ together with the carbon to which they are both bonded form a cyclopropyl, cyclopentyl or cyclohexyl group.

Some embodiments of the present invention pertain to compounds wherein $R_2$ is H or $C_{1-6}$ alkyl; and $R_3$ is H, $C_{2-6}$ alkenyl, $C_{1-6}$ alkyl, halogen or phenyl; wherein said $C_{1-6}$ alkyl is optionally substituted with substituents selected from the group consisting of $C_{1-6}$ alkoxy, hydroxyl, phenoxy and phenyl.

Some embodiments of the present invention pertain to compounds wherein $R_2$ is H or $CH_3$; and $R_3$ is H, $CH_3$ or benzyl.

Some embodiments of the present invention pertain to compounds wherein $R_2$ is H or $CH_3$; and $R_3$ is H, methyl, ethyl, n-propyl, isopropyl, isobutyl, n-butyl, n-pentyl, vinyl, 5 hydroxymethyl, methoxymethyl, benzyl, phenyl or phenoxymethyl.

Some embodiments of the present invention pertain to compounds wherein:

X is N, Z is $CR_7$, and $R_7$ is carboxyl; or
X is $CR_7$, $R_7$ is carboxyl or tetrazolyl, and Z is N;
$R_1$, $R_4$, $R_5$ and $R_6$ are each H;
$R_2$ is H or $CH_3$; and
$R_3$ is H, $CH_3$ or benzyl; or
a pharmaceutically acceptable salt, hydrate or solvate thereof.

Some embodiments of the present invention pertain to compounds wherein:

X is N, Z is $CR_7$, wherein $R_7$ is carboxyl, —$CO_2Et$ or tetrazol-5-yl; or
X is $CR_7$, wherein $R_7$ is carboxyl, —$CO_2Et$ or tetrazolyl, and Z is N;
$R_1$, $R_4$, $R_5$ and $R_6$ are each H;
$R_2$ is H or $CH_3$; and
$R_3$ is H, methyl, ethyl, n-propyl, isopropyl, isobutyl, n-butyl, n-pentyl, vinyl, hydroxymethyl, methoxymethyl, benzyl, phenyl or phenoxymethyl; or
a pharmaceutically acceptable salt, hydrate or solvate thereof.

Some embodiments of the present invention pertain to compounds wherein:

X is N, Z is $CR_7$, and $R_7$ is carboxyl, —$CO_2Et$ or tetrazol-5-yl;
$R_1$, $R_4$, $R_5$ and $R_6$ are each H;
$R_2$ is H or $CH_3$; and
$R_3$ is H, methyl, ethyl, n-propyl, isopropyl, isobutyl, n-butyl, n-pentyl, vinyl, hydroxymethyl, methoxymethyl, benzyl, phenyl or phenoxymethyl; or
a pharmaceutically acceptable salt, hydrate or solvate thereof.

Some embodiments of the present invention pertain to compounds selected from the group consisting of: 3b,4,4a,5-Tetrahydro-2H-cyclopropa[3,4]cyclopenta[1,2-c]pyrazole-3-carboxylic acid; 1a,3,5,5a-Tetrahydro-1H-2,3-diazacyclopropa[a]pentalene-4-carboxylic acid; 1-Benzyl-1a,3,5,5a-tetrahydro-1H-2,3-diaza-cyclopropa[a]pentalene-4-carboxylic acid; and 1,1-Dimethyl-1a,3,5,5a-tetrahydro-1H-2,3-diaza-cyclopropa[a]pentalene-4-carboxylic acid; or a pharmaceutically acceptable salt, hydrate or solvate thereof.

Some embodiments of the present invention pertain to compounds selected from the group consisting of: 4-(2H-Tetrazol-5-yl)-1a,3,5,5a-tetrahydro-1H-2,3-diaza-cyclopropa[a]pentalene; 1,1-Dimethyl-4-(2H-tetrazol-5-yl)-1a,3,5,5a-tetrahydro-1H-2,3-diaza-cyclopropa[a]pentalene; and 1-Benzyl-4-(2H-tetrazol-5-yl)-1a,3,5,5a-tetrahydro-1H-2,3-diaza-cyclopropa[a]pentalene; or a pharmaceutically acceptable salt, hydrate or solvate thereof.

Some embodiments of the present invention pertain to compounds wherein the stereochemistry for the two carbons assigned as 3b and 4a, or 1a and 5a are both R.

Some embodiments of the present invention pertain to compounds wherein the stereochemistry for the two carbons assigned as 3b and 4a, or 1a and 5a are both S.

Some embodiments of the present invention pertain to compounds wherein the stereochemistry for the two carbons assigned as 1a and 5a are both R.

Some embodiments of the present invention pertain to compounds wherein the stereochemistry for the carbon assigned as 1a is R and the stereochemistry for the carbon assigned as 5a is S.

Some embodiments of the present invention pertain to compounds wherein the stereochemistry for the carbon assigned as 1a is S and the stereochemistry for the carbon assigned as 5a is R.

Some embodiments of the present invention pertain to compounds wherein the stereochemistry for the priority group bonded to the carbon assigned as 1 is endo. It is understood that the term "priority group" has the same meaning as defined by "The Cahn, Ingold and Prelog System" by application of sequence rules, for a general review of the CIP system see R. S. Cahn, C. K. Ingold and V. Prelog, *Angew. Chem. Internat. Ed. Eng.* 5, 385–415, (1966); and V. Prelog and G. Helmchen, *Angew. Chem. Internat. Ed. Eng.* 21, 567–583 (1982).

Some embodiments of the present invention pertain to compounds wherein the stereochemistry for the priority group bonded to the carbon assigned as 1 is exo.

In general, the endo and exo terminology applies to $R_2$ and $R_3$ and can be represented by the following formulae, for example, when X is $CR_7$ and Z is N:

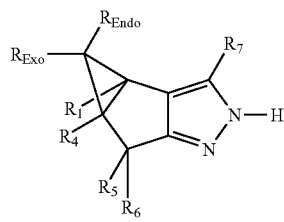

or when X is N and Z is $CR_7$:

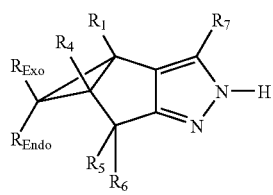

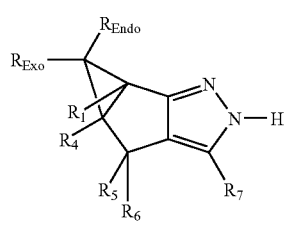

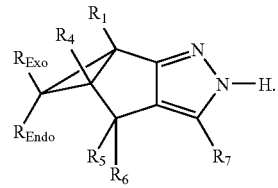

In general, when X is $CR_7$ and Z is N, then the two carbons assigned as 3b and 4a are as shown in Formula (IIa) below:

(IIa)

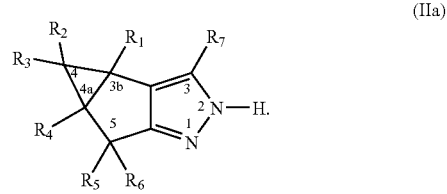

It is understood that compounds of the present invention have the stereochemistry where the $R_1$ and $R_4$ groups are cis with respect to each other. Theses compounds can be generically represented by Formula (IIc) and Formula (IId):

(IIc)

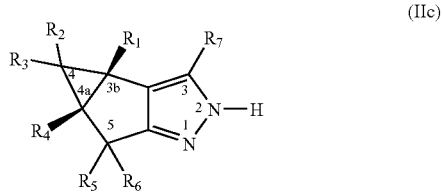

(IId)

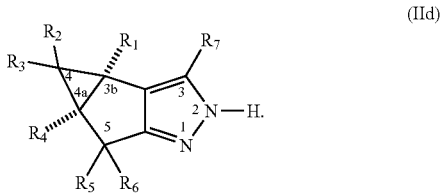

In some embodiments, the carbons assigned as 3b and 4a have the stereochemical designations as represented by Formula (IIc):

(IIc)

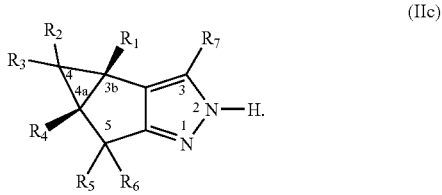

In some embodiments, the carbons assigned as 3b and 4a have the stereochemical designations as represented by Formula (IId):

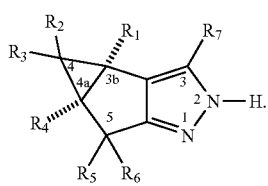
(IId)

Similarly, when X is N and Z is CR$_7$, then the two carbons assigned as 1a and 5a are as shown in Formula (IIe) below:

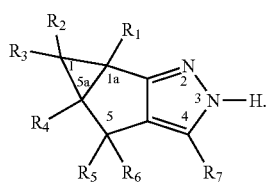
(IIe)

It is understood that compounds of the present invention have the stereochemistry where the R$_1$ and R$_4$ groups are cis with respect to each other. Theses compounds can be generically represented by Formula (IIg) and Formula (IIh):

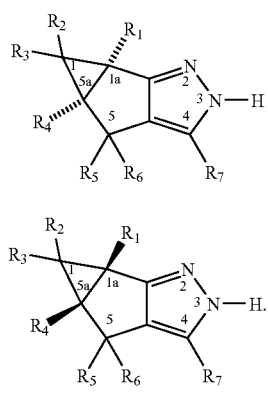
(IIg)

(IIh)

In some embodiments, the carbons assigned as 1a and 5a have the stereochemical designations as represented by Formula (IIg):

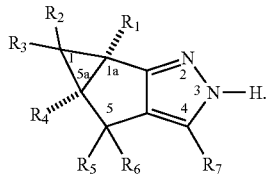
(IIg)

In some embodiments, the carbons assigned as 1a and 5a have the stereochemical designations as represented by Formula (IIh):

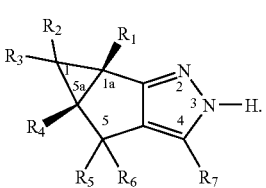
(IIh)

It is understood that the actual "R" and "S" designation for C(3b) and C(4a) in Formulae (IIc) and (IId); and C(1a) and C(5a) in Formulae (IIg) and (IIh) will vary depending on the various groups present. For example, in some embodiments, when R$_1$ to R$_6$ are all hydrogens then the stereochemistry is defined as shown in Formulae (IIj) and (IIk):

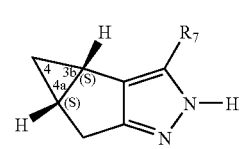
(IIj)

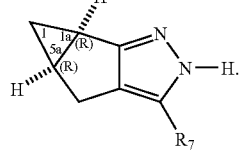
(IIk)

In some embodiments, when R$_1$, R$_2$, R$_4$, R$_5$ and R$_6$ are all hydrogens and R$_3$ is a group such that the carbon of the group is bonded directly to C(4) or C(1), then the stereochemistry is defined as shown in Formulae (IIm) and (IIn). Examples for R$_3$ can be selected from methyl, ethyl, n-propyl, isopropyl, isobutyl, n-butyl, n-pentyl, vinyl, hydroxymethyl, methoxymethyl, benzyl, phenyl and phenoxymethyl; or R$_3$ can be selected from methyl, ethyl, n-propyl, isopropyl, isobutyl, n-butyl, n-pentyl, vinyl, hydroxymethyl, methoxymethyl, benzyl, phenyl, phenoxymethyl, methylsulfanylmethyl, ethoxymethyl, cyclopropyl, 1-but-2-enyl, and allyl:

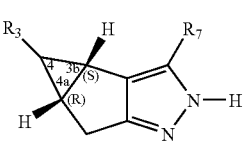
(IIm)

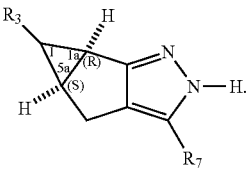
(IIn)

It is understood that all other possible stereochemical representations and designations are embraced by the invention.

Some embodiments of the present invention pertain to compounds as represented in TABLE 1 below.

TABLE 1

| Compd No. | Chemical Structure | Chemical Name |
|---|---|---|
| 1 | 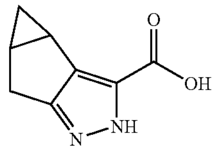 | 3b,4,4a,5-Tetrahydro-2H-cyclopropa[3,4]cyclopenta[1,2-c]pyrazole-3-carboxylic acid |
| 2 | 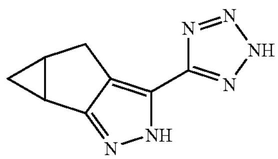 | 4-(2H-Tetrazol-5-yl)-1a,3,5,5a-tetrahydro-1H-2,3-diaza-cyclopropa[a]pentalene |
| 3 | 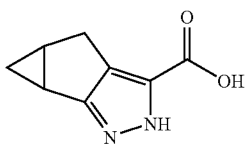 | 1a,3,5,5a-Tetrahydro-1H-2,3-diaza-cyclopropa[a]pentalene-4-carboxylic acid |
| 4 | 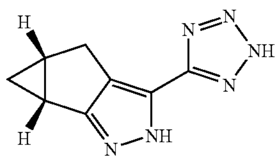 | (1aR,5aR)-4-(2H-Tetrazol-5-yl)-1a,3,5,5a-tetrahydro-1H-2,3-diaza-cyclopropa[a]pentalene |
| 5 | 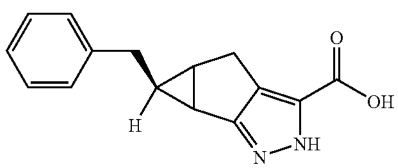 | exo-1-Benzyl-1a,3,5,5a-tetrahydro-1H-2,3-diaza-cyclopropa[a]pentalene-4-carboxylic acid |
| 6 | 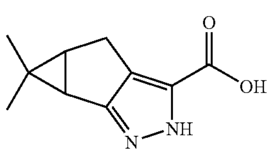 | 1,1-Dimethyl-1a,3,5,5a-tetrahydro-1H-2,3-diaza-cyclopropa[a]pentalene-4-carboxylic acid |
| 7 | 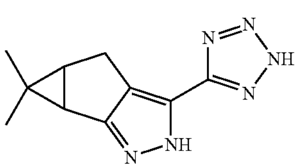 | 1,1-Dimethyl-4-(2H-tetrazol-5-yl)-1a,3,5,5a-tetrahydro-1H-2,3-diaza-cyclopropa[a]pentalene |
| 8 | 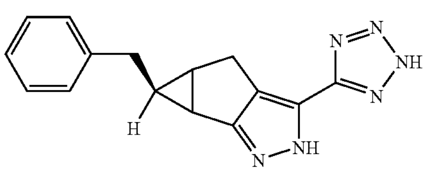 | exo-1-Benzyl-4-(2H-tetrazol-5-yl)-1a,3,5,5a-tetrahydro-1H-2,3-diaza-cyclopropa[a]pentalene |

In some embodiments, compounds of the present invention pertain to the compounds in TABLE 2:

TABLE 2

| Compd No. | Chemical Structure | Chemical Name |
|---|---|---|
| 9 | 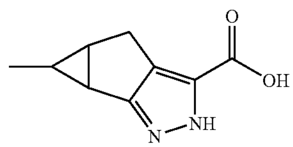 | 1-Methyl-1a,3,5,5a-tetrahydro-1H-2,3-diaza-cyclopropa[a]pentalene-4-carboxylic acid |
| 10 | 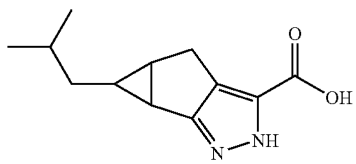 | 1-Isobutyl-1a,3,5,5a-tetrahydro-1H-2,3-diaza-cyclopropa[a]pentalene-4-carboxylic acid |
| 11 | 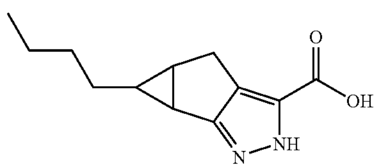 | 1-Butyl-1a,3,5,5a-tetrahydro-1H-2,3-diaza-cyclopropa[a]pentalene-4-carboxylic acid |
| 12 | 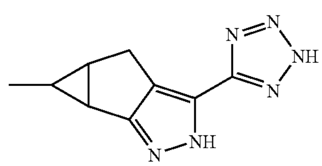 | 1-Methyl-4-(2H-tetrazol-5-yl)-1a,3,5,5a-tetrahydro-1H-2,3-diaza-cyclopropa[a]pentalene |
| 13 | 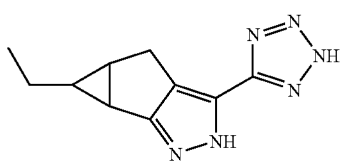 | 1-Ethyl-4-(2H-tetrazol-5-yl)-1a,3,5,5a-tetrahydro-1H-2,3-diaza-cyclopropa[a]pentalene |
| 14 | 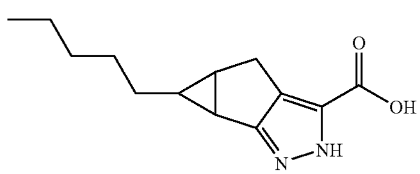 | 1-Pentyl-1a,3,5,5a-tetrahydro-1H-2,3-diaza-cyclopropa[a]pentalene-4-carboxylic acid |
| 15 | 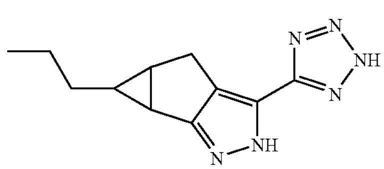 | 1-Propyl-4-(2H-tetrazol-5-yl)-1a,3,5,5a-tetrahydro-1H-2,3-diaza-cyclopropa[a]pentalene |
| 16 | 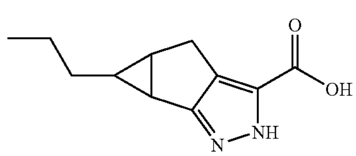 | 1-Propyl-1a,3,5,5a-tetrahydro-1H-2,3-diaza-cyclopropa[a]pentalene-4-carboxylic acid |
| 17 | 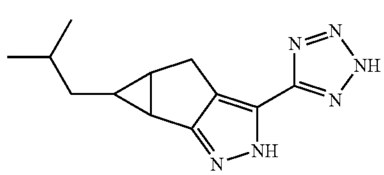 | 1-Isobutyl-4-(2H-tetrazol-5-yl)-1a,3,5,5a-tetrahydro-1H-2,3-diaza-cyclopropa[a]pentalene |

TABLE 2-continued

| Compd No. | Chemical Structure | Chemical Name |
|---|---|---|
| 18 | 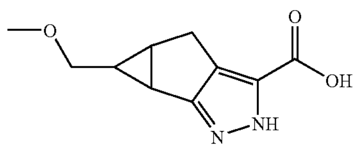 | 1-Methoxymethyl-1a,3,5,5a-tetrahydro-1H-2,3-diaza-cyclopropa[a]pentalene-4-carboxylic acid |
| 19 | 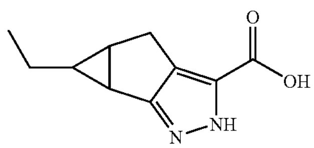 | 1-Ethyl-1a,3,5,5a-tetrahydro-1H-2,3-diaza-cyclopropa[a]pentalene-4-carboxylic acid |
| 20 | 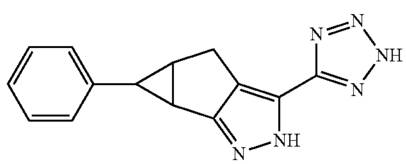 | 1-Phenyl-4-(2H-tetrazol-5-yl)-1a,3,5,5a-tetrahydro-1H-2,3-diaza-cyclopropa[a]pentalene |
| 21 | 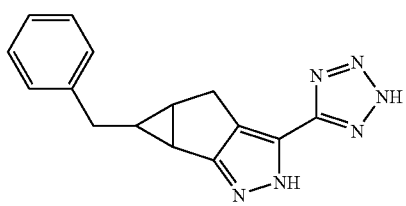 | 1-Benzyl-4-(2H-tetrazol-5-yl)-1a,3,5,5a-tetrahydro-1H-2,3-diaza-cyclopropa[a]pentalene |
| 22 | 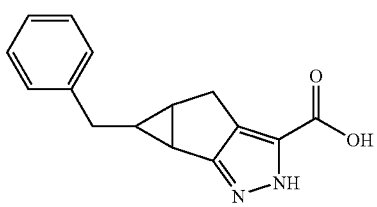 | 1-Benzyl-1a,3,5,5a-tetrahydro-1H-2,3-diaza-cyclopropa[a]pentalene-4-carboxylic acid |
| 23 | 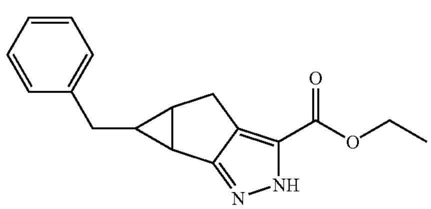 | 1-Benzyl-1a,3,5,5a-tetrahydro-1H-2,3-diaza-cyclopropa[a]pentalene-4-carboxylic acid ethyl ester |
| 24 | 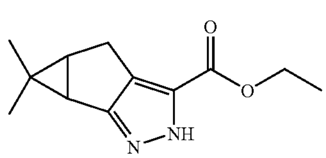 | 1,1-Dimethyl-1a,3,5,5a-tetrahydro-1H-2,3-diaza-cyclopropa[a]pentalene-4-carboxylic acid ethyl ester |
| 25 | 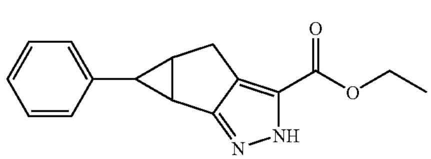 | 1-Phenyl-1a,3,5,5a-tetrahydro-1H-2,3-diaza-cyclopropa[a]pentalene-4-carboxylic acid ethyl ester |

TABLE 2-continued

| Compd No. | Chemical Structure | Chemical Name |
|---|---|---|
| 26 | 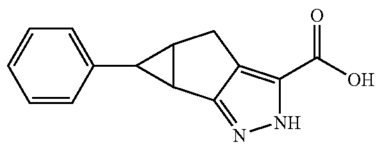 | 1-Phenyl-1a,3,5,5a-tetrahydro-1H-2,3-diaza-cyclopropa[a]pentalene-4-carboxylic acid |
| 27 | 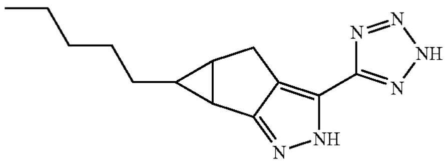 | 1-Pentyl-4-(2H-tetrazol-5-yl)-1a,3,5,5a-tetrahydro-1H-2,3-diaza-cyclopropa[a]pentalene |
| 28 | 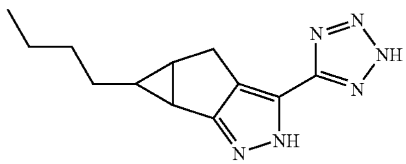 | 1-Butyl-4-(2H-tetrazol-5-yl)-1a,3,5,5a-tetrahydro-1H-2,3-diaza-cyclopropa[a]pentalene |
| 29 | 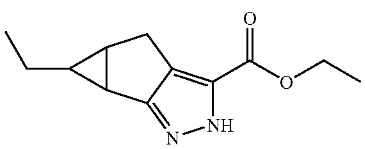 | 1-Ethyl-1a,3,5,5a-tetrahydro-1H-2,3-diaza-cyclopropa[a]pentalene-4-carboxylic acid ethyl ester |
| 30 | 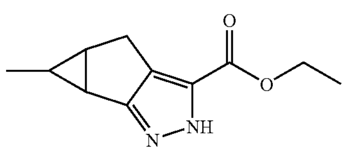 | 1-Methyl-1a,3,5,5a-tetrahydro-1H-2,3-diaza-cyclopropa[a]pentalene-4-carboxylic acid ethyl ester |
| 31 | 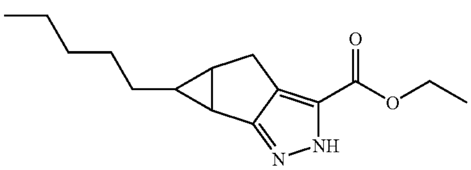 | 1-Pentyl-1a,3,5,5a-tetrahydro-1H-2,3-diaza-cyclopropa[a]pentalene-4-carboxylic acid ethyl ester |
| 32 | 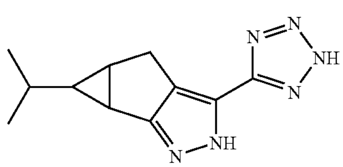 | 1-Isopropyl-4-(2H-tetrazol-5-yl)-1a,3,5,5a-tetrahydro-1H-2,3-diaza-cyclopropa[a]pentalene |
| 33 | 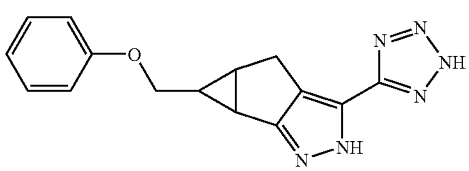 | 1-Phenoxymethyl-4-(2H-tetrazol-5-yl)-1a,3,5,5a-tetrahydro-1H-2,3-diaza-cyclopropa[a]pentalene |
| 34 | 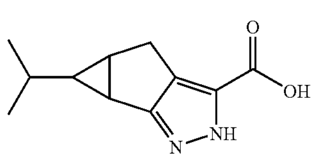 | 1-Isopropyl-1a,3,5,5a-tetrahydro-1H-2,3-diaza-cyclopropa[a]pentalene-4-carboxylic acid |

TABLE 2-continued

| Compd No. | Chemical Structure | Chemical Name |
|---|---|---|
| 35 | 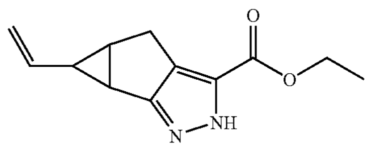 | 1-Vinyl-1a,3,5,5a-tetrahydro-1H-2,3-diaza-cyclopropa[a]pentalene-4-carboxylic acid ethyl ester |
| 36 | 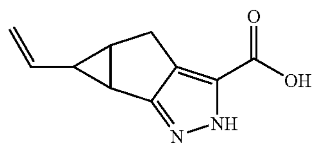 | 1-Vinyl-1a,3,5,5a-tetrahydro-1H-2,3-diaza-cyclopropa[a]pentalene-4-carboxylic acid |
| 37 | 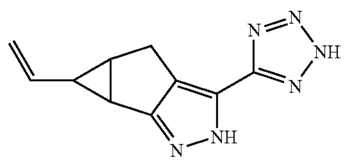 | 4-(2H-Tetrazol-5-yl)-1-vinyl-1a,3,5,5a-tetrahydro-1H-2,3-diaza-cyclopropa[a]pentalene |
| 38 | 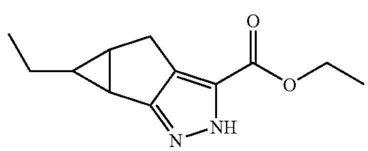 | 1-Ethyl-1a,3,5,5a-tetrahydro-1H-2,3-diaza-cyclopropa[a]pentalene-4-carboxylic acid ethyl ester |
| 39 | 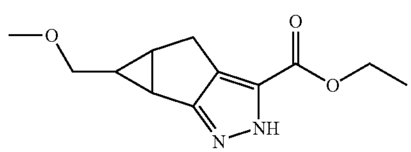 | 1-Methoxymethyl-1a,3,5,5a-tetrahydro-1H-2,3-diaza-cyclopropa[a]pentalene-4-carboxylic acid ethyl ester |
| 40 | 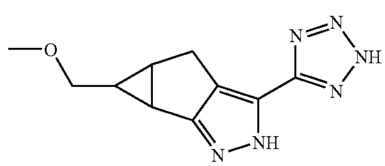 | 1-Methoxymethyl-4-(2H-tetrazol-5-yl)-1a,3,5,5a-tetrahydro-1H-2,3-diaza-cyclopropa[a]pentalene |
| 41 | 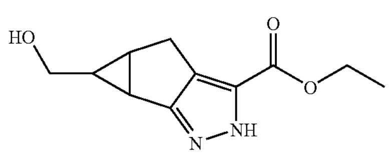 | 1-Hydroxymethyl-1a,3,5,5a-tetrahydro-1H-2,3-diaza-cyclopropa[a]pentalene-4-carboxylic acid ethyl ester |
| 42 | 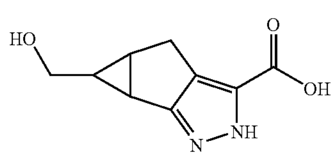 | 1-Hydroxymethyl-1a,3,5,5a-tetrahydro-1H-2,3-diaza-cyclopropa[a]pentalene-4-carboxylic acid |
| 43 | 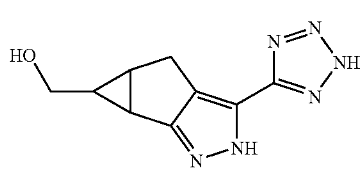 | [4-(2H-Tetrazol-5-yl)-1a,3,5,5a-tetrahydro-1H-2,3-diaza-cyclopropa[a]pentalen-1-yl]-methanol |

In some embodiments, compounds of the present invention pertain to the compounds in TABLE 3:

TABLE 3

| Compd No. | Chemical Structure | Chemical Name |
| --- | --- | --- |
| 44 | 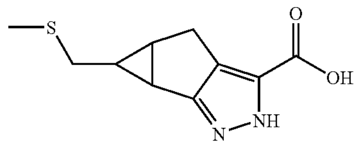 | 1-Methylsulfanylmethyl-1a,3,5,5a-tetrahydro-1H-2,3-diaza-cyclopropa[a]pentalene-4-carboxylic acid |
| 45 | 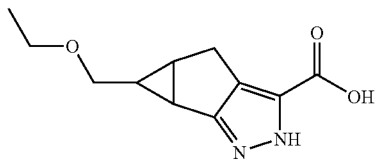 | 1-Ethoxymethyl-1a,3,5,5a-tetrahydro-1H-2,3-diaza-cyclopropa[a]pentalene-4-carboxylic acid |
| 46 | 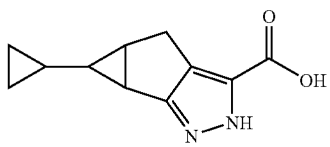 | 1-Cyclopropyl-1a,3,5,5a-tetrahydro-1H-2,3-diaza-cyclopropa[a]pentalene-4-carboxylic acid |
| 47 | 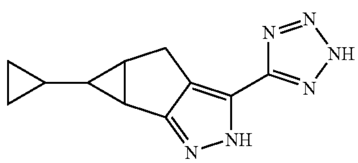 | 1-Cyclopropyl-4-(2H-tetrazol-5-yl)-1a,3,5,5a-tetrahydro-1H-2,3-diaza-cyclopropa[a]pentalene |
| 48 | 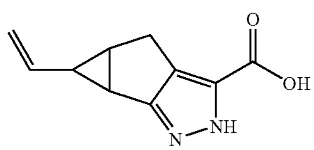 | 1-Vinyl-1a,3,5,5a-tetrahydro-1H-2,3-diaza-cyclopropa[a]pentalene-4-carboxylic acid |
| 49 | 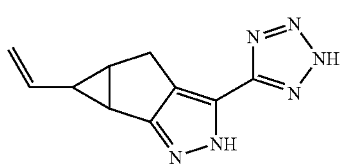 | 4-(2H-Tetrazol-5-yl)-1-vinyl-1a,3,5,5a-tetrahydro-1H-2,3-diaza-cyclopropa[a]pentalene |
| 50 | 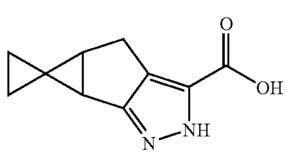 | 1-Spirocyclopropyl-1a,3,5,5a-tetrahydro-1H-2,3-diaza-cyclopropa[a]pentalene-4-carboxylic acid |
| 51 | 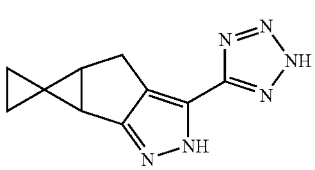 | 1-spirocyclopropyl-4-(2H-tetrazol-5-yl)-1a,3,5,5a-tetrahydro-1H-2,3-diaza-cyclopropa[a]pentalene |
| 52 | 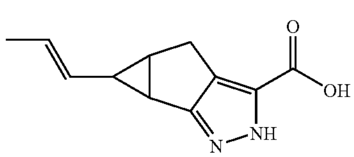 | (E)-1-Propenyl-1a,3,5,5a-tetrahydro-1H-2,3-diaza-cyclopropa[a]pentalene-4-carboxylic acid |

TABLE 3-continued

| Compd No. | Chemical Structure | Chemical Name |
|---|---|---|
| 53 | 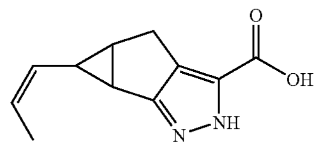 | (Z)-1-Propenyl-1a,3,5,5a-tetrahydro-1H-2,3-diaza-cyclopropa[a]pentalene-4-carboxylic acid |
| 54 | 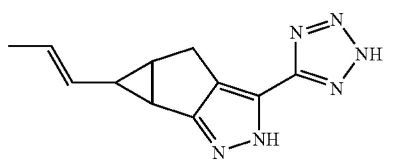 | (E)-1-Propenyl-4-(2H-tetrazol-5-yl)-1a,3,5,5a-tetrahydro-1H-2,3-diaza-cyclopropa[a]pentalene |
| 55 | 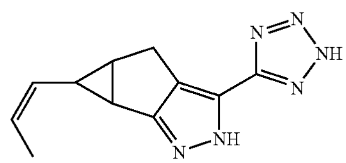 | (Z)-1-Propenyl-4-(2H-tetrazol-5-yl)-1a,3,5,5a-tetrahydro-1H-2,3-diaza-cyclopropa[a]pentalene |
| 56 | 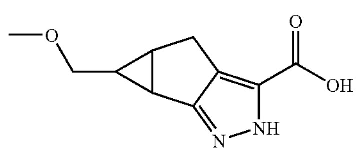 | 1-Methoxymethyl-1a,3,5,5a-tetrahydro-1H-2,3-diaza-cyclopropa[a]pentalene-4-carboxylic acid |
| 57 | 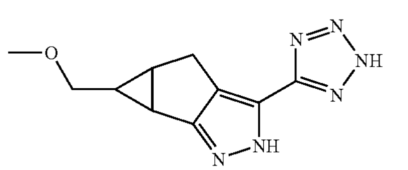 | 1-Methoxymethyl-4-(2H-tetrazol-5-yl)-1a,3,5,5a-tetrahydro-1H-2,3-diaza-cyclopropa[a]pentalene |
| 58 | 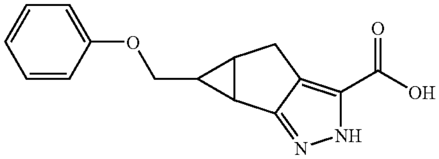 | 1-Phenoxymethyl-1a,3,5,5a-tetrahydro-1H-2,3-diaza-cyclopropa[a]pentalene-4-carboxylic acid |
| 59 | 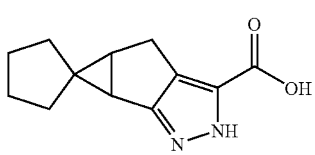 | Spiro[1a,3,5,5a-tetrahydro-1H-2,3-diaza-cyclopropa[a]pentalene-1,1'-cyclopentan]-4-carboxylic acid |
| 60 | 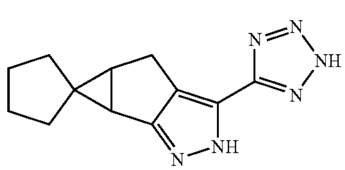 | 5-(Spiro-[1a,3,5,5a-tetrahydro-1H-2,3-diaza-cyclopropa[a]pentalene-1,1'-cyclopentan]-4-yl)-1H-tetrazole |
| 61 | 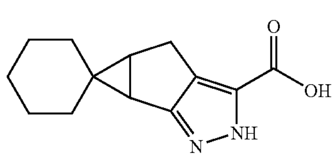 | Spiro[1a,3,5,5a-tetrahydro-1H-2,3-diaza-cyclopropa[a]pentalene-1,1'-cyclohexan]-4-carboxylic acid |

TABLE 3-continued

| Compd No. | Chemical Structure | Chemical Name |
|---|---|---|
| 62 | 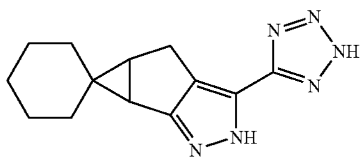 | 5-(Spiro-[1a,3,5,5a-tetrahydro-1H-2,3-diaza-cyclopropa[a]pentalene-1,1'-cyclohexan]-4-yl)-1H-tetrazole |
| 63 | 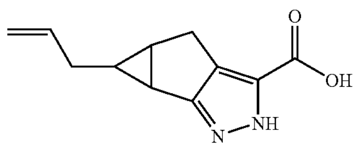 | 1-Allyl-1a,3,5,5a-tetrahydro-1H-2,3-diaza-cyclopropa[a]pentalene-4-carboxylic acid |
| 64 | 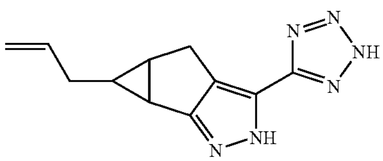 | 1-Allyl-4-(2H-tetrazol-5-yl)-1a,3,5,5a-tetrahydro-1H-2,3-diaza-cyclopropa[a]pentalene |
| 65 | 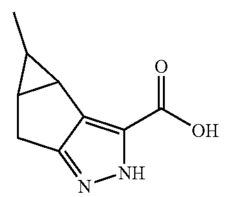 | 4-Methyl-3b,4,4a,5-tetrahydro-2H-cyclopropa[3,4]cyclopenta[1,2-c]pyrazole-3-carboxylic acid |
| 66 | 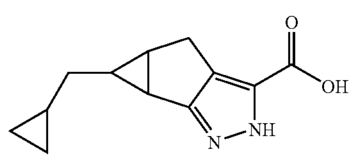 | 1-Cyclopropylmethyl-1a,3,5,5a-tetrahydro-1H-2,3-diaza-cyclopropa[a]pentalene-4-carboxylic acid |

Additionally, compounds of the present invention, for example those compounds found in Tables 1, 2, and 3 including diastereomers and enantiomers thereof, encompass all pharmaceutically acceptable salts, solvates, and particularly hydrates, thereof.

It is understood that the present invention embraces each diastereomer, each enantiomer and mixtures thereof of each compound and generic Formulae disclosed herein just as if they were each individually disclosed with the specific stereochemical designation for each chiral carbon.

For example, one embodiment of the present invention includes a compound with the (3bS, 4aS) or (1aS, 5aS) stereochemistry. One embodiment of the present invention is selected from the group consisting of:

(3bS, 4aS)-3b,4,4a,5-Tetrahydro-2H-cyclopropa[3,4]cyclopenta[1,2-c]pyrazole-3-carboxylic acid; (1aS, 5aS)-4-(2H-Tetrazol-5-yl)-1a,3,5,5a-tetrahydro-1H-2,3-diaza-cyclopropa[a]pentalene; and (1aS, 5as)-1a,3,5,5a-Tetrahydro-1H-2,3-diaza-cyclopropa[a]pentalene-4-carboxylic acid.

Similarly, one embodiment of the present invention includes a compound with the (3bR, 4aR) or (1aR, 5aR) stereochemistry. One embodiment of the present invention is selected from the group consisting of:

(3bR, 4aR)-3b,4,4a,5-Tetrahydro-2H-cyclopropa[3,4]cyclopenta[1,2-c]pyrazole-3-carboxylic acid; (1aR, 5aR)-4-(2H-Tetrazol-5-yl)-1a,3,5,5a-tetrahydro-1H-2,3-diaza-cyclopropa[a]pentalene; and (1aR, 5aR)-1a,3,5,5a-Tetrahydro-1H-2,3-diaza-cyclopropa[a]pentalene-4-carboxylic acid.

In another example, one embodiment of the present invention includes a compound with the endo-(1aR, 5aS) stereochemistry. One embodiment of the present invention is selected from the group consisting of:

endo-(1aR, 5aS)-1-Methyl-1a,3,5,5a-tetrahydro-1H-2,3-diaza-cyclopropa[a]pentalene-4-carboxylic acid; endo-(1aR, 5aS)-1-Isobutyl-1a,3,5,5a-tetrahydro-1H-2,3-diaza-cyclopropa[a]pentalene-4-carboxylic acid; endo-(1aR, 5aS)-1-Butyl-1a,3,5,5a-tetrahydro-1H-2,3-diaza-cyclopropa[a]pentalene-4-carboxylic acid; endo-(1aR, 5aS)-1-Methyl-4-(2H-tetrazol-5-yl)-1a,3,5,5a-tetrahydro-1H-2,3-diaza-cyclopropa[a]pentalene; endo-(1aR, 5aS)-1-Ethyl-4-(2H-tetrazol-5-yl)-1a,3,5,5a-tetrahydro-1H-2,3-diaza-cyclopropa[a]pentalene; endo-1aR, 5aS)-1-Pentyl-1a,3,5,5a-tetrahydro-1H-2,3-diaza-cyclopropa[a]pentalene-4-carboxylic acid; endo-(1aR, 5aS)-1-Propyl-4-(2H-tetrazol-5-yl)-1a,3,5,5a-tetrahydro-1H-2,3-diaza-cyclopropa[a]pentalene; endo-(1aR, 5aS)-1-Propyl-1a,3,5,5a-tetrahydro-1H-2,3-diaza-cyclopropa[a]pentalene-4-carboxylic acid; endo-1aR, 5a)-1-Isobutyl-4-(2H-tetrazol-5-yl)-1a,3,5,5a-tetrahydro-1H-2,3-diaza-cyclopropa[a]pentalene; endo-(1aR, 5aS)-1-Methoxymethyl-1a,3,5,5a-tetrahydro-1H-2,3-diaza-cyclopropa[a]pentalene-4-carboxylic acid; endo-(1aR, 5aS)-1-Ethyl-1a,3,5,5a-tetrahydro-1H-2,3-diaza-cyclopropa[a]pentalene-4-carboxylic acid; endo-(1aR, 5aS)

endo-(1aR, 5aS)-1-Phenyl-4-(2H-tetrazol-5-yl)-1a,3,5,5a-tetrahydro-1H-2,3-diaza-cyclopropa[a]pentalene; endo-(1aR, 5aS)-1-Benzyl-4-2H-tetrazol-5-yl)-1a,3,5,5a-tetrahydro-1H-2,3-diaza-cyclopropa[a]pentalene; endo-(1aR, 5aS)-1-Benzyl-1a,3,5,5a-tetrahydro-1H-2,3-diaza-cyclopropa[a]pentalene-4-carboxylic acid; endo-(1aR, 5aS)-1-Benzyl-1a,3,5,5a-tetrahydro-1H-2,3-diaza-cyclopropa[a]pentalene-4-carboxylic acid ethyl ester; endo-(1aR, 5aS)-1-Phenyl-1a,3,5,5a-tetrahydro-1H-2,3-diaza-cyclopropa[a]pentalene-4-carboxylic acid ethyl ester; endo-(1aR, 5aS)-1-Phenyl-1a,3,5,5a-tetrahydro-1H-2,3-diaza-cyclopropa[a]pentalene-4-carboxylic acid; endo-(1aR, 5aS)-1-Pentyl-4-(2H-tetrazol-5-yl)-1a,3,5,5a-tetrahydro-1H-2,3-diaza-cyclopropa[a]pentalene; endo-(1aR, 5aS)-1-Butyl-4-(2H-tetrazol-5-yl)-1a,3,5,5a-tetrahydro-1H-2,3-diaza-cyclopropa[a]pentalene; endo-(1aR, 5aS)-1-Ethyl-1a,3,5,5a-tetrahydro-1H-2,3-diaza-cyclopropa[a]pentalene-4-carboxylic acid ethyl ester; endo-(1aR, 5aS)-1-Methyl-1a,3,5,5a-tetrahydro-1H-2,3-diaza-cyclopropa[a]pentalene-4-carboxylic acid ethyl ester; endo-(1aR, 5aS)-1-Pentyl-1a,3,5,5a-tetrahydro-1H-2,3-diaza-cyclopropa[a]pentalene-4-carboxylic acid ethyl ester; endo-(1aR, 5aS)-1-Isopropyl-4-(2H-tetrazol-5-yl)-1a,3,5,5a-tetrahydro-1H-2,3-diaza-cyclopropa[a]pe includes a compound with the ntalene; endo-(1aR, 5aS)-1-Phenoxymethyl-4-(2H-tetrazol-5-yl)-1a,3,5,5a-tetrahydro-1H-2,3-diaza-cyclopropa[a]pentalene; endo-(1aR, 5aS)-1-Isopropyl-1a,3,5,5a-tetrahydro-1H-2,3-diaza-cyclopropa[a]pentalene-4-carboxylic acid; endo-(1aR, 5aS)-1-Vinyl-1a,3,5,5a-tetrahydro-1H-2,3-diaza-cyclopropa[a]pentalene-4-carboxylic acid ethyl ester; endo-(1aR, 5aS)-1-Vinyl-1a,3,5,5a-tetrahydro-1H-2,3-diaza-cyclopropa[a]pentalene-4-carboxylic acid; endo-(1aR, 5aS)-4-(2H-Tetrazol-5-yl)-1-vinyl-1a,3,5,5a-tetrahydro-1H-2,3-diaza-cyclopropa[a]pentalene; endo-(1aR, 5aS)-1-Ethyl-1a,3,5,5a-tetrahydro-1H-2,3-diaza-cyclopropa[a]pentalene-4-carboxylic acid ethyl ester; endo-(1aR, 5aS)-1-Methoxymethyl-1a,3,5,5a-tetrahydro-1H-2,3-diaza-cyclopropa[a]pentalene-4-carboxylic acid ethyl ester; endo-(1aR, 5aS)-1-Methoxymethyl-4-(2H-tetrazol-5-yl)-1a,3,5,5a-tetrahydro-1H-2,3-diaza-cyclopropa[a]pentalene; endo-(1aR, 5aS)-1-Hydroxymethyl-1a,3,5,5a-tetrahydro-1H-2,3-diaza-cyclopropa[a]pentalene-4-carboxylic acid ethyl ester; endo-(1aR, 5aS)-1-Hydroxymethyl-1a,3,5,5a-tetrahydro-1H-2,3-diaza-cyclopropa[a]pentalene-4-carboxylic acid; and endo-(1aR, 5aS)-[4-(2H-Tetrazol-5-yl)-1a,3,5,5a-tetrahydro-1H-2,3-diaza-cyclopropa[a]pentalen-1-yl]-methanol.

Another embodiment of the present invention is selected from the group consisting of: endo-(1aR, 5S)-1-Methylsulfanylmethyl-1a,3,5,5a-tetrahydro-1H-2,3-diaza-cyclopropa[a]pentalene-4-carboxylic acid; endo-(1aR, 5aS)-1-Ethoxymethyl-1a,3,5,5a-tetrahydro-1H-2,3-diaza-cyclopropa[a]pentalene-4-carboxylic acid; endo-(1aR, 5aS)-1-Cyclopropyl-1a,3,5,5a-tetrahydro-1H-2,3-diaza-cyclopropa[a]pentalene-4-carboxylic acid; endo-(1aR, 5aS)-1-Cyclopropyl-4-(2H-tetrazol-5-yl)-1a,3,5,5a-tetrahydro-1H-2,3-diaza-cyclopropa[a]pentalene; endo-(1aR, 5aS)-1-Vinyl-1a,3,5,5a-tetrahydro-1H-2,3-diaza-cyclopropa[a]pentalene-4-carboxylic acid; endo-(1aR, 5aS)-4-(2H-Tetrazol-5-yl)-1-vinyl-1a,3,5,5a-tetrahydro-1H-2,3-diaza-cyclopropa[a]pentalene; endo-1aR, 5aS)-1-Spirocyclopropyl-1a,3,5,5a-tetrahydro-1H-2,3-diaza-cyclopropa[a]pentalene-4-carboxylic acid; endo-(1aR, 5aS)-1-spirocyclopropyl-4-(2H-tetrazol-5-yl)-1a,3,5,5a-tetrahydro-1H-2,3-diaza-cyclopropa[a]pentalene; endo-1aR, 5aS)-(E)-1-But-2-enyl-1a,3,5,5a-tetrahydro-1H-2,3-diaza-cyclopropa[a]pentalene-4-carboxylic acid; endo-(1aR, 5aS)-(Z)-1-But-2-enyl-1a,3,5,5a-tetrahydro-1H-2,3-diaza-cyclopropa[a]pentalene-4-carboxylic acid; endo-(1aR, 5aS)-(E)-1-Propenyl-4-(2H-tetrazol-5-yl)-1a,3,5,5a-tetrahydro-1H-2,3-diaza-cyclopropa[a]pentalene; endo-(1aR, 5aS)-(Z)-1-Propenyl-4-(2H-tetrazol-5-yl)-1a,3,5,5a-tetrahydro-1H-2,3-diaza-cyclopropa[a]pentalene; endo-(1aR, 5aS)-1-Methoxymethyl-1a,3,5,5a-tetrahydro-1H-2,3-diaza-cyclopropa[a]pentalene-4-carboxylic acid; endo-(1aR, 5aS)-1-Methoxymethyl-4-(2H-tetrazol-5-yl)-1a,3,5,5a-tetrahydro-1H-2,3-diaza-cyclopropa[a]pentalene; endo-(1aR, 5aS)-1-Phenoxymethyl-1a,3,5,5a-tetrahydro-1H-2,3-diaza-cyclopropa[a]pentalene-4-carboxylic acid; endo-(1aR, 5aS)-Spiro[1a,3,5,5a-tetrahydro-1H-2,3-diaza-cyclopropa[a]pentalene-1,1'-cyclopentan]-4-carboxylic acid; endo-(1aR, 5aS)-5-(Spiro-[1a,3,5,5a-tetrahydro-1H-2,3-diaza-cyclopropa[a]pentalene-1,1'-cyclopentan]-4-yl)-1H-tetrazole; endo-(1aR, 5aS)-Spiro[1a,3,5,5a-tetrahydro-1H-2,3-diaza-cyclopropa[a]pentalene-1,1'-cyclohexan]-4-carboxylic acid; endo-(1aR, 5aS)-5-(Spiro-[1a,3,5,5a-tetrahydro-1H-2,3-diaza-cyclopropa[a]pentalene-1,1'-cyclohexan]-4-yl)-1H-tetrazole; endo-(1aR, 5aS)-1-Allyl-1a,3,5,5a-tetrahydro-1H-2,3-diaza-cyclopropa[a]pentalene-4-carboxylic acid; endo-(1aR, 5aS)-1-Allyl-4-(2H-tetrazol-5-yl)-1a,3,5,5a-tetrahydro-1H-2,3-diaza-cyclopropa[a]pentalene; and endo-(1aR, 5aS)-1-Cyclopropylmethyl-1a,3,5,5a-tetrahydro-1H-2,3-diaza-cyclopropa[a]pentalene-4-carboxylic acid.

It is understood that a compound, as described herein, having exo-(1aR, 5aS), endo-(1aS, 5aR), and exo-(1aS, 5aR) stereochemistry can be written in an analogous manner.

In some embodiments, a compound of the present invention has the structure:

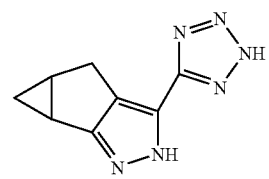

or a pharmaceutically acceptable salt, solvate or hydrate thereof.

In some embodiments, a compound of the present invention has the structure:

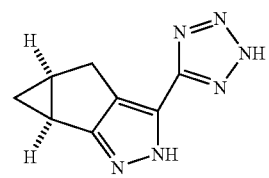

or a pharmaceutically acceptable salt, solvate or hydrate thereof.

In some embodiments, a compound of the present invention has the structure:

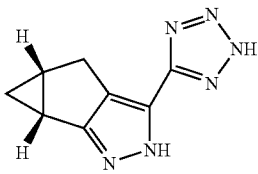

or a pharmaceutically acceptable salt, solvate or hydrate thereof.

In some embodiments, a compound of the present invention has the structure:

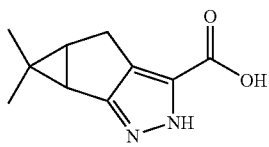

or a pharmaceutically acceptable salt, solvate or hydrate thereof.

In some embodiments, a compound of the present invention has the structure:

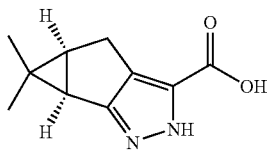

or a pharmaceutically acceptable salt, solvate or hydrate thereof.

In some embodiments, a compound of the present invention has the structure:

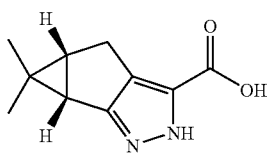

or a pharmaceutically acceptable salt, solvate or hydrate thereof.

In some embodiments, a compound of the present invention has the structure:

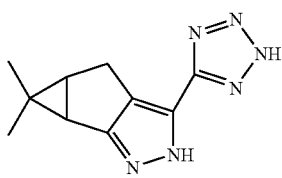

or a pharmaceutically acceptable salt, solvate or hydrate thereof.

In some embodiments, a compound of the present invention has the structure:

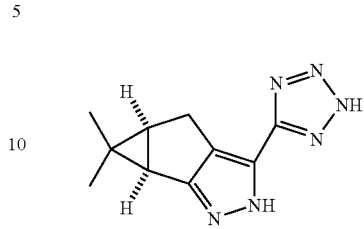

or a pharmaceutically acceptable salt, solvate or hydrate thereof.

In some embodiments, a compound of the present invention has the structure:

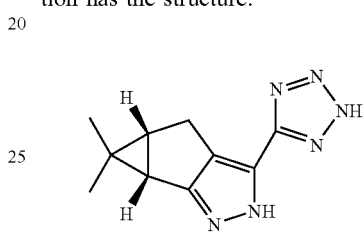

or a pharmaceutically acceptable salt, solvate or hydrate thereof.

In some embodiments, a compound of the present invention has the structure:

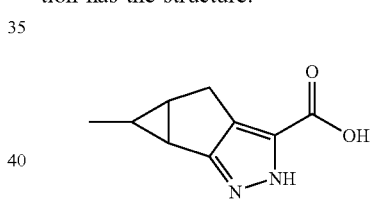

or a pharmaceutically acceptable salt, solvate or hydrate thereof.

In some embodiments, a compound of the present invention has the structure:

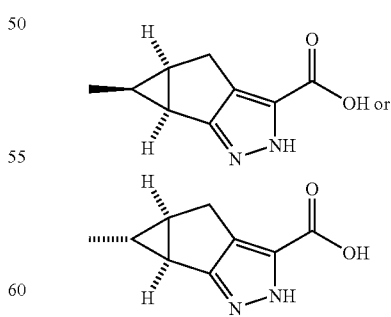

or a pharmaceutically acceptable salt, solvate or hydrate thereof.

In some embodiments, a compound of the present invention has the structure:

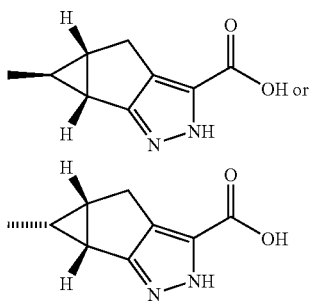

or a pharmaceutically acceptable salt, solvate or hydrate thereof.

In some embodiments, a compound of the present invention has the structure:

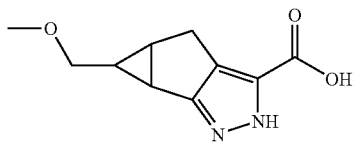

or a pharmaceutically acceptable salt, solvate or hydrate thereof.

In some embodiments, a compound of the present invention has the structure:

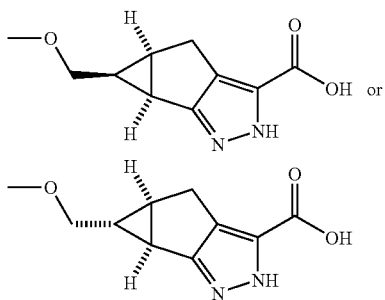

or a pharmaceutically acceptable salt, solvate or hydrate thereof.

In some embodiments, a compound of the present invention has the structure:

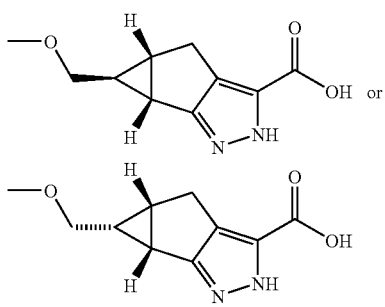

or a pharmaceutically acceptable salt, solvate or hydrate thereof.

In some embodiments, a compound of the present invention has the structure:

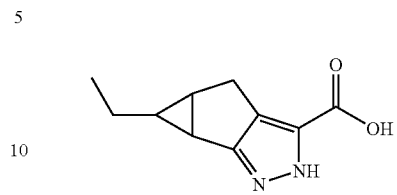

or a pharmaceutically acceptable salt, solvate or hydrate thereof.

In some embodiments, a compound of the present invention has the structure:

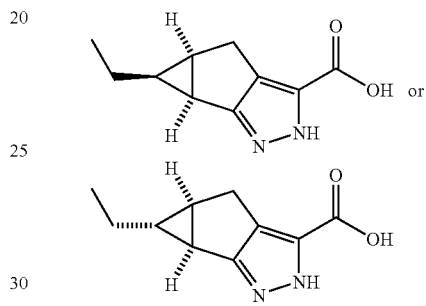

or a pharmaceutically acceptable salt, solvate or hydrate thereof.

In some embodiments, a compound of the present invention has the structure:

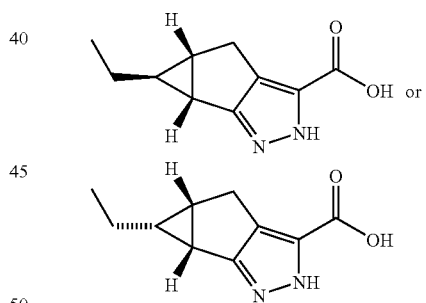

or a pharmaceutically acceptable salt, solvate or hydrate thereof.

Chemistry of the Present Invention

Synthetic Procedures for the Preparation of Compounds of the Invention

Some embodiments of the present invention pertain to synthetic processes for the preparation of novel fused pyrazoles of Formula (Ia). The compounds of the present invention can be readily prepared according to these novel processes utilizing a variety of starting materials that are commercially available or readily prepared by synthetic regimes which would be familiar to one skilled in the art. In the illustrated syntheses outlined below, unless stated otherwise, the labeled substituents have the same definitions as described herein.

One method that can be used to prepare compounds of the invention wherein X is N and Z is C-tetrazol-5-yl utilizes intermediates derived from the cyclic ketone of Formula (A) as illustrated in Reaction Scheme I below:

and Z is C-tetrazol-5-yl. In some instances it can be beneficial to include the presence of a Lewis acid, for example, $AlCl_3$, $ZnBr_2$, and the like, in a suitable solvent, such as, DMF and the like.

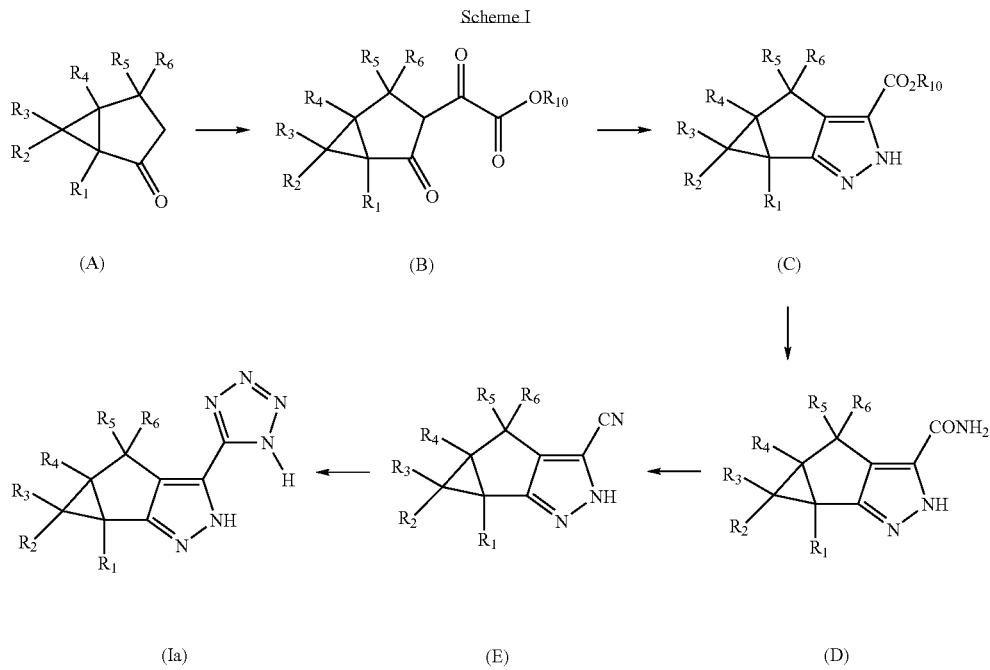

Compounds of Formula (Ia) can be prepared by reacting a cyclic ketone of Formula (A) with a dialkyloxalate of formula $(C(O)OR_{10})_2$, wherein $R_{10}$ is a $C_{1-6}$ alkyl, in the presence of a base and a polar solvent such as, but not limited to, $C_{1-6}$ alkanol, methanol, ethanol, butanol, pentanol, hexanol, 2-methoxyethanol, isopropanol, THF, DMF and the like to give ketoester of Formula (B). Suitable bases include alkali metal alkoxides, for example, sodium methoxide, sodium ethoxide, potassium ethoxide, potassium t-butoxide, and the like; alkali metal amides (i.e., alkali metal-$NR_{11}$ wherein $R_{11}$ is $C_{1-6}$ alkyl or silyl-$C_{1-6}$-alkyl), for example, lithium diisopropylamide, lithium hexamethyldisilazide, sodium hexamethyldisilazide, potassium hexamethyldisilazide and like bases. Ketoester (B) is reacted with hydrazine, either protected or unprotected hydrazine can be used, under suitable conditions to give pyrazole esters of Formula (C). Optionally, the pyrazole can be protected, for example, with a benzyl group and the like. Subsequently, the ester is converted to amide of Formula (D) using methods known to one of skill in the art, for example, treating with ammonia in a polar solvent at temperature from room temperature to the boiling point of the solvent. Amide (D) is reacted with a dehydrating reagent, such as phosphorous oxychloride, phosphorous pentoxide, thionyl chloride, trifluoroacetic anhydride and the like, either neat or in the presence of a nonprotic solvent, such as acetonitrile, DMF, and the like, to give nitrile (E). Nitrile (E) is reacted with an azide (i.e., $N_3$) or azide equivalent, such as, sodium azide, potassium azide, trimethylsilyl azide (i.e., $(CH_3)SiN_3$), and the like to give compounds of Formula (Ia) wherein X is N Other compounds of the invention wherein X is N and Z is C—$CO_2H$ or Z is N and X C—$CO_2H$ can be pepared from intermediate C by hydrolysis to the corresponding acids of Formula (Ic) by lithium hydroxide, sodium hydroxide, potassium hydroxide, potassium trimethylsilanoate or the like. This process is illustrated below for the emobidments wherein X is N and Z is C—$CO_2H$.

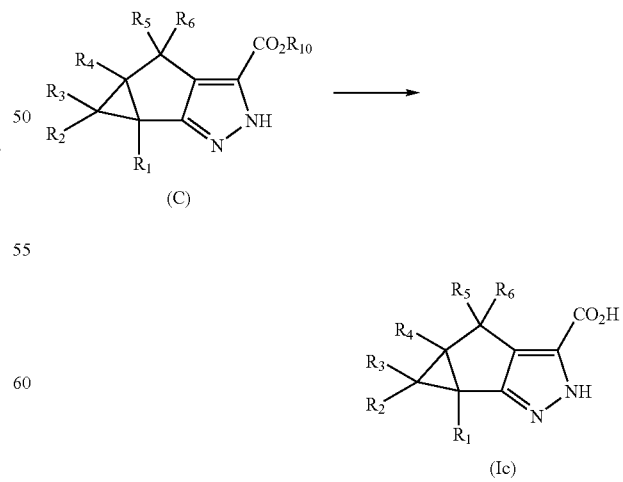

A similar process can also be illustrated for embodiments of the present invention wherein X is C—$CO_2H$ and Z is N.

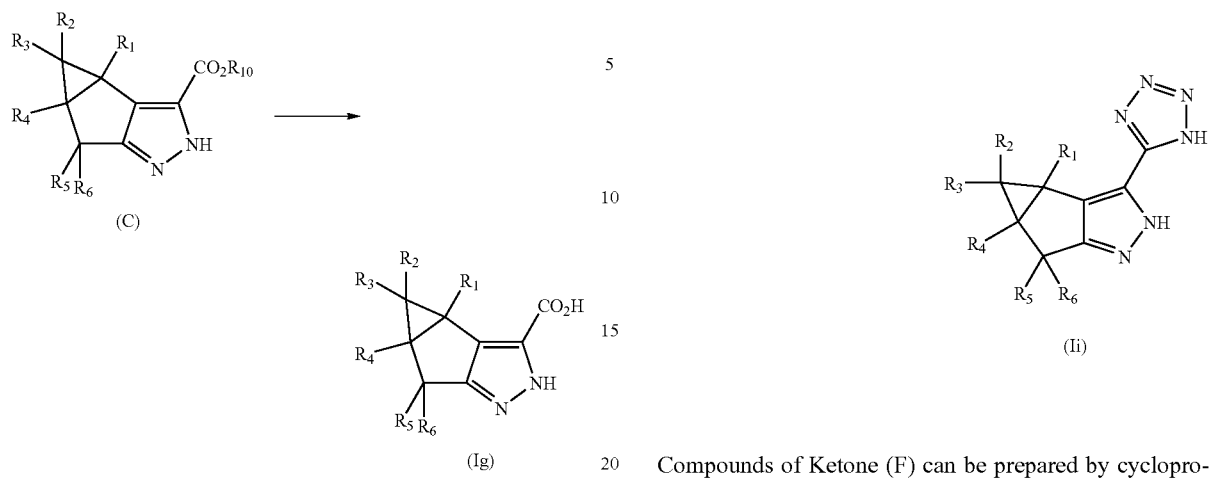

In a similar manner as described above in Scheme I, compounds of the present invention, wherein Z is N and X is C-tetrazolyl or C—CO$_2$H or C—CO$_2$—C$_{1-6}$-alkyl, can be prepared using ketone (F).

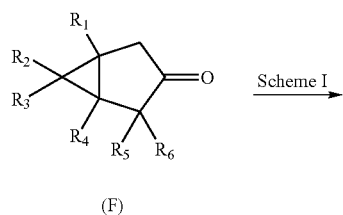

Compounds of Ketone (F) can be prepared by cyclopropanation of the appropriate cyclopentenol by treating with an appropriate carbene or carbenoid generating reagent, such as, but not limited to, diiodoethane with diethylzinc, dibromomethane and sodium hydroxide, and the like. The carbene or carbenoid generating reagent can be selected with the appropriate substitution to either directly introduce R$_2$ and R$_3$ to Ketone (F) or to introduce group(s) (i.e., represented by R$_{12}$ and R$_{13}$) that can be subsequently converted into R$_2$ and R$_3$ groups using methods known in the art. The cyclopentyl alcohol can be oxidized to the cyclic ketone by oxidizing agents such as pyridinium chlorochromate, tetrapropylammonium perrhuthenate, and like oxidizing agents. This process is illustrated below.

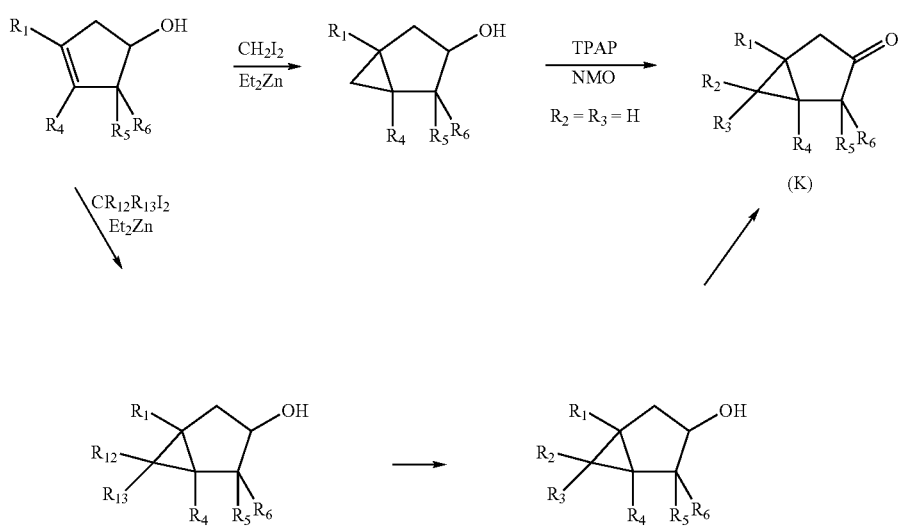

Compounds can be prepared by treating an appropriately substituted suitable 1,2-epoxy-5,6-alkene with a strong base such as lithium tetramethylpiperazide, lithium diisopropylamide, lithium hexamethyldisilazane, sodium hexamethyldisilazane, potassium hexamethyldisilazane and like bases to give Alcohol (M), see Hodson, et al. *J. Am. Chem. Soc.* 2004, 126, 8664. Subsequently, the alcohol can be converted to Ketone (L) using an oxidizing agent, such as, but not limited to, pyridinium chlorochromate, tetrapropylammonium perrhuthenate, and the like.

Chiral (non-racemic) compounds of the invention can be prepared by kinetic hydrolytic resolution of the Epoxide (G) using the published method (Schaus, S. E.; Brandes, B. D.; Larrow, J. F.; Tokunga, M.; Hansen, K. B.; Gould, A. E.; Furrow, M. E.; Jacobsen, E. N. *J. Am. Chem. Soc.* 2002, 124, 1307).

Alternatively, other substituted Ketones (L) can be prepared by addition of the anion generated by reaction of trimethylsulfoxonium iodide and a suitable base like sodiuim hydride, potassium hydride, and the like to an appropriate cyclopentenone.

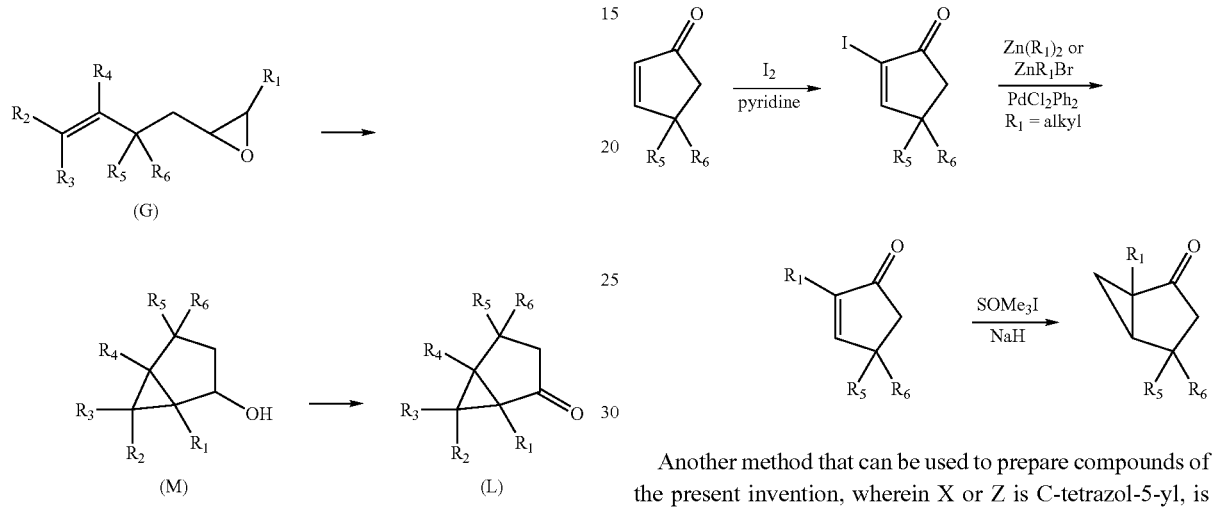

Another method that can be used to prepare compounds of the present invention, wherein X or Z is C-tetrazol-5-yl, is described here. This method allows the option of directly introducing the tetrazol-5-yl group without the need of using multiple steps or an azide reagent. This method is illustrated in the scheme below wherein X is N and Z is C-tetrazol-yl:

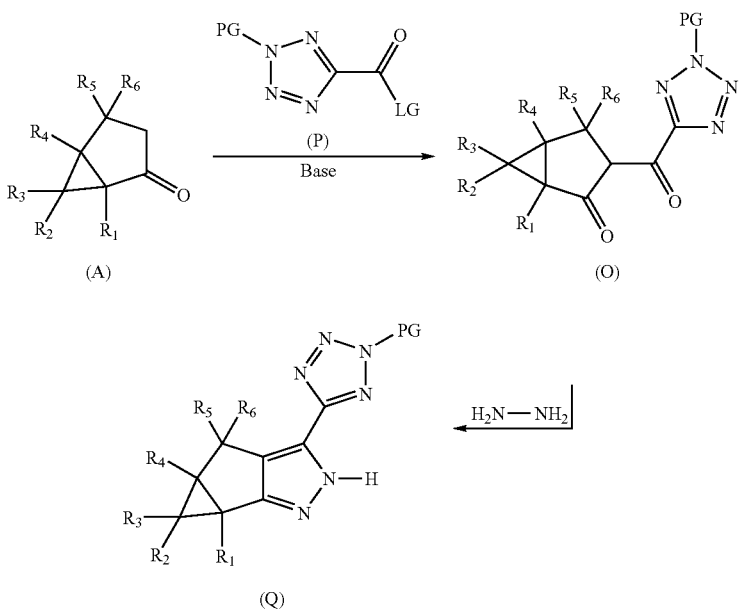

A suitably substituted Ketone (A) can be converted to Diketone (O) using Tetrazole (P) in the presence of base, where PG is a suitable protecting group or metal cation. A suitable base for use in the reaction is one that is soluble in the solvent and can remove a proton from the cyclopentanone, but does not otherwise participate in the reaction. Strong organic bases are particularly useful, such as DBU, DBN, tetramethylguanidine or alkali or alkaline earth metal bases, such as sodium or magnesium alkoxides, and particularly potassium butoxide. Suitable leaving groups (i.e., LG) include groups that can be displaced without affecting the stability of the Tetrazole (P) or the resulting Diketone (O), some examples include esters ($C_{1-4}$ alkoxy or substituted benzyloxy). Suitable solvents include dimethylformamide (DMF), dimethylacetamide (DMAC) dimethylsulfoxide (DMSO), N-methylpyrrolidinone (NMP), and HMPT as well as tetrahydrofuran (THF). In the same reaction or as an additional step after isolation, Diketone (O) is converted to Tetrazole (Q) using hydrazine. The protecting group is subsequently removed to provide compounds of the present invention.

A similar process can also be illustrated for embodiments of the present invention wherein X is C-tetrazol-5-yl and Z is N.

of diastereomeric salts thereof with an optically active acid, and liberating the optically active amine compound by treatment with a base or separation of diastereomeric salts with an optically active base and subsequently liberating the acid by treatment with an acid. Another method for resolving racemates into the optical pure enatiomers is based upon chromatography on an optically active matrix or chiral support. Certain racemic compounds of the present invention can thus be resolved into their optical antipodes, e.g., by fractional crystallization of d- or l-(tartrates, mandelates, or camphorsulphonate) salts for example. The compounds of the present invention can be resolved by the formation of diastereomeric amides or esters by reaction of the compounds of the present invention with an optically active amine or alcohol, such as, but not limited to, (+) or (−) α-methylbenzylamine, (+) or (−) α-methylbenzylalcohol, and the like, separated via fractional recrystallization, chiral chromatography or similar method, and subsequently hydrolyzed.

Additional methods for the resolution of optical isomers known to those skilled in the art can be used and will be apparent to the average worker skilled in the art. Such methods include those discussed by J. Jaques, A. Collet, and

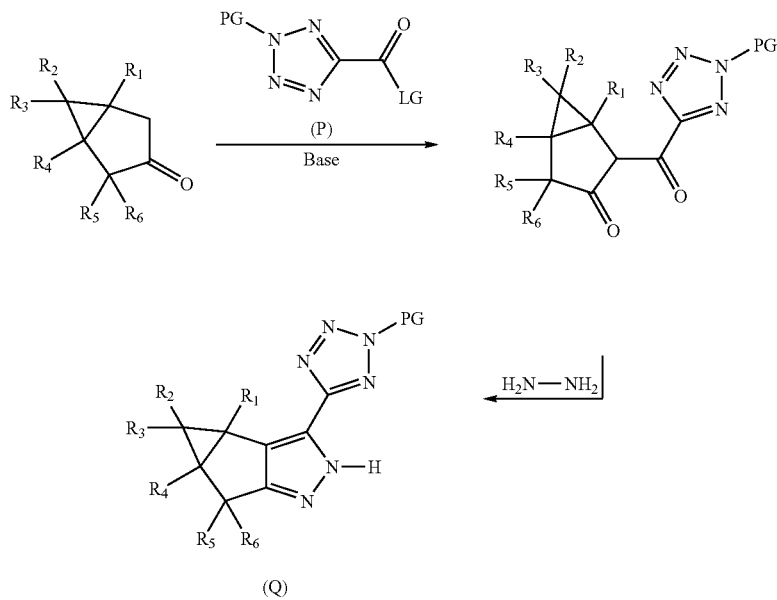

The various organic group transformations and protecting groups utilized herein can be performed by a number of procedures other than those described above. References for other synthetic procedures that can be utillized for the preparation of intermediates or compounds disclosed herein can be found in, for example, Smith, M. B.; and March, J., *Advanced Organic Chemistry*, 5$^{th}$ Edition, Wiley-Interscience (2001); Larock, R. C., *Comprehensive Organic Transformations, A Guide to Functional Group Preparations*, 2$^{nd}$ Edition, VCH Publishers, Inc. (1999), or Wuts, P. G. M.; Greene, T. W.; *Protective Groups in Organic Synthesis*, 3$^{rd}$ Edition, John Wiley and Sons, (1999), all three are incorporated herein by reference in their entirety.

Racemic mixtures can be resolved into the optical pure enatiomers by known methods, for example, by separation S. Wilen in "Enantiomers, Racemates, and Resolutions", John Wiley and Sons, New York (1981).

It is understood that the chemistry described herein is representative and is not intended to be limiting in any manner.

Methods and Uses

Compounds of the present invention are useful in the inhibition of the production of free fatty acids. Further, compounds of the present invention are useful in the inhibition of the production of free fatty acids while resulting in substantially lower or in some instances no measurable flushing side effects. Flushing is a side effect commonly associated with the administration of niacin. Compounds of the present invention typically do not cause vasodilation at doses as high as about 300 mpk as measured using methods know in the art, such as the method shown in Example 7.

In some embodiments, compounds of the present invention cause essentially no measurable flushing in an individual compared to an essentially equally effective dose of niacin. In other embodiments compounds of the present invention cause less than about 80%, 75%, 70%, 65%, 60%, 55%, 50%, 45%, 40%, 35%, 30%, 25%, 20%, 15%, 10%, 5%, or 1% measurable flushing in an individual compared to an essentially equally effective dose of niacin.

Compounds of the present invention can modulate the activity of the RUP25 receptor. The term "modulate" is meant to refer to the ability to increase or decrease activity of the receptor. In some embodiments, compounds of the invention can be used in methods of modulating a RUP25 receptor by contacting the receptor with any one or more of the compound as described herein. In still other embodiments, compounds of the invention can be used in methods of method of modulating a RUP25 receptor for the treatment of a metabolic-related disorder in an individual in need of such modulation comprising contacting the receptor with a therapeutically-effective amount of a compound of Formula (Ia). In some embodiments, compounds of the invention increase activity of the RUP25 receptor. In further embodiments, compounds of the invention are agonists of the RUP25 receptor. The term "agonist", as used herein, refers to agents that can stimulate activity of the receptor (i.e., activate), like the RUP25 receptor. In some embodiments, compounds of the invention are partial agonists of the RUP25 receptor.

Another aspect of the present invention pertains to methods of treatment of a metabolic-related disorder comprising administering to an individual in need of such treatment a therapeutically-effective amount of a compound of Formula (Ia).

Another aspect of the present invention pertains to methods of raising HDL in an individual comprising administering to said individual a therapeutically-effective amount of a compound of Formula (Ia).

Another aspect of the present invention pertains to compounds of Formula (Ia), as described herein, for use in a method of treatment of the human or animal body by therapy.

Another aspect of the present invention pertains to compounds of Formula (Ia), as described herein, for use in a method of treatment of a metabolic-related disorder of the human or animal body by therapy.

Another aspect of the present invention pertains to compounds of Formula (Ia), as described herein, for use in a method of treatment of a metabolic-related disorder of the human or animal body by therapy wherein said metabolic-related disorder is selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to compounds of Formula (Ia), as described herein, for use in a method of treatment of a metabolic-related disorder of the human or animal body by therapy wherein said metabolic-related disorder is selected from the group consisting of dyslipidemia, atherosclerosis, coronary heart disease, insulin resistance and type 2 diabetes.

Another aspect of the present invention pertains to compounds of Formula (Ia), as described herein, for use in a method of treatment of atherosclerosis of the human or animal body by therapy.

Another aspect of the present invention pertains to compounds of Formula (Ia), as described herein, for use in a method of raising HDL of the human or animal body by therapy.

Another aspect of the present invention pertains to uses of the compounds of Formula (Ia), as described herein, for the manufacture of a medicament for use in the treatment of a metabolic-related disorder.

Another aspect of the present invention pertains to uses of the compounds of Formula (Ia), as described herein, for the manufacture of a medicament for use in the treatment of a metabolic-related disorder selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes.

Another aspect of the present invention pertains to uses of the compounds of Formula (Ia), as described herein, for the manufacture of a medicament for use in the treatment of atherosclerosis.

Another aspect of the present invention pertains to uses of the compounds of Formula (Ia), as described herein, for the manufacture of a medicament for use in raising HDL in an individual.

Some embodiments of the present invention relate to methods of treatment of metabolic-related disorders. In some embodiments the metabolic-related disorder is of the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic-related disorder is dyslipidemia, atherosclerosis, coronary heart disease, insulin resistance and type 2 diabetes. In some embodiments the metabolic-related disorder is dyslipidemia. In some embodiments the metabolic-related disorder is atherosclerosis. In some embodiments the metabolic-related disorder is coronary heart disease. In some embodiments the metabolic-related disorder is insulin resistance. In some embodiments the metabolic-related disorder is type 2 diabetes.

In some embodiments related to methods of the present invention, the individual is a mammal. In further embodiments, the mammal is a human.

Another aspect of the present invention pertains to methods of producing a pharmaceutical composition comprising admixing or combining a compound of Formula (Ia), as described herein, and a pharmaceutically acceptable carrier.

Compositions of the Present Invention

Some embodiments of the present invention include pharmaceutical compositions comprising a compound according to Formula (Ia) in combination with a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro, A. R., et al.).

While it is possible that a compound for use in the treatment of the present invention may, in an alternative use, be administered as a raw or pure chemical, it is preferable however to present the compound or "active ingredient" as a pharmaceutical formulation or composition further comprising a pharmaceutically acceptable carrier. Therefore, one aspect of the present invention encompasses pharmaceutical compositions comprising a pharmaceutically acceptable carrier in combination with at least one compound according to Formula (Ia).

The invention provides pharmaceutical formulations comprising a compound of the invention, or a pharmaceutically acceptable salt, hydrate or solvate thereof, together with one or more pharmaceutically acceptable carriers therefor. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form can be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water can be used as a suitable pharmaceutically acceptable carrier.

Compounds of the present invention, or a pharmaceutically acceptable salt, hydrate or solvate thereof, can be used as active ingredients in pharmaceutical compositions, specifically as RUP25 receptor agonists/partial agonists. The term "active ingredient" is defined in the context of a "pharmaceutical composition" and shall mean a component of a pharmaceutical composition that provides the primary pharmacological effect, as opposed to an "inactive ingredient" which would generally be recognized as providing essentially no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses can be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or a pharmaceutically acceptable salt, hydrate or solvate thereof, required for use in treatment will vary not only with the particular salt selected but also with the route of administration, the nature of the condition being treated and the age and condition of the patient. Accordingly, the amount used will ultimately be at the discretion of the attendant physician or clinician. In general, one skilled in the art understands how to extrapolate in vivo data obtained in a model system to another, for example, an animal model to a human. Typically, animal models include, but are not limited to, the rodent diabetes models as described in Example 1, infra; the mouse atherosclerosis model as described in Example 2, infra; or the in vivo animal athosclerosis model as described in Example 5, infra. In some circumstances, these extrapolations may merely be based on the weight of the animal model in comparison to another, such as, a mammal and preferably a human. However, more often, these extrapolations are not simply based on weight differences, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated, on whether further active compounds are administered in addition to the compounds of the present invention as part of a combination therapy. The dosage regimen for treating a disease condition with the compounds and/or compositions of this invention is selected in accordance with a variety factors, such as, those cited above. Thus, the actual dosage regimen employed may vary widely and therefore may deviate from a preferred dosage regimen and one skilled in the art will recognize that dosage and dosage regimen outside these typical ranges can be tested and, where appropriate, can be used in the methods of this invention.

The desired dose may conveniently be presented in a single dose or as divided doses administered at appropriate intervals, for example, as two, three, four or more sub-doses per day. The sub-dose itself can be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it can be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 95 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and can be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention can be formulated as ointments, creams or lotions, or as a transdermal patch.

Ointments and creams may, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract may also be achieved by means of an aerosol formulation in which the active ingredient is provided in a pressurized pack with a suitable propellant. If the compounds of the Formula (Ia) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (Ia) as an aerosol can be prepared by processes well-known to the person skilled in the art. For their preparation, for example, solutions or dispersions of the compounds of the Formula (Ia) in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug can be controlled by provision of a metered valve.

In formulations intended for administration to the respiratory tract, including intranasal formulations, the compound will generally have a small particle size for example of the order of 10 microns or less. Such a particle size can be obtained by means known in the art, for example by micronization. When desired, formulations adapted to give sustained release of the active ingredient can be employed.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin, or blister packs from which the powder can be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions. Such tablets and capsules typically contain from about 0.001 mg to about 1000 mg, about 0.001 mg to about 500 mg, or about 0.001 mg to about 250 mg of a compound of Formula (Ia).

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In general, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Combination Therapy:

While the compounds of the present invention can be administered as the sole active pharmaceutical agent (i.e., mono-therapy), they can also be used in combination with other pharmaceutical agents (i.e., combination-therapy), such as, for the treatment of the diseases/conditions/disorders described herein. Therefore, another aspect of the present invention includes methods of treatment of metabolic related diseases comprising administering to an individual in need of such treatment a therapeutically-effective amount of a compound of the present invention in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, $\beta_3$ adrenergic receptor agonists, dopamine agonists (for example, bromocriptine), melanocyte-stimulating hormone receptor analogs, cannabinoid 1 receptor antagonists [for example, SR1441716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It is understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant disorders. Treatment of such disorders include the use of one or more pharmaceutical agents known in the art that belong to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), anti-platelet agents (for example, aspirin and adenosine diphosphate receptor antagonists that include: clopidogrel, ticlopidine and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic-related disorders.

Some embodiments of the present invention include methods of treatment of a disease, disorder or condition as described herein comprising administering to an individual in need of such treatment a therapeutically effect amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, the pharmaceutical composition further comprises one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer, thiazolidinedione and DP receptor antagonist.

One aspect of the present invention encompasses pharmaceutical compositions comprising at least one compound of the present invention, as described herein. In some embodiments, the pharmaceutical composition further comprises one or more agents selected from the group consisting of, for example, α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione.

Suitable pharmaceutical agents that can be used in conjunction with compounds of the present invention include α-glucosidase inhibitors. α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3dihydroxy-2-propyl)valiolamine (generic name; voglibose), miglitol, and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing $HbA_{1c}$. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include DP receptor antagonists. DP receptor antagonists include those described in WO01/79169, WO03/062200 WO01/66520, WO03/022814, WO03/078409, WO2004/103370, EP 1305286, WO02/094830, and the like. Other representative DP antagonist compounds can be found in WO04/103370. Examples of compounds that are particularly useful for selectively antagonizing the DP receptor include the following:

Compound A

Compound B

Compound C

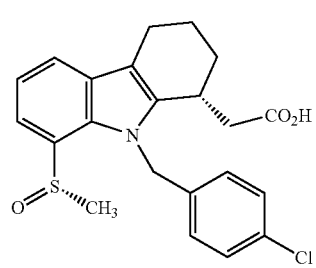

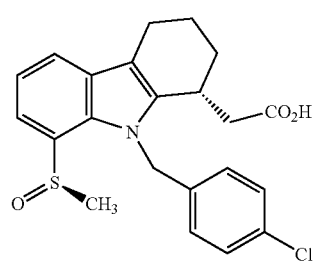

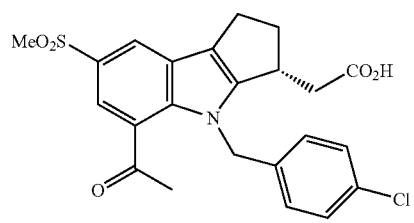

Compound D

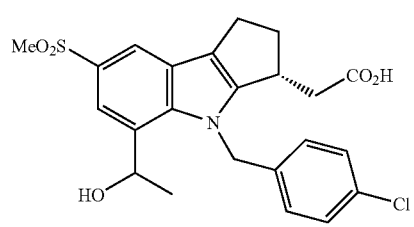

-continued

Compound E

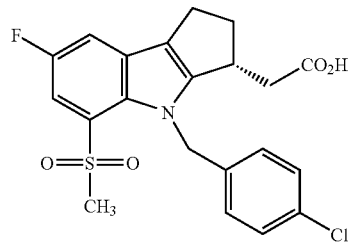

Compound F

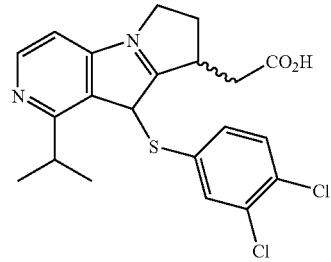

Compound G

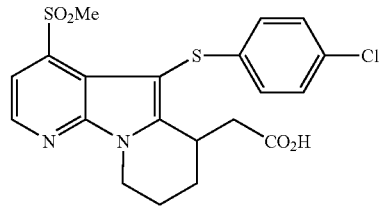

Compound H

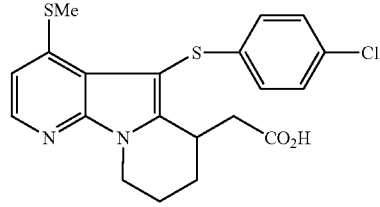

Compound I

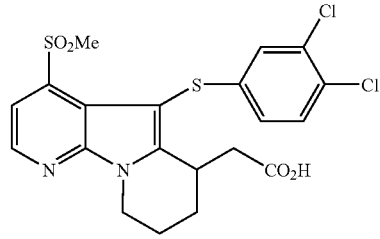

Compound J

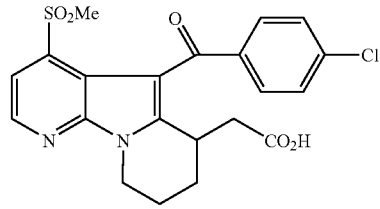

-continued
Compound K
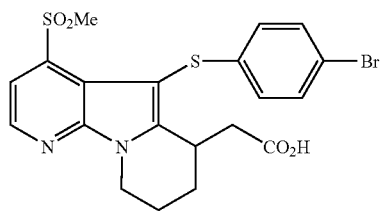
Compound L
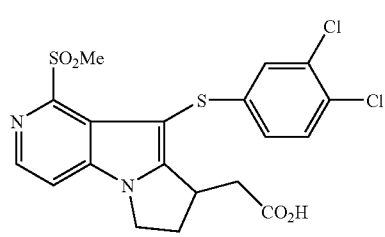
Compound M
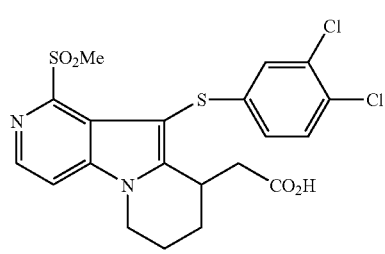
Compound N
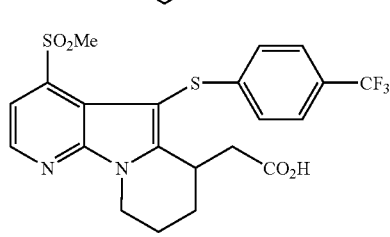
Compound O
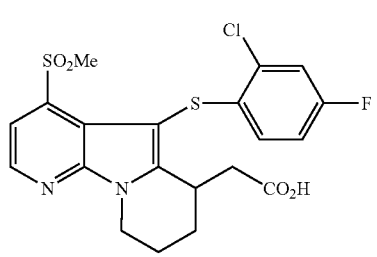
Compound P
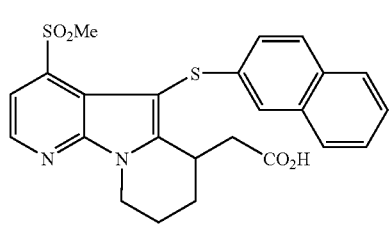
Compound Q
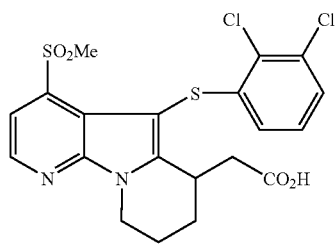
-continued
Compound R
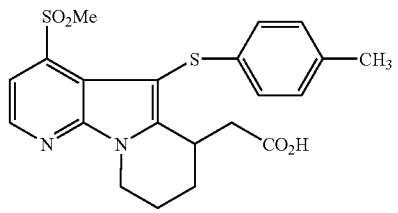
Compound S
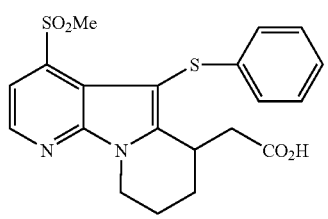
Compound T
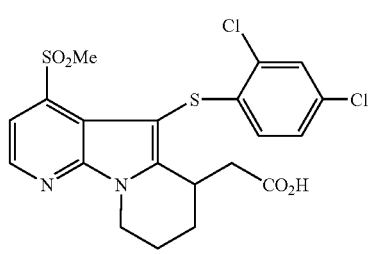
Compound U
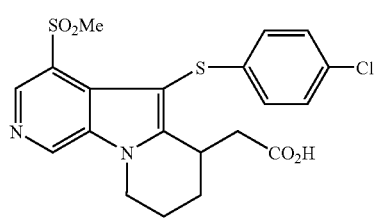
Compound V
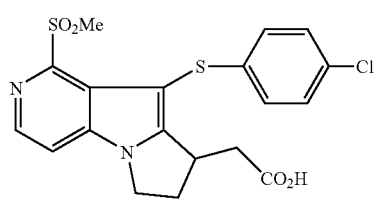
Compound W
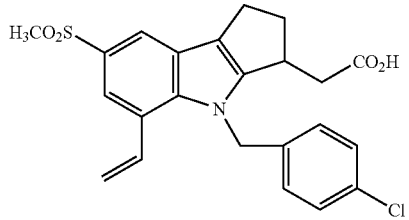

Compound X
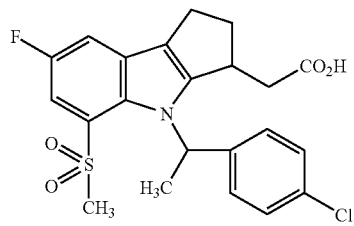
Compound X
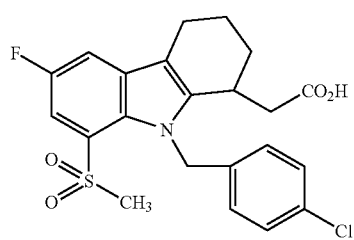
Compound Z
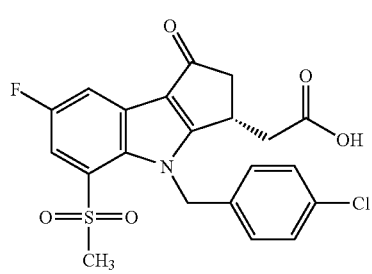
Compound AA
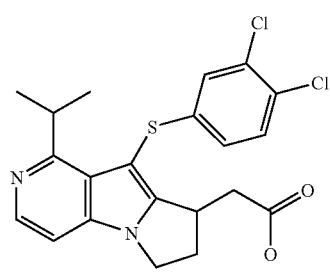
Compound AB
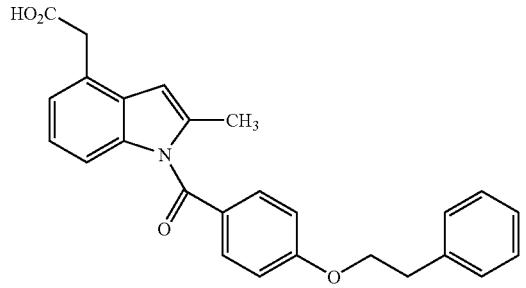
Compound AC
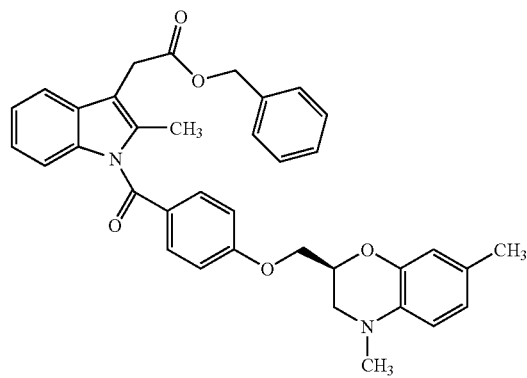
Compound AD
Compound AE
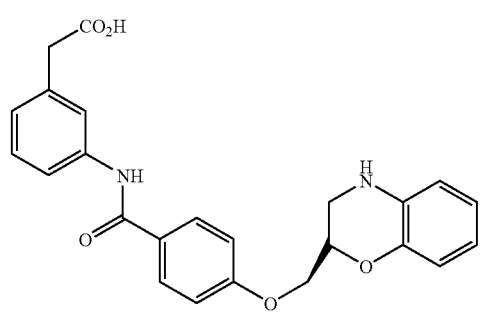
Compound AF
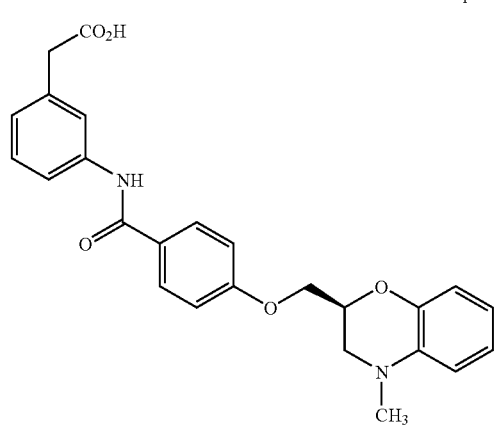
Compound AG
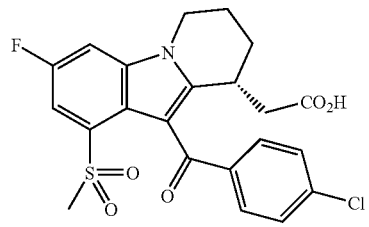

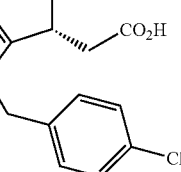

Compound AH

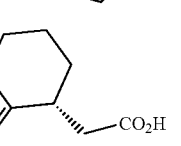

Compound AI

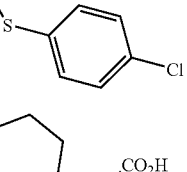

Compound AJ

Included are pharmaceutically acceptable salts, solvates and hydrates thereof. Compound AB can be synthesized in accordance with the description set forth in WO01/66520A1 published on Sep. 13, 2001; Compound AC can be synthesized in accordance with the description set forth in WO03/022814A1 published on Mar. 20, 2003, and Compounds AD and AE can be synthesized in accordance with the description set forth in WO03/078409 published on Sep. 25, 2003.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, ccrivastatin, pitavastatin, BMS's "superstatin", and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of one or more pharmaceutical agents known in the art that belong to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, torcetrapib and like compounds), microsomal triglyceride transfer protein inhibitors (for example, implitapide, and like compounds), cholesterol modulators (for example, NO-1886, and like compounds), bile acid modulators (for example, GT103-279 and like compounds), squalene synthase inhibitors, and 11β-HSD1 inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494) and squalene synthesis inhibitors known in the art.

In accordance with the present invention, the combination can be used by mixing the respective active components either all together or independently with a pharmaceutically acceptable carrier, excipient, binder, diluent, etc., as described herein above, and administering the mixture or mixtures either orally or non-orally as a pharmaceutical composition. When a compound of the present invention is administered as a combination therapy with another active compound the therapeutic agents can be formulated as separate pharmaceutical compositions given at the same time or at different times, or the therapeutic agents can be given as a single composition.

In accordance with the present invention, the combination of a compound of the present invention and pharmaceutical agent can be prepared by mixing the respective active components either all together or independently with a pharmaceutically acceptable carrier, excipient, binder, diluent, etc., as described herein, and administering the mixture or mixtures either orally or non-orally as a pharmaceutical composition. When a compound or a mixture of compounds of the present invention are administered as a combination therapy with another active compound the therapeutic agents can be formulated as separate pharmaceutical compositions given at the same time or at different times, or the therapeutic agents can be given as single separate compositions.

Labeled Compounds and Assay Methods

Another object of the present invention relates to radio-labeled compounds of Formula (Ia) and formulae related thereto that are useful not only in radio-imaging but also in assays, both in vitro and in vivo, for localizing and quantitating RUP25 in tissue samples, including human, and for identifying the RUP25 receptor ligands by inhibition binding of a radio-labeled compound. It is a further object of this invention to include novel RUP25 assays of which comprise such radio-labeled compounds.

The present invention embraces isotopically-labeled compounds of Formula (Ia) and any subgenera herein, such as but not limited to, Formulae (Ia) to (Io). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that can be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro RUP25 labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of the present invention that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence can be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, and are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70–90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943–948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264–S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280–S282.

A radio-labeled RUP25 compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the RUP25 receptor. Accordingly, the ability of a test compound to compete with the "radio-labeled compound of Formula (Ia)" for the binding to the RUP25 receptor directly correlates to its binding affinity.

The labeled compounds of the present invention bind to the RUP25 receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM, and in still yet another embodiment the labeled inhibitor has an IC$_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

The following Examples are provided for illustrative purposes and not as a means of limitation. One of ordinary skill in the art would be able to design equivalent assays and methods based on the disclosure herein, all of which form part of the present invention.

Example 1

Rodent Diabetes Models

Rodent models of type 2 diabetes associated with obesity and insulin resistance have been developed. Genetic models such as db/db and ob/ob [see Diabetes (1982) 31:1–6] in mice and fa/fa in zucker rats have been developed for understanding the pathophysiology of disease and for testing candidate therapeutic compounds [Diabetes (1983) 32:830–838; Annu Rep Sankyo Res Lab (1994) 46:1–57]. The homozygous animals, C57 BL/KsJ-db/db mice developed by Jackson Laboratory are obese, hyperglycemic, hyperinsulinemic and insulin resistant [J Clin Invest (1990) 85:962–967], whereas heterozygotes are lean and normoglycemic. In the db/db model, mice progressively develop insulinopenia with age, a feature commonly observed in late stages of human type 2 diabetes when sugar levels are insufficiently controlled. Since this model resembles that of human type 2 diabetes, the compounds of the present invention are tested for activities including, but not limited to, lowering of plasma glucose and triglycerides. Zucker (fa/fa) rats are severely obese, hyperinsulinemic, and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299–340]}, and the fa/fa mutation may be the rat equivalent of the murine db mutation [Friedman et al, Cell (1992) 69:217–220; Truett et al, Proc Natl Acad Sci USA (1991) 88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type 2 diabetes or other preferred metabolic-related disorders or disorders of lipid metabolism described previously, or in models based on other mammals. Plasma glucose and insulin levels will be tested, as well as other factors including, but not limited to, plasma free fatty acids and triglycerides.

In Vivo Assay for Anti-Hyperglycemic Activity of Compounds of the Invention

Genetically altered obese diabetic mice (db/db) (male, 7–9 weeks old) are housed (7–9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide compounds of the invention, saline, or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

Example 2

Mouse Atherosclerosis Model

Adiponectin-deficient mice generated through knocking out the adiponectin gene have been shown to be predisposed to atherosclerosis and to be insulin resistant. The mice are also a suitable model for ischemic heart disease [Matsuda, M et al. J Biol Chem (2002) July, and references cited therein, the disclosures of which are incorporated herein by reference in their entirety].

Adiponectin knockout mice are housed (7–9 mice/cage) under standard laboratory conditions at 22° C. and 50% relative humidity. The mice are dosed by micro-osmotic pumps, inserted using isoflurane anesthesia, to provide compounds of the invention, saline, or an irrelevant compound to the mice subcutaneously (s.c.). Neointimal thickening and ischemic heart disease are determined for different groups of mice sacrificed at different time intervals. Significant differences between groups (comparing compounds of the invention to saline-treated) are evaluated using Student t-test.

Example 3

In Vitro Biological Activity

A modified Flash Plate™ Adenylyl Cyclase kit (New England Nuclear; Cat. No. SMP004A) was utilized for direct identification of candidate compounds as agonists to hRUP25 in accordance with the following protocol. The term hRUP25 includes the human sequences found in GenBank Accession No. NM_177551 for the nucleotide and GenBank Accession No. NP 808219 for the polypeptide, and naturally-occurring allelic variants, mammalian orthologs, and recombinant mutants thereof.

CHO cells stably transfected with an expression vector encoding hRUP25 and cultured under condition permissive for cell surface expression of the encoded hRUP25 receptor were harvested from flasks via non-enzymatic means. The cells were washed in PBS and resuspended in the manufacturer's Assay Buffer. Live cells were counted using a hemacytometer and Trypan blue exclusion, and the cell concentration was adjusted to $2 \times 10^6$ cells/ml. cAMP standards and Detection Buffer (comprising 2 µCi of tracer [$^{125}$I]-cAMP (100 µl) to 11 ml Detection Buffer) were prepared and maintained in accordance with the manufacturer's instructions. Candidate compounds identified as per above (if frozen, thawed at room temperature) were added to their respective wells (preferably wells of a 96-well plate) at increasing concentrations (3 µl/well; 12 µM final assay concentration). To these wells, 100,000 cells in 50 µl of Assay Buffer were added and the mixture was then incubated for 30 minutes at room temperature, with gentle shaking. Following the incubation, 100 µl of Detection Buffer was added to each well, followed by incubation for 2–24 hours. Plates were counted in a Wallac MicroBeta™ plate reader using "Prot. #31" (as per manufacturer instructions).

Certain compounds of the invention have an $EC_{50}$ in the cAMP Whole Cell method of about 25 µM or less.

Example 4

In vitro Biological Activity $^{35}$S-GTPγS binding assay:

Membranes prepared from Chinese Hamster Ovary (CHO)-K1 cells stably expressing the niacin receptor or vector control (7 μg/assay) were diluted in assay buffer (100 mM HEPES, 100 mM NaCl and 10 mM MgCl$_2$, pH 7.4) in Wallac Scintistrip plates and pre-incubated with test compounds diluted in assay buffer containing 40 μM GDP (final [GDP] was 10 μM) for ~10 minutes before addition of $^{35}$S-GTPγS to 0.3 nM. To avoid potential compound precipitation, all compounds were first prepared in 100% DMSO and then diluted with assay buffer resulting in a final concentration of 3% DMSO in the assay. Binding was allowed to proceed for one hour before centrifuging the plates at 4000 rpm for 15 minutes at room temperature and subsequent counting in a TopCount scintillation counter. Non-linear regression analysis of the binding curves was performed in GraphPad Prism.

Membrane Preparation

Materials:

CHO-K1 cell culture medium: F-12 Kaighn's Modified Cell Culture Medium with 10% FBS, 2 mM L-Glutamine, 1 mM Sodium Pyruvate and 400 μg/mL G418

Membrane Scrape Buffer: 20 mM HEPES
  10 mM EDTA, pH 7.4

Membrane Wash Buffer: 20 mM HEPES
  0.1 mM EDTA, pH 7.4

Protease Inhibitor Cocktail: P-8340, (Sigma, St. Louis, Mo.)

Procedure:
  Aspirate cell culture media off the 15 cm$^2$ plates, rinse with 5 mL cold PBS and aspirate.
  Add 5 mL Membrane Scrape Buffer and scrape cells. Transfer scrape into 50 mL centrifuge tube. Add 50 μL Protease Inhibitor Cocktail.
  Spin at 20,000 rpm for 17 minutes at 4° C.
  Aspirate off the supernatant and resuspend pellet in 30 mL Membrane Wash Buffer. Add 50 μL Protease Inhibitor Cocktail.
  Spin at 20,000 rpm for 17 minutes at 4° C.
  Aspirate the supernatant off the membrane pellet. The pellet may be frozen at −80° C. for later use or it can be used immediately.

Assay

Materials:

Guanosine 5'-diphosphate sodium salt (GDP, Sigma-Aldrich Catalog #87127)

Guanosine 5'-[γ$^{35}$S]thiotriphosphate, triethylammonium salt ([$^{35}$S]GTP-γS, Amersham Biosciences Catalog #SJ1320, ~1000 Ci/mmol)

96 well Scintiplates (Perlin-Elmer #1450-501)

Binding Buffer: 20 mM HEPES, pH 7.4
  100 mM NaCl
  10 mM MgCl$_2$

GDP Buffer: binding buffer plus GDP, ranging from 0.4 to 40 μM, make fresh before assay Procedure:
(total assay volume=100μ well)
25 μL GDP buffer with or without compounds (final GDP 10 μM—so use 40 μM stock)
50 μL membrane in binding buffer (0.4 mg protein/mL)
25 μL [$^{35}$S]GTPγS in binding buffer. This is made by adding 5 μl [$^{35}$S]GTP-γS stock into 10 mL binding buffer (This buffer has no GDP)
  Thaw compound plates to be screened (daughter plates with 5 μL compound@ 2 mM in 100% DMSO)
  Dilute the 2 mM compounds 1:50 with 245 μL GDP buffer to 40 μM in 2% DMSO. Thaw frozen membrane pellet on ice Homogenize membranes briefly until in suspension using a POLYTRON PT3100 (probe PT-DA 3007/2 at setting of 7000 rpm). Determine the membrane protein concentration by Bradford assay. Dilute membrane to a protein concentrations of 0.40 mg/ml in Binding Buffer. (Note: the final assay concentration is 20 μg/well).

Add 25 μL compounds in GDP buffer per well to Scintiplate.

Add 50 μL of membranes per well to Scintiplate.

Pre-incubate for 5–10 minutes at room temperature.

Add 25 μL of diluted [$^{35}$S]GTPγS. Incubate on shaker (Lab-Line model #1314, shake at setting of 4) for 60 minutes at room temperature.

Assay is stopped by spinning plates sealed with plate covers at 2500 rpm for 20 minutes at 22° C.

Read on TopCount NXT scintillation counter −35S protocol.

Certain compounds of the invention have an EC$_{50}$ in the functional in vitro GTPγS binding assay within the range of about 10–100 μM. More advantageous compounds of the invention have an EC$_{50}$ value in this assay within the range of about 1–10 μM. Still more advantages compounds have an EC$_{50}$ value in this assay of less than about 1 μM.

Example 5

In Vivo Animal Model

One utility of the compound of the present invention as a medical agent in the prophylaxis and treatment of a high total cholesterol/HDL-cholesterol ratio and conditions relating thereto is demonstrated by the activity of the compound in lowering the ratio of total cholesterol to HDL-cholesterol, in elevating HDL-cholesterol, or in protection from atherosclerosis in an in vivo pig model. Pigs are used as an animal model because they reflect human physiology, especially lipid metabolism, more closely than most other animal models. An illustrative in vivo pig model not intended to be limiting is presented here.

Yorkshire albino pigs (body weight 25.5±4 kg) are fed a saturated fatty acid rich and cholesterol rich (SFA-CHO) diet during 50 days (1 kg chow 35 kg$^{-1}$ pig weight), composed of standard chow supplemented with 2% cholesterol and 20% beef tallow [Royo T., et al., *European Journal of Clinical Investigation* (2000) 30:843–52; which disclosure is hereby incorporated by reference in its entirety]. Saturated to unsaturated fatty acid ratio is modified from 0.6 in normal pig chow to 1.12 in the SFA-CHO diet. Animals are divided into two groups, one group (n=8) fed with the SFA-CHO diet and treated with placebo and one group (n=8) fed with the SFA-CHO diet and treated with the compound (3.0 mg kg$^{-1}$). Control animals are fed a standard chow for a period of 50 days. Blood samples are collected at baseline (2 days after the reception of the animals), and 50 days after the initiation of the diet. Blood lipids are analyzed.

The Animals are Sacrificed and Necropsied.

Alternatively, the foregoing analysis comprises a plurality of groups each treated with a different dose of the compound. Preferred said doses are selected from the group consisting of: 0.1 mg kg$^{-1}$, 0.3 mg kg$^{-1}$, 1.0 mg kg$^-$, 3.0 mg kg$^{-1}$, 10 mg kg$^{-1}$, 30 mg kg$^{-1}$ and 100 mg kg$^{-1}$. Alternatively, the foregoing analysis is carried out at a plurality of timepoints. Preferred said timepoints are selected from the group consisting of 10 weeks, 20 weeks, 30 weeks, 40 weeks, and 50 weeks.

HDL-Cholesterol

Blood is collected in trisodium citrate (3.8%, 1:10). Plasma is obtained after centrifugation (1200 g 15 min) and immediately processed. Total cholesterol, HDL-cholesterol, and LDL-cholesterol are measured using the automatic analyzer Kodak Ektachem DT System (Eastman Kodak Company, Rochester, N.Y., USA). Samples with value parameters above the range are diluted with the solution supplied by the manufacturer and then re-analyzed. The total cholesterol/HDL-cholesterol ratio is determined. Comparison is made of the level of HDL-cholesterol between groups. Comparison is made of the total cholesterol/HDL-cholesterol ratio between groups.

Elevation of HDL-cholesterol or reduction of the total cholesterol/HDL-cholesterol ratio on administration of the compound is taken as indicative of the compound having the aforesaid utility.

Atherosclerosis

The thoracic and abdominal aortas are removed intact, opened longitudinally along the ventral surface, and fixed in neutral-buffered formalin after excision of samples from standard sites in the thoracic and abdominal aorta for histological examination and lipid composition and synthesis studies. After fixation, the whole aortas are stained with Sudan IV and pinned out flat, and digital images are obtained with a TV camera connected to a computerized image analysis system (Image Pro Plus; Media Cybernetics, Silver Spring, Md.) to determine the percentage of aortic surface involved with atherosclerotic lesions [Gerrity R G et al, *Diabetes* (2001) 50:1654–65; Cornhill J F et al, *Arteriosclerosis, Thrombosis, and Vascular Biology* (1985) 5:415–26; which disclosures are hereby incorporated by reference in their entirety]. Comparison is made between groups of the percentage of aortic surface involved with atherosclerotic lesions.

Reduction of the percentage of aortic surface involved with atherosclerotic lesions on administration of the compound is taken as indicative of the compound having the aforesaid utility.

Example 6

Receptor Binding Assay

In addition to the methods described herein, another means for evaluating a test compound is by determining binding affinities to the RUP25 receptor. This type of assay generally requires a radiolabelled ligand to the RUP25 receptor. Absent the use of known ligands for the RUP25 receptor and radiolabels thereof, compounds of Formula (Ia) can be labelled with a radioisotope and used in an assay for evaluating the affinity of a test compound to the RUP25 receptor.

A radiolabelled RUP25 compound of Formula (Ia) can be used in a screening assay to identify/evaluate compounds. In general terms, a newly synthesized or identified compound (i.e., test compound) can be evaluated for its ability to reduce binding of the "radiolabelled compound of Formula (Ia)" to the RUP25 receptor. Accordingly, the ability to compete with the "radiolabelled compound of Formula (Ia)" or Radiolabelled RUP25 Ligand for the binding to the RUP25 receptor directly correlates to its binding affinity of the test compound to the RUP25 receptor.

Assay Protocol for Determining Receptor Binding for RUP25:

A. RUP25 Receptor Preparation 293 cells (human kidney, ATCC), transiently transfected with 10 ug human RUP25 receptor and 60 µL Lipofectamine (per 15-cm dish), are grown in the dish for 24 hours (75% confluency) with a media change and removed with 10 ml/dish of Hepes-EDTA buffer (20 mM Hepes+10 mM EDTA, pH 7.4). The cells are centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5–50 ug protein) is added to 96-well polyproylene microtiter plates followed by addition of 100 ul of assay buffer and 50 µL of Radiolabelled RUP25 Ligand. For nonspecific binding, 50 µL of assay buffer is added instead of 100 µL and an additional 50 ul of 10 uM cold RUP25 is added before 50 ul of Radiolabelled RUP25 Ligand is added. Plates are then incubated at room temperature for 60–120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 µL of Optiphase Supermix is added to each well, the top of the plates are sealed, and plates are counted in a Trilux Micro-Beta scintillation counter. For compound competition studies, instead of adding 100 µL of assay buffer, 100 µL of appropriately diluted test compound is added to appropriate wells followed by addition of 50 µL of Radiolabelled RUP25 Ligand.

C. Calculations

The test compounds are initially assayed at 1 and 0.1 µM and then at a range of concentrations chosen such that the middle dose would cause about 50% inhibition of a Radio-RUP25 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_d)$$

Where [L] is the concentration of a Radio-RUP25 Ligand used in the assay and $K_d$ is the dissociation constant of a Radio-RUP25 Ligand determined independently under the same binding conditions.

D. Alternative Binding Assay Procedure $^3$H-Nicotinic Acid Binding Competition Assay.

CHO-KI cells stably expressing the niacin receptor were used to make membrane for binding analysis. Cells were grown to ~80% confluence in growth medium (F-12 Kaighn's modified medium (ATCC, #30-2004) containing 10% FBS (GIBCO, #10438-026), 1 mg/ml G418 (GIBCO, #10131-027) and 1× Pen-Strep (Sigma P-0871), harvested by scraping, and centrifuged at 12 000×g, 4° Celsius, 10 minutes. Cell pellets were resuspended in harvest buffer (20 mM HEPES, 10 mM EDTA, pH 7.4) and homogenized with 4×10 second bursts of a 12 mm Polytron homogenizer, setting 5. Lysate was centrifuged at 2 000×g, 4°, 10 minutes to remove unlysed cells and nuclei, and the resulting supernatant centrifuged at 39 000×g, 4°, 45 minutes to pellet membranes. The resulting pellet was resuspended in wash buffer (20 mM HEPES, 0.1 mM EDTA, pH 7.4), homogenized with 3×10 second bursts of a 12 mm Polytron, setting 4, and re-centrifuged at 39 000×g, 4°, 45 minutes. The resulting pellet was resuspended in wash buffer and stored in liquid nitrogen before use. The concentration of membrane proteins in this preparation was determined using the Pierce BCA protein assay, with BSA as a standard.

Equilibrium binding of $^3$H-nicotinic acid was performed in 96-well polypropylene plates. Reactions contained 140 µL membrane diluted in assay buffer (20 mM HEPES, pH 7.4, 1 mM MgCl2, and 0.01% CHAPS; 15–30 µg membrane protein/assay), 20 µL test compounds diluted in assay buffer (compound stocks were in 100% DMSO; final DMSO concentration in the assay was 0.25%), and 40 µL 250 nM tritiated niacin ([5,6-$^3$H]—nicotinic acid: American Radiolabeled Chemicals, Inc., 20 µM in ethanol; final ethanol concentration in each assay was 1.5%). Non-specific binding was determined in the presence of 250 µM unlabeled nicotinic acid. After mixing at 3–4 hours at room temperature, reactions were filtered through Packard Unifilter GF/C plates using a Packard Harvester, and washed with 8×200 µL ice-cold binding buffer. Plates were dried overnight and their backs sealed using PerkinElmer tape designed for GF/C plates. 40 µL PerkinElmer Microscint-20 scintillation fluid was added to each well, the tops sealed, and plates analyzed in a Packard TopCount scintillation counter.

Calculations were preformed as in C above.

Certain compounds of the invention have an $EC_{50}$ in the $^3$H-nicotinic acid binding competition assay within the range of about 10 to about 100 µM. More advantageous compounds of the invention have an $EC_{50}$ value in this assay within the range of about 1 to about 10 µM. Still more advantages compounds have an $EC_{50}$ value in this assay of less than about 1 µM.

Example 7

Flushing via Laser Doppler

Procedure—Male C57B16 mice (~25 g) are anesthetized using 10 mg/ml/kg Nembutal sodium. When antagonists are to be administered they are co-injected with the Nembutal anesthesia. After ten minutes the animal is placed under the laser and the ear is folded back to expose the ventral side. The laser is positioned in the center of the ear and focused to an intensity of 8.4–9.0 V (with is generally ~4.5 cm above the ear). Data acquisition is initiated with a 15 by 15 image format, auto interval, 60 images and a 20 sec time delay with a medium resolution. Test compounds are administered following the 10th image via injection into the peritoneal space. Images 1–10 are considered the animal's baseline and data is normalized to an average of the baseline mean intensities.

Materials and Methods—Laser Doppler Pirimed Pimil; Niacin (Sigma); Nembutal (Abbott labs).

Example 8

Inhibition of Free Fatty-Acid Production, in vivo, in Catheterized Male Sprague-Daly Rats Non-esterified free-fatty acid (NEFA) assays are performed on serum derived from live, freely moving rats. Jugular vein catheters are surgically implanted into the jugular veins and the animals are allowed to recover at least 48 hr post surgery. Food is removed from the animals approximately 16 hours prior to the assay. A draw of ~200 µl blood is pulled from the catheter and represents the baseline NEFA serum sample. Drug is administered intraperitoneally (IP) at various concentrations to individual rats and then ~200 µl blood draws are pulled from the catheter at the indicated time points for further NEFA analysis. NEFA assays are performed according to the manufacturer's specifications (Wako Chemicals, USA; NEFA C) and free fatty acid concentrations are determined via regression analysis of a known standard curve (range of known free fatty acids). Data is analyzed using Excel and PrismGraph.

Example 9

Syntheses of Selected Compounds of the Invention

The compounds of the invention and their synthesis are further illustrated by the following examples. The following examples are provided to further define the invention without, however, limiting the invention to the particulars of these examples. The compounds described herein, supra and infra, are named according to CS Chem Draw Ultra Version 7.0.1 or AutoNom 2000. In certain instances common names are used and it is understood that these common names would be recognized by those skilled in the art. In general, for the Examples provided below, the standard designation of "(±)" directly preceding the chemical name is used to indicate a racemic mixture. The chemical structures shown in the examples are present for illustrative purposes only and are not intended to be limiting unless the chemical name for the example states otherwise.

Chemistry: Proton nuclear magnetic resonance ($^1$H NMR) spectra were recorded on a Varian Mercury Vx-400 equipped with a 4 nucleus auto switchable probe and z-gradient or a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublet, dt=doublet of triplet, t=triplet, q=quartet, m=multiplet, br=broad. Microwave irradiations were carried out using the Emyrs Synthesizer (Personal Chemistry). Thin-layer chromatography (TLC) was performed on silica gel 60 $F_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063–0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shi-

Example 9.1

Preparation of (1aR, 5aR)-(+)-4-(2H-Tetrazol-5-yl)-1a,3,5,5a-tetrahydro-1H-2,3-diaza-cyclopropa[a]pentalene (Compound 4)

Step A: Preparation of bicyclo[3.1.0]hexan-2-ol

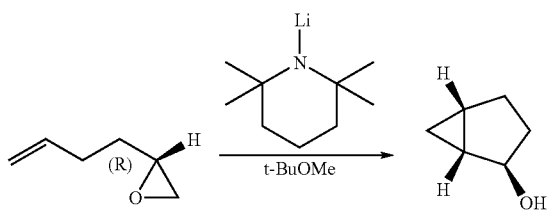

LiTMP was generated by addition of n-BuLi (2.5 M in hexanes, 143 mL, 358 mmol) to a stirred solution of TMP (50.7 g, 359 mmol) in t-BuOMe (1.0 L) at −78° C. The light yellow LiTMP solution was slowly warmed to 0° C. over 45 min. To a stirred solution of (R)-2-but-3-enyl-oxirane (17.6 g, 179 mmol, Schaus, S. E.; et al. *J. Am. Chem. Soc.* 2002, 124, 1307) in t-BuOMe (500 mL) at 0° C. was added the LiTMP solution dropwise via cannula over 50 min. The resultant mixture was stirred at ambient temperature for 18 h then quenched with MeOH (40 mL). The reaction was concentrated to a total volume of 600 mL and the solution was washed with HCl (1N aq., 3×350 mL) and brine (300 mL). The organics were dried over $MgSO_4$, filtered, and concentrated (90 mmHg, 25° C. bath temperature) to give bicyclo[3.1.0]hexan-2-ol as a light yellow oil. The spectral data for bicyclo[3.1.0]hexan-2-ol was similar to the reported literature data, Hodgson, D. M.; Chung, Y. K.; Paris, J.-M. *J. Am. Chem. Soc.* 2004, 126, 8664.

Step B: Preparation of Bicyclo[3.1.0]hexan-2-one

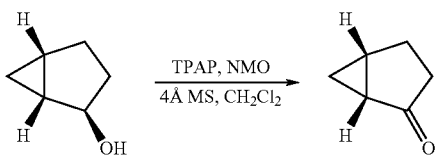

TPAP (1.88 g, 5.35 mmol) was added to a stirring solution of bicyclo[3.1.0]hexan-2-ol (10.5 g, 107 mmol), NMO (25.1 g, 214 mmol), and powdered 4 Å MS (20 g) in $CH_2Cl_2$ (500 mL) at ambient temperature. The mixture was stirred for 2.5 h and filtered through silica gel (80 cm×12 cm) and eluted with $Et_2O/CH_2Cl_2$ (1:1). The organic solvent was carefully evaporated in vacuo (100 mmHg, 25° C. bath temperature) to give bicyclo[3.1.0]hexan-2-one. Spectral data were similar to those previously reported for rac-bicyclo[3.1.0]hexan-2-one (Newman-Evans, R. H.; Simon, R. J.; Carpenter, B. K. *J. Org. Chem.* 1990, 55, 695).

Step C: Preparation of 1a,2,5,5a-Tetrahydro-1H-2,3-diaza-cyclopropa[a]pentalene-4-carboxylic acid ethyl ester

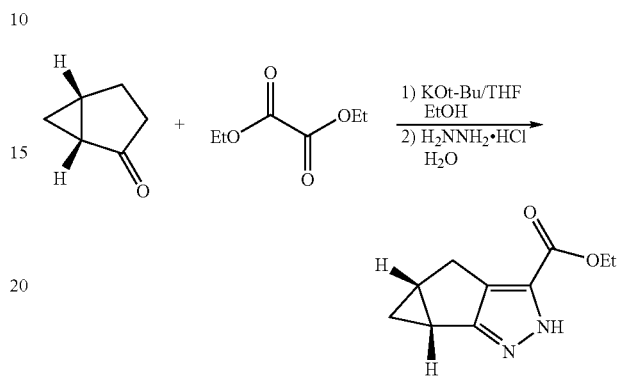

To a solution of bicyclo[3.1.0]hexan-2-one (9.24 g, 96.1 mmol) and diethyl oxalate (14.7 g, 101 mmol) in EtOH (250 mL) at rt under $N_2$ was added a solution of KOt-Bu in THF (106 mL of a 1M solution, 106 mmol). The reaction was stirred for 3.5 h at which time hydrazine hydrochloride (7.90 g, 115 mmol) in $H_2O$ (40 mL) was added. The reaction mixture was stirred for 20 h at rt and acidified to pH ~3 by the addition of HCl (6N aq.). The volatiles were removed in vacuo and the resulting solid was diluted with EtOAc (500 mL) and $H_2O$ (500 mL). The layers were separated and the aqueous phase was back-extracted with EtOAc (300 mL). The combined organics were washed with brine (400 mL), dried over $MgSO_4$, filtered, and concentrated to a crude oil that was determined to be approximately 75–80% pure (wt./wt.) ester by $^1H$ NMR. The title compound was used directly in the next reaction (aminolysis) without further purification. $^1H$ NMR (400 MHz, $CDCl_3$): δ 10.55 (1H, bs), 4.32 (2H, q, J=6.8 Hz), 2.96 (1H, dd, J=16.8, 6.0 Hz), 2.80 (1H, d, J=17.2 Hz), 2.23–2.13 (2H, m), 1.35 (3H, t, J=7.2 Hz), 1.15 (1H, m), 0.34 (1H, m). $^{13}C$ APT NMR (partial) (100 MHz, $CDCl_3$): δ up: 127.4, 61.2, 26.8, 16.8; down: 23.0, 15.4, 14.5. HPLC/MS: Discovery® C18 column (5μ, 50×2.1 mm), 5% v/v $CH_3CN$ (containing 1% v/v TFA) in $H_2O$ (containing 1% v/v TFA) gradient to 99% v/v $CH_3CN$ in $H_2O$, 0.75 mL/min, $t_r$=1.62 min, $ESI^+$=193.1 (M+H).

Step D: Preparation of 1a,2,5,5a-Tetrahydro-1H-2,3-diaza-cyclopropa[a]pentalene-4-carboxylic acid amide

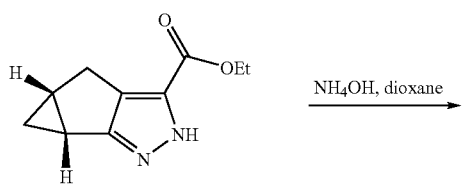

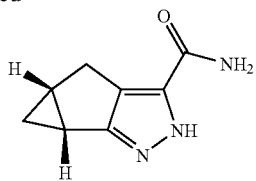

To a solution of the ester from Step C (14.2 g, 73.9 mmol) in dioxane (140 mL) was added ammonium hydroxide (28% $NH_3$ in $H_2O$, 750 mL). The mixture was placed in a 1000 mL pyrex bottle and agitated on a shaker plate for 22 h at rt. The mixture was concentrated in vacuo to a total volume of 100 mL at which time a light yellow precipitate was evident. The mixture was filtered and the solid was washed with $H_2O$ (2×100 mL). Further drying of the solid in vacuo gave 1a,2,5,5a-tetrahydro-1H-2,3-diaza-cyclopropa[a]pentalene-4-carboxylic acid amide [HPLC/MS: Discovery® C18 column (5μ, 50×2.1 mm), 5% v/v $CH_3CN$ (containing 1% v/v TFA) in $H_2O$ (containing 1% v/v TFA) gradient to 99% v/v $CH_3CN$ in $H_2O$, 0.75 mL/min, $t_r$=1.09 min, $ESI^+$=164.0 (M+H)] as a white solid.

Step E: Preparation of 2-Benzyl-1a,2,5,5a-tetrahydro-1H-2,3-diaza-cyclopropa[a]pentalene-4-carbonitrile

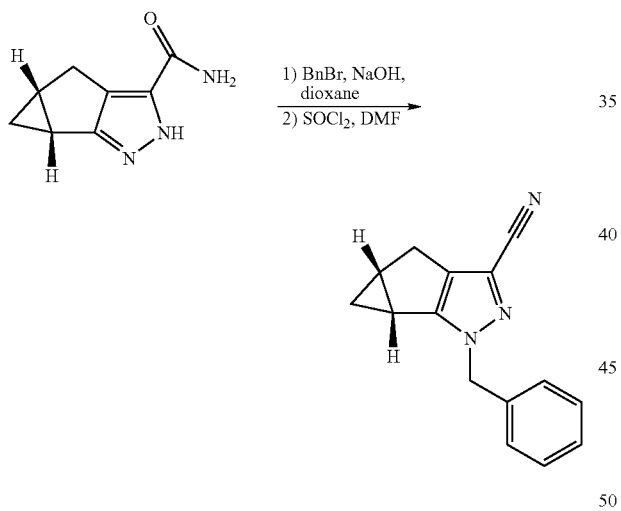

The amide from Step D (9.38 g, 57.9 mmol) was partially dissolved in dioxane (150 mL) and NaOH (5N aq., 23.0 mL, 115 mmol) was added followed by benzyl bromide (10.3 g, 60.2 mmol). The mixture slowly became clear and the reaction stirred for 20 h at rt. The mixture was acidified to pH≈2 by the addition of HCl (6N, aq.) and concentrated to dryness in vacuo. The resultant light yellow solid was washed with $NaHCO_3$ (sat. aq., 100 mL) and $H_2O$ (100 mL). Further drying of the solid in vacuo gave the benzylated product, 2-benzyl-1a,2,5,5a-tetrahydro-1H-2,3-diaza-cyclopropa[a]pentalene-4-carboxylic acid amide as a white solid.

A flask equipped with a drying tube under $N_2$ atmosphere was charged with anhydrous DMF (50 mL). The flask was cooled to 0° C. and thionyl chloride (4.84 mL, 66.5 mmol) was added dropwise over a period of 2 min. After stirring for an additional 10 min, a suspension of 2-benzyl-1a,2,5,5a-tetrahydro-1H-2,3-diaza-cyclopropa[a]pentalene-4-carboxylic acid amide, (14.0 g, 55.3 mmol) in DMF (90 mL) was added over 5 min using an addition funnel. The mixture was slowly warmed to rt and stirred for 20 min at which time additional thionyl chloride (3.05 mL, 41.9 mmol) was added as a pre-mixed solution in DMF (20 mL). The reaction was stirred for an additional 20 min and a second pre-mixed solution of thionyl chloride (6.0 mL, 82.5 mmol) in DMF (20 mL) was added. The reaction was stirred for an additional 15 min and $NaHCO_3$ (sat. aq., 50 mL) was added followed by $H_2O$ (100 mL). The mixture was stirred for 10 min and concentrated to near dryness in vacuo. The residue was diluted with EtOAc (350 mL) and $H_2O$ (250 mL). The layers were separated and the aqueous phase was back-extracted with EtOAc (250 mL). The combined organics were washed with $NaHCO_3$ (sat. aq., 400 mL), and brine (400 mL), dried over $MgSO_4$, filtered, and concentrated to give 2-benzyl-1a,2,5,5a-tetrahydro-1H-2,3-diaza-cyclopropa[a]pentalene-4-carbonitrile as a brown solid. $^1H$ NMR (400 MHz, $CDCl_3$): δ 7.37 (3H, m), 7.25 (2H, m), 5.31 (1H, d, J=14.8 Hz), 5.24 (1H, d, J=14.8 Hz), 2.86, (1H, dd, J=16.4, 6.4 Hz), 2.72 (1H, d, J=16.0 Hz), 2.19 (1H, m), 1.87 (1H, m), 1.07 (1H, m), 0.32 (1H, m). $^{13}C$ APT NMR (100 MHz, $CDCl_3$): δ up: 154.4, 135.3, 130.0, 118.9, 114.3, 55.9, 26.2, 16.9; down: 129.2, 128.6, 128.1, 24.2, 14.4. HPLC/MS: Discovery® C18 column (5μ, 50×2.1 mm), 5% v/v $CH_3CN$ (containing 1% v/v TFA) in $H_2O$ (containing 1% v/v TFA) gradient to 99% v/v $CH_3CN$ in $H_2O$, 0.75 mL/min, $t_r$=2.23 min, $ESI^+$=236.1 (M+H).

Step F: Preparation of 2-Benzyl-4-(2H-tetrazol-5-yl)-1a,2,5,5a-tetrahydro-1H-2,3-diaza-cyclopropa[a]pentalene

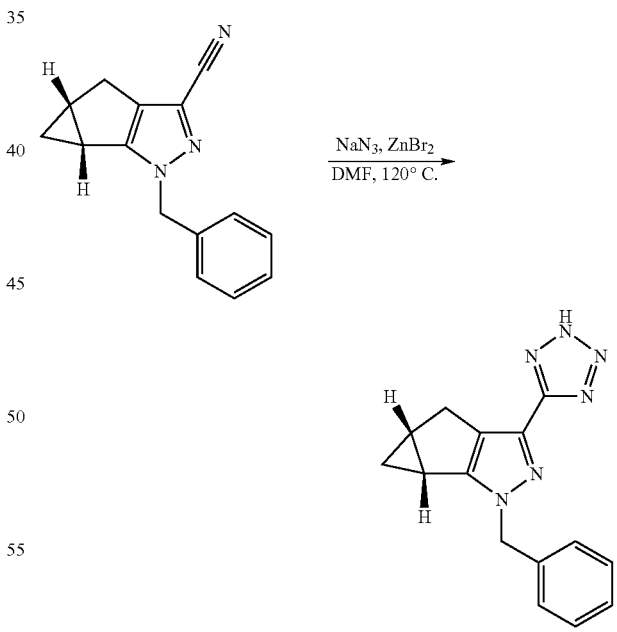

To a solution of 2-benzyl-1a,2,5,5a-tetrahydro-1H-2,3-diaza-cyclopropa[a]pentalene-4-carbonitrile (11.1 g, 47.2 mmol) in DMF (125 mL) was added $ZnBr_2$ (18.4 g, 70.6 mmol) followed by $NaN_3$ (12.2 g, 188 mmol). The mixture was heated to 120° C. and stirred for 18 h under $N_2$ atmosphere. The reaction was cooled to rt and the DMF was removed in vacuo. The crude residue was diluted with EtOAc (200 mL) and HCl (3N aq., ~100 mL) and stirred for 10 min. The layers were separated and the aqueous phase was back-extracted with EtOAc (150 mL). The combined organics were washed with NaOH (1M aq., 2×250 mL) and the organic layers were discarded. The basic aqueous phase was acidified with 6 N HCl to pH ~2 and was extracted with EtOAc (2×250 mL). The extracts were washed with brine (150 mL), dried over MgSO$_4$, filtered, and concentrated to give 2-benzyl4-(2H-tetrazol-5-yl)-1a,2,5,5a-tetrahydro-1H-2,3-diaza-cyclopropa[a]pentalene as a light brown solid. $^1$H NMR (400 MHz, MeOD): δ 7.33 (5H, m), 5.42 (1H, d, J=14.8 Hz), 5.35 (1H, d, J=15.2 Hz), 3.01 (1H, dd, J=16.4, 6.4 Hz), 2.88 (1H, d, J=17.6 Hz), 2.28 (1H, m), 2.11 (1H, M), 1.14 (1H, m), 0.33 (1H, m). HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 ml/min, t$_r$=2.14 min, ESI$^+$=279.3 (M+H).

Step G: Preparation of (1aR,5aR)-4-(2H-Tetrazol-5-yl)-1a,3,5,5a-tetrahydro-1H-2,3-diaza-cyclopropa[a]pentalene (Compound 4)

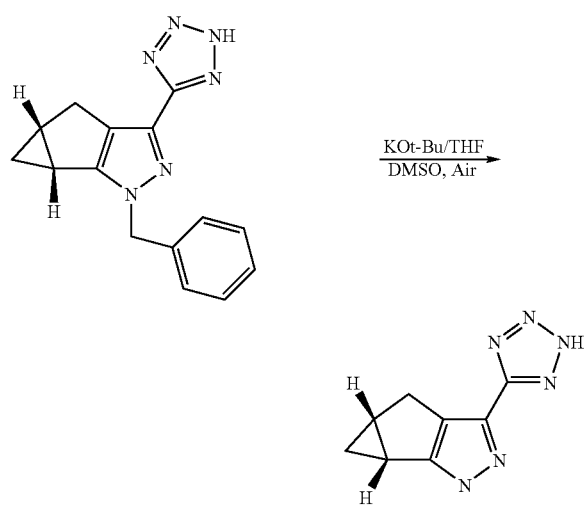

Air was bubbled through a stirring solution of 2-benzyl-4-(2H-tetrazol-5-yl)-1a,2,5,5a-tetrahydro-1H-2,3-diaza-cyclopropa[a]pentalene (10.4 g, 37.4 mmol) and KOt-Bu (374 mL of a 1M solution in THF, 374 mmol) in DMSO (300 mL) for 20 h at rt. The remaining THF was removed in vacuo and the reaction was acidified to pH=2 by the addition of HCl (3M aq). The mixture was concentrated in vacuo to near dryness. The residue was dissolved in HCl (1N aq., 250 mL) and extracted with EtOAc (5×250 mL). The organics were dried over MgSO$_4$, filtered, and concentrated. The product was purified and converted to the ammonium salt by loading material (as a solution in MeOH) on to a column containing Bondesil SCX SPE resin (~250 g). The column was flushed with MeOH (200 mL) to remove unbound impurities. The product was eluted using 2N NH$_3$/MeOH (approx. 200 mL). Concentration of the basic eluant yielded the ammonium salt of Compound 4 as a white solid. $^1$H NMR (400 MHz, MeOD): δ 3.02 (1H, dd, J=16.4, 6.0 Hz), 2.90 (1H, d, J=16.0 Hz), 2.19 (2H, m), 1.17 (1H, m), 0.33 (1H, m). HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.21 min, ESI$^+$=189.0 (M+H). [α]$^{25}_D$+35.7 (c 0.39, MeOH).

Example 9.2

Preparation of (±)-1,1-Dimethyl-4-(2H-tetrazol-5-yl)-1a,3,5,5a-tetrahydro-1H-2,3-diaza-cyclopropa[a]pentalene (Compound 7)

Step A: (±)-2-(4-Methylpent-3-enyl)oxirane

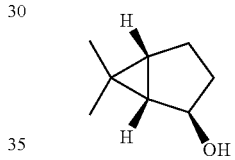

2-(But-3-enyl)oxirane (1.000 g, 10 mmol) and 2-methyl-but-2-ene (10 g, 102 mmol) were stirred at room temperature for 24 hr in a sealed scintillation vial with Zhan catalyst 1 (0.057 g, 0.086 mmol). Solvent was removed under reduced pressure and the residue purified by column chromatography (0–10% EtOAc/n-hexane/silica) to give 2-4-methylpent-3-enyl)oxirane as a colorless oil. $^1$H NMR (CDCl$_3$): δ 5.2–5.1 (m, 1H), 2.95–2.88 (m, 1H), 2.75 (dd, 1H J$_1$=5.0, J$_2$=4.1), 2.48 (dd, 1H J$_1$=5.0, J$_2$=2.8), 2.15 (2H, q, J=7.4), 1.70 (s, 3H), 1.63 (s, 3H), 1.60–1.50 (m, 2H).

Step B: Preparation of (±)-6,6-Dimethyl-bicyclo[3.1.0]hexan-2-ol

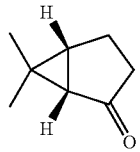

2,2,6,6-Tetramethylpiperidine (9.70 g, 69 mmol) was taken up in MTBE (100 mL) and chilled to −78° C. n-Butyllithium (43 mL, 1.6 M in n-hexane, 69 mmol) was added cautiously and the resulting solution allowed to stir at −78° C. for 30 minutes. The pale yellow solution was added via cannular transfer to a chilled (0° C.) solution of 2-(4-methyl-pent-3-enyl)-oxirane (4.33 g, 34.3 mmol) in MTBE (30 mL) over 30 minutes, allowed to warm slowly to room temperature and stirred under argon for 18 hours. The solution was then added to 1M aqueous hydrochloric acid (50 mL) and extracted into further MTBE (200 mL). Solvent was removed under reduced pressure and the resulting oil purified by column chromatography (0–40% EtOAc/n-hexane, silica). (±)-6,6-Dimethyl-bicyclo[3.1.0]hexan-2-ol was obtained as a yellow oil. $^1$H NMR (CDCl$_3$): δ 4.15–4.10 (m, 1H), 2.10–2.00 (m, 1H), 1.90–1.80 (m, 1H), 1.80–1.70 (m, 1H), 1.62 (br s, OH), 1.56 (ddd, 1H, J$_1$=12.9, J$_2$=9.5, J$_3$=2.9), 1.48 (br s, 1H), 1.14 (dd, 1H, J$_1$=6.3, J$_2$=1.2), 0.99 (s, 3H), 0.93 (s, 3H).

Step C: Preparation of (±)-6,6-Dimethyl-bicyclo[3.1.0]hexan-2-one

A chilled (0° C.) solution of N-methylmorpholine N-oxide (3.11 g, 26.5 mmol) and tetrapropylammonium perrethenate (VII) (0.280 g, 0.796 mmol) in DCM (40 mL) was prepared containing 4 Å molecular sieves (ca 0.3 g). A solution of (±)-6,6-dimethyl-bicyclo[3.1.0]hexan-2-ol (1.67 g, 13.3 mmol) in DCM (10 mL) was added dropwise and the solution allowed to warm to room temperature and stirred for 1 hour under argon. The solution was filtered through a silica plug, solvent removed under reduced pressure and the resulting oil purified by column chromatography (0–100% DCM/n-hexane, silica). 6,6-Dimethyl-bicyclo[3.1.0]hexan-2-one was obtained as a brown oil. $^1$H NMR (CDCl$_3$): δ 2.35–2.15 (m, 2H), 2.10–2.00 (m, 1H), 1.97–1.85 (m, 2H), 1.66 (d, 1H, J=4.7), 1.16 (s, 3H), 1.12 (s, 3H).

Step D: Preparation of (±)-1,1-Dimethyl-1a,3,5,5a-tetrahydro-1H-2,3-diaza-cyclopropa[a]pentalene-4-carboxylic acid ethyl ester

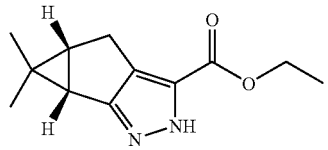

(±)-6,6-Dimethyl-bicyclo[3.1.0]hexan-2-one (1.49 g, 12.0 mmol), diethyl oxalate (2.46 g, 16.8 mmol) and potassium t-butoxide (18.0 mL, 1M in THF, 18.0 mmol) were stirred in ethanol (40 mL) at room temperature for 2 hours. The desired (6,6-dimethyl-2-oxo-bicyclo[3.1.0]hex-3-yl)-oxo-acetic acid ethyl ester was observed by LCMS (m/z (ES$^+$): 247 [M+Na]$^+$, 225 [M+H]$^+$) but not isolated. Hydrazine monohydrochloride (0.168 g, 24.4 mmol) in water (2.0 mL) was added and the solution heated to 80° C. for 18 hours. Solvent was removed under reduced pressure and the resulting oil poured into 0.1M aqueous hydrochloric acid (30 mL) and extracted into DCM (200 mL). Solvent was removed under reduced pressure and the residue purified by column chromatography (0–50% EtOAc/n-hexane, silica) to give (±)-1,1-dimethyl-1a,3,5,5a-tetrahydro-1H-2,3-diaza-cyclopropa[a]pentalene-4-carboxylic acid ethyl ester as a pale yellow oil which solidified upon standing. m/z (ES$^+$): 243 [M+Na]$^+$, 221 [M+H]$^+$, 175 [M-OEt]$^+$; $^1$H NMR (CD$_3$OD): δ 4.4–4.3 (m, 2H, OCH$_2$), 2.90 (dd, 1H, J$_1$=17.5, J$_2$=6.9), 2.65 (d, 1H, J=17.5), 2.1–2.0 (m, 1H), 1.95 (t, 1H, J=12.9), 1.37 (td, J$_1$=7.1, J$_2$=2.0), 1.13 (s, 3H, exo-CH$_3$), 0.74 (d, 3H, J=2.0, endo-CH$_3$).

Step E: Preparation of (±)-1,1-Dimethyl-1a,3,5,5a-tetrahydro-1H-2,3-diaza-cyclopropa[a]pentalene-4-carboxylic acid amide

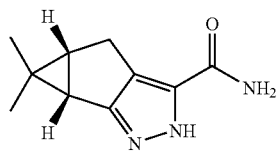

(±)-1,1-Dimethyl-1a,3,5,5a-tetrahydro-1H-2,3-diaza-cyclopropa[a]pentalene-4-carboxylic acid ethyl ester (1.280 g, 5.81 mmol) was taken up in 7M methanolic ammonia (60 mL) in a sealed flask and heated to 100° C. for 18 hours. The resulting suspension was collected by vacuum filtration to give 1,1-dimethyl-1a,3,5,5a-tetrahydro-1H-2,3-diaza-cyclopropa[a]pentalene-4-carboxylic acid amide as a cream solid. Solvent was removed from the mother liquor and the residue purified by preparative HPLC to give further (±)-1,1-dimethyl-1a,3,5,5a-tetrahydro-1H-2,3-diaza-cyclopropa[a]pentalene-4-carboxylic acid amide as a cream solid. m/z (ES$^+$): 192 [M+H]$^+$, 175 [M-NH$_2$]$^+$; $^1$H NMR (CD$_3$OD): δ 2.9–2.65 (m, 1H), 2.55 (t, 1H, J=19.9), 2.0–1.8 (m, 2H), 1.03 (s, 3H), 0.63 (s, 3H).

Step F: Preparation of (±)-1,1-Dimethyl-1a,3,5,5a-tetrahydro-1H-2,3-diaza-cyclopropa[a]pentalene-4-carbonitrile

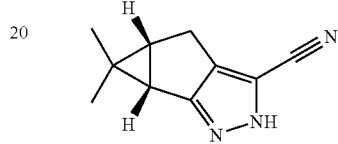

(±)-1,1-Dimethyl-1a,3,5,5a-tetrahydro-1H-2,3-diaza-cyclopropa[a]pentalene-4-carboxylic acid amide (0.532 g, 2.79 mmol) was taken up in THF (150 mL) and trifluoroacetic anhydride (0.936 g, 4.46 mmol) added. The resulting solution was stirred at room temperature under argon for 1 hour. Ethyl acetate (50 mL) was added and solvent removed under reduced pressure. The resulting pale yellow oil was taken up in DCM (100 mL), washed with saturated aqueous sodium bicarbonate solution (40 mL) and solvent removed under reduced pressure. The resulting white solid was taken up as a suspension in DCM (20 mL) and filtered to give (±)-1,1-dimethyl-1a,3,5,5a-tetrahydro-1H-2,3-diaza-cyclopropa[a]pentalene-4-carbonitrile as an off-white solid. m/z (ES): 174 [M+H]$^+$ Step G: Preparation of (±)-1,1-Dimethyl-4-(2H-tetrazol-5-yl)-1a,3,5,5a-tetrahydro-1H-2,3-diaza-cyclopropa[a]pentalene (Compound 7)

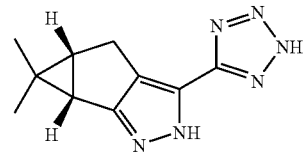

(±)-1,1-Dimethyl-1a,3,5,5a-tetrahydro-1H-2,3-diaza-cyclopropa[a]pentalene-4-carbonitrile (0.184 g, 1.06 mmol) was taken up in 1,4-dioxane (10 mL) with zinc dibromide (0.500 g, 2.22 mmol) and sodium azide (0.300 g, 4.62 mmol) in a heavy walled glass tube. The resulting solution was heated under microwave irradiation to 200° C. for 1 hour. The solution was poured into 1M aqueous hydrochloric acid (10 mL) and extracted into ethyl acetate (50 mL). Solvent was removed under reduced pressure and the resulting oil purified by preparative HPLC to give (±)-1,1-dimethyl-4-(2H-tetrazol-5-yl)-1a,3,5,5a-tetrahydro-1H-2,3-diaza-cyclopropa[a]pentalene as a white solid. m/z (ES$^+$): 217 [M+H]$^+$, 189 [M-N$_2$+H]+; $^1$H NMR (CD$_3$OD): δ 2.87 (dd, 1H, $J_1$=16.5, $J_2$=5.6), 2.67 (dd, 1H, $J_1$=16.5, $J_2$=0.8), 2.1–2.0 (m, 2H), 1.08 (s, 3H), 0.69 (s, 3H).

Example 9.3

Preparation of (±)-1,1-Dimethyl-1a,3,5,5a-tetrahydro-1H-2,3-diaza-cyclopropa[a]pentalene-4-carboxylic acid (Compound 6)

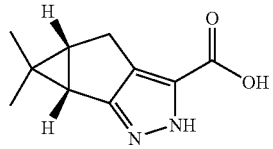

(±)-1,1-Dimethyl-1a,3,5,5a-tetrahydro-1H-2,3-diaza-cyclopropa[a]pentalene-4-carboxylic acid ethyl ester (0.0390 g, 0.177 mmol) was stirred for 18 hours at room temperature in a solution of 1:5:1 methanol:THF:1M aqueous lithium hydroxide (14 mL). Solvent was removed under reduced pressure, the residue was taken up in 1M aqueous hydrochloric acid (5 mL) and extracted into ethyl acetate (40 mL). Solvent was removed under reduced pressure and the residue purified by preparative HPLC to give a white solid. m/z (ES$^+$): 215 [M+Na]$^+$, 193 [M+H]$^+$, 175 [M−OH]$^+$; $^1$H NMR (CD$_3$CN): δ 2.91 (dd, 1H, $J_1$=17.4, $J_2$=6.8), 2.66 (d, 1H, J=17.4), 2.11 (dd, 1H, $J_1$=6.3, $J_2$=1.2), 2.05–1.95 (m, 1H), 1.19 (s, 3H, exo-CH$_3$), 0.77 (d, 3H, J=2.0, endo-CH$_3$).

Example 9.4

Preparation of (±)-exo-1-Benzyl-4-(2H-tetrazol-5-yl)1a,3,5,5a-tetrahydro-1H-2,3-diaza-cyclopropa[a]pentalene (Compound 8)

Compound 8 was synthesized in a similar manner as described in Example 9.2 starting with (E)-2-(5-phenylpent-3-enyl)-oxirane. The intermediates were characterized as shown below for the respective steps.

Step A: (±)-exo-6-Benzyl-bicyclo[3.1.0]hexan-2-ol

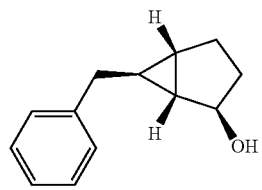

The title compound was prepared in a similar manner as described in Example 9.2, Step B. $^1$H NMR (CDCl$_3$): δ 7.35–7.25 (m, 2H), 7.25–7.15 (m, 3H), 4.25 (d, 1H, J=4.7), 2.54 (d, 2H, J=6.9), 2.00–1.85 (m, 1H), 1.74 (dd, 1H, $J_1$=12.5, $J_2$=8.0), 1.65–1.50 (m, 1H), 1.45–1.35 (m, 1H), 1.35–1.30 (m, 1H), 0.71 (septet, 1H, J=3.3). Contains 15% (±)-endo-6-benzyl-bicyclo[3.1.0]hexan-2-ol.

Step B: (±)-exo-6-Benzyl-bicyclo[3.1.0]hexan-2-one

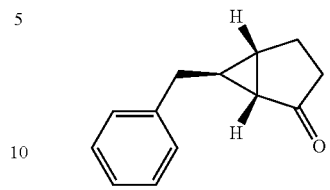

The title compound was prepared in a similar manner as described in Example 9.2, Step C. $^1$H NMR (CDCl$_3$): δ 7.35–7.28 (m, 2H), 7.25–7.20 (m, 3H), 2.78 (dd, 1H, $J_1$=14.9, $J_2$=6.1), 2.60 (dd, 1H, $J_1$=14.9, $J_2$=7.2), 2.20–2.10 (m, 1H), 2.10–2.00 (m, 4H), 1.74 (dd, 1H, $J_1$=5.2, $J_2$=2.4), 1.65–1.55 (m, 1H). Contains 15% (±)-endo-6-benzyl-bicyclo[3.1.0]hexan-2-one.

Step C: (±)-exo-1-Benzyl-1a,3,5,5a-tetrahydro-1H-2,3-diaza-cyclopropa[a]pentalene-4-carboxylic acid ethyl ester

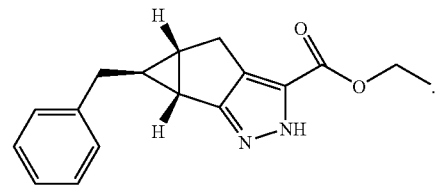

The title compound was prepared in a similar manner as described in Example 9.2, Step D. $^1$H NMR (CD$_3$OD): δ 7.35–7.10 (m, 5H), 4.31 (q, 2H, J=7.1, OCH$_2$), 2.97 (dd, 1H, $J_1$=17.2, $J_2$=6.2), 2.90–2.75 (m, 2H), 2.59 (dd, 1H, $J_1$=15.0, $J_2$=7.5), 2.20–2.15 (m, 1H), 2.15–2.05 (m, 1H), 1.34 (t, 3H, J=7.1), 1.00 (septet, 1H, J=3.5). Contains 15% (±)-endo-1-benzyl-1a,3,5,5a-tetrahydro-1H-2,3-diaza-cyclopropa[a]pentalene-4-carboxylic acid ethyl ester. MS n/z (ES$^+$): 305 [M+Na]$^+$, 283 [M+H]$^+$, 237 [M−OEt]$^+$.

Step D: (±)-exo-1-Benzyl-1a,3,5,5a-tetrahydro-1H-2,3-diaza-cyclopropa[a]pentalene-4-carboxylic acid amide

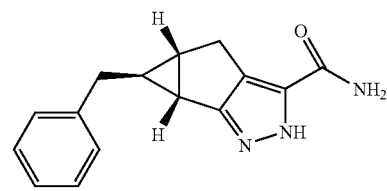

The title compound was prepared in a similar manner as described in Example 9.2, Step E. $^1$H NMR (CD$_3$OD): δ 7.4–7.1 (m, 5H), 2.95 (dd, 1H, $J_1$=16.5, $J_2$=5.4), 2.87 (d, 1H, J=15.6), 2.8–2.6 (m, 2H), 2.25–2.15 (m, 2H), 1.05–0.90 (m, 1H). Contains 15% (±)-endo-1-benzyl-1a,3,5,5a-tetrahydro-1H-2,3-diaza-cyclopropa[a]pentalene-4-carboxylic acid amide. MS m/z (ES$^+$): 276 [M+Na]$^+$, 254 [M+H]$^+$, 237 [M−NH$_2$]$^+$ Step E: (±)-exo-1-Benzyl-1a,3,5,5a-tetrahydro-1H-2,3-diaza-cyclopropa[a]pentalene-4-carbonitrile

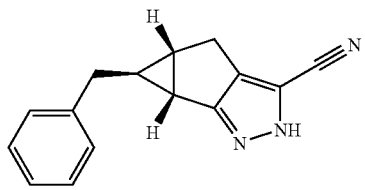

The title compound was prepared in a similar manner as described in Example 9.2, Step F. MS m/z (ES⁺): 236 [M+H]⁺ Contains 15% (±)-endo-1-benzyl-1a,3,5,5a-tetrahydro-1H-2,3-diaza-cyclopropa[a]pentalene-4-carbonitrile.

Step F: (±)-exo-1-Benzyl-4-(2H-tetrazol-5-yl)1a,3,5,5a-tetrahydro-1H-2,3-diaza-cyclopropa[a]pentalene (Compound 8)

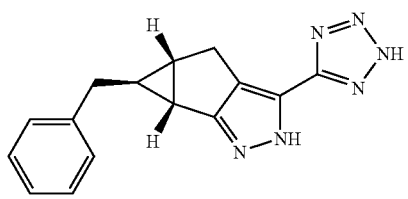

The title compound was prepared in a similar manner as described in Example 9.2, Step G. ¹H NMR (CD₃OD): δ 7.6–7.5 (m, 4H), 7.5–7.4 (m, 1H), 3.29 (dd, 1H, $J_1$=16.2, $J_2$=6.0), 3.18 (d, 1H, J=16.2), 3.01 (dd, 1H, $J_1$=14.7, $J_2$=6.6), 2.90 (dd, 1H, $J_1$=14.7, $J_2$=7.4), 2.55–2.45 (m, 2H), 1.35–1.25 (m, 1H). MS m/z (ES⁺): 301 [M+H]⁺, 279 [M+H]⁺, 251 [M–N₂+H]⁺.

Example 9.5

Preparation of (±)-exo-1-Benzyl-1a,3,5,5a-tetrahydro-1H-2,3-diaza-cyclopropa[a]pentalene-4-carboxylic acid (Compound 5)

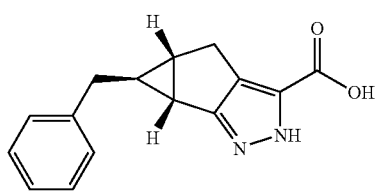

Compounds 5 was synthesized from (±)-exo-1-Benzyl-1a,3,5,5a-tetrahydro-1H-2,3-diaza-cyclopropa[a]pentalene-4-carboxylic acid ethyl ester using a similar method as described in Example 9.3. MS m/z (ES⁺): 277 [M+Na]⁺, 255 [M+H]⁺, 237 [M–OH]⁺; ¹H NMR (CD₃CN): δ 7.3–7.1 (m, 5H), 2.83 (dd, 1H, $J_1$=17.0, $J_2$=5.8), 2.66 (d, 1H, J=17.0), 2.57 (dd, 2H, $J_1$=7.0, $J_2$=4.2), 2.05–1.95 (m, 2H), 0.82 (septet, 1H, J=3.5). Contains 15% (±)-endo-1-benzyl-1a,3,5,5a-tetrahydro-1H-2,3-diaza-cyclopropa[a]pentalene-4-carboxylic acid.

Example 9.6

Preparation of (±)-3b,4,4a,5-Tetrahydro-2H-cyclopropa[3,4]cyclopenta[1,2-c]pyrazole-3-carboxylic acid (Compound 1)

Step A: Preparation of Bicyclo[3.1.0]hexan-3-one

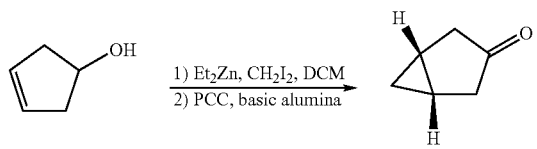

To a solution of cyclopentene-4-ol (5.0 g, 59.5 mmol) and Et₂Zn (12.4 mL, 121 mmol) in DCM (25 mL) under N₂ atmosphere at 0° C. was added CH₂I₂ (9.76 mL, 121 mmol) over 30 min using a syringe pump. The reaction was slowly warmed to rt and stirred overnight at which time the mixture was opened to air and slowly quenched by the addition of dilute HCl (50 mL). The mixture was diluted with EtOAc (100 mL) and filtered. The organic layer was separated, washed with H₂O (100 mL) and brine (100 mL). The organics were dried over MgSO₄, filtered, and concentrated to an oil which was purified by silica gel chromatography (10% EtOAc in hexanes gradient to 30% EtOAc in hexanes) to give the cyclopropyl alcohol as clear oil.

The alcohol (from above) was dissolved in DCM (250 mL) and treated sequentially with basic alumina (10 g) and PCC (15.2 g, 70.6 mmol) at rt. After stirring for 18 h the solution was filtered through a pad of celite atop silica gel using DCM/Et₂O (3:1) as eluant. The solvent was removed in vacuo (250 mbar, 20° C. bath temperature) and the product was purified by bulb-to-bulb distillation at reduced pressure (100 mbar) to give the ketone as a clear oil. ¹H NMR (CDCl₃, 400 MHz): δ 2.60 (2H, m), 2.16 (2H, d, J=20.0 Hz), 1.54 (2H, m), 0.90 (1H, dt, J=6.0, 1.6 Hz), −0.05 (1H, dt, J=6.0, 4.0 Hz).

Step B: Preparation of (±)-3b,4,4a,5-Tetrahydro-1H-cyclopropa[3,4]cyclopenta[1,2-c]pyrazole-3-carboxylic acid ethyl ester

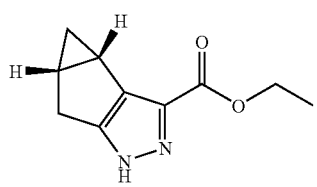

The title ester was prepared in a similar manner as described in Example 9.1, Step C using bicyclo[3.1.0]hexan-3-one.

Step C: Preparation of (±)-3b,4,4a,5-Tetrahydro-2H-cyclopropa[3,4]cyclopenta[1,2-c]pyrazole-3-carboxylic acid (Compound 1)

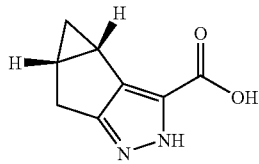

To a solution of ester (43 mg, 0.23 mmol) in THF (2 mL) and H$_2$O (1 mL) was added LiOH H$_2$O (38 mg, 0.90 mmol) at rt. The reaction was heated to 55° C. for 1.5 h. After cooling to rt the mixture was acidified to pH=1 with HCl (6N, aq.). Purification by reverse-phase HPLC [Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 ml/min, λ=214 nm] gave the free acid as a white solid after lyophilization.

HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.24 min, ESI+=165.0 (M+H).

Example 9.7

Preparation of (±)-4-(2H-Tetrazol-5-yl)-1a,3,5,5a-tetrahydro-1H-2,3-diaza-cyclopropa[a]pentalene (Compound 2)

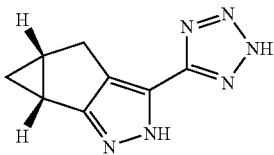

Compound 2 was prepared in a similar manner as described in Example 9.1 using racemic 2-but-3-enyl-oxirane.

Example 9.8

Preparation of (±)-1a,3,5,5a-Tetrahydro-1H-2,3-diaza-cyclopropa[a]pentalene-4-carboxylic acid (Compound 3)

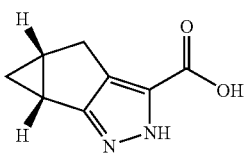

To a solution of the corresponding (±)-ester (50 mg, 0.26 mmol) in dioxane (1 mL) was added NaOH (1N aq., 2 mL) at rt. The reaction was stirred overnight and acidified to pH=1 with HCl (6N, aq.). Purification by reverse-phase HPLC [Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 ml/min, λ=214 nm] gave the free acid as a white solid after lyophilization. HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.09 min, ESI+=164.1 (M+H).

Example 9.9

Preparation of intermediate (±)-6,6-dichloro-spiro[bicyclo[3.1.0]hexane-2,2'-[1,3]dioxolane]

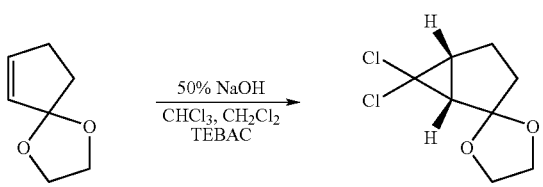

To a solution of 1,4-dioxa-spiro[4.4]non-6-ene (25.23 g, 0.20 mol) in CHCl$_3$ (200 mL) and CH$_2$Cl$_2$ (200 mL) was added triethylbenzylammonium chloride (100 mg) and 50% NaOH solution (200 mL) at rt. This solution was vigorously stirred at 45° C. over 3 days. The reaction mixture was diluted with H$_2$O (300 mL) and extracted with CHCl$_3$ (2×150 mL). The combined organic layer was concentrated in vacuo and the residue was purified by SiO$_2$ column chromatography (0–50% CH$_2$Cl$_2$ in Hexanes) to the title compounds as a colorless liquid. $^1$H NMR (400 MHz, CDCl$_3$): δ 4.06–3.93 (m, 4 H), 2.25–2.01 (m, 5H), 1.89–1.83 (m, 1H).

Example 9.10

Preparation of intermediate (±)-exo-6-chloro-spiro[bicyclo[3.1.0]hexane-2,2'-[1,3]dioxolane] and (±)-endo-6-chloro-spiro[bicyclo[3.1.0]hexane-2,2'-[1,3]dioxolane]

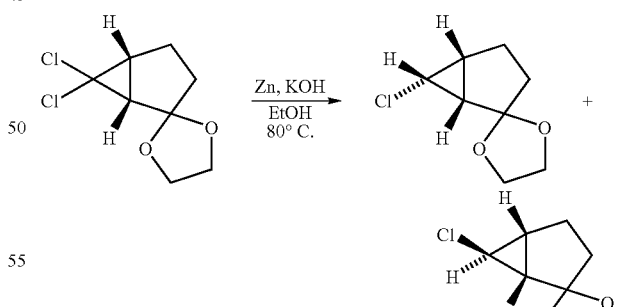

To a solution of (±)-6,6-dichloro-spiro[bicyclo[3.1.0]hexane-2,2'-[1,3]dioxolane] (17.0 g, 81 mmol) and KOH (28.0 g, 0.5 mol) in EtOH (200 mL) was added Zn (62.8 g, 0.96 mol) at rt. The reaction mixture was heated at 80° C. under vigorous stirring overnight. After cooling down the reaction mixture to rt, it was filtered through celite pad and the filtrate was treated with acetic anhydride (47.27 mL, 0.5 mol) under ice bath. After concentration in vacuo, the residue was extracted into hexanes (300 mL) and washed with H$_2$O (2×150 mL) and brine (150 mL). SiO$_2$ column chromatography (20–70% CH$_2$Cl$_2$ in Hexanes) gave both the exo-chloride and endo-chloride.

Exo-chloride: $^1$H NMR (400 MHz, CDCl$_3$): δ 4.07–3.90 (m, 4 H), 2.94 (t, 1H, J=1.9 Hz) 1.95–1.90 (m, 2H), 1.88–1.74 (m, 2H), 1.68–1.62 (m, 1H), 1.45–1.36 (m, 1H).

Endo-chloride: $^1$H NMR (400 MHz, CDCl$_3$): δ 4.02–3.91 (m, 4 H), 3.42 (t, 1H, J=7.5 Hz) 2.22–2.12 (m, 1H), 2.05–1.74 (m, 5H).

Example 9.11

Preparation of Intermediate (±)-endo-6-chloro-exo-6-methyl-spiro[bicyclo[3.1.0]hexane-2,2'-[1,3]dioxolane]

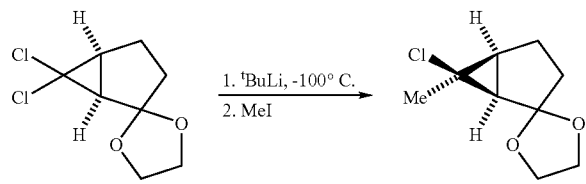

To a solution of (±)-6,6-dichloro-spiro[bicyclo[3.1.0]hexane-2,2'-[1,3]dioxolane] (6.50 g, 31.1 mmol) in 140 mL of THF was dropwise added t-butyl lithium (37.32 mmol, 21.95 mL of 1.7 M solution in pentane) at −100° C. After 20 min, methyl iodide (2.33 mL, 37.32 mmol) was dropwise added to the solution and it slowly warmed to rt. The product was extracted into n-Hexane. Solvent was removed under reduced pressure. SiO$_2$ column chromatography (0–20% EtOAc/n-hexane) gave the title compound as an oil. The $^1$H NMR (400 MHz, CDCl$_3$): δ 4.01–3.91 (m, 4 H), 2.20–2.07 (m, 2H), 1.96–1.82 (m, 2H), 1.63 (dd, 1H, J$_1$=6.8 Hz, J$_2$=5.3 Hz), 1.61 (s, 3 H), 1.54 (dd, 1H, J$_1$=7.6 Hz, J$_2$=1.0 Hz).

Example 9.12

Preparation of Intermediate (±)-6-methylene-spiro[bicyclo[3.1.0]hexane-2,2'-[1,3]dioxolane]

To a solution of (±)-6-chloro-6-methyl-spiro[bicyclo[3.1.0]hexane-2,2'-[1,3]dioxolane] (2.50 g, 13.25 mmol) in DMSO (40 mL) was added a solution of KO$^t$Bu (15.9 mL of 1.0M in THF). The solution heated at 60° C. overnight. After cooling down the reaction mixture to rt, the product was extracted into n-Hexane. Solvent was removed under reduced pressure. SiO$_2$ column chromatography (14–25% EtOAc/n-hexane) gave the title compound. $^1$H NMR (400 MHz, CDCl$_3$): δ 5.55 (s, 1H), 5.42 (t, 1H, J=1.0 Hz), 4.08–3.91 (m, 4H), 2.07–1.97 (m, 2H), 1.90–1.84 (m, 2H), 1.65–1.54 (m, 2H).

Example 9.12a

Preparation of Intermediate (±)-6-spirocyclopropyl-spiro[bicyclo[3.1.0]hexane-2,2'-[1,3]dioxolane]

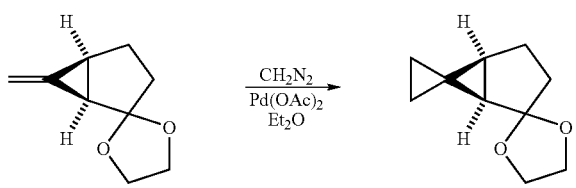

To a solution of (±)-6-methylene-spiro[bicyclo[3.1.0]hexane-2,2'-[1,3]dioxolane] (1.52 g, 10 mmol) in Et$_2$O (20 mL) and CH$_2$N$_2$ (~5 mmol) in Et2O was added Pd(OAc)$_2$ (~20 mg). An additional CH$_2$N$_2$ (~45 mmol) in Et2O was added dropwise to the solution over 1 h at rt. After concentration, SiO$_2$ column chromatography (50–90% CH$_2$Cl$_2$ in Hexanes) gave the product (±)-6-spirocyclopropyl-spiro[bicyclo[3.1.0]hexane-2,2'-[1,3]dioxolane]. $^1$H NMR (400 MHz, CDCl$_3$): δ4.02–3.94 (m, 1H), 3.92–3.86 (m, 3H), 1.96–1.89 (m, 1H), 1.75–1.62 (m, 5H), 0.82–0.86 (m, 2H), 0.79–0.76 (m, 1H), 0.73–0.70 (m, 1H).

Example 9.13

Preparation of endo-substituted Intermediates

General Reaction Scheme:

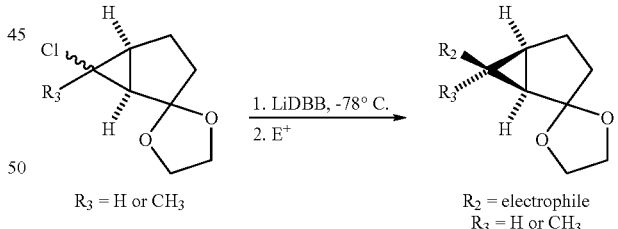

To a solution of 4,4'-di-tert-butyl-biphenyl (5 eq.) in THF was added lithium wire (5 eq.) cut into small pieces at rt. The solution was vigorously stirred at 0° C. for 6 h and cooled down to −78° C. (±)-Endo or exo mono-chloride (1 eq.) dissolved in THF was added to the dark green solution. After 10 min, electrophile (5 eq.) was dropwise added to the solution, it was slowly warmed to rt, and the resulting solution quickly poured into a vigorously stirred hexane/saturated NH$_4$Cl solution mixture under ice bath. The separated organic layer was concentrated and SiO$_2$ column chromatography gave the endo-substituted product.

Example 9.13a (±)-exo-4-Methyl-spiro[bicyclo[3.1.0]hexane-2,2'-[1,3]dioxolane]

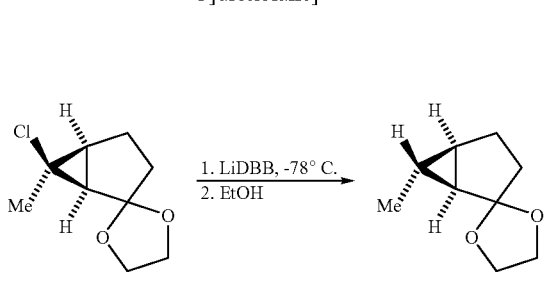

¹H NMR (400 MHz, CDCl₃): δ 4.05–3.87 (m, 4H), 1.90–1.80 (m, 1H), 1.76 (dd, 1H, J₁=12.3 Hz, J₂=8.0 Hz), 1.61 (dd, 1H, J₁=13.8 Hz, J₂=8.4 Hz), 1.45 (ddd, 1H, J₁=13.8 Hz, J₂=11.8 Hz, J₃=8.2 Hz), 1.18–1.14 (m, 1H), 1.10 (ddd, 1H, J₁=6.1 Hz, J₂=2.9 Hz, J₃=1.1 Hz), 1.00 (d, 3H, J=6.0 Hz), 0.88 (qdd, 1H, J₁=6.0 Hz, J₂=3.0 Hz, J₃=3.0 Hz).

Example 9.13b (±)-endo-6-Methyl-spiro[bicyclo[3.1.0]hexane-2,2'-[1,3]dioxolane]

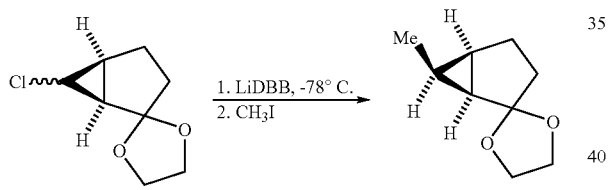

¹H NMR (400 MHz, CDCl₃): δ 3.98–3.88 (m, 4H), 2.10–2.00 (m, 1H), 1.91 (dd, 1H, J₁=14.3 Hz, J₂=10.7 Hz), 1.69 (ddd, 1H, J₁=13.2 Hz, J₂=9.3 Hz, J₃=1.4 Hz), 1.59–1.45 (m, 2H), 1.38 (ddd, 1H, J₁=8.6 Hz, J₂=6.5 Hz, J₃=1.3 Hz), 1.15 (d, 3H, J=6.6 Hz), 0.97 (qdd, 1H, J₁=6.6 Hz, J₂=7.5 Hz, J₃=7.5 Hz).

Example 9.13c (±)-endo-6-Ethyl-spiro[bicyclo[3.1.0]hexane-2,2'-[1,3]dioxolane]

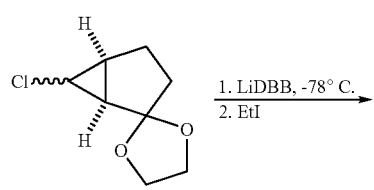

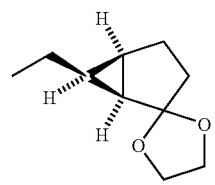

¹H NMR (400 MHz, CDCl₃): δ 3.99–3.88 (m, 4H), 2.09–1.91 (m, 2H), 1.73–1.50 (m, 4H), 1.45–1.35 (m, 2H), 1.15 (t, 3H, J=7.4 Hz), 0.78 (qdd, 1H, J₁=7.4 Hz, J₂=7.5 Hz).

Example 9.13d (±)-endo-6-Formyl-spiro[bicyclo[3.1.0]hexane-2,2'-[1,3]dioxolane]

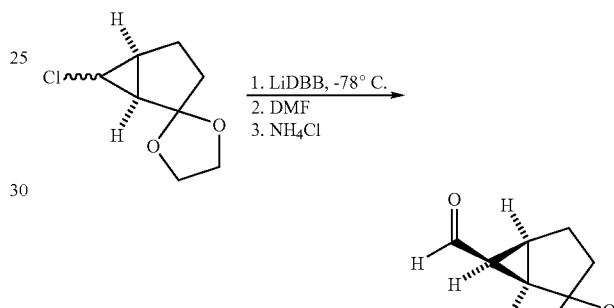

¹H NMR (400 MHz, CDCl₃): δ 9.60 (d, 1H, J=6.3 Hz), 4.05–3.93 (m, 4H), 2.34–2.19 (m, 2H), 2.15–2.06 (m, 3H), 1.91–1.76 (m, 2H).

Example 9.13e (±)-exo-6-Formyl-spiro[bicyclo[3.1.0]hexane-2,2'-[1,3]dioxolane]

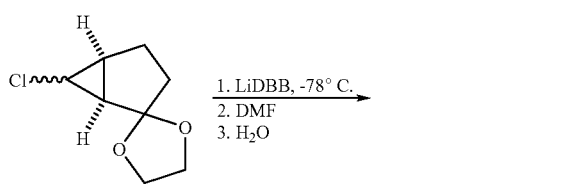

¹H NMR (400 MHz, CDCl₃): δ 9.27 (d, 1H, J=4.0 Hz), 4.08–4.02 (m, 1H), 3.99–3.91 (m, 3H), 2.13–1.99 (m, 4H), 1.90 (dd, 1H, $J_1$=12.7 Hz, $J_2$=8.0 Hz), 1.72 (dd, 1H, $J_1$=14.0 Hz, $J_2$=8.7 Hz), 1.59–1.50 (m, 1H).

Example 9.14

Preparation of Intermediate (±)-endo-6-vinyl-spiro[bicyclo[3.1.0]hexane-2,2'-[1,3]dioxolane]

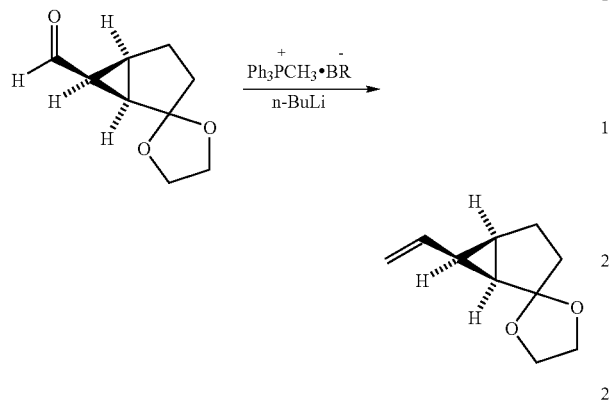

To a solution of methyltriphenylphosphonium bromide (2.55 g, 7.14 mmol) in 40 mL of THF was added n-butyl lithium (7.14 mmol, 4.46 mL of 1.6 M solution in hexane) at rt. After 2 h, a solution of endo-6-formyl-spiro[bicyclo[3.1.0]hexane-2,2'-[1,3]dioxolane] (1.0 g, 5.95 mmol) in 8 mL of THF was added to the reaction mixture at rt and it was stirred overnight. The product was extracted into n-Hexane. Solvent was removed under reduced pressure. $SiO_2$ column chromatography (0–20% EtOAc/n-hexane) gave the title compound as an oil. $^1$H NMR (400 MHz, $CDCl_3$): δ 5.87 (ddd, 1H, $J_1$=17.0 Hz, $J_2$=10.2 Hz, $J_3$=8.6 Hz), 5.30 (ddd, 1H, $J_1$=17.0 Hz, $J_2$=2.0 Hz, $J_3$=1.0 Hz), 5.18 (ddd, 1H, $J_1$=10.2 Hz, $J_2$=2.0 Hz, $J_3$=1.0 Hz), 4.00–3.88 (m, 4H), 2.12–2.02 (m, 1H), 1.90 (dd, 1H, $J_1$=14.5 Hz, $J_2$=10.3 Hz), 1.80–1.56 (m, 5H).

Example 9.14a

Preparation of Intermediate (±)-exo-6-vinyl-spiro[bicyclo[3.1.0]hexane-2,2'-[1,3]dioxolane]

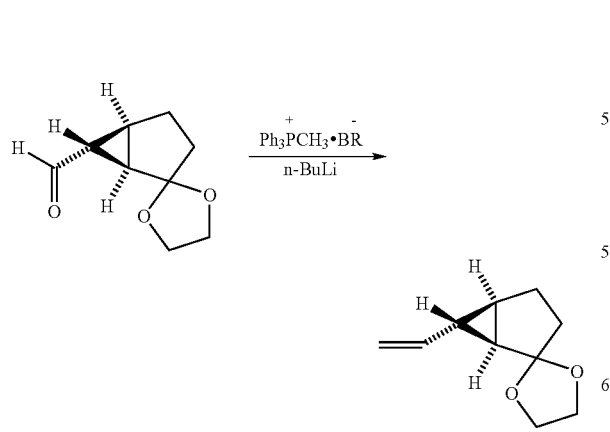

The title compound was prepared in a similar manner as described in Example 9.14.

$^1$H NMR (400 MHz, $CDCl_3$): δ 5.35 (ddd, 1H, $J_1$=17.0 Hz, $J_2$=10.2 Hz, $J_3$=8.6 Hz), 5.05 (ddd, 1H, $J_1$=17.0 Hz, $J_2$=1.5 Hz, $J_3$=0.4 Hz), 4.96 (dd, 1H, $J_1$=10.3 Hz, $J_2$=1.6 Hz), 4.06–4.00 (m, 1H), 3.99–3.88 (m, 3H), 1.98–1.88 (m, 1H), 1.84 (dd, 1H, $J_1$=12.1 Hz, $J_2$=8.1 Hz), 1.66 (dd, 1H, $J_1$=14.2 Hz, $J_2$=8.8 Hz), 1.56–1.43 (m, 4H).

Example 9.14b

Preparation of Intermediate (±)-endo-6-(1-propenyl)-spiro[bicyclo[3.1.0]hexane-2,2'-[1,3]dioxolane]

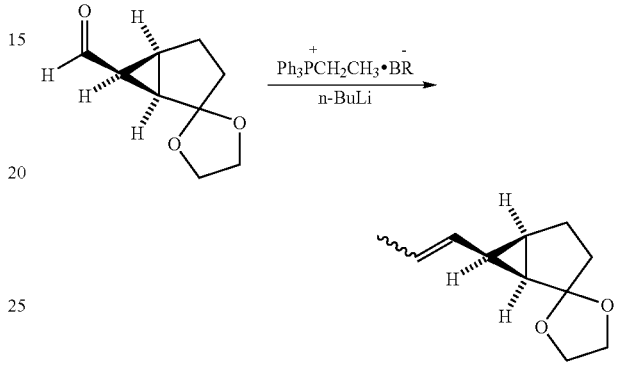

The title compound was prepared in a similar manner as described in Example 9.14.

$^1$H NMR (400 MHz, $CDCl_3$): δ 5.75–5.68 (m, 1H), 5.52–5.47 (m, 1H), 3.99–3.88 (m, 4H), 2.06–1.96 (m, 1H), 1.89–1.70 (m, 5H), 1.68–1.52 (m, 4H).

Example 9.14c

Preparation of Intermediate (±)-endo-6-cyclopropyl-spiro[bicyclo[3.1.0]hexane-2,2'-[1,3]dioxolane]

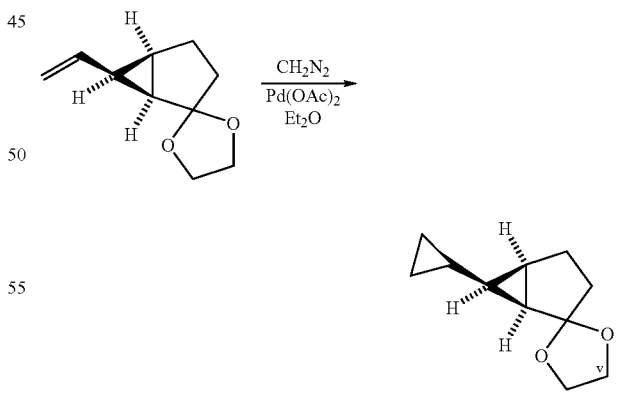

The title compound was prepared in a similar manner as described in Example 9.12a.

$^1$H NMR (400 MHz, $CDCl_3$): δ 4.02–3.88 (m, 4H), 2.09–1.99 (m, 1H), 1.91–1.50 (m, 3H), 1.48–1.39 (m, 2H), 1.22–1.17 (m, 1H), 0.78–0.71 (m, 1H), 0.65–0.52 (m, 2H), 0.33–0.26 (m, 2H).

Example 9.15

Preparation of Ketone Intermediates

General Reaction Scheme:

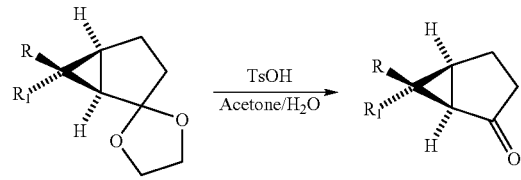

A solution of the protected ketone in acetone/H₂O (4/1) was treated with catalytic amount of TsOH at rt. The solution was stirred overnight. Acetone was removed in vacuo and the product was extracted with hexanes (3×). The combined organic layer was washed with 5% NaHCO₃ solution and brine, dried (MgSO₄), and concentrated in vacuo to afford the product ketone.

Example 9.15a (±)-exo-6-Methyl-bicyclo[3.1.0]hexane-2-one

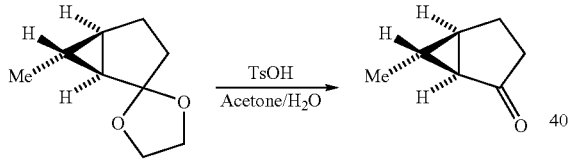

$^1$H NMR (400 MHz, CDCl$_3$): δ 2.14–1.98 (m, 4H), 1.85 (q, 1H, J=4.8 Hz), 1.52 (dd, 1H, J$_1$=5.0 Hz, J$_2$=2.5 Hz), 1.36–1.30 (m, 1H), 1.12 (d, 3H, J=6.0 Hz).

Example 9.15b (±)-endo-6-Methyl-bicyclo[3.1.0]hexane-2-one

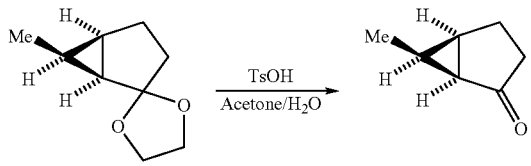

$^1$H NMR (400 MHz, CDCl$_3$): δ 2.32–2.21 (m, 2), 2.13–2.08 (m, 1H), 1.97–1.84 (m, 3H), 1.55–1.48 (m, 1H), 1.15 (d, 3H, J=6.6 Hz).

Example 9.15c (±)-endo-6-Ethyl-bicyclo[3.1.0]hexane-2-one

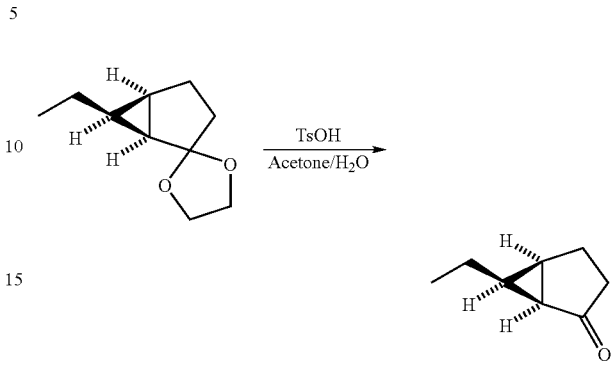

$^1$H NMR (400 MHz, CDCl$_3$): δ 2.34–2.20 (m, 2H), 2.15 (q, 1H, J=6.0 Hz), 2.00–1.87 (m, 3H), 1.48–1.36 (m, 3H), 1.04 (t, 3H, J=6.5 Hz).

Example 9.15d (±)-endo-6-Vinyl-bicyclo[3.1.0]hexane-2-one

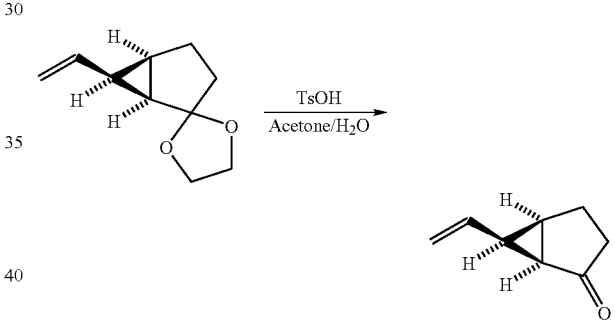

$^1$H NMR (400 MHz, CDCl$_3$): δ 5.67 (ddd, 1H, J$_1$=17.0 Hz, J$_2$=10.3 Hz, J$_3$=8.5 Hz), 5.37 (dt, 1H, J$_1$=17.0 Hz, J$_2$=1.4 Hz), 5.27 (dt, 1H, J$_1$=10.3 Hz, J$_2$=1.5 Hz), 2.32–2.21 (m, 3H), 2.20–2.14 (m, 1H), 2.10–2.07 (m, 1H), 2.03–1.93 (m, 2H).

Example 9.15e (±)-6-Spirocyclopropyl-bicyclo[3.1.0]hexane-2-one

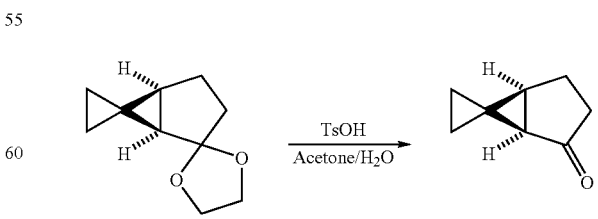

$^1$H NMR (400 MHz, CDCl$_3$): δ2.33 (t, 1H, J=5.0 Hz), 2.26–2.04 (m, 4H), 1.99–1.91 (m, 1H), 1.03 (t, 2H, J=7.2 Hz), 0.88–0.78 (m, 2H).

Example 9.15f (±)-exo-6-Vinyl-bicyclo[3.1.0]hexane-2-one

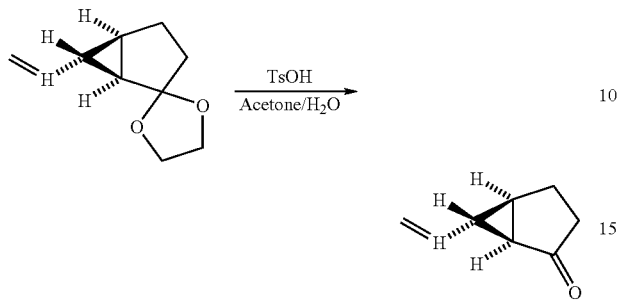

¹H NMR (400 MHz, CDCl₃): δ 5.35 (ddd, 1H, J₁=17.0 Hz, J₂=10.2 Hz, J₃=8.5 Hz), 5.15 (ddd, 1H, J₁=17.0 Hz, J₂=1.2 Hz, J₃=0.4 Hz), 4.99 (dd, 1H, J₁=10.2 Hz, J₂=1.1 Hz), 2.20–2.05 (m, 5H), 1.95–1.91 (m, 1H), 1.83 (q, 1H, J₁=2.5 Hz).

Example 9.15g (±)-endo-6-(1-propenyl)-bicyclo[3.1.0]hexane-2-one

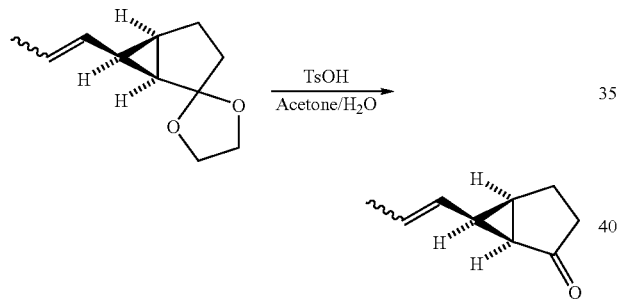

¹H NMR (400 MHz, CDCl₃): δ 5.82–5.75 (m, 1H), 5.33–5.26 (m, 1H), 2.30–1.89 (m, 7H), 1.76–1.70 (m, 3H).

Example 9.15h (±)-endo-6-cyclopropyl-bicyclo[3.1.0]hexane-2-one

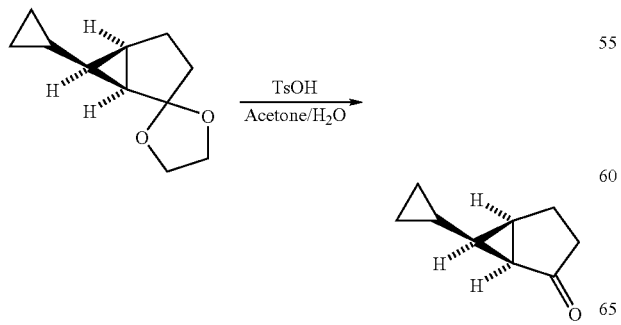

¹H NMR (400 MHz, CDCl₃): δ 2.32–2.09 (m, 5H), 1.86–1.82 (m, 1H), 1.16–1.09 (m, 1H), 0.71–0.65 (m, 1H), 0.61–0.56 (m, 2H), 0.39–0.29 (m, 2H).

Example 9.16

Preparation of (±)-exo-1-methyl-1a,3,5,5a-tetrahydro-1H-2,3-diaza-cyclopropa[a]pentalene-4-carboxylic acid ethyl ester

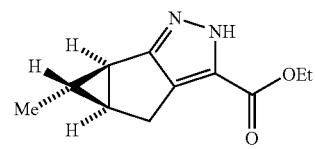

The title compound was prepared in a similar manner as described in Example 9.2, Step D. MS m/z (ES⁺): 207.2 [M+H]⁺, 229.4 [M+Na]⁺; ¹H NMR (400 MHz, CDCl₃): δ 4.37–4.31 (m, 2H), 2.97 (dd, 1H, J₁=17.1 Hz, J₂=5.7 Hz), 2.86 (d, 1H, J=17.1 Hz), 2.01–1.97 (m, 2H), 1.36 (t, 3H, J=7.1 Hz), 1.13 (d, 3H, J=6.1 Hz), 0.78–0.72 (m, 1H).

Example 9.17

Preparation of (±)-exo-1-methyl-1a,3,5,5a-tetrahydro-1H-2,3-diaza-cyclopropa[a]pentalene-4-carboxylic acid

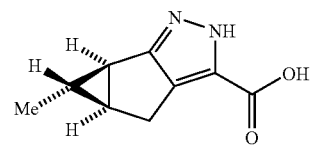

The title compound was prepared in a similar manner as described in Example 9.3. MS m/z (ES⁺): 179.1 [M+H]⁺, 201.5 [M+Na]⁺; ¹H NMR (400 MHz, CDCl₃): δ 3.02 (dd, 1H, J₁=18.5 Hz, J₂=6.3 Hz), 2.91 (d, 1H, J=18.5 Hz), 2.09 (dd, 1H, J₁=5.6 Hz, J₂=2.2 Hz), 1.78 (dd, 1H, J₁=9.7 Hz, J₂=5.9 Hz), 1.17 (d, 3H, J=6.0 Hz), 0.74 (qdd, 1H, J₁=6.0 Hz, J₂=3.0 Hz, J₃=3.0 Hz).

Example 9.18

Preparation of (±)-exo-1-methyl-4-(2H-tetrazol-5-yl)1a,3,5,5a-tetrahydro-1H-2,3-diaza-cyclopropa[a]pentalene Step A: Preparation of (±)-exo-1-methyl-1a,3,5,5a-tetrahydro-1H-2,3-diaza-cyclopropa[a]pentalene-4-carboxylic acid amide

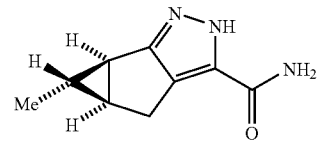

The title compound was prepared in a similar manner as described in Example 9.1, Step D. MS m/z (ES⁺): 178.1 [M+H]⁺, 200.1 [M+Na]⁺; ¹H NMR (400 MHz, DMSO-d₆):

δ 2.84 (dd, 1H, $J_1$=18.0 Hz, $J_2$=6.4 Hz), 2.69 (d, 1H, J=18.0 Hz), 1.97 (dd, 1H, $J_1$=5.8 Hz, $J_2$=2.3 Hz), 1.68 (dd, 1H, $J_1$=9.5 Hz, $J_2$=6.0 Hz), 1.08 (d, 3H, J=6.0 Hz), 0.63 (qdd, 1H, $J_1$=6.0 Hz, $J_2$=3.0 Hz, $J_3$=3.0 Hz).

Step B: Preparation of (±)-exo-1-methyl-1a,3,5,5a-tetrahydro-1H-2,3-diaza-cyclopropa[a]pentalene-4-carbonitrile

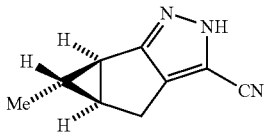

The title compound was prepared in a similar manner as described in Example 9.2, Step F. MS m/z (ES$^+$): 160.2 [M+H]$^+$, 319.1 [2M+H]$^+$; $^1$H NMR (400 MHz, DMSO-$d_6$): δ 2.80 (dd, 1H, $J_1$=15.9 Hz, $J_2$=4.4 Hz), 2.71 (d, 1H, J=15.9 Hz), 2.04–1.97 (m, 2H), 1.05 (d, 3H, J=6.1 Hz), 0.72–0.65 (m, 1H).

Step C: Preparation of (±)-exo-1-methyl-4-(2H-tetrazol-5-yl)-1a,3,5,5a-tetrahydro-1H-2,3-diaza-cyclopropa[a]pentalene

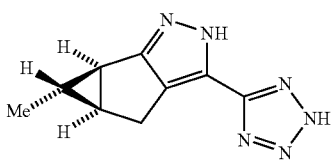

The title compound was prepared in a similar manner as described in Example 9.2, Step G. MS m/z (ES$^+$): 203.5 [M+H]$^+$, 225.4 [M+Na]$^+$; $^1$H NMR (400 MHz, DMSO-$d_6$): δ 2.89 (ddd, 1H, $J_1$=16.2 Hz, $J_2$=4.7 Hz, $J_3$=1.6 Hz), 2.81 (d, 1H, J=16.2 Hz), 2.02–1.98 (m, 2H), 1.08 (d, 3H, J=6.1 Hz), 0.70 (qdd, 1H, $J_1$=6.1 Hz, $J_2$=3.0 Hz, $J_3$=3.0 Hz).

Example 9.19

Preparation of (±)-endo-1-methyl-1a,3,5,5a-tetrahydro-1H-2,3-diaza-cyclopropa[a]pentalene-carboxylic acid ethyl ester

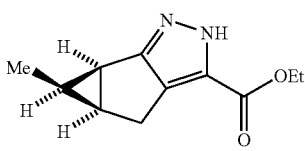

The title compound was prepared in a similar manner as described in Example 9.2, Step D. MS m/z (ES$^+$): 207.1 [M+H]$^+$, 229.2 [M+Na]$^+$; $^1$H NMR (400 MHz, CDCl$_3$): δ 4.37–4.30 (m, 2H), 2.92 (dd, 1H, $J_1$=17.5 Hz, $J_2$=6.8 Hz), 2.65 (d, 1H, J=17.5 Hz), 2.33 (t, 1H, J=6.8 Hz), 2.33 (dd, 1H, $J_1$=15.0 Hz, $J_2$=6.8 Hz), 1.38 (t, 3H, J=7.1 Hz), 1.39–1.30 (m, 1H), 0.71 (d, 3H, J=6.5 Hz).

Example 9.20

Preparation of (±)-endo-1-methyl-1a-3,5,5a-tetrahydro-1H-2,3-diaza-cyclopropa[a]pentalene-4-carboxylic acid

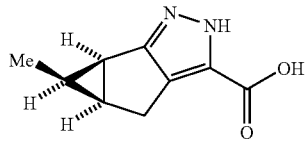

The title compound was prepared in a similar manner as described in Example 9.3. MS m/z (ES$^+$): 179.1 [M+H]$^+$, 357.1 [2M+H]$^+$; $^1$H NMR (400 MHz, CD$_3$OD): δ 2.89 (dd, 1H, $J_1$=17.3 Hz, $J_2$=6.7 Hz), 2.64 (d, 1H, J=17.2 Hz), 2.30–2.18 (m, 2H)), 1.34 (qdd, 1H, $J_1$=6.4 Hz, $J_2$=7.0 Hz, $J_3$=7.0 Hz), 0.69 (d, 3H, J=6.4 Hz).

Example 9.21

Preparation of (±)-endo-1-methyl-(2H-tetrazol-5-yl)-1a,3,5,5a-tetrahydro-1H-2,3-diaza-cyclopropa[a]pentalene Step A: Preparation of (±)-endo-1-methyl-1a-3,5,5a-tetrahydro-1H-2,3-diaza-cyclopropa[a]pentalene-4-carboxylic acid amide

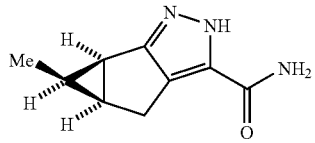

The title compound was prepared in a similar manner as described in Example 9.2, Step E. MS m/z (ES$^+$): 178.1 [M+H]$^+$, 355.2 [2M+H]$^+$; $^1$H NMR (400 MHz, CD$_3$OD): δ 2.88 (dd, 1H, $J_1$=16.5 Hz, $J_2$=4.8 Hz), 2.66 (d, 1H, J=16.8 Hz), 2.30–2.22 (m, 2H)), 1.32 (qdd, 1H, $J_1$=6.4 Hz, $J_2$=7.0 Hz, $J_3$=7.0 Hz), 0.69 (d, 3H, J=6.4 Hz).

Step B: Preparation of (±)-endo-1-methyl-1a-3,5,5a-tetrahydro-1H-2,3-diaza-cyclopropa[a]pentalene-4-carbonitrile

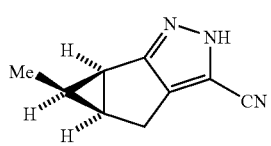

The title compound was prepared in a similar manner as described in Example 9.2, Step F. MS m/z (ES$^+$): 160.1 [M+H]$^+$, 319.4 [2M+H]$^+$; $^1$H NMR (400 MHz, CD$_3$OD): δ 2.84 (dd, 1H, $J_1$=16.6 Hz, $J_2$=6.7 Hz), 2.59 (d, 1H, J=16.6 Hz), 2.36–2.27 (m, 2H)), 1.39 (qdd, 1H, $J_1$=6.4 Hz, $J_2$=7.0 Hz, $J_3$=7.0 Hz), 0.69 (d, 3H, J=6.4 Hz).

Step C: Preparation of (±)-endo-1-methyl-4-(2H-tetrazol-5-yl)-1a,3,5,5a-tetrahydro-1H-2,3-diaza-cyclopropa[a]pentalene

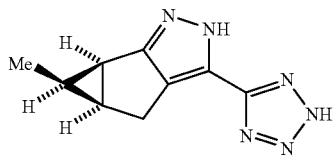

The title compound was prepared in a similar manner as described in Example 9.2, Step G. MS m/z (ES⁺): 203.4 [M+H]⁺, 405.4 [2M+H]⁺; ¹H NMR (400 MHz, CDCl₃): δ 3.18 (dd, 1H, $J_1$=17.3 Hz, $J_2$=6.5 Hz), 2.95 (d, 1H, J=17.4 Hz), 2.60–2.53 (m, 2H)), 1.67 (qdd, 1H, $J_1$=6.5 Hz, $J_2$=7.0 Hz, $J_3$=7.0 Hz), 0.82 (d, 3H, J=6.5 Hz).

Example 9.22

Preparation of (±)-endo-1-ethyl-1a-3,5,5a-tetrahydro-1H-2,3-diaza-cyclopropa[a]pentalene-1-carboxylic acid ethyl ester

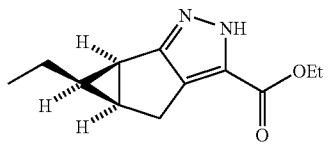

The title compound was prepared in a similar manner as described in Example 9.2, Step D. MS m/z (ES⁺): 221.3 [M+H]⁺, 243.3 [M+Na]⁺; ¹H NMR (400 MHz, CDCl₃): δ 4.38–4.30 (m, 2H), 2.92 (dd, 1H, $J_1$=17.5 Hz, $J_2$=6.9 Hz), 2.65 (d, 1H, J=17.5 Hz), 2.35 (ddd, 1H, $J_1$=7.6 Hz, $J_2$=6.2 Hz, $J_3$=1.3 Hz), 2.21 (dd, 1H, $J_1$=14.4 Hz, $J_2$=6.7 Hz), 1.37 (t, 3H, J=7.1 Hz), 1.23–1.17 (m, 1H), 1.11–1.01 (m, 1H), 0.91–0.83 (m, 4H).

Example 9.23

Preparation of (±)-endo-1-ethyl-1a-3,5,5a-tetrahydro-1H-2,3-diaza-cyclopropa[a]pentalene-4-carboxylic acid

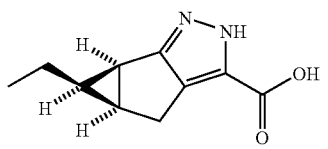

The title compound was prepared in a similar manner as described in Example 9.3. MS m/z (ES⁺): 193.0 [M+H]⁺, 215.0 [M+Na]⁺; ¹H NMR (400 MHz, DMSO-d₆): δ 2.80 (dd, 1H, $J_1$=17.2 Hz, $J_2$=6.8 Hz), 2.49 (d, 1H, J=17.2 Hz), 2.24 (ddd, 1H, $J_1$=7.6 Hz, $J_2$=6.2 Hz, $J_3$=1.0 Hz), 2.15 (dd, 1H, $J_1$=14.4 Hz, $J_2$=6.4 Hz), 1.18–1.11 (m, 1H), 1.03–0.93 (m, 1H), 0.81 (t, 3H, J=6.9 Hz), 0.77–0.68 (m, 1H).

Example 9.24

Preparation of (±)-endo-1-ethyl-4-(2H-tetrazol-5-yl)-1a,3,5,5a-tetrahydro-1H-2,3-diaza-cyclopropa[a]pentalene Step A: Preparation of (±)-endo-1-ethyl-1a-3,5,5a-tetrahydro-1H-2,3-diaza-cyclopropa[a]pentalene-1-carboxylic acid amide

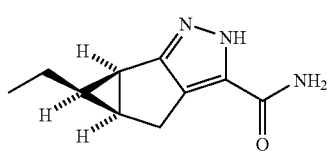

The title compound was prepared in a similar manner as described in Example 9.1, Step D. MS m/z (ES⁺): 192.0 [M+H]⁺, 383.2 [2M+H]⁺.

Step B: Preparation of (±)-endo-1-ethyl-1a-3,5,5a-tetrahydro-1H-2,3-diaza-cyclopropa[a]pentalene-1-carbonitrile

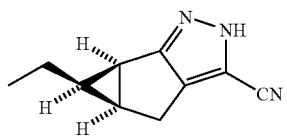

The title compound was prepared in a similar manner as described in Example 9.2, Step F. MS m/z (ES⁺): 174.1 [M+H]⁺, 347.4 [2M+H]⁺.

Step C: Preparation of (±)-endo-1-ethyl-4-(2H-tetrazol-5-yl)-1a,3,5,5a-tetrahydro-1H-2,3-diaza-cyclopropa[a]pentalene

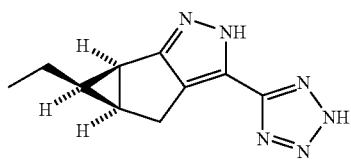

The title compound was prepared in a similar manner as described in Example 9.2, Step G. MS m/z (ES⁺): 217.1 [M+H]⁺, 433.1 [2M+H]⁺; ¹H NMR (400 MHz, CD₃OD): δ 2.91 (dd, 2H, $J_1$=14.6 Hz, $J_2$=6.1 Hz), 2.07–2.03 (m, 1H), 1.88–1.79 (m, 1H), 1.66–1.57 (m, 1H), 1.17 (dd, 1H, $J_1$=7.7 Hz, $J_2$=4.7 Hz), 1.09 (t, 3H, J=7.4 Hz), 0.56 (dd, 1H, $J_1$=3.2 Hz).

Example 9.25

Preparation of (±)-endo-1-vinyl-1a,3,5,5a-tetrahydro-1H-2,3-diaza-cyclopropa[a]pentalene-4-carboxylic acid ethyl ester

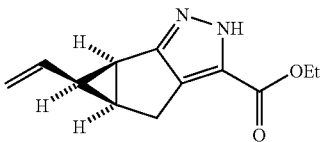

The title compound was prepared in a similar manner as described in Example 9.2, Step D. MS m/z (ES$^+$): 219.2 [M+H]$^+$, 241.1 [M+Na]$^+$; $^1$H NMR (400 MHz, CDCl$_3$): δ 5.31–5.23 (m, 1H), 5.05–4.95 (m, 1H), 4.39–4.31 (m, 2H), 2.99 (dd, 1H, J$_1$=17.5 Hz, J$_2$=6.7 Hz), 2.76 (d, 1H, J=17.5 Hz), 2.60 (ddd, 1H, J$_1$=7.6 Hz, J$_2$=6.0 Hz, J$_3$=1.2 Hz), 2.42 (dd, 1H, J$_1$=15.0 Hz, J$_2$=6.0 Hz), 1.99 (ddd, 1H, J$_1$=8.0 Hz, J$_2$=8.0 Hz, J$_3$=8.0 Hz), 1.37 (t, 3H, J=7.1 Hz).

Example 9.26

Preparation of (±)-endo-1-vinyl-1a,3,5,5a-tetrahydro-1H-2,3-diaza-cyclopropa[a]pentalene-carboxylic acid

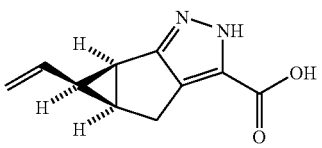

The title compound was prepared in a similar manner as described in Example 9.3. MS m/z (ES$^+$): 191.2 [M+H]$^+$, 381.3 [2M+H]$^+$; $^1$H NMR (400 MHz, DMSO-d$_6$): δ 5.25 (dd, 1H, J$_1$=16.9 Hz, J$_2$=2.3 Hz), 4.99 (dd, 1H, J$_1$=10.4 Hz, J$_2$=2.4 Hz), 4.85 (ddd, 1H, J$_1$=16.9 Hz, J$_2$=10.4 Hz, J$_3$=9.2 Hz), 2.88 (dd, 1H, J$_1$=17.3 Hz, J$_2$=6.6 Hz), 2.57–2.50 (m, 2H), 2.39 (dd, 1H, J$_1$=14.5 Hz, J$_2$=6.2 Hz), 1.94 (ddd, 1H, J$_1$=8.4 Hz, J$_2$=8.4 Hz, J$_3$=8.4 Hz).

Example 9.27

Preparation of

Step A: Preparation of (±)-endo-1-vinyl-1a,3,5,5a-tetrahydro-1H-2,3-diaza-cyclopropa[a]pentalene-4-carboxylic acid amide

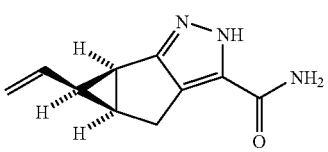

The title compound was prepared in a similar manner as described in Example 9.1, Step D. MS m/z (ES$^+$): 190.2 [M+H]$^+$, 379.2 [2M+H]$^+$; $^1$H NMR (400 MHz, DMSO-d$_6$): δ 5.25 (dd, 1H, J$_1$=16.9 Hz, J$_2$=2.3 Hz), 4.98 (dd, 1H, J$_3$=10.4 Hz, J$_2$=2.4 Hz), 4.90–4.81 (m, 1H), 2.88 (bd, 1H, J=13.6 Hz), 2.64–2.49 (m, 2H), 2.40 (dd, 1H, J$_1$=13.7 Hz, J$_2$=6.9 Hz), 1.92 (ddd, 1H, J$_1$=8.4 Hz, J$_2$=8.4 Hz, J$_3$=8.4 Hz).

Step B: Preparation of (±)-endo-1-vinyl-1a,3,5,5a-tetrahydro-1H-2,3-diaza-cyclopropa[a]pentalene-4-carbonitrile

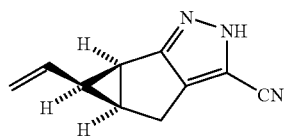

The title compound was prepared in a similar manner as described in Example 9.2, Step F. MS m/z (ES$^+$): 172.3 [M+H]$^+$, 343.3 [2M+H]$^+$; $^1$H NMR (400 MHz, CDCl$_3$): δ 5.30 (dd, 1H, J$_1$=16.9 Hz, J$_2$=2.0 Hz), 5.08 (dd, 1H, J$_1$=10.4 Hz, J$_2$=2.0 Hz), 4.93 (ddd, 1H, J$_1$=16.9 Hz, J$_2$=10.4 Hz, J$_3$=8.5 Hz), 2.96 (dd, 1H, J$_1$=16.9 Hz, J$_2$=6.7 Hz), 2.73 (d, 1H, J=16.9 Hz), 2.60–2.49 (m, 2H), 2.03 (ddd, 1H, J$_1$=8.3 Hz, J$_2$=8.3 Hz, J$_3$=8.3 Hz).

Step C: Preparation of (±)-endo-4-(2H-tetrazol-5-yl)-1-vinyl-1a,3,5,5a-tetrahydro-1H-2,3-diaza-cyclopropa[a]pentalene

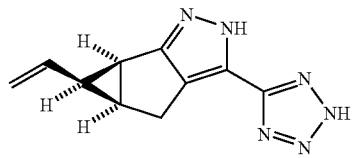

The title compound was prepared in a similar manner as described in Example 9.1, Step F. MS m/z (ES$^+$): 215.2 [M+H]$^+$, 429.3 [2M+H]$^+$; $^1$H NMR (400 MHz, CD$_3$OD): δ 5.30–5.25 (m, 1H), 5.07–4.99 (m, 2H), 3.05 (dd, 1H, J$_1$=16.6 Hz, J$_2$=6.6 Hz), 2.82 (d, 1H, J=16.6 Hz), 2.62 (dd, 1H, J$_1$=7.5 Hz, J$_2$=6.1 Hz), 2.55 (dd, 1H, J$_1$=13.5 Hz, J$_2$=7.0 Hz), 2.06–2.00 (m, 1H).

Example 9.28

Preparation of (±)-endo-1-Benzyl-4-(2H-tetrazol-5-yl)-1a,3,5,5a-tetrahydro-1H-2,3-diaza-cyclopropa[a]pentalene

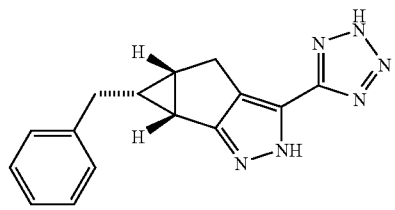

The title compound was obtained by HPLC purification from the mixture of diastereomers as described in Example 9.4, Step F. MS: m/z (ES+): 301 [M+Na]+, 279 [M+H]+, 251 [M−N2+H]+; ¹H NMR (CD₃OD): δ 7.2–7.05 (m, 2H), 7.03 (t, 1H, J=6.8), 6.97 (d, 2H, J=7.4), 3.0–2.8 (m, 1H), 2.77 (d, 1H, J=16.7), 2.5–2.3 (m, 3H), 2.02 (dd, 1H, J₁=14.5, J₂=8.9), 1.55–1.45 (m, 1H).

Example 9.29

Preparation of (±)-exo-1-Propyl-1a,3,5,5a-tetrahydro-1H-2,3-diaza-cyclopropa[a]pentalene-4-carboxylic acid ethyl ester Step A: Preparation of (±)-exo-6-Propyl-bicyclo[3.1.0]hexan-2-ol

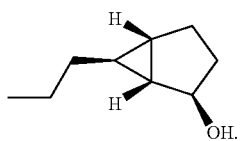

The title compound was prepared in a similar manner as described in Example 9.2, Step B. ¹H NMR (CDCl₃): δ 4.21 (d, 1H, J=4.8), 1.95–1.80 (m, 1H), 1.67 (dd, 1H, J₁=12.5, J₂=8.2), 1.53 (dd, 1H, J₁=14.2, J₂=8.3), 1.48–1.28 (m, 4H), 1.20–1.05 (m, 3H), 0.88 (t, 3H, j=7.3), 0.37 (septet, 1H, J=3.3). Contains ca 30% (±)endo-6-n-propyl-bicyclo[3.1.0]hexan-2-ol.

Step B: Preparation of (±)-exo-6-Propyl-bicyclo[3.1.0]hexan-2-one

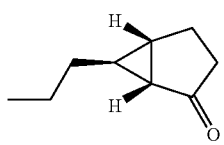

The title compound was prepared in a similar manner as described in Example 9.2, Step C. ¹H NMR (CDCl₃): δ 2.15–1.95 (m, 4H), 1.9–1.8 (m, 1H), 1.53 (d, 1H, J=5.0), 1.50–1.35 (m, 2H), 1.35–1.25 (m, 3H), 0.91 (t, 3H, J=7.3). Contains ca 30% (±)endo-6-n-propyl-bicyclo[3.1.0]hexan-2-one.

Step C: Preparation of (±)-exo-1-Propyl-1a,3,5,5a-tetrahydro-1H-2,3-diaza-cyclopropa[a]pentalene-4-carboxylic acid ethyl ester

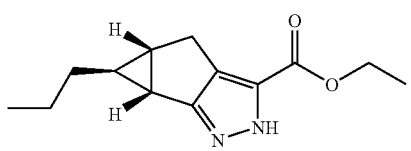

The title compound was prepared in a similar manner as described in Example 9.2, Step D. MS: m/z (ES+): 257 [M+Na]+, 235 [M+H]+, 189 [M−OEt]+; ¹H NMR (CDCl₃): δ 4.25 (q, 2H, J=7.1, OCH2), 2.86 (dd, 1H, J₁=17.1, J₂=6.2), 2.74 (d, 1H, J=17.1), 1.95–190 (m, 1H), 1.87–1.80 (m, 1H), 1.40–1.10 (m, 7H, including 1.27 (t, 3H, J=7.2)), 0.85 (t, 3H, J=7.2), 0.60 (septet, 1H, J=3.4). Contains ca 30% (±)-endo-1-n-propyl-1a,3,5,5a-tetrahydro-1H-2,3-diaza-cyclopropa[a]pentalene-4-carboxylic acid ethyl ester.

Example 9.30

Preparation of (±)-exo-1-Propyl-1a,3,5,5a-tetrahydro-1H-2,3-diaza-cyclopropa[a]pentalene-4-carboxylic acid

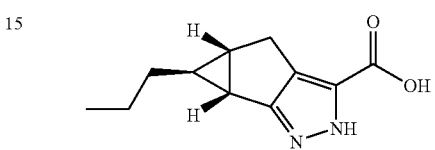

The title compound was prepared in a similar manner as described in Example 9.3. MS: m/z (ES+): 229 [M+Na]+, 207 [M+H]+, 189 [M−OH]+; ¹H NMR (CD₃OD): δ 2.95–2.85 (m, 1H), 2.79 (d, 1H, J=16.8), 2.00–1.90 (m, 2H), 1.47 (m, 2H, J=7.1), 1.40–1.25 (m, 2H), 0.96 (t, 3H, J=7.3), 0.63 (m, 1H, J=3.4).

Example 9.31

Preparation of (±)-exo-1-Propyl-4-(2H-tetrazol-5-yl)-1a,3,5,5a-tetrahydro-1H-2,3-diaza-cyclopropa[a]pentalene Step A: Preparation of (±)-exo-1-Propyl-1a,3,5,5a-tetrahydro-1H-2,3-diaza-cyclopropa[a]pentalene-4-carboxylic acid amide

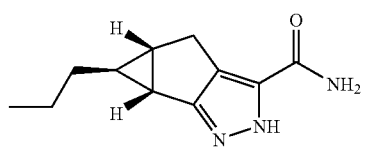

The title compound was prepared in a similar manner as described in Example 9.2, Step E. MS: m/z (ES+): 206 [M+H]hu +, 189 [M−NH2]+; ¹H NMR (CD₃OD): δ 2.92 (dd, 1H, J₁=16.4, J₂=5.8), 2.82 (d, 1H, J=16.5), 2.05–1.90 (m, 2H), 1.47 (pentet, 2H, J=7.1), 1.38–1.28 (m, 2H), 0.96 (t, 3H, J=7.3), 0.66 (septet, 1H, J=3.3).

Step B: Preparation of (±)-exo-1-Propyl-1a,3,5,5a-tetrahydro-1H-2,3-diaza-cyclopropa[a]pentalene-4-carbonitrile

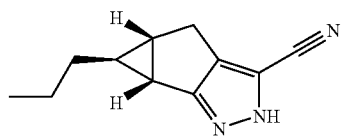

The title compound was prepared in a similar manner as described in Example 9.2, Step F. MS: m/z (ES+): 188 [M+H]$^+$; $^1$H NMR (CD$_3$OD): δ 2.88 (dd, 1H, J$_1$=16.3, J$_2$=6.0), 2.76 (d, 1H, J=16.2), 2.1–2.0 (m, 2H), 1.47 (pentet, 2H, J=7.3), 1.40–1.28 (m, 2H), 0.96 (t, 3H, J=7.3), 0.71 (septet, 1H, J=3.3).

Step C: Preparation of (±)-exo-1-Propyl-4-(2H-tetrazol-5-yl-1a,3,5,5a-tetrahydro-1H-2,3-diaza-cyclopropa[a]pentalene

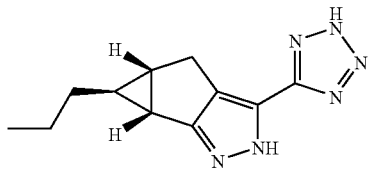

The title compound was prepared in a similar manner as described in Example 9.2, Step G. MS: m/z (ES+): 231 [M+H]$^+$, 203 [M−N2+H]$^+$; $^1$H NMR (CD$_3$OD): δ 3.00 (dd, 1H, J$_1$=10.1, J$_2$=6.1), 2.91(d, 1H, J=16.2), 2.07 (m, 2H), 1.50 (sextet, 2H, J=7.3), 1.35 (septet, 2H, J=7.0), 0.99 (t, 3H, J=6.1), 0.74 (septet, 1H, J=3.3).

Example 9.32

Preparation of (±)-endo-1-Propyl-1a,3,5,5a-tetrahydro-1H-2,3-diaza-cyclopropa[a]pentalene-4-carboxylic acid

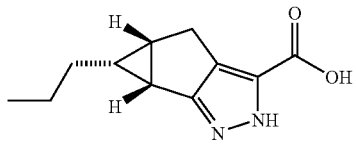

The title compound was prepared in a similar manner as described in Example 9.3 using the mixture of diastereomers described in Example 9.29, Step C. MS: m/z (ES+): 229 [M+Na]$^+$, 207 [M+H]$^+$, 189 [M−OH]$^+$.

Example 9.33

Preparation of (±)-endo-1-Propyl-4-(2H-tetrazol-5-yl)-1a,3,5,5a-tetrahydro-1H-2,3-diaza-cyclopropa[a]pentalene Step A: Preparation of (±)-endo-1-Propyl-1a,3,5,5a-tetrahydro-1H-2,3-diaza-cyclopropa[a]pentalene-4-carboxylic acid amide

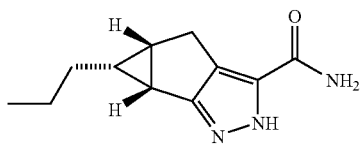

The title compound was prepared in a similar manner as described in Example 9.2, Step E. MS: m/z (ES+): 206 [M+H]$^+$, 189 [M−NH2]$^+$; $^1$H NMR (CDCl$_3$): δ 6.45 (br s, 1H), 5.95 (br s, 1H), 2.93 (dd, 1H, J$_1$=16.6, J$_2$=6.6), 2.68 (d, 1H, J=16.6), 2.4–2.3 (m, 2H), 1.4–1.2 (m, 3H), 1.15–1.00 (m, 1H), 0.88–0.78 (m, 4H).

Step B: Preparation of (±)-endo-1-Propyl-1a,3,5,5a-tetrahydro-1H-2,3-diaza-cyclopropa[a]pentalene-4-carbonitrile

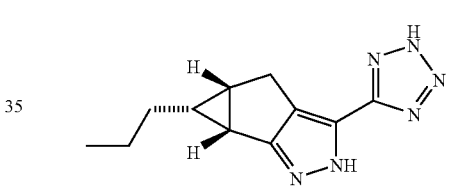

The title compound was prepared in a similar manner as described in Example 9.2, Step F. MS: m/z (ES+): 188 [M+H]$^+$; $^1$H NMR (CD$_3$OD): δ 2.85 (dd, 1H, J$_1$=16.6, J$_2$=6.6), 2.60 (d, 1H, J=16.6), 2.4–2.3 (m, 2H), 1.45–1.20 (m, 3H), 1.15–1.05 (m, 1H), 0.78–0.65 (m, 1H).

Step C: Preparation of (±)-endo-1-Propyl-4-(2H-tetrazol-5-yl)-1a,3,5,5a-tetrahydro-1H-2,3-diaza-cyclopropa[a]pentalene The title compound was prepared in a similar manner as described in Example 9.2, Step G. MS: m/z (ES+): 231 [M+H]$^+$, 203 [M−N2+H]$^+$; $^1$H NMR (CD$_3$OD): δ 2.97 (dd, 1H, J$_1$=10.2, J$_2$=6.4), 2.72 (d, 1H, J=18.3), 2.40–2.34 (m, 2H), 1.42–1.28 (m, 3H), 1.20–1.11 (m, 1H), 0.86–0.77 (m, 4H including 0.85 (t, 3H, J=7.4)).

Example 9.34

Preparation of (±)-exo-1-Butyl-1a,3,5,5a-tetrahydro-1H-2,3-diaza-cyclopropa[a]pentalene-4-carboxylic acid ethyl ester Step A: Preparation of (±)-(E)-2-(Oct-3-enyl)oxirane

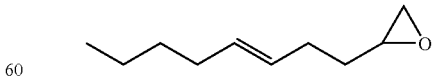

2-(But-3-enyl)oxirane (1.000 g, 10.2 mmol) and hex-1-ene (9.12 g, 102 mmol) were stirred at room temperature for 24 hr in a sealed scintillation vial with Zhan Catalyst-1 (0.057 g, 0.086 mmol). Solvent was removed under reduced pressure and the residue purified by column chromatography (0–10% EtOAc/n-hexane/silica) to give (±)-(E)-2-(oct-3- enyl)oxirane as a colorless oil. ¹H NMR (CDCl₃): δ 5.5–5.4 (m, 2H), 3.0–2.9 (m, 1H), 2.8–2.7 (m, 1H), 2.5–2.45 (m, 1H), 2.2–2.1 (m, 2H), 1.99 (q, 2H, J=5.7), 1.65–1.55 (m, 2H), 1.35–1.25 (m, 4H), 0.95–0.85 (m, 3H). Contains ca 20% (Z)-2-(oct-3-enyl)oxirane.

Step B: Preparation of (±)-exo-6-Butyl-bicyclo[3.1.0]hexan-2-ol

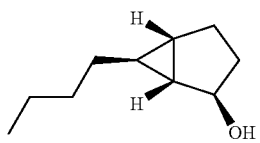

The title compound was prepared in a similar manner as described in Example 9.2, Step B. ¹H NMR (CDCl₃): δ 4.21 (d, 1H, J=4.8), 1.95–1.80 (m, 1H), 1.69 (dd, 1H, J₁=12.6, J₂=8.0), 1.54 (dd, 1H, J₁=11.6, J₂=5.7), 1.48–1.25 (m, 6H), 1.25–1.05 (m, 3H), 0.95–0.85 (m, 3H), 0.36 (septet, 1H, J=3.3). Contains ca 20% (±)-endo-6-n-butyl-bicyclo[3.1.0]hexan-2-ol.

Step C: Preparation of (±)-exo-6-Butyl-bicyclo[3.1.0]hexan-2-one

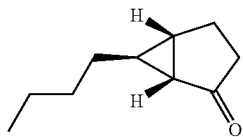

The title compound was prepared in a similar manner as described in Example 9.2, Step C. ¹H NMR (CDCl₃): δ 2.15–1.95 (m, 4H), 1.9–1.8 (m, 1H), 1.54 (t, 1H, J=2.4), 1.45–1.20 (m, 7H), 0.95–0.85 (m, 3H). Contains ca 20% (±)-endo-6-n-butyl-bicyclo[3.1.0]hexan-2-one.

Step D: Preparation of (±)-exo-1-Butyl-1a,3,5,5a-tetrahydro-1H-2,3-diaza-cyclopropa[a]pentalene-4-carboxylic acid ethyl ester

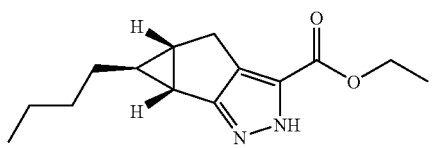

The title compound was prepared in a similar manner as described in Example 9.2; Step D. MS: m/z (ES+): 249 [M+H]⁺, 203 [M−OEt]⁺; ¹H NMR (CDCl₃): δ 4.30 (q, 2H, J=7.2, OCH2), 2.91 (dd, 1H, J₁=17.0, J₂=6.2), 2.79 (d, 1H, J=17.0), 1.98–1.93 (m, 1H), 1.89 (dd, 1H, J₁=9.8, J₂=6.0), 1.45–1.10 (m, 9H, including 1.32 (t, 3H, J=7.1)), 0.87 (t, 3H, J=6.8), 0.70–0.60 (m, 1H). Contains ca 30% (±)-endo-1-n-butyl-1a,3,5,5a-tetrahydro-1H-2,3-diaza-cyclopropa[a]pentalene-4-carboxylic acid ethyl ester.

Example 9.35

Preparation of (±)-exo-1-Butyl-1a,3,5,5a-tetrahydro-1H-2,3-diaza-cyclopropa[a]pentalene-4-carboxylic acid

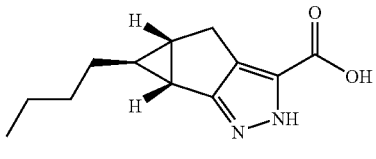

The title compound was prepared in a similar manner as described in Example 9.3. MS: m/z (ES+): 221 [M+H]⁺, 203 [M−OH]⁺; ¹H NMR (CD₃OD): δ 2.95–2.85 (m, 1H), 2.78 (d, 1H, J=16.9), 2.00–1.90 (m, 2H), 1.5–1.25 (m, 6H), 0.93 (t, 3H, J=7.0), 0.62 (septet, 1H, J=3.3).

Example 9.36

Preparation of (±)-exo-1-Butyl-4-(2H-tetrazol-5-yl)-1a,3,5,5a-tetrahydro-1H-2,3-diaza-cyclopropa[a]pentalene Step A: Preparation of (±)-exo-1-Butyl-1a,3,5,5a-tetrahydro-1H-2,3-diaza-cyclopropa[a]pentalene-4-carboxylic acid amide

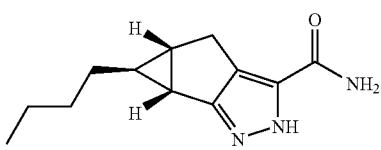

The title compound was prepared in a similar manner as described in Example 9.2, Step E. MS: m/z (ES+): 220 [M+H]⁺, 203 [M−NH2]⁺; ¹H NMR (CD₃OD): δ 2.92 (dd, 1H, J₁=16.4, J₂=5.9), 2.82 (d, 1H, J=16.0), 2.05–1.90 (m, 2H), 1.50–1.30 (m, 6H), 0.93 (t, 3H, J=7.0), 0.65 (septet, 1H, J=3.3).

Step B: Preparation of (±)-exo-1-Butyl-1a,3,5,5a-tetrahydro-1H-2,3-diaza-cyclopropa[a]pentalene-4-carbonitrile

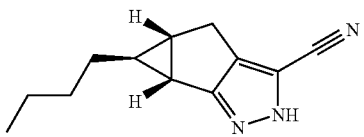

The title compound was prepared in a similar manner as described in Example 9.2, Step F. MS: m/z (ES+): 202 [M+H]⁺; ¹H NMR (CD₃OD): δ 2.89 (dd, 1H, J1=16.3, J₂=6.0), 2.76 (d, 1H, J=16.2), 2.1–2.0 (m, 2H), 1.50–1.30 (m, 6H), 0.93 (t, 3H, J=7.0), 0.70 (septet, 1H, J=3.3).

Step C: Preparation of (±)-exo-1-Butyl-4-(2H-tetrazol-5-yl)-1a,3,5,5a-tetrahydro-1H-2,3-diaza-cyclopropa[a]pentalene

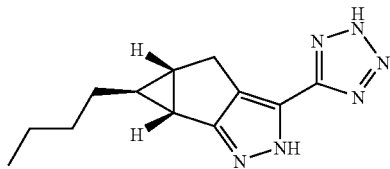

The title compound was prepared in a similar manner as described in Example 9.2, Step G. MS: m/z (ES+): 245 [M+H]+, 217 [M−N2+H]+; $^1$H NMR (CD$_3$OD): δ 2.99 (dd, 1H, J$_1$=10.2, J$_2$=6.0), 2.90 (d, 1H, J=16.2), 2.10–2.00 (m, 2H), 1.49–1.32 (m, 6H), 0.93 (t, 3H, J=7.0), 0.72 (septet, 1H, J=3.3).

Example 9.37

Preparation of (±)-endo-1-Butyl-1a,3,5,5a-tetrahydro-1H-2,3-diaza-cyclopropa[a]pentalene-4-carboxylic acid

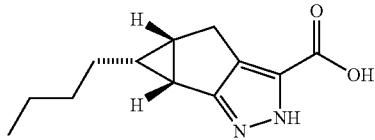

The title compound was prepared in a similar manner as described in Example 9.3 using the mixture of diastereomers described in Example 9.34, Step D. MS: m/z (ES+): 221 [M+H]+, 203 [M−OH]+.

Example 9.38

Preparation of (±)-endo-1-Butyl-4-(2H-tetrazol-5-yl)-1a,3,5,5a-tetrahydro-1H-2,3-diaza-cyclopropa[a]pentalene Step A: Preparation of (±)-endo-1-n-Butyl-1a,3,5,5a-tetrahydro-1H-2,3-diaza-cyclopropa[a]pentalene-4-carboxylic acid amide

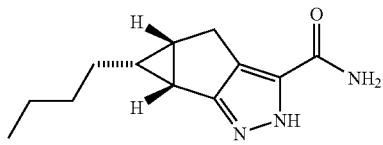

The title compound was prepared in a similar manner as described in Example 9.2, Step E using the mixture of diastereomers described in Example 9.36, Step D. MS: m/z (ES+): 220 [M+H]+, 203 [M−NH2]+; $^1$H NMR (CD$_3$OD): δ 2.87 (dd, 1H, J$_1$=16.7, J$_2$=6.3), 2.66 (d, 1H, J=16.7), 2.35–2.20 (m, 2H), 1.35–1.15 (m, 5H), 1.15–1.05 (m, 1H), 0.85–0.70 (m, 4H).

Step B: Preparation of (±)-endo-1-Butyl-1a,3,5,5a-tetrahydro-1H-2,3-diaza-cyclopropa[a]pentalene-4-carbonitrile

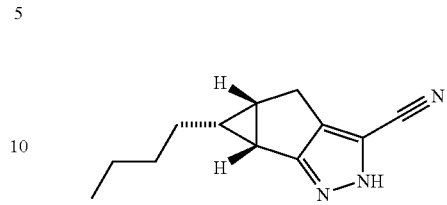

The title compound was prepared in a similar manner as described in Example 9.2, Step F. MS: m/z (ES+): 202 [M+H]+; $^1$H NMR (CD$_3$OD): δ 2.86 (dd, 1H, J$_1$=16.5, J$_2$=6.5), 2.60 (d, 1H, J=16.4), 2.4–2.3 (m, 2H), 1.4–1.1 (m, 6H), 0.85–0.79 (m, 3H), 0.78–0.68 (m, 1H).

Step C: Preparation of (±)-endo-1-Butyl-4-(2H-tetrazol-5-yl)-1a,3,5,5a-tetrahydro-1H-2,3-diaza-cyclopropa[a]pentalene

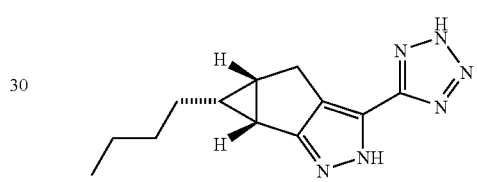

The title compound was prepared in a similar manner as described in Example 9.2, Step G. MS: m/z (ES+): 245 [M+H]+, 217 [M−N2+H]+; $^1$H NMR (CD$_3$OD): δ 2.97 (dd, 1H, J$_1$=10.0, J$_2$=6.4), 2.78 (d, 1H, J=16.6), 2.38 (pentet, 2H, J=5.4), 1.40–1.14 (m, 6H), 0.85–0.79 (m, 3H), 0.88–0.79 (m, 4H including 0.81 (t, 3H, J=7.2)).

Example 9.39

Preparation of (±)-endo-1-Pentyl-1a,3,5,5a-tetrahydro-1H-2,3-diaza-cyclopropa[a]pentalene-4-carboxylic acid ethyl ester Step A: Preparation of (±)-endo-6n-Pentyl-bicyclo[3.1.0]hexan-2-ol

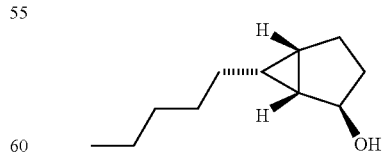

The title compound was prepared in a similar manner as described in Example 9.2, Step B. $^1$H NMR (CDCl$_3$): δ 4.17 (dd, 1H, J$_1$=5.0, J$_2$=1.0), 2.15–2.00 (m, 1H), 1.80–1.45 (m, 3H),1.40–1.25 (m, 8H), 1.22–1.15 (m, 3H), 0.95–0.85 (m, 3H), 0.75 (pentet, 1H, J=8.4).

Step B: Preparation of (±)-endo-6-Pentyl-bicyclo[3.1.0]hexan-2-one

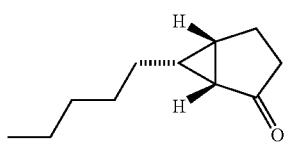

The title compound was prepared in a similar manner as described in Example 9.2, Step C. $^1$H NMR (CDCl$_3$): δ 2.35–2.20 (m, 2H), 2.14 (dd, 1H, J$_1$=11.8, J$_2$=5.9), 2.05–1.85 (m, 3H), 1.50–1.20 (m, 9H), 0.95–0.85 (m, 3H).

Step C: Preparation of (±)-endo-1-Pentyl-1a,3,5,5a-tetrahydro-1H-2,3-diaza-cyclopropa[a]pentalene-4-carboxylic acid ethyl ester

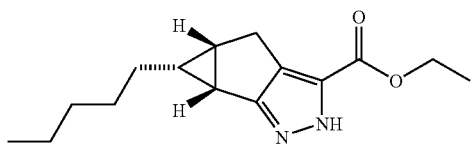

The title compound was prepared in a similar manner as described in Example 9.2, Step D. MS: m/z (ES+): 263 [M+H]$^+$, 217 [M−OEt]$^+$; $^1$H NMR (CDCl$_3$): δ 4.40–4.30 (m, 2H), 2.91 (dd, 1H, J$_1$=17.5, J$_2$=6.8), 2.66 (d, 1H, J=17.5), 2.33 (ddd, 1H, J$_1$=7.7, J$_2$=6.2, J$_3$=1.2), 2.20 (dd, 1H, J$_1$=14.6, J$_2$=6.5), 1.35–1.15 (m, 10H), 1.10–0.95 (m, 1H), 0.87 (t, 3H, J=6.9).

Example 9.40

Preparation of (±)-endo-1-Pentyl-1a,3,5,5a-tetrahydro-1H-2,3-diaza-cyclopropa[a]pentalene-4-carboxylic acid

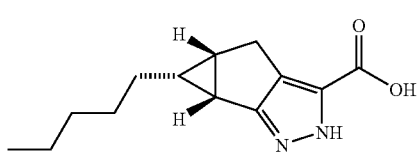

The title compound was prepared in a similar manner as described in Example 9.3. MS: m/z (ES+): 235 [M+H]$^+$, 217 [M−OH]$^+$; $^1$H NMR (CD$_3$OD): δ 2.86 (dd, 1H, J$_1$=17.2, J$_2$=6.7), 2.40 (d, 1H, J=17.2), 2.33–2.28 (m, 1H), 2.28–2.20 (m, 1H), 1.40–1.15 (m, 7H), 1.13–1.05(m, 1H), 0.88–0.82 (m, 3H), 0.82–0.73(m, 1H).

Example 9.41

Preparation of (±)-endo-1-Pentyl-4-(2H-tetrazol-5-yl)-1a,3,5,5a-tetrahydro-1H-2,3-diaza-cyclopropa[a]pentalene

Step A: Preparation of (±)-endo-1-Pentyl-1a,3,5,5a-tetrahydro-1H-2,3-diaza-cyclopropa[a]pentalene-4-carboxylic acid amide

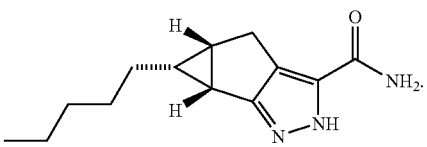

The title compound was prepared in a similar manner as described in Example 9.2, Step E. MS: m/z (ES+): 234 [M+H]$^+$, 217 [M−NH2]$^+$; $^1$H NMR (CD$_3$OD): δ 2.89 (dd, 1H, J$_1$=16.8, J$_2$=6.2), 2.67 (d, 1H, J=16.8), 2.35–2.25 (m, 2H), 1.40–1.15 (m, 7H), 1.15–1.05 (m, 1H), 0.90–0.70 (m, 4H).

Step B: Preparation of (±)-endo-1-Pentyl-1a,3,5,5a-tetrahydro-1H-2,3-diaza-cyclopropa[a]pentalene-4-carbonitrile

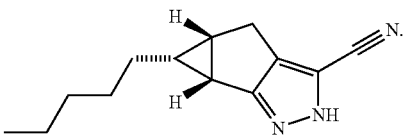

The title compound was prepared in a similar manner as described in Example 9.2, Step F. MS: m/z (ES+): 216 [M+H]$^+$.

Step C: Preparation of (±)-endo-1-Pentyl-4-(2H-tetrazol-5-yl)-1a,3,5,5a-tetrahydro-1H-2,3-diaza-cyclopropa[a]pentalene

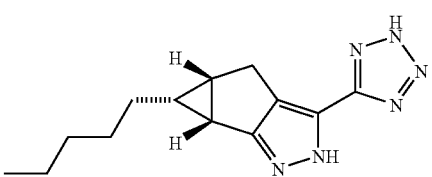

The title compound was prepared in a similar manner as described in Example 9.2, Step G. MS: m/z (ES+): 260 [M+H]$^+$, 232 [M−N2+H]$^+$; $^1$H NMR (CD$_3$OD): δ 2.96 (dd, 1H, J$_1$=16.5, J$_2$=6.4), 2.75 (d, 1H, J=16.5), 2.40–2.33 (m, 2H), 1.40–1.12 (m, 8H), 0.86–0.78 (m, 4H).

Example 9.42

Preparation of (±)-exo-1-Isopropyl-1a,3,5,5a-tetrahydro-1H-2,3-diaza-cyclopropa[a]pentalene-4-carboxylic acid ethyl ester Step A: Preparation of (±)-exo-6-Isopropyl-bicyclo[3.1.0]hexan-2-ol

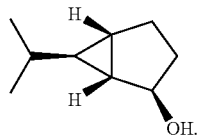

The title compound was prepared in a similar manner as described in Example 9.2, Step B. $^1$H NMR (CDCl$_3$): δ 4.19 (d, 1H, J=4.8), 1.94–1.85 (m, 2H), 1.65 (dd, 1H, J$_1$=12.5, J$_2$=8.2),1.53 (dd, 1H, J$_1$=14.2, J$_2$=8.4), 1.36–1.26 (m, 1H), 1.22–1.20 (m, 1H), 1.14–1.12(m, 1H), 0.95–0.87 (m, 7H), 0.37 (m, 1H).

Step B: Preparation of (±)-exo-6-Isopropyl-bicyclo[3.1.0]hexan-2-one

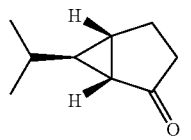

The title compound was prepared in a similar manner as described in Example 9.2, Step C. $^1$H NMR (CDCl$_3$): δ 2.07–1.93 (m, 4H), 1.86–1.84 (m, 1H), 1.53 (d, 1H, J=5.2), 1.05–1.02 (m, 2H), 0.98(d, 3H, J=5.1), 0.93(d, 3H, J=5.7).

Step C: Preparation of (±)-exo-1-Isopropyl-1a,3,5,5a-tetrahydro-1H-2,3-diaza-cyclopropa[a]pentalene-4-carboxylic acid ethyl ester

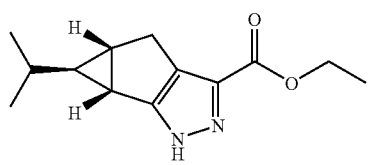

The title compound was prepared in a similar manner as described in Example 9.2, Step D. MS: m/z (ES+): 235 [M+H]$^+$, 189 [M–OEt]$^+$; $^1$H NMR (CDCl$_3$): δ 4.33 (q, 2H, J=5.9), 2.90 (dd, 1H, J$_1$=17.1, J$_2$=5.3), 2.77 (d, 1H, J=17.1), 1.91–1.89 (m, 1H), 1.30 (t, 3H, J=10.1), 1.24–1.19 (m, 1H), 1.06–1.03 (m, 1H), 0.97 (d, 6H, J=11.5), 0.45 (m, 1H).

Example 9.43

Preparation of (±)-exo-1-Isopropyl-1a,3,5,5a-tetrahydro-1H-2,3-diaza-cyclopropa[a]pentalene-4-carboxylic acid

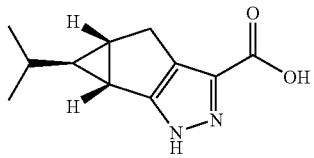

The title compound was prepared in a similar manner as described in Example 9.3. MS: m/z (ES+): 207 [M+H]$^+$, 189 [M–OH]$^+$; $^1$H NMR (CD$_3$OD): δ 2.95–2.93 (m, 1H), 2.90 (d, 1H, J=16.7), 2.00 (m, 2H), 1.08–1.03(m, 7H (including d, 6H, J=12.4)), 0.43 (septet, 1H, J=4.1).

Example 9.44

Preparation of (±)-exo-1-Isopropyl-4-(2H-tetrazol-5-yl)-1a,3,5,5a-tetrahydro-1H-2,3-diaza-cyclopropa[a]pentalene

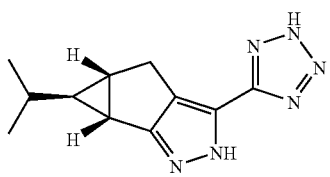

(±)-exo-6-Isopropyl-bicyclo[3.1.0]hexan-2one (0.200 g, 1.45 mmol) and 1H-tetrazole-5-carboxylic acid ethyl ester sodium salt (0.238 mg, 1.45 mmol) were dissolved into DMF (5 mL) and chilled to 0° C. Potassium tert-butoxide (1.0 M in THF, 3.20 mL, 3.20 mmol) was added slowly and the resulting solution stirred at 0° C. for 1 hour. Hydrochloric acid (3.0N, 1.00 mL, 2.90 mmol) was then added slowly, followed by the drop-wise addition of hydrazine monohydrate (0.080 mL, 1.67 mmol). The reaction mixture was allowed to warm to room temperature and stirred overnight. DMF was removed under reduced pressure and the reaction mixture was dissolved in DMSO (5 mL) and purified by HPLC to give (±)-exo-1-isopropyl-4-(2H-tetrazol-5-yl)-1a,3,5,5a-tetrahydro-1H-2,3-diaza-cyclopropa[a]pentalene as an off-white solid. MS: m/z (ES+): 231 [M+H]$^+$, 203 [M–N2+H]$^+$; $^1$H NMR (CD$_3$OD): δ 2.83 (dd, 1H, J$_1$=14.6, J$_2$=5.6), 2.65(d, 1H, J=16.1), 1.95–1.86 (m, 2H), 0.81–0.88 (m, 7H (including d, 6H, J=12.9)), 0.31(septet, 1H, J=3.3).

Example 9.45

Preparation of (±)-exo-1-Isobutyl-1a,3,5,5a-tetrahydro-1H-2,3-diaza-cyclopropa[a]pentalene-4-carboxylic acid ethyl ester Step A: Preparation of (±)exo-Isobutyl-bicyclo[3.1.0]hexan-2-ol

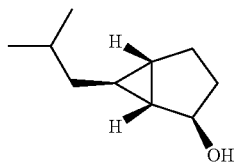

The title compound was prepared in a similar manner as described in Example 9.2, Step B. ¹H NMR (CDCl₃): δ 4.22(m, 1H), 1.95–1.80 (m, 1H), 1.72–1.45 (m, 4H,), 1.40–1.20 (m, 1H), 1.20–1.16(m, 1H), 1.15–1.00(m, 2H), 0.97–0.83 (m, 6H) 0.37 (septet, 1H). Contains ca 30% (±)endo-6-isobutyl-bicyclo[3.1.0]hexan-2-ol.

Step B: Preparation of (±)exo-6-Isobutyl-bicyclo[3.1.0]hexan-2-one

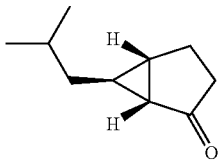

The title compound was prepared in a similar manner as described in Example 9.2, Step C. ¹H NMR (CDCl₃): δ 2.13–1.97 (m, 4H), 1.88–1.82 (m, 1H), 1.74–1.66 (m, 1H), 1.55–1.51(d, 1H, J=5.1), 1.32–1.23(m, 2H), 1.15–1.07(m, 1H) 0.95(d, 3H, J=2.5), 0.92(d, 3H, J=2.5). Contains ca 30% (±)endo-6-isobutyl-bicyclo[3.1.0]hexan-2-one.

Step C: Preparation of (±)-exo-1-Isobutyl-1a,3,5,5a-tetrahydro-1H-2,3-diaza-cyclopropa[a]pentalene-4-carboxylic acid ethyl ester

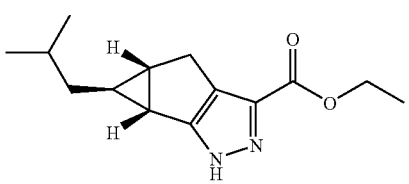

The title compound was prepared in a similar manner as described in Example 9.2, Step D. MS: m/z (ES+): 249 [M+H]⁺, 203 [M–OEt]⁺; ¹H NMR (CDCl₃): δ 4.30 (q, 2H, J=7.1), 2.91 (dd, 1H, J₁=17.0, J₂=6.2), 2.77 (d, 1H, J=17.0), 1.98–1.93 (m, 2H), 1.59–1.49 (m, 1H), 1.43–1.34(t, 3H, J=6.9), 1.24–1.15 (m, 1H), 0.85(m, 7H), 0.64–0.57 (m, 1H). Contains ca 30% (±)-endo-1-Isobutyl-1a,3,5,5a-tetrahydro-1H-2,3-diaza-cyclopropa[a]pentalene-4-carboxylic acid ethyl ester.

Example 9.46

Preparation of (±)-exo-1-Isobutyl-1a,3,5,5a-tetrahydro-1H-2,3-diaza-cyclopropa[a]pentalene-4-carboxylic acid

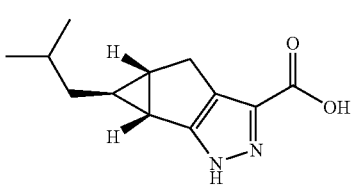

The title compound was prepared in a similar manner as described in Example 9.3. MS: m/z (ES+): 221 [M+H]⁺, 203 [M–OH]⁺; ¹H NMR (CD₃OD): δ 2.95–2.90 (m, 1H), 2.80 (d, 1H, J=16.9), 1.96(m, 2H), 1.78–1.72 (m, 1H),1.26–1.23 (m, 2H), 0.98–0.94 (m, 6H), 0.62 (septet, 1H, J=3.3).

Example 9.47

Preparation of (±)-exo-1-Isobutyl-4-(2H-tetrazol-5-yl)-1a,3,5,5a-tetrahydro-1H-2,3-diaza-cyclopropa[a]pentalene

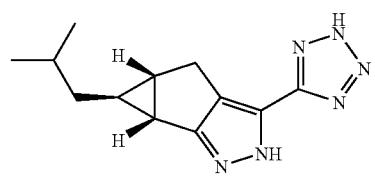

The title compound was prepared in a similar manner as described in Example 9.44. MS: m/z (ES+): 245 [M+H]⁺, 217 [M–N2+H]⁺; ¹H NMR (CD₃OD): δ 2.99 (dd, 1H, J₁=16.2, J₂=5.6), 2.91 (d, 1H, J=16.0), 2.10–2.00 (m, 2H), 1.78–1.71(m, 1H),1.30–1.23(m, 2H), 0.96 (m, 6H), 0.73 (septet, 1H, J=3.2).

Example 9.48

Preparation of (±)-endo-1-Isobutyl-1a,3,5,5a-tetrahydro-1H-2,3-diaza-cyclopropa[a]pentalene-1-carboxylic acid

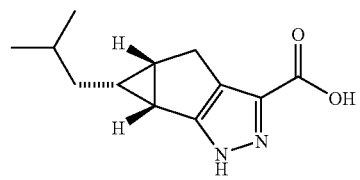

The title compound was prepared in a similar manner as described in Example 9.3 using the mixture of diastereomers described in Example 9.45, Step C. MS: m/z (ES+): 221 [M+H]⁺, 203 [M–OH]⁺; ¹H NMR (CD₃OD): δ 2.94–2.88 (dd, 1H, J=6.7), 2.65 (d, 1H, J=17.5), 2.35–2.24 (m, 2H), 1.63–1.54 (m, 1H),1.34–1.27(m, 1H), 1.07–0.98(m, 1H) 0.90(d, 3H, J=6.6), 0.84(d, 3H, J=6.6), 0.66 (septet, 1H, J=3.1).

Example 9.49

Preparation of (±)-endo-1-Isobutyl-4-(2H-tetrazol-5-yl)1a,3,5,5a-tetrahydro-1H-2,3-diaza-cyclopropa[a]pentalene

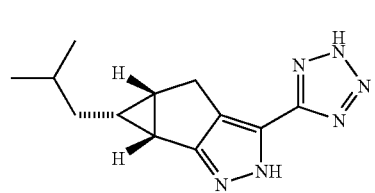

The title compound was prepared in a similar manner as described in Example 9.44 using the mixture of diastereomers described in Example 9.45, Step B. MS: m/z (ES+): 245 [M+H]$^+$, 217 [M−N2+H]$^+$; $^1$H NMR (CD$_3$OD): δ 2.84 (dd, 1H, J$_1$=16.5, J$_2$=6.6), 2.62 (d, 1H, J=16.6), 2.38 (m, 2H), 1.50–1.43(m, 1H), 1.22–1.18(m, 1H), 1.00–0.94(m, 1H), 0.76(d, 3H, J=6.6), 0.70(d, 3H, J=6.6), 0.59–0.52(m, 1H).

Example 9.50

Preparation of (±)-endo-1-Phenyl-4-(2H-tetrazol-5-yl)-1a,3,5,5a-tetrahydro-1H-2,3-diazocyclopropan[a]pentalene Step A: Preparation of (Z)-Ethyl 5-phenylpent-4-enoate

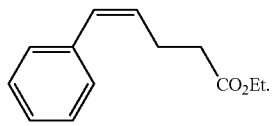

3-Ethoxycarbonylpropyltriethylphosphonium bromide (5.488 g, 12.00 mmol), benzaldehyde (3.820 g, 36.00 mmol) and potassium tert-butoxide (4.040 g, 36.00 mmol) were taken up in MTBE (300 mL) at room temperature and was stirred overnight. The reaction mixture was washed with water (1×100 mL) and the aqueous phase was extracted with MTBE (3×100 mL). Solvent was removed from the combined organic phase under reduced pressure and the resulting oil purified by column chromatography (0–10% EtOAc/n-hexane, silica) to give (Z)-ethyl 5-phenylpent-4-enoate as a pale yellow oil. $^1$H NMR (CDCl$_3$): δ 7.36–7.31 (m, 2H), 7.28–7.21 (m, 3H), 6.47 (d, 1H, J=11.6, Ph-CH), 5.63 (dt, 1H, J$_1$=11.6, J$_2$=7.2), 4.14 (q, 2H, J=7.2), 2.66 (dq, 2H, J$_1$=7.3, J$_2$=1.7), 2.43 (t, 2H, J=7.6), 1.24 (t, 3H, J=7.1). Contains ca. 33% (E)-ethyl 5-phenylpent-4-enoate Step B: Preparation of (Z)-5-Phenylpent-4-enal

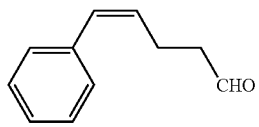

(Z)-Ethyl 5-phenylpent-4-enoate (1.600 g, 7.833 mmol) was taken up in dichloromethane (100 mL) under N2 and chilled to −78° C. DIBAL (1M in hexanes, 9 mL, 9.0 mmol) was added and the reaction mixture was stirred at −78° C. for 3 hours. The excess DIBAL was quenched with the slow addition of methanol (25 mL). The resulting solution was poured into a saturated solution of sodium/potassium tartarate (400 mL). Further hexane (150 mL) was added and the mixture was stirred at room temperature over night. The organic phase was collected and solvent removed under reduced pressure. The resulting oil was purified by column chromatography (0–20% EtOAc/n-hexane, silica) to give (Z)-5-phenylpent-4-enal as a pale yellow oil. $^1$H NMR (CDCl$_3$): δ 9.77 (s, 1H), 7.36–7.29 (m, 2H), 7.25–7.21 (m, 3H), 6.49 (d, 1H, J=11.5), 5.62 (dt, 1H, J$_1$=11.6, J$_2$=7.2, Ph-CHCH), 2.70–2.62 (m, 2H), 2.60–2.55 (m, 2H). Contains ca. 16% (E)-5-phenylpent-4-enal.

Step C: Preparation of (Z)-2-(4-Phenylbut-3-enyl)oxirane

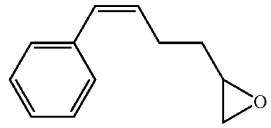

(Z)-5-Phenylpent-4-enal (0.475 g, 2.97 mmol) and dibromomethane (0.626 g, 3.60 mmol) were taken up in THF (20 mL) and chilled to −78° C. under argon n-butyl lithium (1.6M in hexane, 2.0 mL, 3.20 mmol) was added dropwise over 5 minutes. The resulting mixture was warmed slowly to room temperature and stirred overnight. The reaction mixture was poured into saturated aqueous NH4Cl (20 mL), extracted with MTBE (2×30 mL) and solvent removed under reduced pressure. The resulting oil was purified by column chromatography (0–20% EtOAc/n-hexane, silica) to give (Z)-2-(4-Phenylbut-3-enyl)oxirane as a pale yellow oil. $^1$H NMR (CDCl$_3$): δ 7.32–7.27 (m, 2H), 7.25–7.19 (m, 3H), 6.47 (d, 1H, J=11.7), 5.68 (J$_1$=11.6, J$_2$=7.3), 2.97–2.93 (m, 1H), 2.77–2.74 (m, 1H), 2.55–2.52 (m, 1H), 2.53–2.48 (m, 2H), 1.76–1.67 (m, 2H). Contains ca. 18% (E)-2-4-phenylbut-3-enyl)oxirane.

Step D: Preparation of (±)-endo-6-Phenylbicyclo[3.1.0]hexan-2-ol

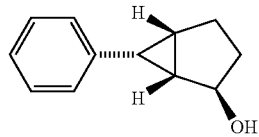

The title compound was prepared in a similar manner as described in Example 9.2, Step B. $^1$H NMR (CDCl$_3$): δ 7.31–7.17 (m, 5H), 4.20 (d, 1H, J=5.2), 2.20 (t, 1H, J=8.6), 2.13–2.03 (m, 2H), 1.92–1.79 (m, 2H), 1.78–1.63 (m, 2H), 0.51–0.40 (m, 1H, Ph-CH).

Step E: Preparation of (±)-endo-6Phenylbicyclo[3.1.0]hexan-2-one

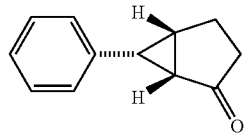

The title compound was prepared in a similar manner as described in Example 9.2, Step C. $^1$H NMR (CDCl$_3$): δ 7.32–7.24 (m, 5H), 2.80 (t, 1H, J=8.6), 2.45–2.36 (m, 1H), 2.32–2.15 (m, 2H), 2.08–1.82 (m, 2H), 0.98–0.86 (m, 1H, Ph-CH)

Step F: Preparation of (±)-endo-1-Phenyl-4-(2H-tetrazol-5-yl)1a,3,5,5a-tetrahydro-1H-2,3-diazocyclopropan[a]pentalene

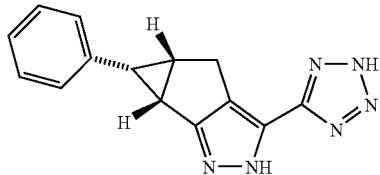

The title compound was prepared in a similar manner as described in Example 9.44. MS: m/z (ES+): 265 [M+H]+, 237 [M−N2+H]+; $^1$H NMR (CD$_3$OD): δ 7.50–6.90 (m, 5H), 3.05–2.96 (dd, 1H, $J_1$=16.4, $J_2$=6.3), 2.84–2.76 (m, 1H), 2.76–2.67 (m, 1H), 2.64 (t, 1H, J=8.1), 1.40–1.25 (m, 1H).

Example 9.51

Preparation of (±)-exo-1-Phenoxymethyl-4-(2H-tetrazol-5-yl)-1a,2,5,5a-tetrahydro-1H-2,3-diazacyclopropa[a]pentalene

Step A: tert-Butyl-dimethyl-(5-oxiranyl-pent-2-enyloxy)-silane

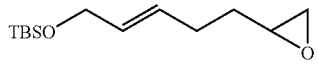

The title compound was prepared in a similar manner as described in Example 9.2, Step A. $^1$H NMR (400 MHz, CDCl$_3$): δ 5.65 (1H, dt, J=15.3, 6.2 Hz), 5.57 (1H, dt, J=15.3, 4.9 Hz), 4.11 (2H, m), 2.91 (1H, m), 2.73 (1H, m), 2.46(1H, dd, J=5.0, 2.7 Hz), 2.19 (2H, m), 1.61 (2H, m), 0.89 (9H, s), 0.05 (6H, s).

Step B: Preparation of (±)-exo-6-(tert-Butyl-dimethyl-silanyloxymethyl)-bicyclo[3.1.0]hexan-2-ol

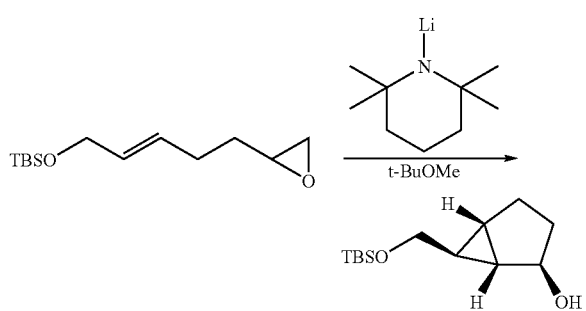

LiTMP was generated by addition of n-BuLi (2.5 M in hexanes, 51 mL, 124 mmol) to a stirred solution of TMP (17.5 g, 124 mmol) in t-BuOMe (400 mL) at −78° C. The light yellow LiTMP solution was slowly warmed to 0° C. To a stirred solution of tert-butyl-dimethyl-(5-oxiranyl-pent-2-enyloxy)-silane (15.0 g, 62 mmol) in t-BuOMe (200 mL) at 0° C. was added the LiTMP solution dropwise via cannula. The resultant mixture was stirred at ambient temperature for 18 h, and then quenched with MeOH (20 mL). The reaction was concentrated to a total volume of 300 mL and the solution was washed with NH$_4$Cl (sat., aq., 3×150 mL) and brine (150 mL). The organics were dried over MgSO$_4$, filtered, concentrated and purified on a silica gel column, (5% EtOAc in hexane, gradient to 30% EtOAc in hexane) to give the title compound as a light yellow oil. $^1$H NMR (400 MHz, CDCl$_3$): δ 4.25 (1H, d, J=4.8 Hz), 3.49 (1H, dd, J=10.8, 6.2 Hz), 3.44 (1H, dd, J=10.8, 6.4 Hz), 1.93 (1H, m), 1.72 (1H, dd, J=12.6, 8.1 Hz), 1.57 (1H, dd, J=14.5, 8.4 Hz), 1.38–1.24 (4H, m), 0.89 (9H, s), 0.71 (1H, m), 0.04 (6H, s).

Step C: Preparation of (±)-exo-6-(tert-Butyl-dimethyl-silanyloxymethyl)-bicyclo[3.1.0]hexan-2-one

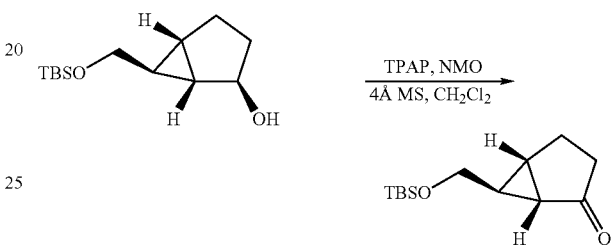

TPAP (0.181 g, 0.52 mmol) was added to a stirring solution of (±)-exo-6-(tert-Butyl-dimethyl-silanyloxymethyl)-bicyclo[3.1.0]hexan-2-ol (2.5 g, 10.3 mmol), NMO (2.4 g, 20.6 mmol), and 4 Å MS (3 g) in CH$_2$Cl$_2$ (50 mL) at ambient temperature. The mixture was stirred for 3 h, filtered through celite, poured on silica gel and eluted with Et$_2$O/CH$_2$Cl$_2$ (1:1). The organic solvent was evaporated in vacuo to give the title compound. $^1$H NMR (400 MHz, CDCl$_3$): δ 3.69 (1H, dd, J=10.8, 4.8 Hz), 3.58 (1H, dd, J=10.8, 5.3 Hz), 2.15 (1H, m), 2.05 (4H, m), 1.72 (1H, m), 1.51 (1H, m), 0.87 (9H, s), 0.04 (6H, s).

Step D: Preparation of (±)-exo-1-Hydroxymethyl-1a-3,5,5a-tetrahydro-1H-2,3-diaza-cyclopropa[a]pentalene-4-carboxylic acid ethyl ester

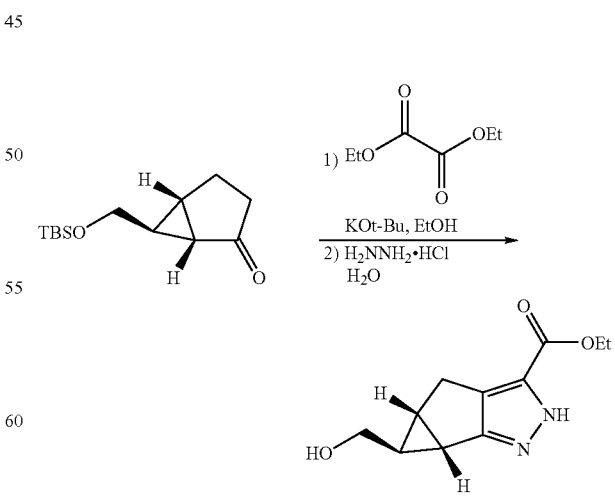

To a solution of ketone (2.2 g, 9.2 mmol) and diethyl oxalate (1.35 g, 9.2 mmol) in EtOH (35 mL) at rt under N$_2$ was added a solution of KOt-Bu in THF (10.1 mL of a 1 M solution, 10.1 mmol). The reaction was stirred for 4 h at which time hydrazine hydrochloride (0.756 g, 11 mmol) in H₂O (4 mL) was added. The reaction mixture was stirred for 20 h at rt and acidified to pH ~3 by the addition of HCl (6N aq.). The volatiles were removed in vacuo and the resulting solid was diluted with EtOAc (50 mL) and H₂O (50 mL). The layers were separated and the aqueous phase was back-extracted with EtOAc. The combined organics were washed with brine, dried over MgSO₄, filtered, and concentrated to give the title compound. The compound was used directly in the next reaction with no further purification. ¹H NMR (400 MHz, CDCl₃): δ 4.23 (2H, q, J=7.1 Hz), 3.41 (1H, dd, J=11.4, 5.9 Hz), 3.28 (1H, dd, J=11.4, 6.8 Hz), 2.84 (1H, dd, J=16.9, 6.2 Hz), 2.69 (1H, d, J=16.9 Hz), 2.05 (2H, m), 1.26 (3H, t, J=7.1 Hz), 0.78 (1H, m). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=1.54 min, ESI⁺=223.2 (M+H).

Step E: Preparation of 1-Hydroxymethyl-1a-2,5,5a-tetrahydro-1H-2,3-diaza-cyclopropa[a]pentalene-4-carboxylic acid amide

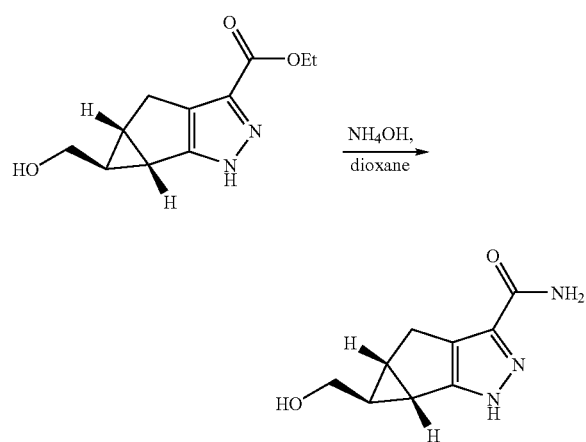

To a solution of ester (5.3 g, 23.9 mmol) in dioxane (80 mL) was added ammonium hydroxide (28% NH₃ in H₂O, 400 mL). The mixture was placed in a 500 mL pyrex bottle and agitated on a shaker plate for 22 h at rt. The mixture was concentrated in vacuo to a total volume of 100 mL at which time a light yellow precipitate was evident. The mixture was filtered and the solid was washed with H₂O. Further drying of the solid gave the title as a white solid. The compound was used directly in the next reaction with no further purification. ¹H NMR (400 MHz, DMSO-d₆): δ 7.29 (1H, bs), 7.12 (1H, s), 4.62 (1H, bs), 3.39 (1H, dd, J=11.4, 6.0 Hz), 3.28 (1H, dd, J=16.4, 5.3 Hz), 2.82 (1H, dd, J=16.4, 5.3 Hz), 2.73 (1H, d, J=17.8), 2.03 (2H, m), 1.75 (1H, s), 0.76 (1H, m). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=1.49 min, ESI⁺=194.0 (M+H).

Step F: Preparation of (±)-exo-2-Benzyl-1-hydroxymethyl-1a-2,5,5a-tetrahydro-1H-2,3-diaza-cyclopropa[a]pentalene-4-carboxylic acid amide

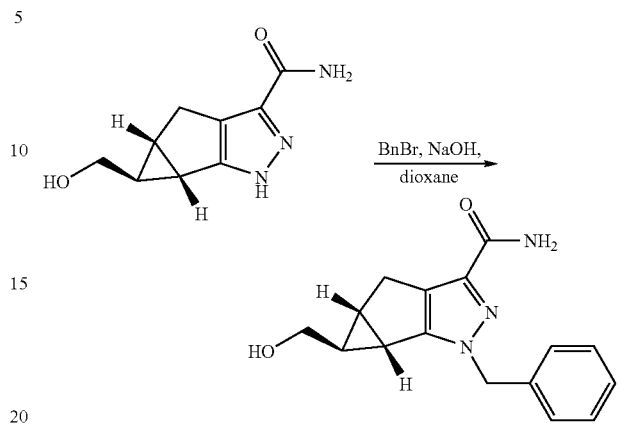

The amide was partially dissolved in dioxane (60 mL) and NaOH (5N aq., 10.0 mL, 50.0 mmol) was added followed by benzyl bromide (4.25 g, 24.9 mmol). The mixture slowly became clear and the reaction stirred for 20 h at rt. The mixture was acidified to pH≈2 by the addition of HCl (6N, aq.) and concentrated to dryness in vacuo. The resultant residue was dissolved in EtOAc and washed with NaHCO₃ (sat. aq., 50 mL) and H₂O (50 mL). The residue was purified on a silica gel column (40% EtOAc in hexane, gradient to 75% EtOAc in hexane) to give the benzylated product. ¹H NMR (400 MHz, CDCl₃): δ 7.38 (3H, m), 7.26 (2H, m), 6.64 (1H, bs), 5.30 (1H, d, J=15.0 Hz), 5.23 (1H, d, J=15.0 Hz), 3.55 (1H, m), 3.19 (1H, m), 2.96 (1H, dd, J=16.6, 6.2 Hz), 2.88 (1H, d, J=16.6 Hz), 2.07 (1H, m), 1.76 (1H, m), 1.05 (1H, bs), 0.90 (1H, m). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=1.81 min, ESI⁺=284.2 (M+H).

Step G: Preparation of (±)-exo-2-Benzyl-1-chloromethyl-1a-2,5,5a-tetrahydro-1H-2,3-diaza-cyclopropa[a]pentalene-4-carbonitrile

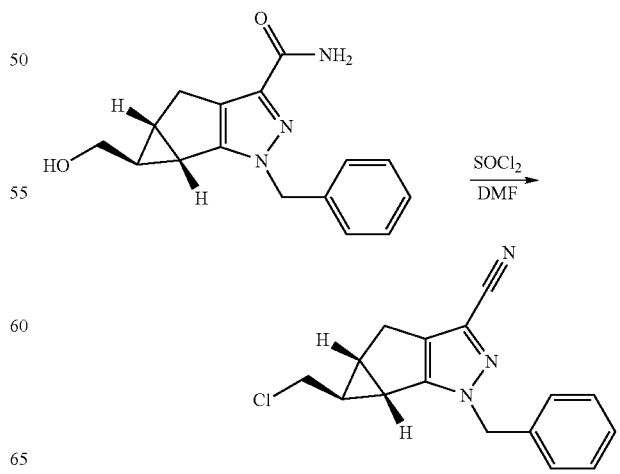

A flask charged with anhydrous DMF (4 mL) under $N_2$ atmosphere was cooled to 0° C. and thionyl chloride (0.77 mL, 10.6 mmol) was added dropwise. After stirring for 5 min, a suspension of the amide (1.0 g, 3.5 mmol) in DMF (4 mL) was added dropwise. The mixture was slowly warmed to rt and stirred for 20 h, and $NaHCO_3$ (sat. aq., 10 mL) was added followed by $H_2O$ (15 mL). The mixture was stirred for 10 min and concentrated to near dryness in vacuo. The residue was diluted with EtOAc (20 mL) and $H_2O$ (20 mL). The layers were separated and the aqueous phase was back-extracted with EtOAc (20 mL). The combined organics were washed with $NaHCO_3$ (sat. aq., 30 mL), and brine (30 mL), dried over $MgSO_4$, filtered, and concentrated to give the title compound as a brown oil. The compound was used directly in the next reaction with no further purification. $^1$H NMR (400 MHz, $CDCl_3$): δ 7.38 (3H, m), 7.31 (2H, m), 5.30 (1H, d, J=14.8), 5.26 (1H, d, J=14.8 Hz), 3.47 (1H, dd, J=11.4, 6.6 Hz), 3.22 (1H, dd, J=11.4, 8.1 Hz), 2.89 (1H, dd, J=16.5, 6.4 Hz), 2.79 (1H, d, J=16.5 Hz), 2.20 (1H, m), 1.92 (1H, m), 1.09 (1H, m). HPLC/MS: Alltech® Prevail C18 column (5μ, 50×4.6 mm), 5% v/v $CH_3CN$ (containing 1% v/v TFA) in $H_2O$ (containing 1% v/v TA) gradient to 99% v/v $CH_3CN$ in $H_2O$, 3.5 mL/min, $t_r$=3.02 min, $ESI^+$=284.4 (M+H).

Step H: Preparation of (±)-exo-2-Benzyl-1-phenoxymethyl-1a-2,5,5a-tetrahydro-1H-2,3-diaza-cyclopropa[a]pentalene-4-carbonitrile

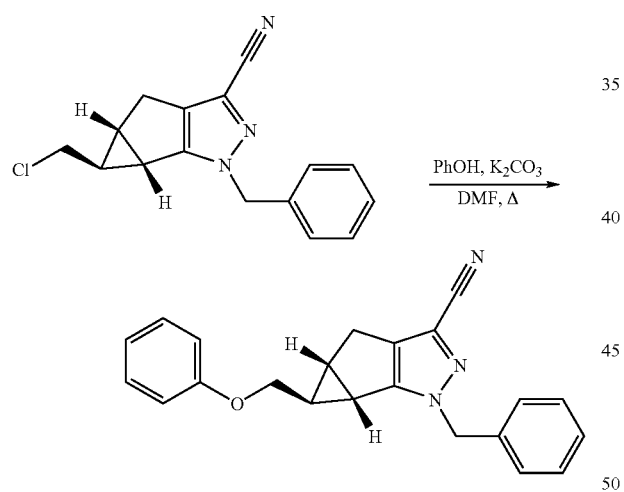

The nitrile (0.300 g, 1.06 mmol), phenol (0.141 g, 1.5 mmol), and $K_2CO_3$ (0.277 g, 2.0 mmol) were dissolved in DMF (6 mL). The reaction vessel was sealed and heated in a microwave reactor to 120° C. for 40 minutes. After cooling to ambient temperature, the reaction mixture was taken up in ethyl acetate and washed once with water, once with brine, dried over MgSO4, and concentrated in vacuo. The resulting residue was purified by reverse-phase HPLC: Phenomenex® Luna C18 column (10μ, 250×21.2 mm), 5% (v/v) $CH_3CN$ (containing 1% v/v TFA) in $H_2O$ (containing 1% v/v TFA) gradient to 95% $H_2O$, 20 ml/min, λ=214 nm to give the title compound as a white solid after lyophilization. HPLC/MS: Alltech® Prevail C18 column (5μ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=3.50 min, $ESI^+$=342.3 (M+H).

Step I: Preparation of (±)-exo-2-Benzyl-1-phenoxymethyl-4-(2H-tetrazol-5-yl)1a,2,5,5a-tetrahydro-1H-2,3-diaza-cyclopropa[a]pentalene

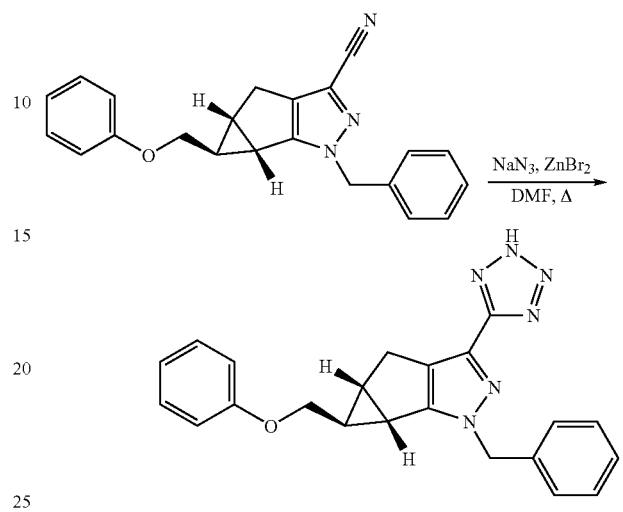

The nitrile (0.30 g, 0.88 mmol), $ZnBr_2$ (0.400 g, 1.76 mmol), and NaN3 (0.345 g, 5.31 mmol) were dissolved in DMF (5 mL). The reaction vessel was sealed and heated in a microwave reactor to 190° C. for 15 minutes. After cooling to ambient temperature, the reaction mixture was acidified by the addition of HCl (1N, aq.) and purified by reverse-phase HPLC: Phenomenex® Luna C18 column (10μ, 250× 21.2 mm), 5% (v/v) $CH_3CN$ (containing 1% v/v TFA) in $H_2O$ (containing 1% v/v TFA) gradient to 95% $H_2O$, 20 ml/min, λ=214 nm to give the title compound as a white solid after lyophilizing. HPLC/MS: Alltech® Prevail C18 column (5μ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=2.71 min, $ESI^+$=384.9 (M+H).

Step J: Preparation of (±)-exo-1-Phenoxymethyl-4-(2H-tetrazol-5-yl)-1a,2,5,5a-tetrahydro-1H-2,3-diaza-cyclopropa[a]pentalene

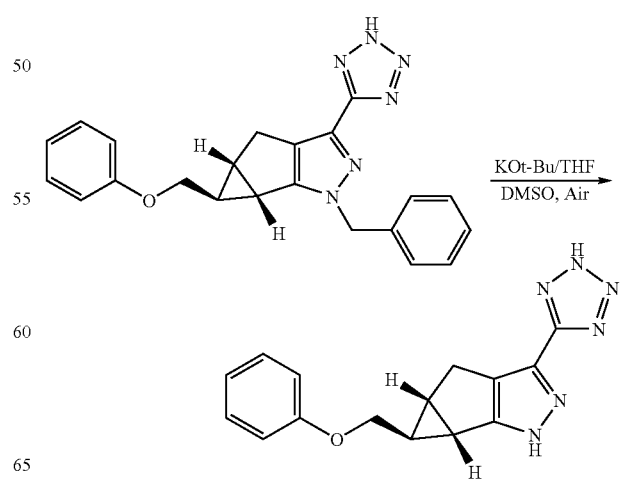

Air was bubbled through a stirring solution of protected compound (0.150 g, 0.39 mmol) and KOt-Bu (4.0 mL of a 1M solution in THF, 4.0 mmol) in DMSO (4 mL) for 2 h at rt. The remaining THF was removed in vacuo and the reaction mixture was diluted with EtOAc (20 mL) and H₂O (20 mL). The layers were separated and the organic layer was washed with brine, dried over MgSO₄, concentrated, and purified by reverse-phase HPLC: Phenomenex® Luna C18 column (10μ, 250×21.2 mm), 5% (v/v) CH₃CN (containing 1% v/v TFA) in H₂O (containing 1% v/v TFA) gradient to 95% H₂O, 20 ml/min, λ=214 nm to give the title compound as a white solid after lyophilizing. ¹H NMR (400 MHz, DMSO-d₆): δ 7.28 (2H, m), 6.94 (3H, m), 4.06 (1H, dd, J=10.5, 6.1 Hz), 3.83 (1H, dd, J=10.4, 7.9 Hz), 2.98 (1H, dd, J=16.3, 6.1 Hz), 2.88 (1H, d, J=16.6 Hz), 2.40 (1H, m), 2.34 (1H, m), 1.21 (1H, m). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=2.08 min, ESI⁺=295.4 (M+H).

Example 9.52

Preparation of (±)-exo-1-Methoxymethyl-1a,3,5,5a-tetrahydro-1H-2,3-diaza-cyclopropa[a]pentalene-4-carboxylic acid Step A: Preparation of (±)-exo-2-Benzyl-1-hydroxymethyl-1a,2,5,5a-tetrahydro-1H-2,3-diaza-cyclopropa[a]pentalene-4-carboxylic acid ethyl ester

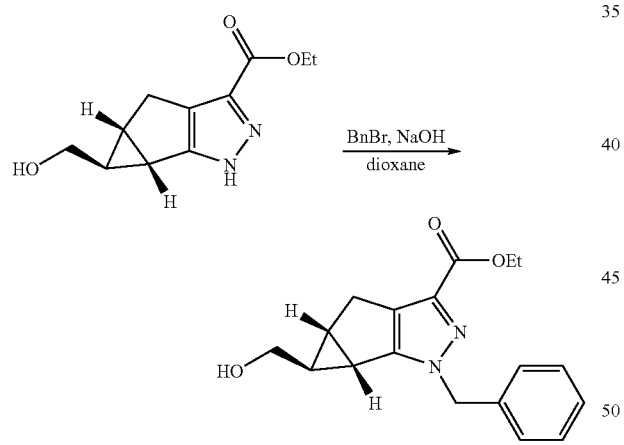

The ester (1.5 g, 6.75 mmol) was dissolved in DMF (20 mL) and K₂CO₃ (1.84 g, 13.5 mmol) was added followed by benzyl bromide (1.73 g, 10.1 mmol). The reaction stirred for 20 h at rt. The mixture was diluted with EtOAc and washed with water and brine, dried over MgSO₄, and concentrated to dryness in vacuo. The residue was purified on a silica gel column (40% EtOAc in hexane, gradient to 75% EtOAc in hexane) to give the benzylated product as a white solid. ¹H NMR (400 MHz, CDCl₃): δ 7.38 (3H, m), 7.30 (2H, m), 5.42 (1H, d, J=14.9 Hz), 5.29 (1H, d, J=14.9 Hz), 4.36 (2H, q, J=7.1 Hz), 3.14 (1H, m), 2.91 (1H, dd, J=16.7, 6.3 Hz), 2.82 (1H, d, J=16.7 Hz), 2.03 (1H, m), 1.67 (1H, m), 1.37 (3H, t, J=7.1 Hz), 0.85 (1H, m). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=2.11 min, ESI⁺=313.2 (M+H).

Step B: Preparation of (±)-exo-2-Benzyl-1-methoxymethyl-1a,2,5,5a-tetrahydro-1H-2,3-diaza-cyclopropa[a]pentalene-4-carboxylic acid ethyl ester

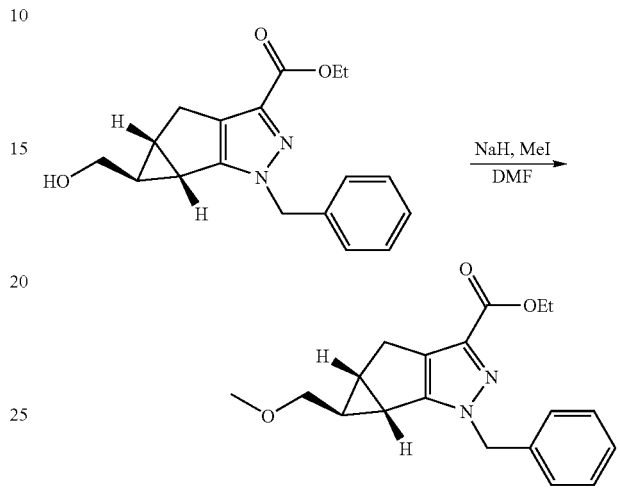

To a solution of the alcohol (0.350 g, 1.1 mmol) in DMF (5 mL) was added NaH (60% dispersion, 0.088 g, 2.2 mmol) at 0° C. under N₂. The mixture was stirred for 10 min and MeI (0.239 g, 1.7 mmol) was added. The reaction mixture stirred at ambient temperature for 20 h, and quenched with water. The mixture was extracted with EtOAc (2×10 mL) and the combined organic layers were washed with water (10 mL), dried over MgSO₄, and concentrated in vacuo. The residue was purified on a silica gel column, eluting with hexane:EtOAc (6:4) to give the title compound. HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=2.65 min, ESI⁺=327.4 (M+H).

Step C: Preparation of (±)-exo-1-Methoxymethyl-1a,3,5,5a-tetrahydro-1H-2,3-diaza-cyclopropa[a]pentalene-4-carboxylic acid

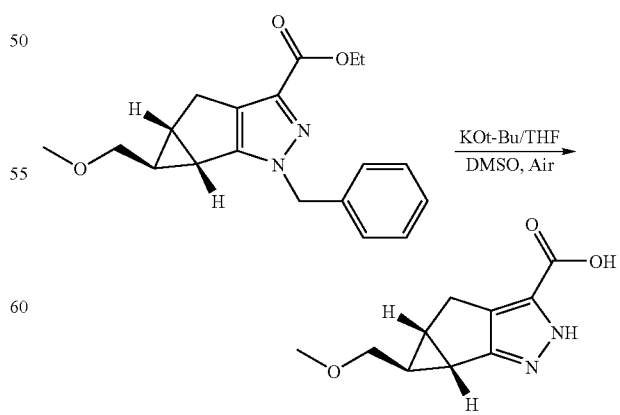

Air was bubbled through a stirring solution of the ester (0.075 g, 0.23 mmol) and KOt-Bu (2.3 mL of a 1M solution in THF, 2.3 mmol) in DMSO (2.5 mL) for 1 h at rt. The remaining THF was removed in vacuo and the reaction was acidified by the addition of HCl (3M aq.) and purified by reverse-phase HPLC: Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 ml/min, λ=214 nm to give title compound as a white solid after lyophilization. $^1$H NMR (400 MHz, DMSO-d$_6$): δ 13.0 (1H, bs), 3.31 (1H, dd, J=16.7, 6.4 Hz), 3.24 (3H, s), 3.22 (1H, dd, J=10.5, 7.2 Hz), 2.84 (1H, dd, J=16.9, 6.2 Hz), 2.69 (1H, d, J=14.8 Hz), 2.09 (1H, m), 2.04 (1H, m), 0.84 (1H, m). HPLC/MS: Alltech (Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.36 min, ESI$^+$=208.9 (M+H).

Example 9.53

Preparation of (1aR,5aR-(+)-4-(2H-Tetrazol-5-yl)-1a,3,5,5a-tetrahydro-1H-2,3-diaza-cyclopropa[a]pentalene

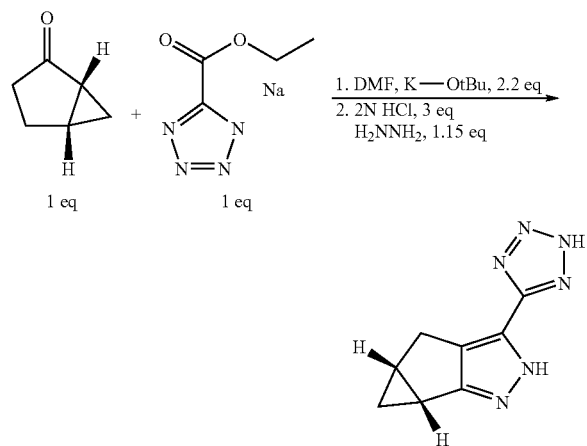

PROCEDURE: Ketone was dissolved in DMF. Tetrazole was then added to the solution. The resulting suspension was cooled to 0° C. Potassium-t-Butoxide solution in DMF was added slowly to the mixture keeping the temperature <10° C. The mixture was stirred at 0° C. for 1 hour. 2N HCl solution was then added slowly, followed by the dropwise addition of hydrazine hydrate (64% hydrazine). The reaction mixture was allowed to warm to room temperature overnight.

WORK UP: DMF was removed and the residue was partitioned with water, extract (7x) with EtOAc. The organic was dried over MgSO$_4$, filtered, concentrate in vacuo. The crude product was purified on reverse phase column (25% CH$_3$CN+0.1% TFA, 75% water+0.1% TFA, wavelength=265 nm) (10 minutes run). Separate isomers on SFC (AS (21×250mmn), 30% MeOH+0.1% TFA). Repurify on reverse phase column (25% CH$_3$CN+0.1% TFA, 75% water+0.1% TFA, wavelength=265 nm) (10 minutes run) in order to eliminate yellow color. The white solid was dissolved in hot water and allowed to crystallize to provide pure white/colorless crystals.

Example 9.54

Preparation of (+)-endo-1-methyl-1a,2,5,5a-tetrahydro-1H-2,3-diaza-cyclopropa[a]pentalene-4-carboxylic acid and exo-1-methyl-1a,2,5,5a-tetrahydro-1H-2,3-diaza-cyclopropa[a]pentale-4-carboxylic acid Step A: Preparation of (R)-5-(chloromethyl)tetrahydrofuran-2-ol

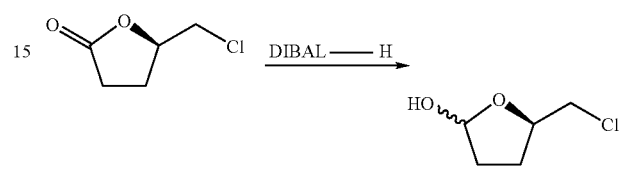

To a solution of (R)-5-(chloromethyl)dihydrofuran-2 (3H)-one (6.69 g, 49.7 mmol, see Movassaghi, M.; Jacobsen, E. N. *J. Am. Chem. Soc.* 2002, 124, 245 for preparation) in DCM (150 mL) under N$_2$ at −78° C. was added diisobutylaluminum hydride (1M DCM, 62.1 ml, 62.1 mmol) over 15 minutes. The mixture was stirred at −78° C. for 30 min at which time MeOH (~10 mL) was added and the mixture was removed from cooling. Rochelle salt (150 mL sat. aqueous) was added and the mixture was stirred for 1 h while warming to rt. The organic phase was removed and the aqueous phase was extracted with EtOAc (2×). The combined organics were dried over MgSO$_4$, filtered, and concentrated to give (R)-5-(chloromethyl)tetrahydrofuran-2-ol (6.65 g, 48.7 mmol, 98% yield), a clear oil, as a mixture of epimers (1.25:1). $^1$H NMR (400 MHz, CDCl$_3$): Major epimer: δ 5.62 (1H, m), 4.48 (1H, dq, J=7.6, 5.6 Hz), 3.67 (1H, dd, J=10.8, 5.6 Hz), 3.61 (1H, dd, J=11.2, 6.0 Hz), 2.65 (1H, m), 2.24 (1H, dq, J=12.4, 8.0 Hz), 2.10–1.72 (3H, m). Minor epimer: δ 5.30 (1H, m), 4.29 (1H, m), 3.53 (2H, m), 2.65 (1H, m), 2.10–1.72 (4H, m).

Step B: Preparation of cis/trans-(R)-2-(pent-3-enyl)oxirane

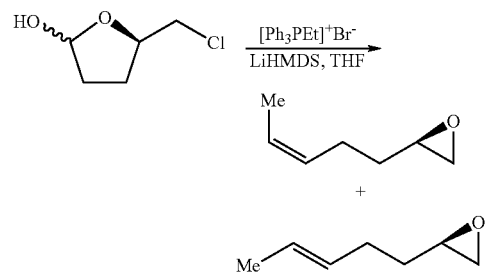

To a suspension of ethyl triphenylphosphonium bromide (5.57 g, 15.0 mmol) in THF (15 mL) at 0° C. was added lithiumbis(trimethylsilyl)amide 1M THF (15.0 ml, 15.0 mmol). The solution was stirred for 0.5 h at which time the (R)-5-(chloromethyl)tetrahydrofuran-2-ol (1.00 g, 7.32 mmol) was added at 0° C. as a solution in THF (15 mL). The resulting solution was allowed to warm to rt and stirred overnight. The mixture was quenched with H$_2$O and extracted with Et$_2$O (2×), dried over MgSO$_4$, filtered, and concentrated. The mixture was purified by silica gel chromatography (1% Et₂O in pentane gradient to 5% Et₂O in pentane) to give the (R)-2-(pent-3-enyl)oxirane, a clear oil, as an inseparable mixture of olefin isomers (cis:trans=2.3:1). ¹H NMR (400 MHz, CDCl₃): δ 5.55–5.26 (2H, m), 2.93 (1H, m), 2.76 (1H, m), 2.49 (from cis isomer, 0.7H, dd, J=6.0, 2.8 Hz), 2.48 (from trans isomer, 0.3H, dd, J=6.0, 2.8 Hz), 2.21 (from cis isomer, 1.4H, q, J=7.6 Hz), 2.14 (from trans isomer, 0.6H, m), 1.67–1.56 (5H, m).

Step C: Preparation of (1S,2S,5R,6S)-6-methylbicyclo[3.1.0]hexan-2-ol and (1S,2S,5R,6R)-6-methylbicyclo[3.1.0]hexan-2-ol

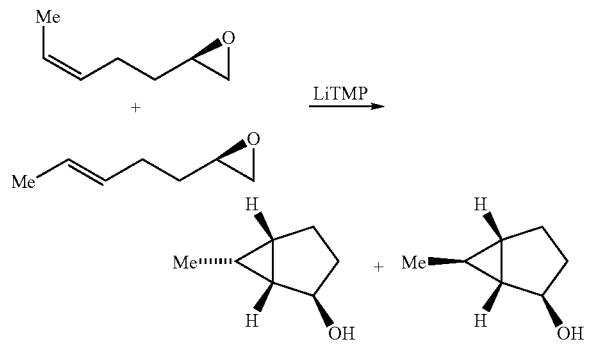

The intramolecular cyclopropanation of (R)-2-(pent-3-enyl)oxirane (980 mg, 8.74 mmol) was performed as described previously in Example 9.1, Step A to give (1S,2S,5R,6S)-6-methylbicyclo[3.1.0]hexan-2-ol and (1S,2S,5R,6R)-6-methylbicyclo[3.1.0]hexan-2-ol as an inseparable mixture after silica gel chromatography.

(1S,2S,5R,6S)-6-methylbicyclo[3.1.0]hexan-2-ol:
¹H NMR (400 MHz, CDCl₃): δ 4.15 (1H, d, J=4.8 Hz), 2.08 (1H, m), 1.75–1.25 (5H, m), 0.90 (5H, m).

(1S,2S,5R,6R)-6-methylbicyclo[3.1.0]hexan-2-ol:
¹H NMR (400 MHz, CDCl₃): δ 4.21 (1H, d, J=4.8 Hz), 1.88 (1H, m), 1.75–1.25 (4H, m), 1.15 (1H, m), 1.07 (1H, m), 0.96 (3H, d, J=6.0 Hz), 0.41 (1H, m).

Step D: Preparation of (1S,5R)-6-methylbicyclo[3.1.0]hexan-2-one

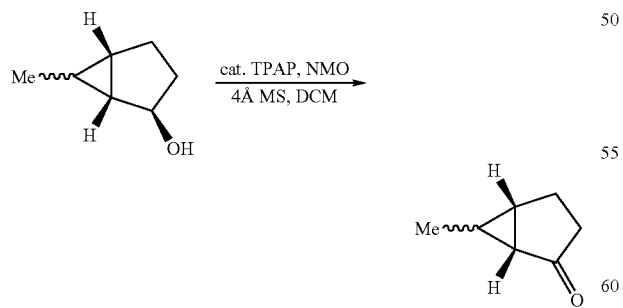

The oxidation of (1S,2S,5R,6S)-6-methylbicyclo[3.1.0]hexan-2-ol/(1S,2S,5R,6R)-6-methylbicyclo[3.1.0]hexan-2-ol (658 mg, 5.87 mmol) was performed as described previously in Example 9.1, Step B to give (1S,5R)-6-methylbicyclo[3.1.0]hexan-2-one. The spectral data was identical to that of (±)-(1S,5R)-6-methylbicyclo[3.1.0]hexan-2-one (as shown previously).

Step E: Preparation of (1R,1aR,5aS)-1-methyl-1a,2,5,5a-tetrahydro-1H-2,3-diaza-cyclopropa[a]pentalene-4-carboxylic acid ethyl ester and (1S,1aR,5aS)-1-methyl-1a,2,5,5a-tetrahydro-1H-2,3-diaza-cyclopropa[a]pentalene-4-carboxylic acid ethyl ester

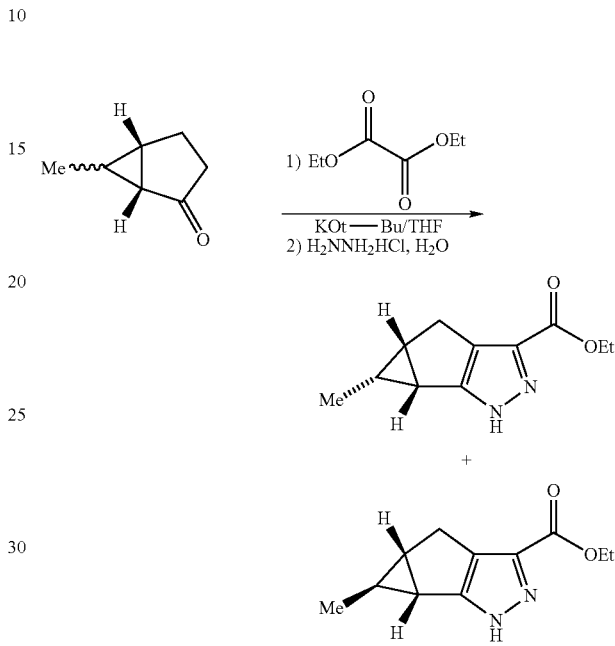

The preparation of the enantiopure endo-methyl pyrazole derivative and exo-methyl pyrazole derivative was performed as described previously in Example 9.1, Step C (for racemic variants). Separation of the isomers was performed by reverse-phase HPLC: Phenomenex® Luna C18 column (10μ, 250×100 mm), 5% (v/v) CH₃CN (containing 1% v/v TFA) in H₂O (containing 1% v/v TFA) gradient to 50% H₂O, 60 ml/min, λ=254 nm to give the endo-methyl-pyrazole followed by the exo-methyl-pyrazole.

Step F: Preparation of (1R,1aR,5aS)-1-methyl-1a,2,5,5a-tetrahydro-1H-2,3-diaza-cyclopropa[a]pentalene-4-carboxylic acid

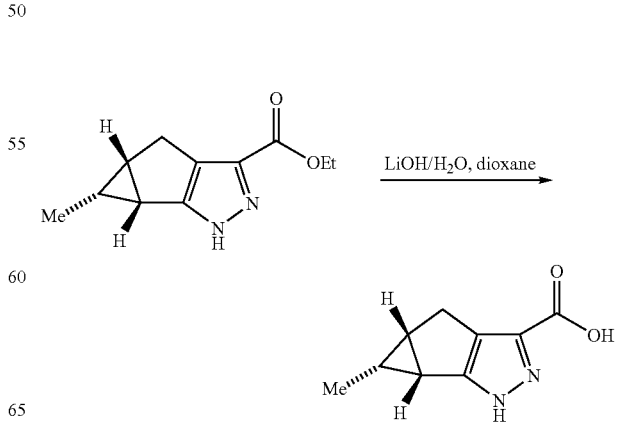

The ester hydrolysis was performed as shown previously in Example 9.3 to give the corresponding acid $[\alpha]^{25}_D$+67.6 (c 0.524, MeOH). Spectral data were identical to the racemic material.

Step G: Preparation of (1S,1aR,5aS)-methyl-1a,2,5,5a-tetrahydro-1H-2,3-diaza-cyclopropa[a]pentalene-4-carboxylic acid

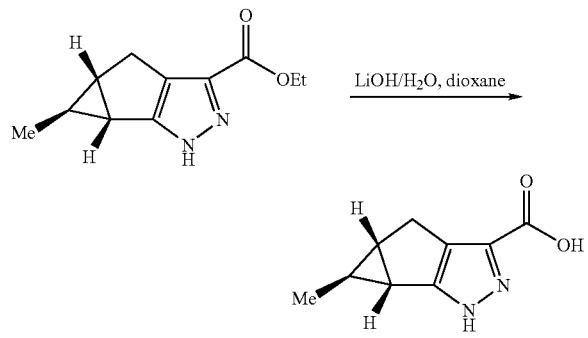

The ester hydrolysis was performed as shown previously in Example 9.3 to give the corresponding acid. Spectral data were identical to the racemic material.

Example 9.55

Preparation of (−)-endo-1-methyl-1a,2,5,5a-tetrahydro-1H-2,3-diaza-cyclopropa[a]pentalene-4-carboxylic acid and exo-1-methyl-1a,2,5,5a-tetrahydro-1H-2,3-diaza-cyclopropa[a]pentalene-4-carboxylic acid

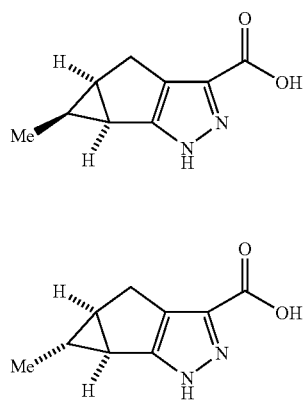

The above compounds were prepared as pure enantiomers by the identical synthetic route as described previously in Example 9.3 using (S)-5-(chloromethyl)dihydrofuran-2(3H)-one as the starting lactone (see Movassaghi, M.; Jacobsen, E. N. *J. Am. Chem. Soc.* 2002, 124, 245 for preparation). Rotation data for endo-methyl compound: $[\alpha]^{25}_D$−93.0 (c 0.552, MeOH).

Example 9.56

Preparation of endo-1-ethyl-1a,2,5,5a-tetrahydro-1H-2,3-diaza-cyclopropa[a]pentalene-4-carboxylic acid and exo-1-ethyl-1a,2,5,5a-tetrahydro-1H-2,3-diaza-cyclopropa[a]pentalene-4-carboxylic acid Step A: Preparation of (R)-4-(hex-3-ynyl)-2,2-dimethyl-1,3-dioxolane

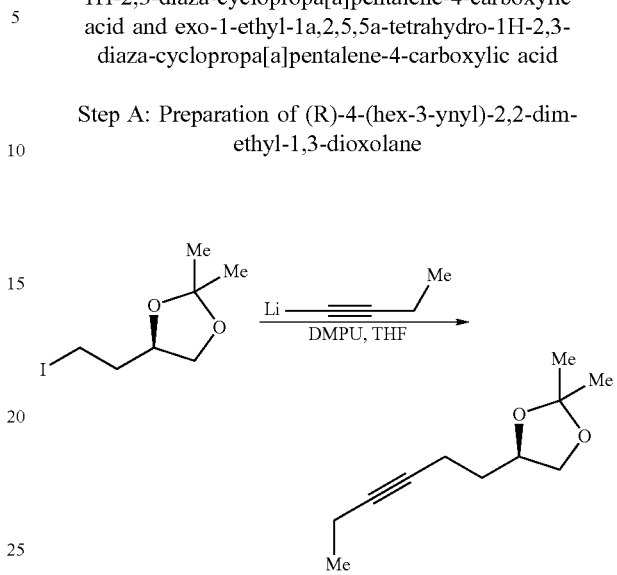

To a flask cooled to −78° C. under $N_2$ was added 2-butyne gas via syringe needle until approximately ~3 mL of liquid had condensed in the flask. THF (120 mL) was then added followed by DMPU (18.9 ml, 156 mmol). The flask was purged with $N_2$ and n-butyllithium (2.5M hexanes, 18.7 ml, 46.9 mmol) was added via syringe over 5 min and stirred for an additional 15 min at which time (R)-4-(2-iodoethyl)-2,2-dimethyl-1,3-dioxolane (10.0 g, 39.1 mmol) was added as a solution in THF (30 mL) [preparation of enantiopure (R)-4-(2-iodoethyl)-2,2-dimethyl-1,3-dioxolane from commercially available (R)-2-(2,2-dimethyl-1,3-dioxolan-4-yl)ethanol was performed using the procedure described by: Taber. D. F.; Xu, M.; Hartnett, J. C. *J. Am. Chem. Soc.* 2002, 124, 13121]. The reaction was slowly warmed to rt and stirred a total of 3 h. The mixture was quenched with sat. $NH_4Cl$, and extracted with $Et_2O$ (2×). The organics were washed with $H_2O$, and brine, dried over $MgSO_4$, filtered, and concentrated. The material was purified by silica gel chromatography (5% EtOAc in hexanes gradient to 15% EtOAc in hexanes) to give (R)-4-(hex-3-ynyl)-2,2-dimethyl-1,3-dioxolane as a clear oil. $^1$H NMR (400 MHz, CDCl$_3$): δ 4.19 (1H, m), 4.08 (1H, dd, J=8.0, 6.0 Hz), 3.58 (1H, dd, J=7.6, 6.8 Hz), 2.26 (2H, m), 2.15 (2H, qt, J=5.2, 2.4 Hz), 1.81 (1H, m), 1.68 (1H, m), 1.40 (3H, s), 1.36 (3H,s), 1.11 (3H, t, J=7.6 Hz).

Step B: Preparation of (R,Z)-4-(hex-3-enyl)-2,2-dimethyl-1,3-dioxolane

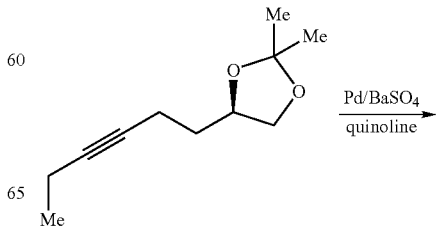

-continued

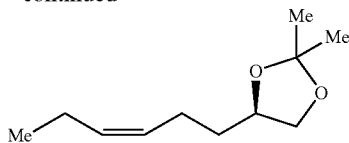

To a solution of (R)-4-(hex-3-ynyl)-2,2-dimethyl-1,3-dioxolane (6.49 g, 35.6 mmol) in hexanes (100 mL) was added 5% palladium on BaSO$_4$ (1.14 g), and quinoline (freshly distilled from Zn dust, 0.631 ml, 5.34 mmol). The flask was then purged with H$_2$ and stirred under an H$_2$ atmosphere for 2 h. The reaction mixture was filtered through celite and washed sequentially with 1N HCl (2×) and brine. The organics were dried over MgSO$_4$, filtered, and concentrated to give (R,Z)-4-(hex-3-enyl)-2,2-dimethyl-1,3-dioxolane which was used without further purification. This material contained approximately 7% of the trans olefin isomer which was carried through the synthetic route as a mixture (data not shown for minor isomer) eventually producing the corresponding exo-ethyl pyrazole acid derivative after separation by reverse phase HPLC (vide infra). $^1$H NMR (400 MHz, CDCl$_3$): δ 5.40 (1H, m), 5.31 (1H, m), 4.06 (2H, m), 3.52 (1H, t, J=4.8 Hz), 2.09 (4H, m), 1.71 (1H, m), 1.54 (1H, m), 1.41 (3H, s), 1.35 (3H, s), 0.96 (3H, t, J=Hz).

Step C: Preparation of (R,Z)-oct-5-ene-1,2-diol

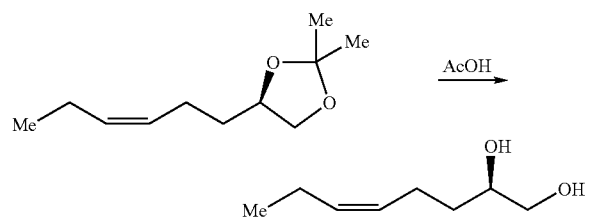

(R,Z)-4-(hex-3-enyl)-2,2-dimethyl-1,3-dioxolane (5.95 g, 32.3 mmol) was stirred in 80% aq. AcOH (50 mL) for 20 h. The mixture was concentrated in vacuo and purified by silica gel chromatography (40% EtOAc in hexanes gradient to 70% EtOAc in hexanes) to give (R,Z)-oct-5-ene-1,2-diol as a clear oil. $^1$H NMR (400 MHz, CDCl$_3$): δ 5.45 (1H, m), 5.36 (1H, m), 3.75 (1H, m), 3.67 (1H, dd, J=10.8, 2.8 Hz), 3.45 (1H, dd, J=11.2, 7.6 Hz), 2.16 (2H, m), 2.04 (2H, m), 1.50 (2H, m), 0.96 (3H, t, J=7.6 Hz).

Step D: Preparation of (R,Z)-2-(hex-3-enyl)oxirane

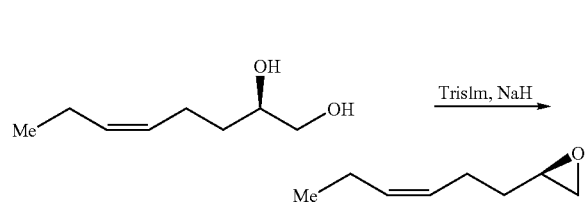

To a solution of (R,Z)-oct-5-ene-1,2-diol (8.50 g, 58.9 mmol) in THF (230 mL) at 0° C. was added NaH (60% dispersion in mineral oil, 7.06 g, 177 mmol) (7.06 g as dispersion). The mixture was warmed to ambient temperature and stirred for 40 min. The reaction was cooled to 0° C. and triisopropylbenzenesulfonyl chloride (20.7 g, 61.8 mmol) was added. The reaction was warmed to room temp, stirred for 1 h, quenched with H$_2$O and extracted with Et$_2$O. The organics were washed with brine, dried over MgSO$_4$, filtered, and concentrated. Purification by silica gel chromatography (2% Et$_2$O in pentane gradient to 8% Et$_2$O in pentane) gave (R,Z)-2-(hex-3-enyl)oxirane. It was determined that slight racemization occurred at this step (98% ee to 84% ee). In order to ensure optical purity the enantioenriched product was further resolved using Jacobsen's hydrolytic kinetic resolution (HKR, Step E). $^1$H NMR (400 MHz, CDCl$_3$): δ 5.41 (1H, m), 5.35 (1H, m), 2.93 (1H, m), 2.75 (1H, dd, J=5.2, 4.4 Hz), 2.49 (1H, dd, J=5,2, 2.8 Hz), 2.20 (2H, q, J=6.8 Hz), 2.06 (2H, quin, 7.6 Hz), 1.59 (2H, m), 0.97 (3H, t, J=7.6 Hz).

Step E: Preparation of (R,Z)-2-(hex-3-enyl)oxirane

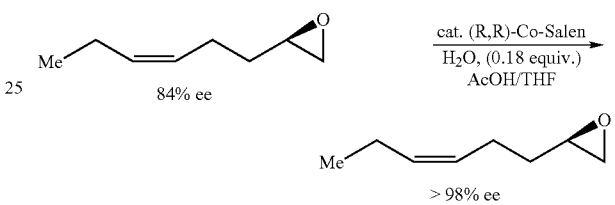

To a flask containing enantioenriched (R,Z)-2-(hex-3-enyl)oxirane (5.04 g, 39.9 mmol) and THF (0.4 mL) at 0° C. was added sequentially (R,R)—Co-Salen catalyst (150 mg, 0.248 mmol), AcOH (60.0 mg, 1.00 mmol), and H$_2$O (130 mg, 7.22 mmol). The mixture was warmed to rt and stirred for 20 h. Purification by silica gel chromatography (2% Et$_2$O in pentane gradient to 10% Et$_2$O in pentane) gave enantiopure (R,Z)-2-(hex-3-enyl)oxirane.

Step F: Preparation of (1S,2S,5R,6S)-6-ethylbicyclo[3.1.0]hexan-2-ol

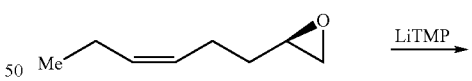

The intramolecular cyclopropanation of (R,Z)-2-(hex-3-enyl)oxirane (3.00 g, 23.8 mmol) was performed as described previously in Example 9. 1, Step A to give (1S,2S,5R,6S)-6-ethylbicyclo[3.1.0]hexan-2-ol as a clear oil. $^1$H NMR (400 MHz, CDCl$_3$): δ 4.18 (1H, m), 2.08 (1H, m), 1.79–1.51 (4H, m), 1.40 (2H, m), 1.20 (2H, m), 0.96 (3H, t, J=7.6 Hz), 0.74 (1H, m).

Step G: Preparation of (1S,5R,6S)-6-ethylbicyclo[3.1.0]hexan-2-one

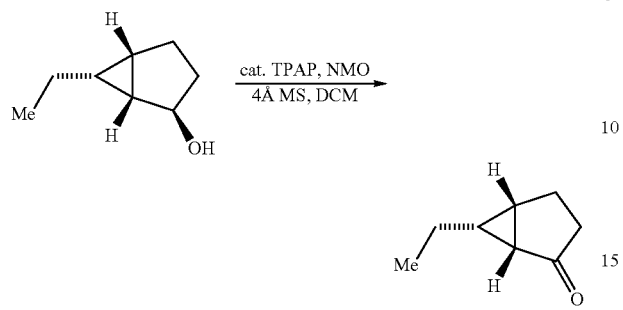

The oxidation of (1S,2S,5R,6S)-6-ethylbicyclo[3.1.0]hexan-2-ol (1.75 g, 13.9 mmol) was performed as described previously in Example 9.1, Step B to give (1S,5R,6S)-6-ethyl-bicyclo[3.1.0]hexan-2-one as a clear oil. The spectral data were identical to (±)-(1S,5R,6S)-6-ethylbicyclo[3.1.0]hexan-2-one.

Step H: Preparation of (1R,1aR,5aS)-1-ethyl-1a,2,5,5a-tetrahydro-1H-2,3-diaza-cyclopropa[a]pentalene-4-carboxylic acid

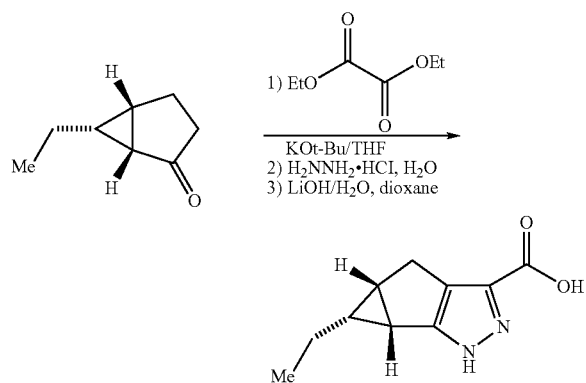

The preparation of enantiopure endo-ethyl pyrazole derivative from the corresponding ketone was performed in a similar fashion to that of the racemic endo-ethyl pyrazole compound, in Example 9.54, Steps E and F. The spectral data were identical.

Step I: Preparation of (1S,1aR,5aS)-1-ethyl-1a,2,5,5a-tetrahydro-1H-2,3-diaza-cyclopropa[a]pentalene-4-carboxylic acid

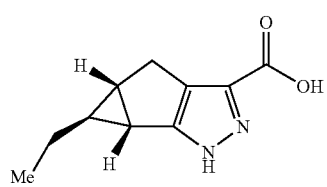

The enantiopure exo-ethyl pyrazole derivative was isolated by rev. phase HPLC as a minor impurity from the above synthetic route.

Example 9.57

Preparation of (±)-endo-1-methylsulfanylmethyl-1a,2,5,5a-tetrahydro-1H-2,3-diaza-cyclopropa[a]pentalene-4-carboxylic acid

Step A: Preparation of (±)-endo-spiro[bicyclo[3.1.0]hexane-2,2'-[1,3]dioxolane]-ylmethyl methanesulfonate

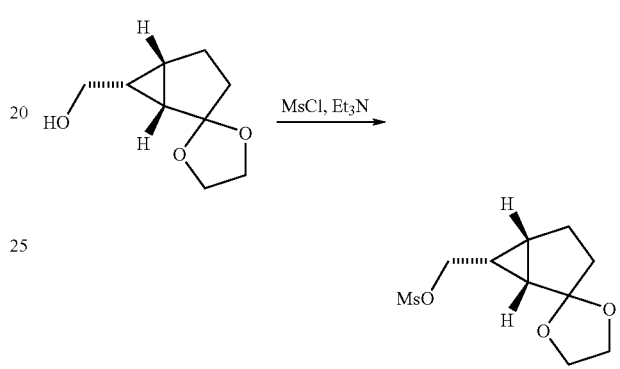

To a solution of (±)-endo-spiro[bicyclo[3.1.0]hexane-2,2'-[1,3]dioxolane]-6-ylmethanol (350 mg, 2.06 mmol) in DCM (12 mL) under $N_2$ was added $Et_3N$ (561 µl, 4.11 mmol). The flask was cooled to 0° C. and methanesulfonyl chloride (318 µl, 4.11 mmol) was added drop wise. After stirring for 5 min the flask was warmed to rt and stirred for 1 h (reaction near completion by TLC). The DCM was evaporated and the mixture was quenched with $H_2O$. The mixture was extracted with EtOAc (2×) and the combined extracts were dried over $MgSO_4$, filtered, and concentrated to give (±)-(1R,5R,6S)-spiro[bicyclo[3.1.0]hexane-2,2'-[1,3]dioxolane]-6-ylmethyl methanesulfonate. $^1H$ NMR (400 MHz, $CDCl_3$): δ 4.63 (1H, dd, J=11.2, 6.3 Hz), 4.34 (1H, dd, J=11.2, 9.3 Hz), 4.01–3.85 (4H, m), 3.04 (3H, s), 2.11 (2H, m), 1.89 (1H, m), 1.78 (1H, m), 1.70 (1H, m), 1.63 (1H, m), 1.35 (1H, m). The material was used immediately in the next reaction without further purification.

Step B: Preparation of (±)-endo-6-(methylthiomethyl)spiro[bicyclo[3.1.0]hexane-2,2'-[1,3]dioxolane]

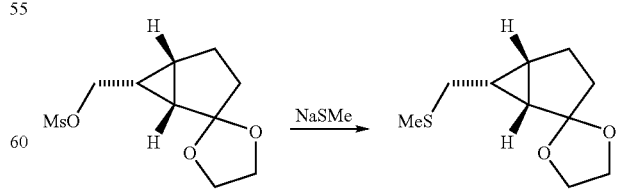

To a solution of crude (±)-endo-spiro[bicyclo[3.1.0]hexane-2,2'-[1,3]dioxolane]-6-ylmethyl methanesulfonate (250 mg, 1.01 mmol) in DMF (5.0 mL) was added sodium thiomethoxide (176 mg, 2.52 mmol). The solution became quite viscous initially and was stirred at rt overnight. The mixture was partitioned between EtOAc and H₂O. The layers were separated and the aqueous phase was back-extracted with EtOAc. The combined organics were dried over MgSO₄, filtered, and concentrated. Purification by silica gel chromatography (3% EtOAc in hexanes gradient to 12% EtOAc in hexanes) gave (±)-endo-6-(methylthiomethyl)spiro-[bicycle[3.1.0]hexane-2,2'-[1,3]dioxolane] as a clear oil. ¹H NMR (400 MHz, CDCl₃): δ 3.99–3.87 (4H, m), 2.87 (1H, dd, J=13.5, 5.4 Hz), 2.54 (1H, dd, J=13.4, 8.8 Hz), 2.19 (3H,s), 2.14–1.96 (2H, m), 1.80 (1H, m), 1.68–1.53 (3H, m), 1.18 (1H, qd, J=8.6, 5.4 Hz).

Step C: Preparation of (±)-endo-6-methylthiomethyl)-bicyclo[3.1.0]hexan-2-one

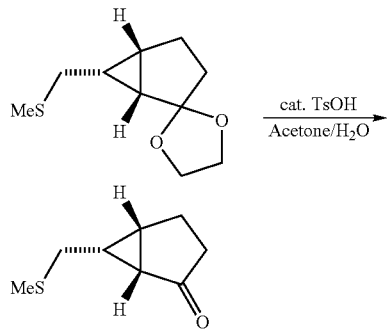

To a solution of (±)-endo-6-(methylthiomethyl)spiro[bicyclo[3.1.0]hexane-2,2'-[1,3]dioxolane] (190 mg, 0.949 mmol) in Acetone/H₂O (4:1, 5 mL) was added p-toluenesulfonic acid monohydrate (9.02 mg, 47.4 μmol). Stirred at rt for 2 h. Concentrated in vacuo to remove acetone. Extracted w/EtOAc (2×) and washed organics with brine. Dried over MgSO₄, filtered, and concentrated to give (±)-endo-6-methylsulfanylmethyl-bicyclo[3.1.0]hexan-2-one as a clear oil. ¹H NMR (400 MHz, CDCl₃): δ 2.63 (1H, dd, J=13.6, 6.5 Hz), 2.53 (1H, dd, J=13.6 8.6 Hz), 2.32 (2H, m), 2.24 (1H, m), 2.17 (3H, s), 1.99 (3H, m), 1.75 (1H, m).

Step D: Preparation of (±)-endo-1-(methylthiomethyl)-1a,2,5,5a-tetrahydro-1H-2,3-diaza-cyclopropa[a]pentalene-4-carboxylic acid ethyl ester

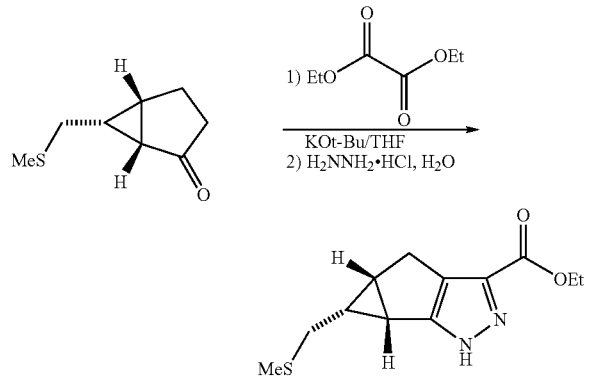

(±)-endo-6-(methylthiomethyl)bicyclo[3.1.0]hexan-2-one (52.0 mg, 0.333 mmol) was converted to the corresponding endo-1-methylsulfanylmethyl-1a,2,5,5a-tetrahydro-1H-2,3-diaza-cyclopropa[a]pentalene-4-carboxylic acid ethyl ester as described previously in Example 9.1, Step C. ¹H NMR (400 MHz, CDCl₃): δ 11.2–9.4 (1H, bs), 4.34 (2H, m), 2.96 (1H, dd, J=17.7, 6.8 Hz), 2.75 (1H, d, J=17.7 Hz), 2.50(1H, m), 2.32(1H, m), 2.15 (2H, m), 2.08 (3H, s), 1.57 (1H, m), 1.37 (3H, t, J=7.1 Hz). HPLC/MS: Alltech® Prevail C18 column (5 μ, 50×4.6 mm), 5% v/v CH₃CN (containing 1% v/v TFA) in H₂O (containing 1% v/v TFA) gradient to 99% v/v CH₃CN in H₂O, 3.5 mL/min, t$_r$=2.29 min, ESI⁺=253.3 (M+H).

Step E: Preparation of (±)-endo-1-(methylthiomethyl)-1a,2,5,5a-tetrahydro-1H-2,3-diaza-cyclopropa[a]pentalene-4-carboxylic acid

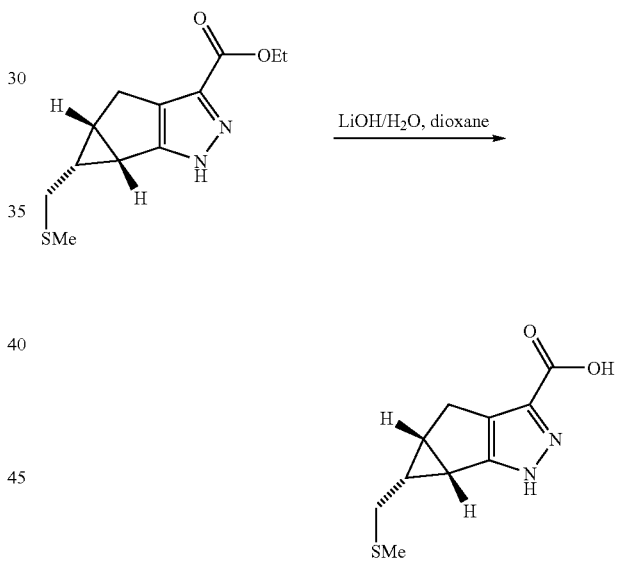

The ester hydrolysis of endo-1-(methylthiomethyl)-1a,2,5,5a-tetrahydro-1H-2,3-diaza-cyclopropa[a]pentalene-4-carboxylic acid ethyl ester (34.0 mg, 0.135 mmol) was performed as described previously in Example 9.3 to give endo-1-(methylthiomethyl)-1a,2,5,5a-tetrahydro-1H-2,3-diaza-cyclopropa[a]pentalene-4-carboxylic acid as a white solid after lyophilization. ¹H NMR (400 MHz, d₆-DMSO): δ 13.6–12.1 (1H, bs), 2.82 (1 H, dd, J=17.4, 6.8 Hz), 2.57 (1H, d, J=17.4 Hz), 2.40 (1H, m), 2.23 (1H, m), 2.08 (1H, dd, J=13.4, 7.1 Hz), 1.99 (4H,m), 1.48 (1H, m). HPLC/MS: Alltech® Prevail C18 column (5 μ, 50×4.6 mm), 5% v/v CH₃CN (containing 1% v/v TFA) in H₂O (containing 1% v/v TFA) gradient to 99% v/v CH₃CN in H₂O, 3.5 mL/min, t$_r$=1.59 min, ESI⁺=225.3 (M+H).

Example 9.58

Preparation of (±)-exo-1-ethoxymenthyl-1a,2,5,5a-tetrahydro-1H-2,3-diaza-cyclopropa[a]pentalene-4-carboxylic acid (±)-endo-ethoxymethyl-1a,2,5,5a-tetrahydro-1H-2,3-diaza-cyclopropa[a]pentalene-4-carboxylic acid Step A: Preparation of cis and trans (±)-2-(5-thoxy-pent-3-enyl)-oxiranehexane-2,2'-[1,3]dioxolane]-ylmethyl methanesulfonate

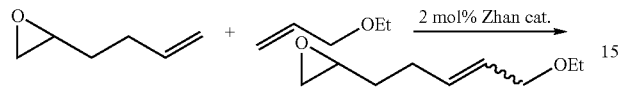

The cross metathesis of (±)-2-(but-3-enyl)oxirane (3.80 g, 38.7 mmol) with ethyl allyl ether (10.0 g, 116 mmol) was performed as described previously in Example 9.2, Step A to give (±)-2-(5-ethoxypent-3-enyl)oxirane as an inseparable mixture of olefin isomers (trans:cis=10:1) after silica gel chromatography. ¹H NMR (400 MHz, CDCl₃): trans isomer: δ 5.73 (1H, m), 5.63 (1H, m), 3.91 (2H, m), 3.48 (2H, q, J=7.0 Hz), 2.93 (1H, m), 2.75 (1H, dd, J=5.0, 2.7 Hz), 2.22 (2H, m), 1.63 (2H, m), 1.21 (3H, t, J=7.0 Hz). cis isomer: δ 5.62 (2H, m), 4.04 (2H, m), 3.48 (2H, q, J=7.0 Hz), 2.93 (1H, m), 2.75 (1H, m), 2.49 (1H, m), 2.22 (2H, m), 1.63 (2H, m), 1.22 (3H, t, J=7.0 Hz).

Step B: Preparation of (±)-exo-6-(ethoxymethyl) bicyclo[3.1.0]hexan-2-ol and (±)-endo-6-(ethoxymethyl)bicyclo[3.1.0]hexan-2-ol

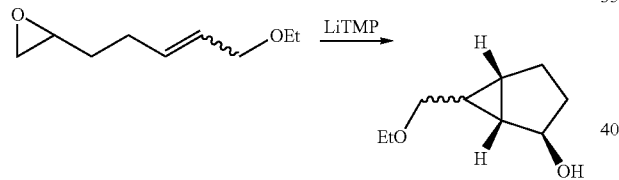

The intramolecular cyclopropanation of (±)-2-(5-ethoxypent-3-enyl)oxirane (3.34 g, 23.6 mmol) was performed as described previously in Example 9.1, Step A to give (±)-exo-6-(ethoxymethyl)-bicycle[3.1.0]hexan-2-ol/(±)-endo-6-(ethoxymethyl)bicyclo[3.1.0]hexan-2-ol (rel. ratio 10:1) as a clear oil. ¹H NMR (400 MHz, CDCl₃): δ 4.29 (1H, m), 3.47 (2H, q, J=7.1 Hz), 3.24 (2H, m), 1.94 (1H, m), 1.75 (1H, dd, J=12.6, 8.1 Hz), 1.56 (1H, m), 1.40–1.28 (4H, m), 1.20 (3H, t, J=7.1 Hz), 0.78 (1H, m).

Step C: Preparation of (±)-exo-6-(ethoxymethyl) bicyclo[3.1.0]hexan-2-one

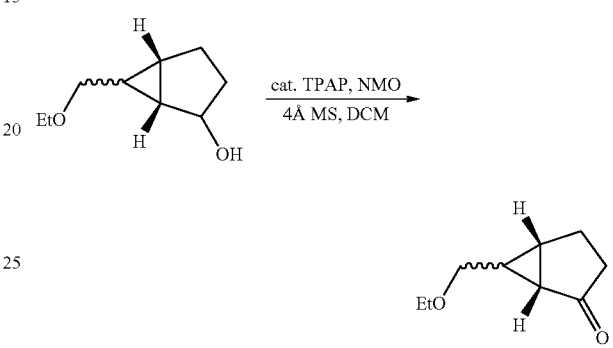

The oxidation of (±)-endo-6-(ethoxymethyl)bicyclo[3.1.0]hexan-2-ol/(±)-exo-6-(ethoxymethyl)bicyclo[3.1.0]hexan-2-ol (290 mg, 1.86 mmol) was performed as described previously in Example 9.1, Step B to give (±)-6-(ethoxymethyl)bicyclo[3.1.0]hexan-2-one as a clear oil. (exo isomer). ¹H NMR (400 MHz, CDCl₃): δ 3.46 (3H, m), (1H, dd, J=10.4, 6.7 Hz), 2.19–2.01 (5H, m), 1.70 (1H, dd, J=5.2, 2.6 Hz), 1.59 (1H, m), 1.20 (3H, t, J=7.0 Hz).

Step D: Preparation of (±)-exo-1-ethoxymethyl-1a,2,5,5a-tetrahydro-1H-2,3-diaza-cyclopropa[a]pentalene-4-carboxylic acid and (±)-endo-ethoxymethyl-1a,2,5,5a-tetrahydro-1H-2,3-diaza-cyclopropa[a]pentalene-4-carboxylic acid

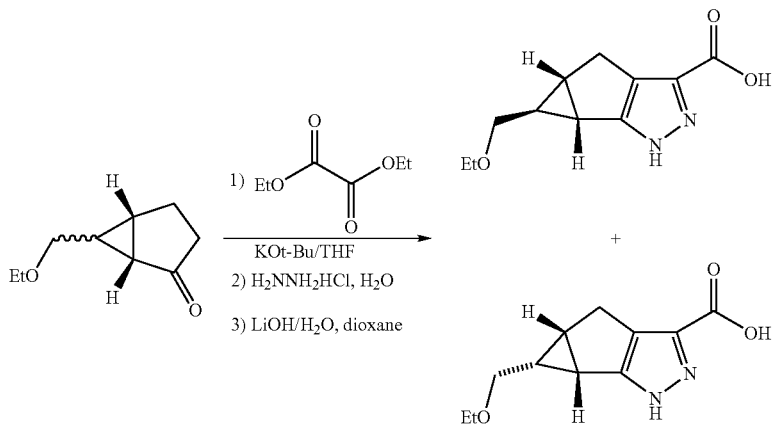

The preparation of the (±)-exo-ethoxymethyl pyrazole/(±)-endo-ethoxymethyl pyrazole acid derivatives was performed as described previously in Example 9.56, Step H. Separation of the isomers was performed by reverse-phase HPLC: Phenomenex® Luna C18 column (10 μ, 250×50 mm), 5% (v/v) CH$_3$CN (containing 1% v/v TFA) in H$_2$O (containing 1% v/v TFA) gradient to 50% H$_2$O, 60 ml/min, λ=254 nm to give the endo-methyl-pyrazole followed by the exo-methyl-pyrazole obtained as white solids after lyophilization.

(±)-exo-1-ethoxymethyl-1a,2,5,5a-tetrahydro-1H-2,3-diaza-cyclopropa[a]pentalene-4-carboxylic acid $^1$H NMR (400 MHz, CDCl$_3$): δ 13.50–12.03 (1H, bs), 3.42 (2H, q, J=7.0 Hz), 3.35 (1H, dd, J=10.5, 6.2), 3.23 (1H, dd, J=10.5, 7.3 Hz), 2.84 (1H, dd, J=16.9, 6.2 Hz), 2.69 (1H, d, J=17.0 Hz), 2.09 (1H, m), 2.03 (1H, m), 1.11 (3H, t, J=7.0 Hz), 0.83 (1H, m). HPLC/MS: Alltech® Prevail C18 column (5 μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.56 min, ESI$^+$=223.2 (M+H).

(±)-endo-1-ethoxymethyl-1a,2,5,5a-tetrahydro-1H-2,3-diaza-cyclopropa[a]pentalene-4-carboxylic acid $^1$H NMR (400 MHz, CDCl$_3$): δ 3.30–3.15 (2H, m), 3.01 (1H, dd, J=10.7, 6.8 Hz), 2.91 (1H, dd, J=10.7, 7.6 Hz), 2.80 (1H, dd, J=17.3, 6.8 Hz), 2.57 (1H, d, J=17.3 Hz), 2.35 (1H, m), 2.24 (1H, m), 1.45 1=(1H, m), 1.10 (1H, m), 1.00 (3H, t, J=7.0 Hz). HPLC/MS: Alltech® Prevail C18 column (5 μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.42 min, ESI$^+$=223.2 (M+H).

Example 9.59

Preparation of (±)-endo-1-cyclopropyl-1a,3,5,5a-tetrahydro-1H-2,3-diaza-cyclopropa[a]pentalene-4-carboxylic acid ethyl ester

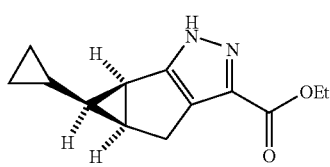

The title compound was prepared in a similar manner as described in Example 9.2, Step D. MS m/z (ES$^+$): 233.4 [M+H]$^+$, 255.4 [M+Na]$^+$; $^1$H NMR (400 MHz, CDCl$_3$): δ 4.37–4.31 (m, 2H), 2.98(dd, 1H, J$_1$=17.4 Hz, J$_2$=6.4 Hz), 2.88 (d, 1H, J=17.4 Hz), 2.37–2.34 (m, 1H), 2.24–2.18 (m, 1H), 1.37 (t, 3H, J=7.2 Hz), 0.74(q, 1H, J=8.4 Hz), 0.49–0.43(m, 1H), 0.32–0.25 (m, 1H), 0.24–0.17 (m, 2H), −0.02−−0.12 (m, 1H).

Example 9.60

Preparation of (±)-endo-1-cyclopropyl-1a,3,5,5a-tetrahydro-1H-2,3-diaza-cyclopropa[a]pentalene-4-carboxylic acid

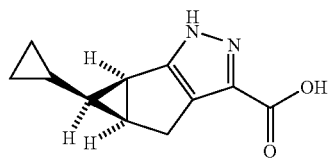

The title compound was prepared in a similar manner as described in Example 9.3. MS m/z (ES$^+$): 205.3 [M+H]$^+$; $^1$H NMR (400 MHz, CDCl$_3$): δ 3.06(dd, 1H, J$_1$=18.9 Hz, J$_2$=5.9 Hz), 2.99 (d, 1H, J=18.7 Hz), 2.43(t, 1H, J=8.2 Hz), 2.05(q, 1H, J=6.1 Hz), 0.85(q, 1h, J=8.3 Hz), 0.55–0.50 (m, 1H), 0.41–0.36 (m, 1H), 0.29–0.21(m, 2H), 0.08–0.00 (m, 1H).

Example 9.61

Preparation of (±)-endo-1-cyclopropyl-4-(2H-tetrazol-5-yl)-1a,3,5,5a-tetrahydro-1H-2,3-diaza-cyclopropa[a]pentalene Step A: Preparation of (±)-endo-1-cyclopropyl-1a,3,5,5a-tetrahydro-1H-2,3-diaza-cyclopropa[a]pentalene-4-carboxylic acid amide

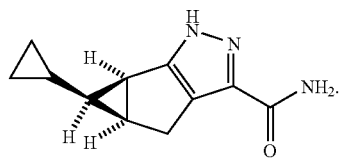

The title compound was prepared in a similar manner as described in Example 9.1, Step D. MS m/z (ES$^+$): 204.5 [M+H]$^+$, 226.4 [M+Na]$^+$; $^1$H NMR (400 MHz, CD$_3$OD): δ 2.99(dd, 1H, J$_1$=16.7 Hz, J$_2$=5.9 Hz), 2.93 (d, 1H, J=16.6 Hz), 2.37–2.29 (m, 2H), 0.80 (q, 1H, J=8.2 Hz), 0.54–0.48 (m, 1H), 0.33–0.25 (m, 2H), 0.22–0.18 (m, 1H), 0.01−−0.05 (m, 1H).

Step B: Preparation of (±)-endo-1-cyclopropyl-1a,3,5,5a-tetrahydro-1H-2,3-diaza-cyclopropa[a]pentalene-4-carbonitrile

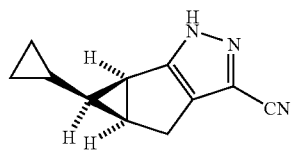

The title compound was prepared in a similar manner as described in Example 9.2, Step F. MS m/z (ES$^+$): 186.1 [M+H]$^+$, 371.2 [2M+H]$^+$; $^1$H NMR (400 MHz, CD$_3$OD): δ 2.96 (dd, 1H, J$_1$=16.5 Hz, J$_2$=6.2 Hz), 2.86 (d, 1H, J=16.4 Hz), 2.41–2.35 (m, 2H), 0.87(q, 1H, J=8.2 Hz), 0.57–0.52 (m, 1H), 0.34–0.27 (m, 2H), 0.22–0.18 (m, 1H), −0.02−−0.11 (m, 1H).

Step C: Preparation of (±)-endo-1-cyclopropyl-4-(2H-tetrazol-5-yl)-1a,3,5,5a-tetrahydro-1H-2,3-diaza-cyclopropa[a]pentalene

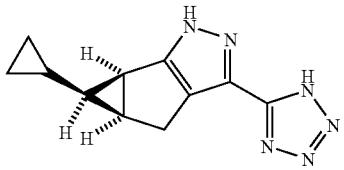

The title compound was prepared in a similar manner as described in Example 9.2, Step G. MS m/z (ES+): 229.3 [M+H]+, 251.2 [M+Na]+; ¹H NMR (400 MHz, CD₃OD): δ 2.99 (dd, 2H, J₁=16.7 Hz, J₂=6.0 Hz), 2.92 (d, 1H, J=16.7 Hz), 2.36–2.29 (m, 2H), 0.80 (q, 1H, J=8.3 Hz), 0.53–0.47 (m, 1H), 0.32–0.24 (m, 2H), 0.21–0.17(m, 1H), 0.01–-0.07 (m, 1H).

Example 9.62

Preparation of (±)-exo-1-vinyl-1a,3,5,5a-tetrahydro-1H-2,3-diaza-cyclopropa[a]pentalene-4-carboxylic acid ethyl ester

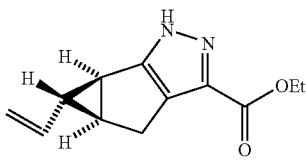

The title compound was prepared in a similar manner as described in Example 9.2, Step D. MS m/z (ES+): 219.3 [M+H]+, 241.1 [M+Na]+; ¹H NMR (400 MHz, CDCl₃): δ 5.53–5.44 (m, 1H), 5.04 (dd, 1H, J₁=17.1 Hz, J₂=1.0 Hz), 4.94(dd, 1H, J₁=10.34 Hz, J₂=1.4 Hz), 4.33 (q, 2H, J=7.2 Hz), 3.02 (dd, 1H, J₁=17.3 Hz, J₂=6.1 Hz), 2.90 (d, 1H, J=17.3 Hz), 2.34–2.30 (m, 1H), 2.21–2.17 (m, 1H), 1.35 (t, 3H, J=7.2 Hz), 1.33–1.29 (m, 1H).

Example 9.63

Preparation of (±)-exo-1-vinyl-1a,3,5,5a-tetrahydro-1H-2,3-diaza-cyclopropa[a]pentalene-4-carboxylic acid

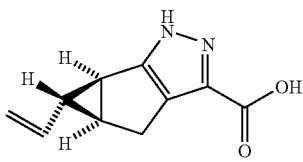

The title compound was prepared in a similar manner as described in Example 9.3. MS m/z (ES+): 191.3 [M+H]+; ¹H NMR (400 MHz, DMSO-d₆): δ 5.57–5.48 (m, 1H), 5.13(dd, 1H, J₁=17.1 Hz, J₂=1.6 Hz), 4.97(dd, 1H, J1=10.3 Hz, J2=1.7 Hz), 2.98 (dd, 1H, J₁=18.2 Hz, J₂=6.3 Hz), 2.80(d, 1H, J=18.2 Hz), 2.36 (dd, 1H, J₁=6.1 Hz, J₂=2.6 Hz), 2.07–2.03 (m, 1H), 1.37 (dt, 1H, J₁=8.8 Hz, J₂=3.1 Hz).

Example 9.64

Preparation of (±)-exo-4-(2H-tetrazol-5-yl)-1-vinyl-1a,3,5,5a-tetrahydro-1H-2,3-diaza-cyclopropa[a]pentalene

Step A: Preparation of (±)-exo-1-vinyl-1a,3,5,5a-tetrahydro-1H-2,3-diaza-cyclopropa[a]pentalene-4-carboxylic acid amide

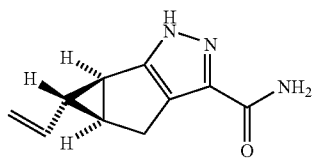

The title compound was prepared in a similar manner as described in Example 9.1, Step D. MS m/z (ES+): 190.3 [M+H]+, 379.2 [2M+H]+; ¹H NMR (400 MHz, DMSO d₆): δ 5.58–5.49(m, 1H), 5.09 (dd, 1H, J₁=17.1 Hz, J₂=1.6 Hz), 4.94 (dd, 1H, J₁=10.3 Hz, J₂=1.6 Hz), 2.94 (dd, 1H, J₁=17.1 Hz, J₂=6.1 Hz), 2.78 (d, 1H, J=17.1 Hz), 2.29 (dd, 1H, J₁=5.8 Hz, J₂=2.1 Hz), 2.25–2.21 (m, 1 H), 1.26–1.23 (m, 1H).

Step B: Preparation of (±)-exo-1-vinyl-1a,3,5,5a-tetrahydro-1H-2,3-diaza-cyclopropa[a]pentalene-4-carbonitrile

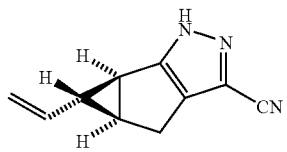

The title compound was prepared in a similar manner as described in Example 9.2, Step F. MS m/z (ES+): 172.3 [M+H]+, 343.1 [2M+H]+; ¹H NMR (400 MHz, CDCl₃): δ 5.52–5.43 (m, 1H), 5.09 (dd, 1H, J₁=17.0 Hz, J₂=0.6 Hz), 5.00 (dd, 1H, J₁=10.3 Hz, J₂=1.2 Hz), 2.99 (dd, 1H, J1=16.7 Hz, J2=6.3 Hz), 2.88 (d, 1H, J=16.7 Hz), 2.34–2.28 (m, 2H), 1.39–1.36 (m, 1H).

Step C: Preparation of (±)-exo-4-(2H-tetrazol-5-yl)-1-vinyl-1a,3,5,5a-tetrahydro-1H-2,3-diaza-cyclopropa[a]pentalene

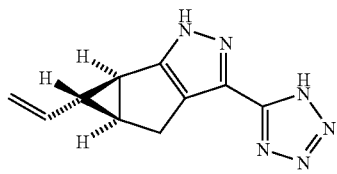

The title compound was prepared in a similar manner as described in Example 9.2, Step G. MS m/z (ES+): 215.3 [M+H]+, 429.4 [2M+H]+; ¹H NMR (400 MHz, CD₃OD): δ 5.62–5.53 (m, 1H), 5.12 (d, 1H, J=17.1 Hz), 4.99 (d, 1H, J=10.4 Hz), 3.14–3.08 (m, 1H), 3.02 (d, 1H, J=16.5 Hz), 2.38 (s, 1H), 2.07–2.04 (m, 1H), 1.42–1.39 (m, 1H).

Example 9.65

Preparation of (±)-1-spirocyclopropyl-1a,3,5,5a-tetrahydro-1H-2,3-diaza-cyclopropa[a]pentalene-4-carboxylic acid ethyl ester

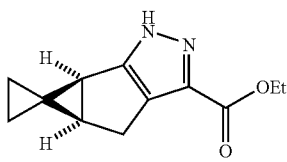

The title compound was prepared in a similar manner as described in Example 9.2, Step D. MS m/z (ES+): 219.4 [M+H]+, 241.2 [M+Na]+; ¹H NMR (400 MHz, CDCl₃): δ 4.37–4.31(m, 2H), 2.97 (dd, 1H, J₁=17.0 Hz, J₂=6.1 Hz), 2.70 (d, 1H, J=17.0 Hz), 2.58 (d, 1H, J=5.5 Hz), 2.52 (t, 1H, J=5.8 Hz), 1.37 (t, 3H, J=7.1 Hz), 1.07–1.02 (m, 1H), 0.98–0.93(m, 1H), 0.53–0.46 (m, 2H).

Example 9.66

Preparation of (±)-1-spirocyclopropyl-1a,3,5,5a-tetrahydro-1H-2,3-diaza-cyclopropa[a]pentalene-4-carboxylic acid

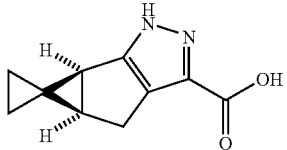

The title compound was prepared in a similar manner as described in Example 9.3. MS m/z (ES+): 191.3 [M+H]+, 213.2 [M+Na]+; ¹H NMR (400 MHz, CD₃OD): δ 3.03 (dd, 1H, J₁=18.1 Hz, J₂=6.1 Hz), 2.78 (d, 1H, J=17.8 Hz), 2.63 (d, 1H, J=5.7 Hz), 2.34 (t, 1H, J=5.7 Hz), 1.12–1.03 (m, 2H), 0.68–0.63 (m, 1H), 0.54–0.49 (m, 1H).

Example 9.67

Preparation of (±)-1-spirocyclopropyl-4-(2H-tetrazol-5-yl)-1a,3,5,5a-tetrahydro-1H-2,3-diaza-cyclopropa[a]pentalene Step A: Preparation of (±)-1-spirocyclopropyl-1a,3,5,5a-tetrahydro-1H-2,3-diaza-cyclopropa[a]pentalene-4-carboxylic acid amide

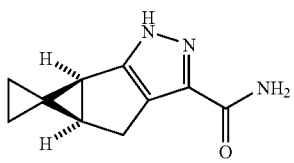

The title compound was prepared in a similar manner as described in Example 9.1, Step D. MS m/z (ES+): 190.2 [M+H]+, 379.3 [2M+H]+; ¹H NMR (400 MHz, DMSO-d₆): δ 2.90 (dd, 1H, J₁=16.2 Hz, J₂=5.4 Hz), 2.66 (d, 1H, J=16.4 Hz), 2.54 (2H, overlapped with DMSO), 1.07–1.03(m, 1H), 0.99–0.95 (m, 1H), 0.55–0.50 (m, 1H), 0.39–0.34 (m, 1H).

Step B: Preparation of (±)-1-spirocyclopropyl-1a,3,5,5a-tetrahydro-1H-2,3-diaza-cyclopropa[a]pentalene-4-carbonitrile

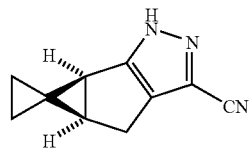

The title compound was prepared in a similar manner as described in Example 9.2, Step F. MS m/z (ES+): 172.3 [M+H]+, 343.4 [2M+H]+; ¹H NMR (400 MHz, CDCl₃): δ 2.93 (dt, 1H, J₁=16.4 Hz, J₂=3.0 Hz), 2.68 (d, 1H, J=16.3 Hz), 2.61 (d, 2H, J=3.0 Hz), 1.12–1.08 (m, 1H), 1.02–0.98 (m, 1H), 0.57–0.53 (m, 1H), 0.51–0.46 (m, 1H).

Step C: Preparation of (±)-1-spirocyclopropyl-4-(2H-tetrazol-5-yl)-1a,3,5,5a-tetrahydro-1H-2,3-diaza-cyclopropa[a]pentalene

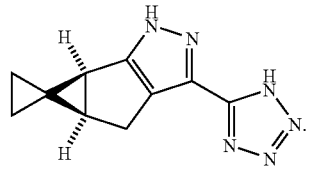

The title compound was prepared in a similar manner as described in Example 9.2, Step G. MS m/z (ES+): 215.2 [M+H]+, 429.2 [2M+H]+; ¹H NMR (400 MHz, MeOD): δ 3.06 (dd, 1H, J₁=16.1 Hz, J₂=6.1 Hz), 2.85 (d, 1H, J=16.1 Hz), 2.68 (t, 1H, J=5.8 Hz), 2.64 (d, 1H, J=5.4 Hz), 1.11 (quintet, 1H, J=4.4 Hz), 1.03 (q, 1H, J=4.0 Hz), 0.61 (q, 1H, J=4.6 Hz), 0.49 (q, 1H, J=4.3 Hz).

Example 9.68

Preparation of (±)-endo-1-propenyl-1a,3,5,5a-tetrahydro-1H-2,3-diaza-cyclopropa[a]pentalene-4-carboxylic acid ethyl ester

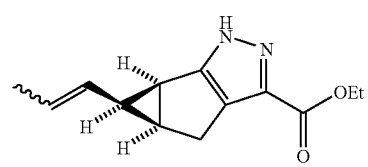

The title compound was prepared in a similar manner as described in Example 9.2, Step D. MS m/z (ES+): 233.4 [M+H]+, 255.3 [M+Na]+;

Example 9.69

Preparation of (±)-endo-1-propenyl-1a,3,5,5a-tetrahydro-1H-2,3diaza-cyclopropa[a]pentalene-4-carboxylic acid

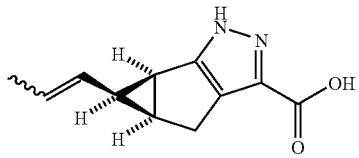

The title compound was prepared in a similar manner as described in Example 9.3. MS m/z (ES+): 205.2 [M+H]+;

Example 9.70

Preparation of (±)-endo-1-propenyl-4-(2H-tetrazol-5-yl)-1a,3,5,5a-tetrahydro-1H-2,3-diaza-cyclopropa[a]pentalene Step A: Preparation of (±)-endo-1-propenyl-1a,3,5,5a-tetrahydro-1H-2,3-diaza-cyclopropa[a]pentalene-4-carboxylic acid amide

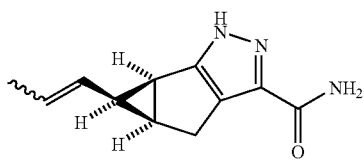

The title compound was prepared in a similar manner as described in Example 9.2, Step E. MS m/z (ES+): 204.1 [M+H]+;

Step B: Preparation of (±)-endo-1-propenyl-1a,3,5,5a-tetrahydro-1H-2,3-diaza-cyclopropa[a]pentalene-4-carbonitrile

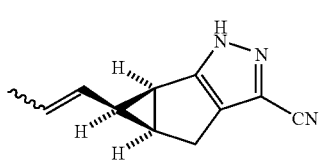

The title compound was prepared in a similar manner as described in Example 9.2, Step F. MS m/z (ES+): 186.1 [M+H]+, 371.1 [2M+H]+;

Step C: Preparation of (±)-endo-1-propenyl-4-(2H-tetrazol-5-yl)-1a,3,5,5a-tetrahydro-1H-2,3-diaza-cyclopropa[a]pentalene

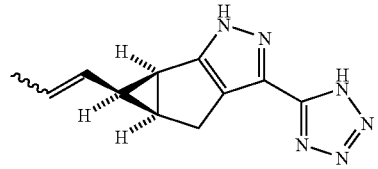

The title compound was prepared as an isomeric mixture (1.7:1) in a similar manner as described in Example 9.2, Step G. MS m/z (ES+): 229.4 [M+H]+, 457.3 [2M+H]+; Major isomer: $^1$H NMR (400 MHz, MeOD): δ 5.59–5.51 (m, 1H), 4.69–4.62 (m, 1H), 3.02 (dd, 1H, $J_1$=6.5 Hz, $J_2$=4.0 Hz), 2.78 (d, 1H, J=16.5 Hz), 2.64–2.55 (m, 2H), 2.15 (q, 1H, J=8.0 Hz), 1.76 (dd, 3H, $J_1$=6.8 Hz, $J_2$=1.6 Hz). Minor isomer: $^1$H NMR (400 MHz, MeOD): δ 5.79–5.71 (m, 1H), 4.75–4.69 (m, 1H), 3.06 (dd, 1H, $J_1$=6.5 Hz, $J_2$=4.0 Hz), 2.83 (d, 1H, J=15.5 Hz), 2.58–2.49 (m, 2H), 2.00 (q, 1H, J=8.0 Hz), 1.55 (dd, 3H, $J_1$=6.5 Hz, $J_2$=1.5 Hz).

Example 9.71

Preparation of 1-methoxymethyl-1a,2,5,5a-tetrahydro-1H-2,3-diaza-cyclopropa[a]pentalene-4-carboxylic acid Step A: Preparation of spiro[bicyclo[3.1.0]hexane-2,2'-[1,3]dioxolane]-6-ylmethanol

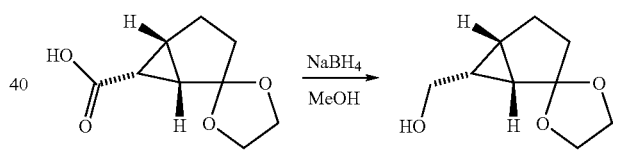

NaBH$_4$ (90 mg, 2.38 mmol) was dissolved in MeOH (2 mL) and added drop wise to a solution of aldehyde (400 mg, 2.38 mmol) dissolved in MeOH (8 mL). Reaction was stirred at ambient temperature for 10 min and then quenched with 10% NaOH. The mixture was extracted with ether, dried over MgSO$_4$, and concentrated in vacuo. The residue was purified by column chromatography (50% EtOAc/n-hexane/silica) to give 200 mg of the title compound. $^1$H NMR (400 MHz, CDCl$_3$): δ 4.07–3.88 (5H, m), 3.64 (1H, ddd, J=12.5, 10.4, 2.2 Hz), 2.79 (1H, dd, J=11.0, 2.2 Hz), 2.18–2.05 (2H, m), 1.82–1.60 (4H, m), 1.40–1.30 (1H, m).

Step B: Preparation of 6-endo-(methoxymethyl) spiro[bicyclo[3.1.0]hexane-2,2'-[1,3]dioxolane]

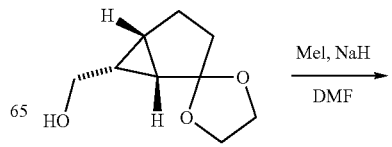

-continued

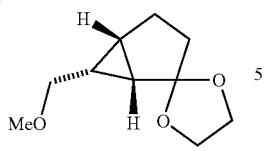

The title compound was prepared in a similar manner as described in Example 9.52, Step B. ¹H NMR (400 MHz, CDCl₃): δ 4.00–3.82 (4H, m), 3.77 (1H, dd, J=10.5, 5.4), 3.44 (1H, dd, J=10.5, 8.5 Hz), 3.40 (3H, s), 2.16–2.04 (1H, m), 2.04–1.96 (1H, m) 1.87–1.79 (1H, m), 1.72–1.65 (1H, m), 1.64–1.54 (2H, m), 1.28–1.15 (1H, m).

Step C: Preparation of 6-endo-methoxymethyl-bicyclo[3.1.0]hexan-2-one

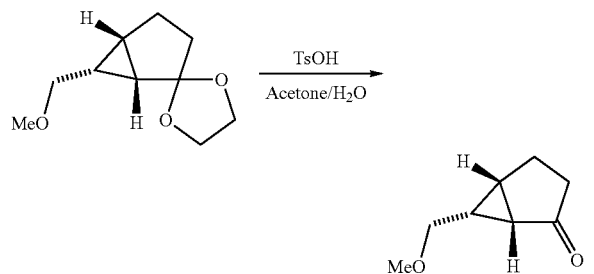

The title compound was prepared in a similar manner as described in Example 9.15. ¹H NMR (400 MHz, CDCl₃): δ 3.55 (1H, dd, J=10.8, 6.4 Hz), 3.45 (1H, dd, J=10.8, 8.5 Hz), 3.37 (3H, s), 2.36–2.23 (3H, m), 2.05–1.98 (3H, m), 1.82–1.73 (1H, m).

Step D: Preparation of 1-endo-methoxymethyl-1a,2,5,5a-tetrahydro-1H-2,3-diaza-cyclopropa[a]pentalene-4-carboxylic acid ethyl ester

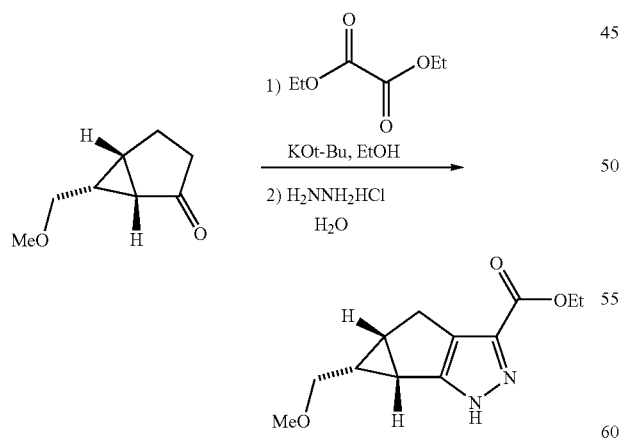

The title compound was prepared in a similar manner as described in Example 9.51, Step D. HPLC/MS: Alltech® Prevail C18 column (5µ, 50×4.6 mm), 5% v/v CH₃CN (containing 1% v/v TFA) in H₂O (containing 1% v/v TFA) gradient to 99% v/v CH₃CN in H₂O, 3.5 mL/min, t_r=1.84 min, ESI⁺=236.9 (M+H).

Step E: Preparation of 1-endo-methoxymethyl-1a,2,5,5a-tetrahydro-1H-2,3-diaza-cyclopropa[a]pentalene-4-carboxylic acid

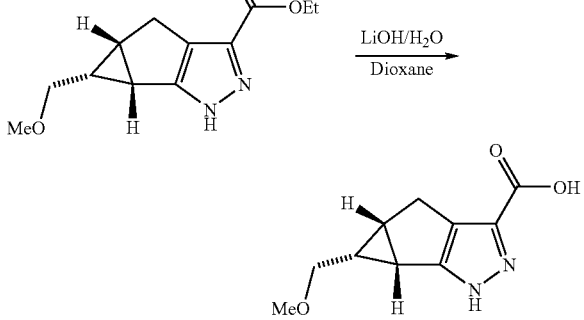

To a solution of ester (0.090 g, 0.38 mmol) in dioxane was added 1M aq. lithium hydroxide (1.0 ml, 1.0 mmol). The solution was stirred overnight at ambient temperature and made acidic by the addition of 1 N HCl. The mixture was concentrated and purified by reverse-phase HPLC: Phenomenex® Luna C18 column (10µ, 250×21.2 mm), 5% (v/v) CH₃CN (containing 1% v/v TFA) in H₂O (containing 1% v/v TFA) gradient to 95% H₂O, 20 ml/min, λ=214 nm to give the title compound as a white solid after lyophilization. HPLC/MS: Alltech® Prevail C18 column (5µ, 50×4.6 mm), 5% v/v CH₃CN (containing 1% v/v TFA) in H₂O (containing 1% v/v TFA) gradient to 99% v/v CH₃CN in H₂O, 3.5 mL/min, t_r=1.17 min, ESI⁺=209.1 (M+H).

Example 9.72

Preparation of 1-endo-methoxymethyl-4-(1H-tetrazol-5-yl)-1a,2,5,5a-tetrahydro-1H-2,3-diaza-cyclopropa[a]pentalene

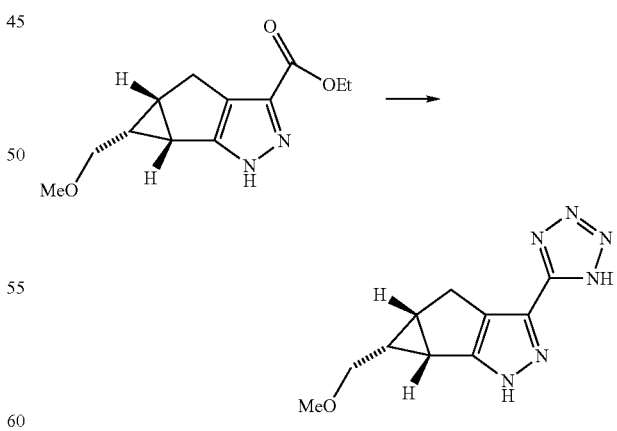

The title compound was prepared in a similar manner as described in Example 9.2, Steps E, F, and G. HPLC/MS: Alltech® Prevail C18 column (5µ, 50×4.6 mm), 5% v/v CH₃CN (containing 1% v/v TFA) in H₂O (containing 1% v/v ThA) gradient to 99% v/v CH₃CN in H₂O, 3.5 mL/min, t_r=1.27 min, ESI⁺=233.0 (M+H).

Example 9.73

Preparation of 1-endo-phenoxymethyl-1a,2,5,5a-tetrahydro-1H-2,3-diaza-cyclopropa[a]pentalene-4-carboxylic acid

Step A: Preparation of 6-endo-(phenoxymethyl)spiro[bicyclo[3.1.0]hexane-2,2'-[1,3]dioxolane]

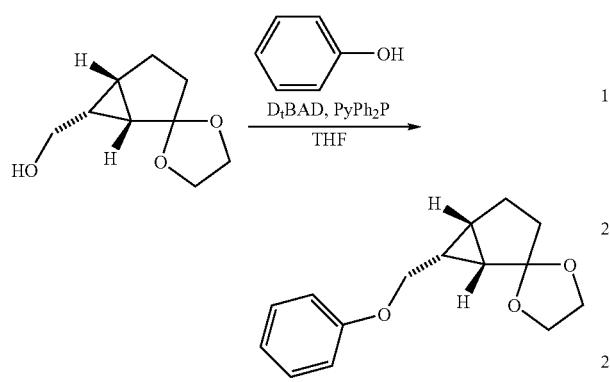

The alcohol (170 mg, 1.0 mmol), phenol (141.2 mg, 1.5 mmol), PyPh₂P (395 mg, 1.5 mmol), and D$_t$BAD (345 mg, 1.5 mmol) were dissolved in THF (5 mL) and stirred at ambient temperature overnight. 1N HCl was added to the reaction mixture and was extracted with ether (3×). The combined organic layers were washed with brine, dried over MgSO₄, and concentrated. The residue was purified by column chromatography (0–25% EtOAc/n-hexane/silica) to give the title compound. ¹H NMR (400 MHz, CDCl₃): δ 7.31–7.25 (2H, m), 6.99–6.92 (3H, m), 4.41 (1H, dd, J=10.6, 5.2 Hz), 4.03–3.89 (5H, m), 2.18–2.08 (1H, m), 2.08–1.99 (1H, m), 1.92–1.84 (1H, m), 1.81–1.75 (1H, m), 1.70–1.63 (1H, m), 1.63–1.56 (1H, m), 1.44–1.35 (1H, m).

Step B: Preparation of 6-endo-phenoxymethyl-bicyclo[3.1.0]hexan-2-one

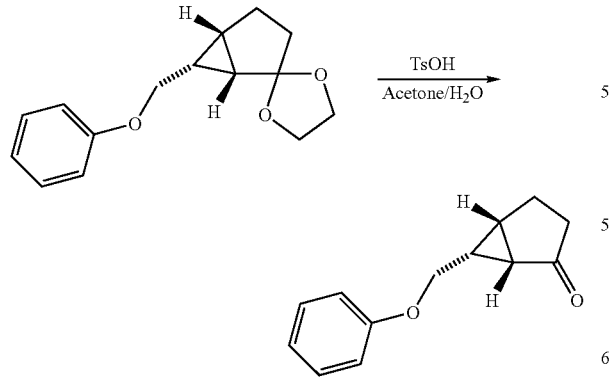

The title compound was prepared in a similar manner as described in Example 9.15 ¹H NMR (400 MHz, CDCl₃): δ 7.32–7.25 (2H, m), 7.00–6.94 (1H, m), 6.92–6.88 (2H, m), 4.19 (1H, dd, J=10.6, 6.1 Hz), 3.96 (1H, dd, J=10.6, 8.9 Hz), 2.38–2.32 (3H, m), 2.13–1.94 (4H, m).

Step C: Preparation of 1-endo-phenoxymethyl-1a,2,5,5a-tetrahydro-1H-2,3-diaza-cyclopropa[a]pentalene-4-carboxylic acid ethyl ester

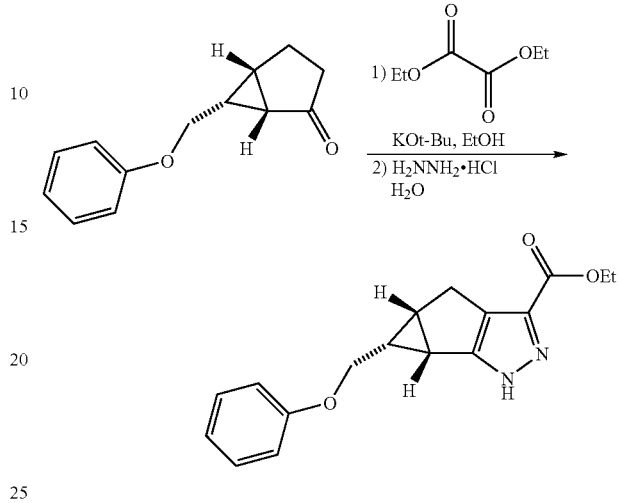

The title compound was prepared in a similar manner as described in Example 9.51, Step D. ¹H NMR (400 MHz, CDCl₃): δ 7.27–7.21 (2H, m), 6.91 (1H, t, J=7.3 Hz), 6.83–6.79 (2H, m), 4.39–4.25 (2H, m), 3.88–3.82 (1H, m), 3.48 (1H, dd, J=10.4, 8.3 Hz), 3.02 (1H, dd, J=17.8, 6.8 Hz), 2.84 (1H, d, 17.8 Hz), 2.61–2.56 (1H, m), 2.50–2.43 (1H, m), 1.85–1.76 (1H, m), 1.35 (3H, t, J=7.1 Hz). HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, t$_r$=2.56 min, ESI⁺=299.1 (M+H).

Step D: Preparation of 1-endo-phenoxymethyl-1a,2,5,5a-tetrahydro-1H-2,3-diaza-cyclopropa[a]pentalene-4-carboxylic acid (Compound _)

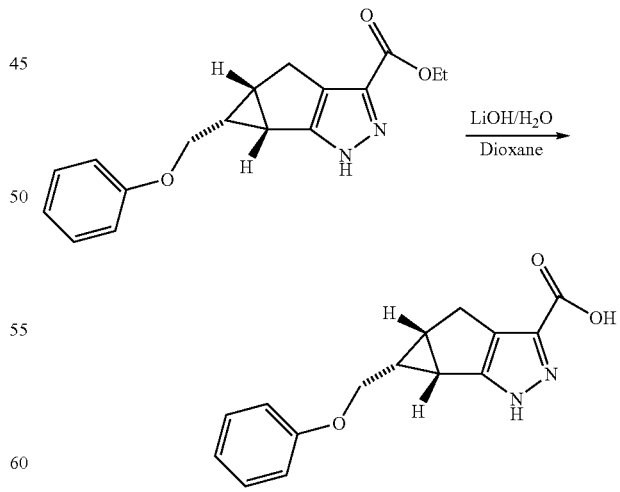

To a solution of ester (0.025 g, 0.084 mmol) in dioxane was added 1M aq. Lithium hydroxide (0.23 ml, 0.23 mmol). The solution was stirred at 60° C. for 3 hr and made acidic by the addition of 1N HCl. The mixture was concentrated and purified by reverse-phase HPLC: Phenomenex® Luna C18 column (10μ, 250×21.2 mm), 5% (v/v) CH₃CN (containing 1% v/v TFA) in H₂O (containing 1% v/v TFA) gradient to 95% H₂O, 20 ml/rnin, λ=214 nm to give the title compound as a white solid after lyophilization. HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=2.01 min, ESI⁺=271.0 (M+H).

Example 9.74

Preparation of 1-endo-phenoxymethyl-4-(1H-tetrazol-5-yl)-1a,2,5,5a-tetrahydro-1H-2,3-diaza-cyclopropa[a]pentalene

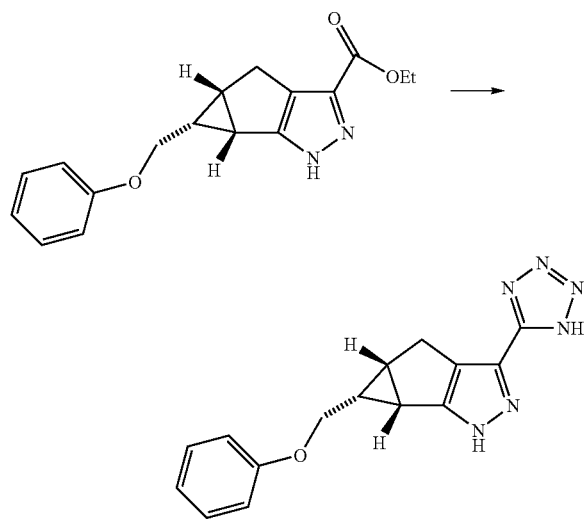

The title compound was prepared in a similar manner as described in Example 9.2, Steps E, F, and G. HPLC/MS: Alltech® Prevail C18 column (5μ, 50×4.6 mm), 5% v/v CH₃CN (containing 1% v/v TFA) in H₂O (containing 1% v/v TFA) gradient to 99% v/v CH₃CN in H₂O, 3.5 mL/min, $t_r$=1.96 min, ESI⁺=295.3 (M+H).

Example 9.75

Preparation of 1-exo-methylsulfanylmethyl-1a,2,5,5a-tetrahydro-1H-2,3-diaza-cyclopropa[a]pentalene-4-carboxylic acid Step A: Preparation of 2-(5-methylsulfanyl-pent-3-enyl)oxirane

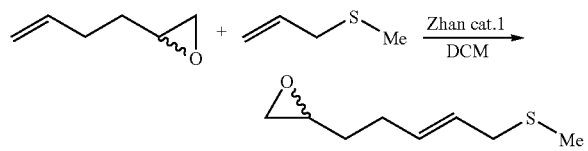

Epoxide (5.57 g, 56.7 mmol) and Allyl methyl sulfide (1.000 g, 11.3 mmol) were stirred at 20° C. for 24 hr with Zhan catalyst 1 (MW=661.07, 0.150 g, 0.23 mmol, ex ZannanPharma). Solvent was removed under reduced pressure. The residual oil was purified by column chromatography (0–10% EtOAc/n-hexane/silica) to give the title compound as an oil. ¹H NMR (400 MHz, CDCl₃): δ 5.60–5.43 (2H, m), 3.07 (2H, d, J=7.2 Hz), 2.96–2.91 (1H, m), 2.78–2.74 (1H, m), 2.49 (1H, dd, J=5.0, 2.7 Hz), 2.28–2.19 (2H, m), 2.02 (3H, s), 1.70–1.57 (2H, m).

Step B: Preparation of (±)-exo-6-methylsulfanylmethyl-bicyclo[3.1.0]hexan-2-ol

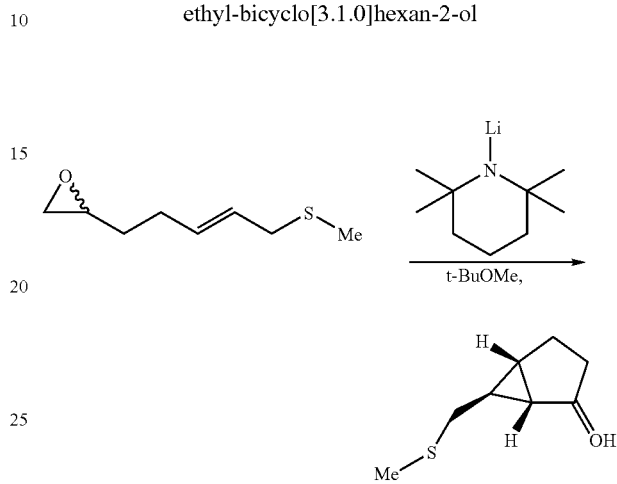

The title compound was prepared in a similar manner as described in Example 9.51, Step B. ¹H NMR (400 MHz, CDCl₃): δ 4.28 (1H, t, J=5.0 Hz), 2.41 (2H, d, J=7.0 Hz), 2.14 (3H, s), 2.00–1.89 (1H, m), 1.75 (1H, dd, 12.7, 8.1 Hz), 1.58 (1H, dd, J=14.6, 8.6 Hz), 1.40–1.28 (4H, m), 0.72–0.66 (1H, m).

Step C: Preparation of (±)-6-exo-methylsulfanylmethyl-bicyclo[3.1.0]hexan-2-one

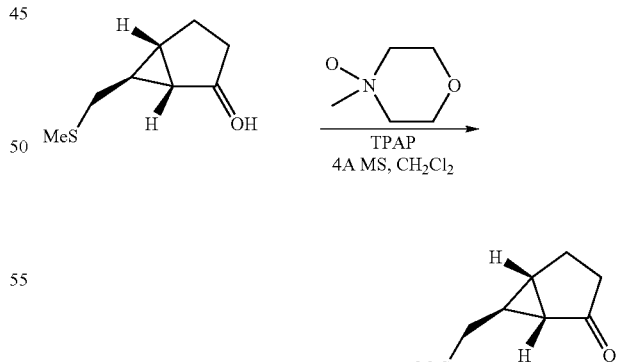

The title compound was prepared in a similar manner as described in Example 9.51, Step C. ¹H NMR (400 MHz, CDCl₃): δ 2.65 (1H, dd, J=13.5, 5.8 Hz), 2.38 (1H, dd, J=13.5, 7.7 Hz), 2.18 (3H, s), 2.16–2.03 (4H, m), 2.00 (1H, dd, J=9.1, 5.1 Hz), 1.78 1H, dd, J=5.3, 2.5 Hz), 1.56–1.51 (1H, m).-

Step D: Preparation of (±)-1-exo-methylsulfanylm-
ethyl-1a,2,5,5a-tetrahydro-1H-2,3-diaza-cyclopropa
[a]pentalene-4-carboxylic acid ethyl ester

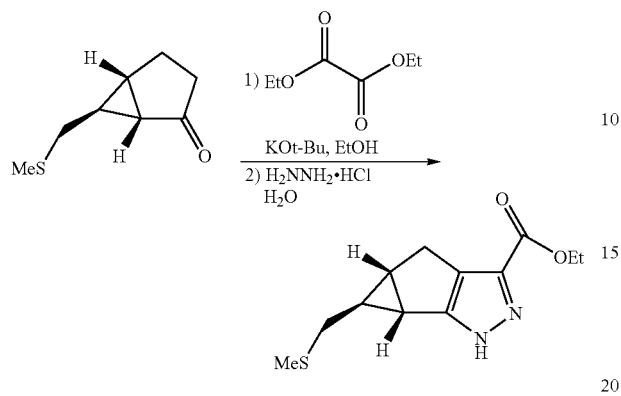

The title compound was prepared in a similar manner as described in Example 9.51, Step D. HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.35 min, ESI$^+$=253.1 (M+H).

Step E: Preparation of (±)-endo-1-methylsulfanylm-
ethyl-1a,2,5,5a-tetrahydro-1H-2,3-diaza-cyclopropa
[a]pentalene-4-carboxylic acid

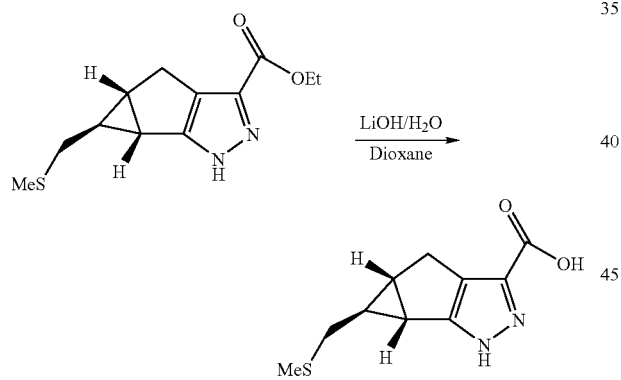

To a solution of ester (40 mg, 159 mmol) in dioxane was added 1M aq. lithium hydroxide (428 μl, 428 μmol). The solution was stirred at ambient temp overnight and made acidic by the addition of 1N HCl. The mixture was concentrated and purified by reverse-phase HPLC: Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 ml/min, λ=214 nm to give the title compound as a white solid after lyophilization. $^1$H NMR (400 MHz, CD$_3$OD): δ 2.94 (1H, dd, J=16.9, 5.9 Hz), 2.82 (1H, d, 16.8 Hz), 2.53 (2H, d, J=7.0 Hz), 2.14 (3H, s), 2.16–2.08 (2H, m), 0.92–0.86 (1H, m). HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.64 min, ESI$^+$=225.2 (M+H).

Example 9.76

Preparation of (±)-Spiro[1a,3,5,5a-tetrahydro-1H-2,
3-diaza-cyclopropa[a]pentalene-1,1'-cyclopentan]-4-
carboxylic acid Step A: Preparation of (±)-Spiro-[bicyclo[3.1.0]
hexane-6-1'-cyclopentan]-2-ol

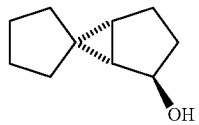

The title compound was prepared in a similar manner as described in Example 9.2, Steps A & B. $^1$H NMR (CDCl$_3$): δ 4.11 (d, 1H, J=4.8), 2.05–1.98(m, 1H), 1.69–1.46(m, 8H),1.40–1.26 (m, 5H).

Step B: Preparation of (±)-Spiro-[bicyclo[3.1.0]
hexane-6-1'-cyclopentan]-2-one

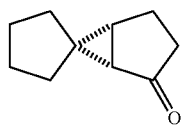

The title compound was prepared in a similar manner as described in Example 9.2, Step C. $^1$H NMR (CDCl$_3$): δ 2.23–2.11 (m, 2H), 2.02–1.90 (m, 3H), 1.77–1.73(m, 3H), 1.70–1.50 (m, 5H), 1.48–1.24 (m, 1H).

Step C: Preparation of (±)-Spiro[1a,3,5,5a-tetrahy-
dro-1H-2,3-diaza-cyclopropa[a]pentalene-1,1'-cyclo-
pentan]-4-carboxylic acid ethyl ester

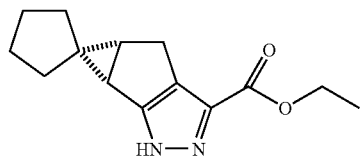

The title compound was prepared in a similar manner as described in Example 9.2, Step D. MS: m/z (ES$^+$): 247 [M+H]$^+$, 201 [M–OEt]$^+$ Step D: Preparation of (±)-Spiro[1a,3,5,5a-tetrahy-
dro-1H-2,3-diaza-cyclopropa[a]pentalene-1,1'-cyclo-
pentan]carboxylic acid

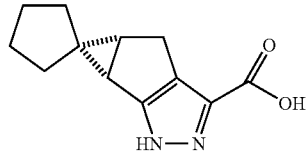

The title compound was prepared in a similar manner as described in Example 9.3. MS: m/z (ES$^{30}$): 219 [M+H]$^+$, 201 [M–OH]$^+$. $^1$H NMR (CD$_3$OD): δ 2.94 (dd, 1H, J$_1$=17.1, J$_2$=2.1), 2.72 (d, 1H, J=17.1, 2.17 (s, 2H), 1.78–1.53 (m, 6H), 1.34–1.24 (m, 1H), 0.94–0.84 (m, 1H).

Example 9.77

Preparation of (±)-5-(Spiro-[1a,3,5,5a-tetrahydro-1H-2,3-diaza-cyclopropa[a]pentalene-1,1'-cyclopentan]-4-yl)-1H-tetrazole

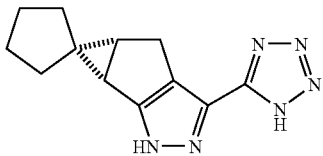

The title compound was prepared in a similar manner as described in Example 9.44. MS: m/z (ES+): 243 [M+H]+, 215 [M−N$_2$+H]+. $^1$H NMR (CD$_3$OD): δ 2.88 (dd, 1H, J$_1$=12.3 J$_2$=6.1), 2.72 (d, 1H, J=16.6), 2.18–2.07 (m, 2H), 1.63–1.40 (m, 6H), 1.28–1.13 (m, 1H), 0.83–0.71 (m, 1H).

Example 9.78

Preparation of (±)-Spiro[1a,3,5,5a-tetrahydro-1H-2,3-diaza-cyclopropa[a]pentalene-1,1'-cyclohexan]-4-carboxylic acid Step A: Preparation of (±)-Spiro-[bicyclo[3.1.0]hexane-6-1'-cyclohexan]-2-ol

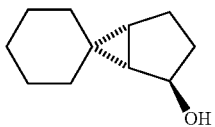

The title compound was prepared in a similar manner as described in Example 9.2, Steps A & B. $^1$H NMR (CDCl$_3$): δ 4.14 (br s, 1H), 2.05–2.00 (m, 1H), 2.0–1.1(m, 15H).

Step B: Preparation of (±)-Spiro-[bicyclo[3.1.0]hexane-6-1'-cyclohexan]-2-one

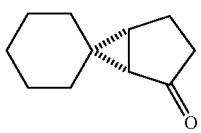

The title compound was prepared in a similar manner as described in Example 9.2, Step C. $^1$H NMR (CDCl$_3$): δ 2.39–2.28 (m, 1H), 2.28–2.14 (m, 1H), 2.10–1.99 (m, 2H), 1.97–1.82 (m, 2H), 1.64 (d, 1H, J=5.2), 1.60–1.44 (m, 7H), 1.33–1.25 (m, 2H).

Step C: Preparation of (±)-Spiro[1a,3,5,5a-tetrahydro-1H-2,3-diaza-cyclopropa[a]pentalene-1,1'-cyclohexan]-4-carboxylic acid ethyl ester

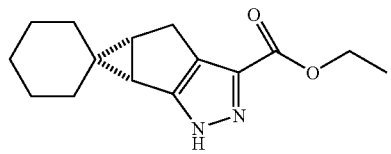

The title compound was prepared in a similar manner as described in Example 9.2, Step D. MS: m/z (ES+): 283 [M+Na]+, 261 [M+H]+, 215 [M−OEt]+. $^1$H NMR (CDCl$_3$): δ 5.30 (br s, 1H, NH), 4.41–4.27 (m, 2H), 2.89 (dd, 1H, J$_1$=17.5, J$_2$=6.9), 2.64 (d, 1H, J=17.5), 2.08 (d, 1H, J=6.1), 1.98 (t, 1H, J=6.3), 1.62–1.42 (m, 4H), 1.40–1.25 (m, 7H, including 1.36 (t, 3H, J=7.1), 1.10–0.90 (m, 2H).

Step D: Preparation of (±)-Spiro[1a,3,5,5a-tetrahydro-1H-2,3-diaza-cyclopropa[a]pentalene-1,1'-cyclohexan]-4-carboxylic acid

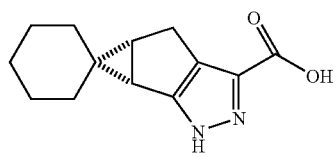

The title compound was prepared in a similar manner as described in Example 9.3. MS: m/z (ES+): 255 [M+Na]+, 233 [M+H]+. $^1$H NMR (CDCl$_3$): δ 2.70 (dd, 1H, J$_1$=18.5, J$_2$=7.0), 2.46–2.40 (m, 2H), 1.90 (d, 1H, J=6.2), 1.60 (t, 1H, J=6.5), 1.40–1.15 (m, 7H), 1.10–0.88 (m, 2H).

Example 9.79

Preparation of (±)-5-(Spiro-[1a,3,5,5a-tetrahydro-1H-2,3-diaza-cyclopropa[a]pentalene-1,1'-cyclohexan]-4-yl)-1H-tetrazole

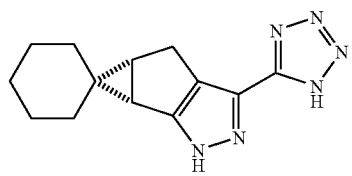

The title compound was prepared in a similar manner as described in Example 9.44. MS: m/z (ES+): 279 [M+Na]+, 257 [M+H]+, 229 [M−N$_2$+H]+. $^1$H NMR (CD$_3$OD): δ 3.20–2.90 (m, 1H), 2.75 (dd, 1H, J$_1$=16.5, J$_2$=1.0), 2.15–2.08 (m, 2H), 1.67–1.40 (m, 6H), 1.40–1.24 (m, 2H), 1.21–1.12 (m, 1H), 1.07–0.98 (m, 1H).

Example 9.80

Preparation of (±)-exo-1-allyl-1a,2,5,5a-tetrahydro-1H-2,3-diaza-cyclopropa[a]pentalene-4-carboxylic acid

Step A: Preparation of cyclobutyldiphenylsulfonium trifluoromethanesulfonate

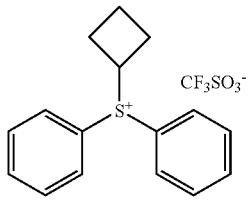

A solution of cyclobutanol (1.00 g, 13.9 mmol) in 25 ml of DCM was chilled to −20° C. and dry pyridine (1.35 ml, 16.6 mmol) added, followed by trifluoromethanesulfonic anhydride (2.33 ml, 13.9 mmol) (in 5 ml of DCM). The solution was allowed to warm to room temperature over 1 hr. Pentane (40 mL) was added and the resulting mixture shaken and filtered. The filtrate was concentrated under reduced pressure with a room temperature bath until all volatile solvents were removed. The residual oil was chilled to −20° C. and diphenylsulfane (10.2 ml, 61.0 mmol) added. The mixture was stirred at 25° C. for 20 hr, warmed to 45 ° C. for 30 minutes and cooled to room temperature. Pentane was added, the solution shaken and the resulting solid collected by vacuum filtration to give cyclobutyldiphenylsulfonium trifluoromethanesulfonate (1.82 g, 4.86 mmol, 35.0%). MS: m/z (ES$^+$): 241 [C$_{16}$H$_{17}$S]$^+$. $^1$H NMR (D$_6$-DMSO): δ 8.10 (dt, 4H, J$_1$=7.8, J$_2$=3.1), 7.84–7.72 (m, 6H), 5.90–5.78 (m, 1H), 5.15 (ddd, 2H, J$_1$=14.9, J$_2$=10.3, J$_3$=1.4), 4.48 (t, 2H, J=14.2), 2.45 (dd, 2H, J$_1$=13.8, J$_2$=7.1).

Step B: Preparation of (±)-exo-6-allyl-bicyclo[3.1.0]hexan-2-one

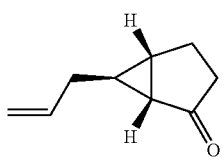

A solution of cyclobutyldiphenylsulfonium trifluoromethanesulfonate (1.820 g, 4.86 mmol) in 30 ml of THF was chilled to −78° C. and t-butyllithium, 1.7M in pentane (2.700 ml, 4.59 mmol) added dropwise. After 30 minutes, cyclopent-2-enone (0.190 ml, 2.35 mmol) in THF (3 mL) was added and the solution stirred at −78 ° C. for 2 hr. The reaction was quenched with the addition of sat. NaHCO$_3$ and warmed to room temperature. The product was extracted into DCM, solvent removed under reduced pressure and purified by column chromatography (0–20% EtOAc/n-hexane/silica) to give (±)-exo-6-allyl-bicyclo[3.1.0]hexan-2-one as a colorless oil (0.178 g, 1.31 mmol, 55.6%). Contains ca 50% (±)-endo-6-allyl-bicyclo[3.1.0]hexan-2-one $^1$H NMR (CDCl$_3$): δ 5.95–5.75 (m, 1H), 5.20–5.00 (m, 2H), 2.38–2.20 (m, 1H), 2.20–1.90 (m, 5H), 1.65–1.50 (m, 2H), 1.40–1.32 (m, 2H).

Step C: Preparation of (±)-exo-1-allyl-1a,3,5,5a-tetrahydro-1H-2,3-diaza-cyclopropa[a]pentalene-4-carboxylic acid ethyl ester

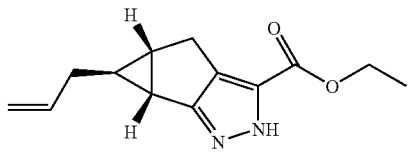

The title compound was prepared in a similar manner as described in Example 9.2, Step D. MS: m/z (ES$^+$): 255 [M+Na]$^+$, 233 [M+H]$^+$, 187 [M−OEt]$^+$. $^1$H NMR (CDCl$_3$): δ 5.91–5.81 (m, 1H), 5.02 (dd, 1H, J$_1$=17.2, J$_2$=1.6), 4.92 (dd, 1H, J$_1$=10.3, J$_2$=1.6), 4.34 (q, 2H J=7.1), 2.97 (dd, 1H, J$_1$=17.1, J$_2$=6.3), 2.86 (d, 1H, J=17.1), 2.22–2.14 (m, 2H), 2.11–2.00 (m, 2H), 1.36 (t, 3H, J=7.1), 0.80 (septet, 1H, J=3.4).

Step D: Preparation of (±)-exo-1-allyl-1a,3,5,5a-tetrahydro-1H-2,3-diaza-cyclopropa[a]pentalene-4-carboxylic acid

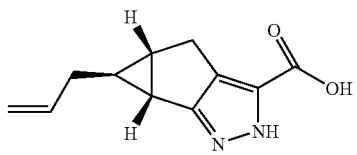

The title compound was prepared in a similar manner as described in Example 9.3. MS: m/z (ES$^+$): 227 [M+Na]$^+$, 205 [M+H]$^+$, 187 [M−OH]$^+$. $^1$H NMR (CD$_3$CN): δ 6.00–5.88 (m, 1H), 5.13 (dq, 1H, J$_1$=17.2, J$_2$=1.7), 5.03 (dq, 1H, J$_1$=10.3, J$_2$=2.1), 2.92 (dd, 1H, J$_1$=16.8, J$_2$=5.8), 2.78 (d, 1H, J=17.0), 2.3–2.0 (m, 4H), 0.71 (septet, 1H, J=3.4).

Example 9.81

Preparation of (±)-exo-1-allyl-4-(2H-tetrazol-5-yl)-1a,3,5,5a-tetrahydro-1H-2,3-diaza-cyclopropa[a]pentalene

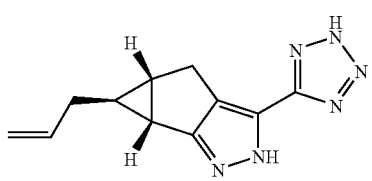

The title compound was prepared in a similar manner as described in Example 9.44. MS: m/z (ES$^+$): 251 [M+Na]$^+$, 229 [M+H]$^+$, 201 [M−N$_2$+H]$^+$. $^1$H NMR (CD$_3$CN): δ 5.98–5.84 (m, 1H, CH=CH$_2$), 5.12 (ddd, 1H, J$_1$=17.2, J$_2$=3.6, J$_3$=1.7, CH=CHH), 5.01 (d, 1H,ddd, 1H), J$_1$=10.2, J$_2$=3.3, J$_3$=1.4, CH=CHH), 2.98 (ddd 1H, J$_1$=16.3, J$_2$=4.8, J$_3$=1.6), 2.88 (d, 1H, J=16.3), 2.14–2.04 (m, 2H), 0.80 (septet, 1H, J=3.4).

Example 9.82

Preparation of (±)-endo-1-allyl-1a,2,5,5a-tetrahydro-1H-2,3-diaza-cyclopropa[a]pentalene-4-carboxylic acid Step A: Preparation of (±)-endo-1-allyl-1a,3,5,5a-tetrahydro-1H-2,3-diaza-cyclopropa[a]pentalene-4-carboxylic acid ethyl ester

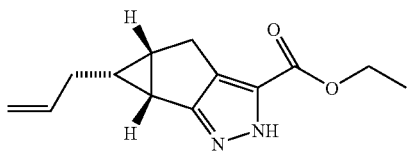

The title compound was prepared in a similar manner as described in Example 9.2, Step D using the mixture of diastereomers described in Example 9.80, Step B. MS: m/z (ES$^+$): 255 [M+Na]$^+$, 233 [M+H]$^+$, 187 [M−OEt]$^+$. $^1$H NMR (CDCl$_3$): δ 5.84–5.74 (m, 1H), 5.00 (dd, 1H, J$_1$=17.2, J$_2$=1.7), 4.95 (dd, 1H, J$_1$=10.2, J$_2$=1.5), 4.39–4.31 (m, 2H), 2.95 (dd, 1H, J$_1$=17.5, J$_2$=6.9), 2.70 (d, 1H, J=17.5), 2.44 (t, 1H, J=7.6), 2.31 (dd, 1H, J$_1$=14.5, J$_2$=6.5), 1.79–1.66 (m, 2H), 1.42–1.33 (m, 4H, including 1.37 (t, 3H, J=7.1)).

Step B: Preparation of (±)-endo-1-allyl-1a,3,5,5a-tetrahydro-1H-2,3-diaza-cyclopropa[a]pentalene-4-carboxylic acid

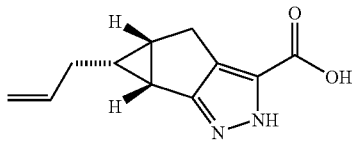

The title compound was prepared in a similar manner as described in Example 9.3. MS: m/z (ES$^+$): 227 [M+Na]$^+$, 205 [M+H]$^+$, 187 [M−OH]$^+$. $^1$H NMR (CD$_3$CN): δ 5.68–5.56 (m, 1H), 4.81 (dq, 1H, J$_1$=15.5, J$_2$=1.7),5.03 (dq, 1H, J$_1$=10.2, J$_2$=1.4), 2.68 (dd, 1H, J$_1$=17.4, J$_2$=6.8), 2.43 (d, 1H, J=17.3), 2.17–2.12 (m, 1H), 2.10–2.03 (m, 1H), 1.61–1.50 (m, 1H), 1.45–1.36 (m, 1H), 1.13 (pentet, 1H, J=7.8).

Example 9.83

Preparation of (±)-endo-1-allyl-4-(2H-tetrazol-5-yl)-1a,3,5,5a-tetrahydro-1H-2,3-diaza-cyclopropa[a]pentalene

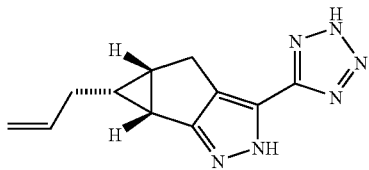

The title compound was prepared in a similar manner as described in Example 9.44 using the mixture of diastereomers described in Example 9.80, Step B. MS: m/z (ES$^+$): 251 [M+Na]$^+$, 229 [M+H]$^+$, 201 [M−N$_2$+H]$^+$. $^1$H NMR (CD$_3$CN): δ 5.77–5.68 (m, 1H), 4.92–4.80 (m, 2H), 2.88 (dd, 1H, J$_1$=16.7, J$_2$=6.8), 2.64 (d, 1H, J=16.7), 2.37–2.30 (m, 1H), 2.30–2.23 (m, 1H), 1.75–1.67 (m, 1H), 1.55–1.476 (m, 1H), 1.29 (pentet, 1H, J=7.9).

Example 9.84

Preparation of (±)-exo-4-methyl-3b,4,4a,5 tetrahydro-1H-cyclopropa[3,4]cyclopenta[1,2-c]pyrazole-3-carboxylic acid Step A: Preparation of (±)-exo-4-methyl-3b,4,4a,5-tetrahydro-1H-cyclopropa[3,4]cyclopenta[1,2-c]pyrazole-3-carboxylic acid ethyl ester

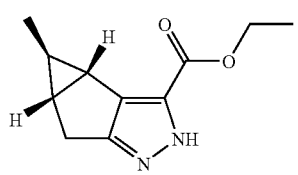

The title compound was prepared in a similar manner as described in Example 9.2, Step D from a 1:1 mixture of 6-exo-methylbicyclo[3.1.0]hexan-3-one and 6-endo-methylbicyclo[3.1.0]hexan-3-one (see P. S. Mariano, E. Bay, D. G. Watson, T. Rose, and C. Bracken, *J. Org. Chem.* 1980, 45, 1753; J. Nishimura, N. Kawabata, J. Furukawa, *Tetrahedron.* 1969, 25, 2647). MS: m/z (ES$^+$): 229 [M+Na]$^+$, 207 [M+H]$^+$, 161 [M−OEt]$^+$. $^1$H NMR (CDCl$_3$): δ 4.39 (t, 2H, J=7.2), 2.96 (dd, 1H, J$_1$=16.9, J$_2$=6.6), 2.82 (d, 1H, J=16.8), 2.03–2.01 (m, 1H), 1.89–1.85 (m, 1H), 1.40 (t, 3H, J=7.2), 1.14 (d, 3H, J=6.1), 0.69–0.64 (m, 1H).

Step B: Preparation of (±)-exo-4-methyl-3b,4,4a,5-tetrahydro-1H-cyclopropa[3,4]cyclopenta[1,2-c]pyrazole-3-carboxylic acid

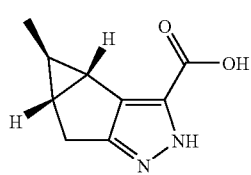

The title compound was isolated during the reaction described in Example 9.84, Step A. MS: m/z (ES$^+$): 179 [M+H]$^+$, 161 [M−OH]$^+$. $^1$H NMR (CD$_3$CN): δ 2.90 (dd, 1H, J$_1$=16.5, J$_2$=6.6), 2.74 (d, 1H, J=16.0), 2.02–1.99 (m, 1H), 1.88–1.78 (m, 1H), 1.13 (d, 3H, J=6.1), 0.62–0.55 (m, 1H).

Example 9.85

Preparation of (±)-endo-4-methyl-3b,4,4a,5-tetrahydro-1H-cyclopropa[3,4]cyclopenta[1,2-c]pyrazole-3-carboxylic acid

Step A: Preparation of (±)-endo-4-methyl-3b,4,4a,5tetrahydro-1H-cyclopropa[3,4]cyclopenta[1,2-c]pyrazole-3-carboxylic acid ethyl ester

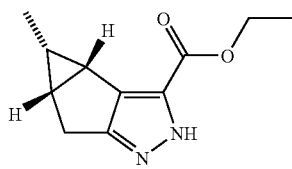

The title compound was prepared in a similar manner as described in Example 9.2, Step D using the mixture of diastereomers described in Example 9.84, Step A. MS: m/z (ES$^+$): 229 [M+Na]$^+$, 207 [M+H]$^+$, 161 [M−OEt]$^+$.

Step B: Preparation of (±)-endo-4-methyl-3b,4,4a,5tetrahydro-1H-cyclopropa[3,4]cyclopenta[1,2-c]pyrazole-3-carboxylic acid

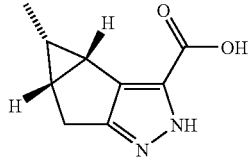

The title compound was isolated during the reaction described in Example 9.85, Step A. MS: z/z (ES$^+$): 179 [M+H]$^+$, 161 [M−OH]$^+$. $^1$H NMR (CD$_3$CN): δ 2.83 (dd, 1H, $J_1$=16.8, $J_2$=6.9), 2.55 (d, 1H, J=16.9), 2.29 (t, 1H, J=6.9), 2.10 (dd, 1H, $J_1$=14.4, $J_2$=6.6), 1.37–1.31 (m, 1H), 0.61 (d, 3H, J=6.4).

Example 9.86

Preparation of (±)-endo-1-cyclopropylmethyl-1a,3,5,5a-tetrahydro-1H-2,3-diaza-cyclopropa[a]pentalene-4-carboxylic acid

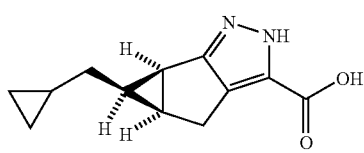

Step A: Preparation of 4-(2-Iodo-ethyl)-2,2-dimethyl-[1,3]dioxolane

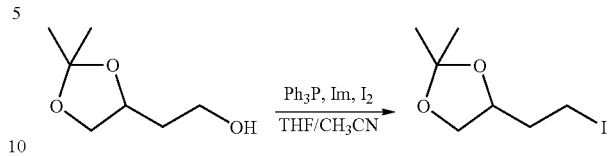

Triphenylphosphine (172 mmol, 45 g) and imidazole (172 mmol, 12 g) were dissolved in THF/acetonitrile (3:1, 300 ml). The mixture was cooled under an ice bath, and iodine (172 mmol, 44 g) was added in four portions with vigorous stirring over 20 minutes. The resulting slurry was warmed to 20° C. and then cooled to 0° C. (±)-2-(2,2-Dimethyl-[1,3]dioxolan-4-yl)-ethanol (156 mmol, 25 g) was added dropwise to the reaction mixture over 15 minutes. The mixture was stirred at room temperature overnight. The mixture was concentrated, diluted with 5% sodium bicarbonate solution and extracted with hexane. The combined organic layer was dried with MgSO$_4$ and concentrated. Silica gel chromatography gave 4-(2-iodo-ethyl)-2,2-dimethyl-[1,3]dioxolane as a clear oil; $^1$H NMR (400 MHz, CDCl$_3$): δ 4.18–4.12 (m, 1H), 4.06 (dd, 1H, $J_1$=8.0 Hz, $J_2$=6.1 Hz), 3.55 (dd, 1H, $J_1$=8.0 Hz, $J_2$=6.5 Hz), 3.28–3.17 (m, 2 H), 2.11–1.98 (m, 2H), 1.38 (s, 3H), 1.33 (s, 3H).

Step B: Preparation of [4-(2,2-Dimethyl-[1,3]dioxolan-4-yl)-but-1-ynyl]-trimethyl-silane

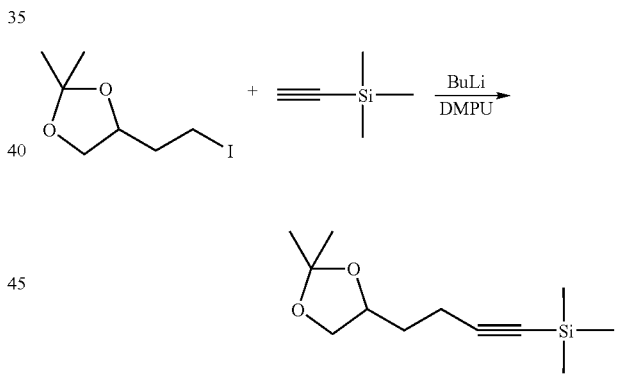

To a solution of TMS-acetylene (72 mmol, 7.1 g) in 150 ml anhydrous THF and DMPU (27 ml, 222 mmol) was slowly added 2.5 M (78 mmol, 31 ml) BuLi in Hexane at −78° C. and then 4-(2-Iodo-ethyl)-2,2-dimethyl-[1,3]dioxolane was added to the mixture. It was stirred at −78° C. for 15 minutes and slowly warmed up to room temperature. The reaction mixture was quenched with sat. NH$_4$Cl and extracted by EtOAc. The combined organic layer was washed with H$_2$O and brine, dried by MgSO$_4$ and concentrated. Silica gel chromatography (2~10% EtOAc/Hexane) afforded 4-(2,2-Dimethyl-[1,3]dioxolan-4-yl)-but-1-ynyl]-trimethyl-silane as a clear oil; $^1$H NMR (400 MHz, CDCl$_3$): δ 4.19–4.12 (m, 1H), 4.07 (dd, 1H, $J_1$=8.0 Hz, $J_2$=6.0 Hz), 3.57 (dd, 1H, $J_1$=8.0 Hz, $J_2$=6.9 Hz), 2.39–2.26 (m, 2H), 1.86–1.79 (m, 1H), 1.76–1.68 (m, 1H), 1.39 (s, 3H), 1.34 (s, 3H), 0.13 (s, 9H).

Step C: Preparation of 4-But-3-ynyl-2,2-dimethyl-[1,3]dioxolane

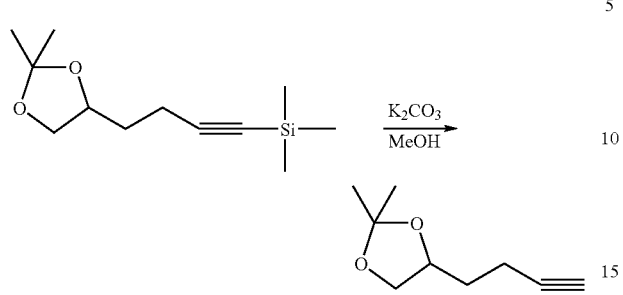

To a solution of 4-(2,2-Dimethyl-[1,3]dioxolan-4-yl)-but-1-ynyl]-trimethyl-silane (44 mmol, 10.0 g) in 40 ml methanol, was added $K_2CO_3$ (49 mmol, 6.7 g,). The mixture was stirred at room temperature for 4 h. The reaction mixture was concentrated, diluted with $NH_4Cl$ solution and extracted with EtOAc. The combined organic layer was dried with $MgSO_4$ and concentrated. Silica gel chromatography (4~12% EtOAc/Hexane) afforded 4-But-3-ynyl-2,2-dimethyl-[1,3]dioxolane as a clear oil; $^1$H NMR (400 MHz, $CDCl_3$): δ 4.21–4.15 (m, 1H), 4;05 (dd, 1H, $J_1$=8.0 Hz, $J_2$=6.0 Hz), 3.55 (dd, 1H, $J_1$=8.0 Hz, $J_2$=6.9 Hz), 2.31–2.26 (m, 2H), 1.94 (t, 1H, J=2.6 Hz), 1.84–1.75 (m, 1H), 1.73–1.68 (m, 1H), 1.38 (s, 3H), 1.33 (s, 3H).

Step D: Preparation of 4-(5-Cyclopropyl-pent-3-ynyl)-2,2-dimethyl-[1,3]dioxolane

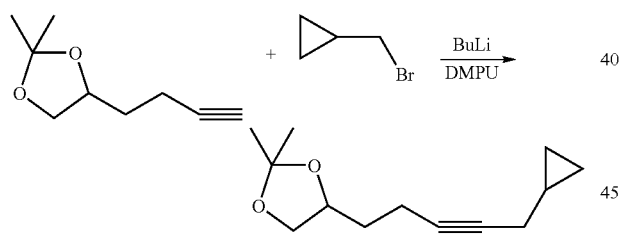

To a solution of 4-But-3-ynyl-2,2-dimethyl-[1,3]dioxolane (6 mmol, 1.0 g) in 40 ml anhydrous THF and anhydrous DMPU (26 mmol, 3 g) was added a solution of 2.5M BuLi in hexane (9.01 mmol, 3.6 mL) at −78° C. It was stirred at −78 ° C. for 15 minutes and slowly warmed up to room temperature. The reaction mixture was quenched with sat. $NH_4Cl$ and extracted by EtOAc. The combined organic layer was washed with $H_2O$ and brine, dried by $MgSO_4$ and concentrated. Silica gel chromatography (2~10% EtOAc/Hexane) 4(5-Cyclopropyl-pent-3-ynyl)-2,2-dimethyl-[1,3]dioxolane as a clear oil; $^1$H NMR (400 MHz, $CDCl_3$): δ 4.22–5.15 (m, 1H), 4.07 (dd, 1H, $J_3$=8.0 Hz, $J_2$=6.0 Hz), 3.57 (dd, 1H, $J_1$=7.9 Hz, $J_2$=7.1 Hz), 2.29–2.23 (m, 2H), 2.20–2.16 (m, 2H), 1.83–1.77 (m, 1H), 1.72–1.65 (m, 1H), 1.40 (s, 3H), 1.35 (s, 3H), 0.91–0.86 (m, 1H), 0.46–0.41(m, 2H), 0.21–0.17 (m, 2H).

Step E: Preparation of 4-(5-Cyclopropyl-pent-3-enyl)-2,2-dimethyl-[1,3]dioxolane

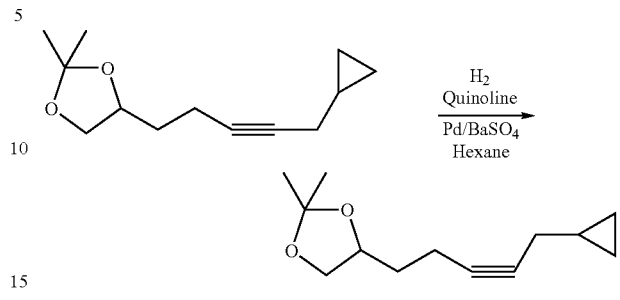

To a solution of 4-(5-Cyclopropyl-pent-3-ynyl)-2,2-dimethyl-[1,3]dioxolane (1.92 mmol, 0.40 g) in hexane (5 mL) was added quinoline (0.192 mmol, 24.8 mg), followed by addition of 5% Pd on $BaSO4$ (0.384 mmol). Stirred at room temperature under $H_2$ atmosphere for 4 hrs. TLC showed reaction completed. Filtered through celite and concentrated. Diluted with hexane, washed with $NH_4Cl$, brine and dried over $MgSO_4$. Silica gel chromatography (2~7% EtOAc/Hexane) 4-(5-Cyclopropyl-pent-3-enyl)-2,2-dimethyl-[1,3]dioxolane as clear oil $^1$H NMR (400 MHz, $CDCl_3$): δ 5.52–5.45 (m, 1H), 5.40–5.34 (m, 1H), 4.11–4.04 (m, 1H), 4.02 (dd, 1H, $J_1$=8.0 Hz, $J_2$=6.0 Hz), 3.51 (t, 1H, J=7.5 Hz), 2.17–2.04 (m, 2H), 1.97 (t, 2H, J=7.0 Hz), 1.74–1.66 (m, 1H), 1.58–1.49 (m, 1H), 1.41 (s, 3H), 1.35 (s, 3H), 0.73–0.68 (m, 1H), 0.43–0.39 (m, 2H), 0.08–0.04 (m, 2H).

Step F: Preparation of 7-Cyclopropyl-hept-5-ene-1,2-diol

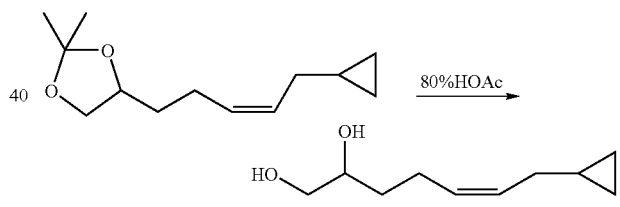

Stirred 4-(5-Cyclopropyl-pent-3-enyl)-2,2-dimethyl-[1,3]dioxolane (0.30 g, 1.4 mmol) in 80% AcOH (5 mL) overnight at room temperature. Concentrated and purified by silica gel chromatography (70~90% EtOAc in hexanes) to collect 7-Cyclopropyl-hept-5-ene-1,2-diol as a clear oil. $^1$H NMR (400 MHz, $CDCl_3$): δ 5.52–5.47 (m, 1H), 5.41–5.35 (m, 1H), 3.77–3.71 (m, 1H), 3.66 (d, 1H, J=11.2 Hz), 3.46 (dd, 1H, $J_1$=11.2 Hz, $J_2$=7.7 Hz), 2.19–2.10 (m, 2H), 1.97 (t, 2H, J=7.1 Hz), 1.53–1.46 (m, 2H), 0.74–0.68 (m, 1H), 0.44–0.39 (m, 2H), 0.08–0.04(m, 2H).

Step G: Preparation of 2-(4Cyclopropyl-but-2-enyl)-oxirane

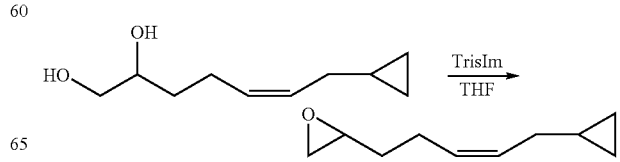

To a solution of 7-Cyclopropyl-hept-5-ene-1,2-diol (1.45 g, 9.28 mmol) in THF (30 mL) was added 60% sodium hydride (1.1 g, 27.84 mmol) at 0° C. The mixture was slowly warmed to room temperature and stirred for 1 h. TrisIm (3.41 g, 10.2 mmol) was added in one portion at 0° C. followed stirring at room temperature for 1.5 h. The mixture was quenched with water and extracted with Et$_2$O. The organics were washed with brine, dried over MgSO$_4$, filtered, and concentrated. Purification by silica gel chromatography (7% EtOAc in hexanes gradient to 14% EtOAc in hexanes) gave 2-(4-Cyclopropyl-but-2-enyl)-oxirane as a clear oil; $^1$H NMR (400 MHz, CDCl$_3$): δ 5.54–5.48 (m, 1H), 5.44–5.37 (m, 1H), 2.94–2.91 (m, 1H), 2.75 (dd, 1H, J$_1$=4.9 Hz, J$_2$=4.1 Hz), 2.48 (dd, 1H, J$_1$=5.0 Hz, J$_2$=2.7 Hz), 2.19 (q, 2H, J=7.3 Hz), 1.98 (t, 2H, J=7.0 Hz), 1.62–1.56 (m, 2H), 0.75–0.66 (m, 1H), 0.44–0.39 (m, 2H), 0.09–0.05(m, 2H).

Step H: Preparation of
6-Cyclopropylmethyl-bicyclo[3.1.0]hexan-2-ol

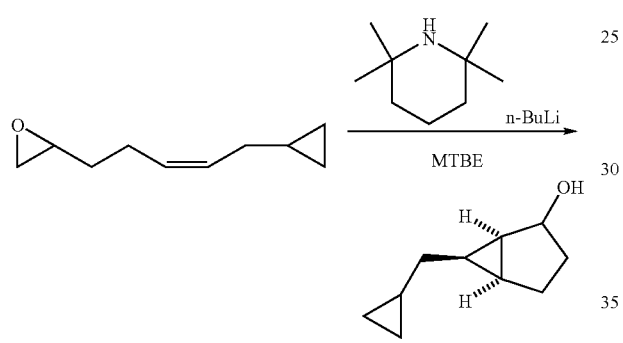

To a solution of tetramethylpiperidine (0.624 ml, 3.7 mmol) in MTBE (5 mL) was added n-butyllithium 2.5M hexanes (1.5 ml, 3.7 mmol) at −78° C. The solution was slowly warmed to approx 0° C. and was added via cannula to a solution of 2-(4-cyclopropyl-but-2-enyl)-oxirane (0.288 g, 1.898 mmol) in MTBE (2 mL) over 10 min at 0° C. The mixture was allowed to warm to rt, stirred overnight, washed with 1N HCl (2×), and brine. The organics were dried over MgSO$_4$, filtered, and concentrated to give 6-cyclopropylmethyl-bicyclo[3.1.0]hexan-2-ol as clear oil; $^1$H NMR (400 MHz, CDCl$_3$): δ 4.19 (d, 1H, J=5.5 Hz), 2.15–2.06 (m, 1H), 1.75 (dd, 1H, J$_1$=11.0 Hz, J$_2$=9.7 Hz), 1.69–1.52(m, 4H), 1.42 (dd, 1H, J$_1$=8.1 Hz, J$_2$=6.2 Hz), 0.98–0.87 (m, 2H), 0.75–0.68 (m, 1H), 0.46–0.41 (m, 2H), 0.03 (dd, 2H, J$_1$=9.1 Hz, J$_2$=4.7 Hz).

Step I: Preparation of
6-Cyclopropylmethyl-bicyclo[3.1.0]hexan-2-one

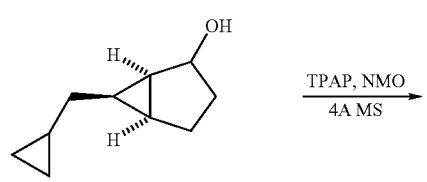

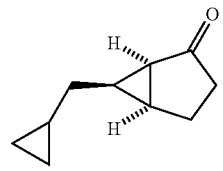

To a solution of 6-cyclopropylmethyl-bicyclo[3.1.0]hexan-2-ol (220 mg, 1.45 mmol) in 10 mL DCM was added sequentially 4 A Molecular sieves (200 mg), NMO (N-Methyl morpholine N-oxide) (339 mg, 2.90 mmol), TPAP label (25.448 mg, 0.0725 mmol). The mixture was stirred overnight at room temperature and plugged through silica gel (3:1 DCM: Et$_2$O) to give 6-cyclopropylmethyl-bicyclo [3.1.0]hexan-2-one as a clear oil; $^1$H NMR (400 MHz, CDCl$_3$): δ 2.32–2.21 (m, 2H), 2.16 (dd, 1H, J$_1$=13.4 Hz, J$_2$=5.4 Hz), 1.97–1.86 (m, 3H), 1.61–1.53 (m, 1H), 1.38–1.28 (m, 2H), 0.82–0.73 (m, 1H), 0.49–0.44 (m, 2H), 0.09–0.05 (m, 2H).

Step J: Preparation of (±)-endo-1-cyclopropylmethyl-
1a,3,5,5a-tetrahydro-1H-2,3-diaza-cyclopropa[a]
pentalene-4-carboxylic acid ethyl ester

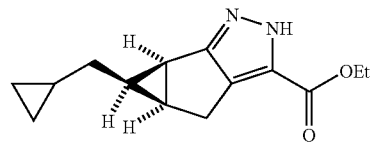

The title compound was prepared in a similar manner as described in Example 9.2, Step D. MS m/z (ES$^+$): 247.3 [M+H]$^+$, 269.1 [M+Na]$^+$; $^1$H NMR (400 MHz, CDCl$_3$): δ 4.38–4.29 (m, 2H), 2.93 (dd, 1H, J$_1$=17.4 Hz, J$_2$=6.8 Hz), 2.65 (d, 1H, J=17.4 Hz), 2.40 (t, 1H, J=6.9 Hz), 2.23 (dd, 1H, J$_1$=14.0 Hz, J$_2$=6.7 Hz), 1.40–1.35 (m, 1H), 1.37 (t, 3H, J=7.1 Hz), 1.03–0.96 (m, 1H), 0.78–0.64 (m, 2H), 0.39–0.32 (m, 2H), −0.02–−0.12 (m, 2H).

Step K: Preparation of (±)-endo-1-cyclopropylm-
ethyl-1a,3,5,5a-tetrahydro-1H-2,3-diaza-cyclopropa
[a]pentalene-4-carboxylic acid

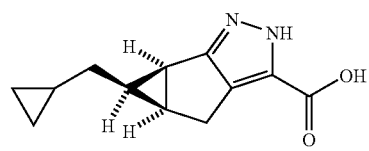

The title compound was prepared in a similar manner as described in Example 9.3. MS m/z (ES$^+$): 219.3 [M+H]$^+$; $^1$H NMR (400 MHz, CD$_3$OD): δ 2.95 (dd, 1H, J$_1$=18.5 Hz, J$_2$=6.9 Hz), 2.69 (d, 1H, J=18.5 Hz), 2.40 (t, 1H, J=6.9 Hz), 2.17 (dd, 1H, J$_1$=14.0 Hz, J$_2$=6.7 Hz), 1.47–1.42 (m, 1H), 1.15–1.08 (m, 1H), 0.86–0.79 (m, 1H), 0.76–0.68 (m, 1H), 0.44–0.36 (m, 2H), 0.02–−0.11 (m, 2H).

Throughout this application, various publications, patents and published patent applications are cited. The disclosures of these publications, patents and published patent applications referenced in this application are hereby incorporated by reference in their entirety into the present disclosure. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human GPCRs, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The invention claimed is:

1. A compound of Formula (Ia):

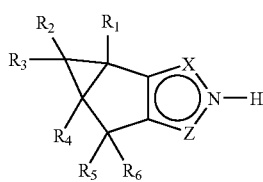

(Ia)

or a pharmaceutically acceptable salt, hydrate or solvate thereof,
wherein:
X is N and Z is $CR_7$, or X is $CR_7$ and Z is N;
$R_1$ and $R_4$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol;
$R_2$ and $R_3$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, arylsulfinyl, arylsulfonyl, arylthio, carbamimidoyl, carbo-$C_{1-6}$ alkoxy, carboxamide, carboxy, cyano, $C_{3-7}$ cycloalkyl, $C_{3-7}$ cycloalkyloxy, $C_{2-6}$ dialkylamino, $C_{1-6}$ dialkylcarboxamide, $C_{1-6}$ dialkylthiocarboxamide, $C_{1-6}$-dialkylamido, $C_{1-6}$-dialkylthioamido, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxocycloalkyl, phenoxy, phenyl, sulfonamide, sulfonic acid and thiol; wherein said $C_{1-6}$ alkyl is optionally substituted with substituents selected from the group consisting of $C_{1-6}$ acyl, $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, nitro, phenoxy and phenyl; or
$R_2$ and $R_3$ together with the carbon to which they are both bonded form a $C_{3-6}$ cycloalkyl;
$R_5$ and $R_6$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{1-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, carbo-$C_{1-6}$-alkoxy, carboxamide, carboxy, cyano, $C_{3-7}$ cycloalkyl, $C_{2-6}$ dialkylamino, $C_{1-6}$ dialkylcarboxamide, $C_{1-6}$ dialkylthiocarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, nitro, sulfonamide and thiol; and
$R_7$ is carbo-$C_{1-6}$-alkoxy, carboxy or tetrazol-5-yl.

2. The compound according to claim 1, or a pharmaceutically acceptable salt, hydrate or solvate thereof, wherein:
$R_2$ and $R_3$ are each selected independently from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{1-6}$ alkylthiocarboxamide, $C_{2-6}$ alkynyl, $C_{2-6}$ alkylsulfonamide, $C_{1-6}$ alkylsulfinyl, $C_{1-6}$ alkylsulfonyl, $C_{1-6}$ alkylthio, $C_{1-6}$ alkylthioureyl, $C_{1-6}$ alkylureyl, amino, $C_{1-6}$-alkylamido, amino-$C_{1-6}$-alkylsulfonyl, $C_{1-6}$-alkylthioamido, arylsulfinyl, arylsulfonyl, arylthio, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ dialkylcarboxamide, $C_{1-6}$ dialkylthiocarboxamide, $C_{1-6}$-dialkylamido, $C_{1-6}$-dialkylthioamido, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxocycloalkyl, phenoxy, phenyl, sulfonamide, sulfonic acid and thiol; wherein said $C_{1-6}$ alkyl is optionally substituted with substituents selected from the group consisting of $C_{1-6}$ acyl, $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, nitro, phenoxy and phenyl.

3. The compound according to claim 2, or a pharmaceutically acceptable salt, hydrate or solvate thereof, provided that $R_1$ and $R_4$ are cis to each other.

4. The compound according to claim 3, or a pharmaceutically acceptable salt, hydrate or solvate thereof, wherein X is N; Z is $CR_7$; and $R_7$ is carbo-$C_{1-6}$-alkoxy or carboxy.

5. The compound according to claim 3, or a pharmaceutically acceptable salt, hydrate or solvate thereof, wherein X is N; Z is $CR_7$; and $R_7$ is carboxy.

6. The compound according to claim 3, or a pharmaceutically acceptable salt, hydrate or solvate thereof, wherein X is N; Z is $CR_7$; and $R_7$ is tetrazol-5-yl.

7. The compound according to claim 3, or a pharmaceutically acceptable salt, hydrate or solvate thereof, wherein X is $CR_7$; $R_7$ is carbo-$C_{1-6}$-alkoxy or carboxy; and Z is N.

8. The compound according to claim 3, or a pharmaceutically acceptable salt, hydrate or solvate thereof, wherein X is $CR_7$; $R_7$ is carboxy; and Z is N.

9. The compound according to claim 3, or a pharmaceutically acceptable salt, hydrate or solvate thereof, wherein X is $CR_7$; $R_7$ is tetrazol-5-yl; and Z is N.

10. The compound according to claim 3, or a pharmaceutically acceptable salt, hydrate or solvate thereof, wherein $R_1$ is H or halogen.

11. The compound according to claim 3, or a pharmaceutically acceptable salt, hydrate or solvate thereof, wherein $R_1$ is H.

12. The compound according to claim 3, or a pharmaceutically acceptable salt, hydrate or solvate thereof, wherein $R_4$ is H or halogen.

13. The compound according to claim 3, or a pharmaceutically acceptable salt, hydrate or solvate thereof, wherein $R_4$ is H.

14. The compound according to claim 3, or a pharmaceutically acceptable salt, hydrate or solvate thereof, wherein $R_1$ and $R_4$ are both H.

15. The compound according to claim 3, or a pharmaceutically acceptable salt, hydrate or solvate thereof, wherein $R_5$ is H or halogen.

16. The compound according to claim 3, or a pharmaceutically acceptable salt, hydrate or solvate thereof, wherein $R_5$ is H.

17. The compound according to claim 3, or a pharmaceutically acceptable salt, hydrate or solvate thereof, wherein $R_6$ is H or halogen.

18. The compound according to claim 3, or a pharmaceutically acceptable salt, hydrate or solvate thereof, wherein $R_6$ is H.

19. The compound according to claim 3, or a pharmaceutically acceptable salt, hydrate or solvate thereof, wherein $R_5$ and $R_6$ are both H.

20. The compound according to claim 3, or a pharmaceutically acceptable salt, hydrate or solvate thereof, wherein $R_1$, $R_4$, $R_5$ and $R_6$ are each H.

21. The compound according to claim 3, or a pharmaceutically acceptable salt, hydrate or solvate thereof, wherein $R_2$ and $R_3$ are each selected independently from the group consisting of H, $C_{1-6}$ alkyl and halogen; wherein said $C_{1-6}$ alkyl is optionally substituted with substituents selected from the group consisting of $C_{1-6}$ acyloxy, $C_{1-4}$ alkoxy, $C_{1-6}$ alkylamino, $C_{1-6}$ alkylsulfinyl, $C_{1-6}$ alkylsulfonyl, $C_{1-6}$ alkylthio, amino, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, phenoxy and phenyl.

22. The compound according to claim 3, or a pharmaceutically acceptable salt, hydrate or solvate thereof, wherein $R_2$ is H or $C_{1-6}$ alkyl; and $R_3$ is H, $C_{1-6}$ alkyl or halogen; wherein said $C_{1-6}$ alkyl is optionally substituted with substituents selected from the group consisting of $C_{1-6}$ acyloxy, $C_{1-6}$ alkoxy, $C_{1-6}$ alkylamino, $C_{1-6}$ alkylsulfinyl, $C_{1-6}$ alkylsulfonyl, $C_{1-6}$ alkylthio, amino, $C_{3-7}$ cycloalkyloxy, $C_{2-6}$ dialkylamino, $C_{1-6}$ haloalkoxy, $C_{1-6}$ haloalkylsulfinyl, $C_{1-6}$ haloalkylsulfonyl, $C_{1-6}$ haloalkylthio, hydroxyl, phenoxy and phenyl.

23. The compound according to claim 1, or a pharmaceutically acceptable salt, hydrate or solvate thereof, wherein $R_2$ is H or $C_{1-6}$ alkyl; and $R_3$ is H, $C_{2-6}$ alkenyl, $C_{1-6}$ alkyl, $C_{3-7}$ cycloalkyl, halogen or phenyl; wherein said $C_{1-6}$ alkyl is optionally substituted with substituents selected from the group consisting of $C_{1-6}$ alkoxy, $C_{1-4}$ alkylthio, hydroxyl, phenoxy and phenyl; or $R_2$ and $R_3$ together with the carbon to which they are both bonded form a cyclopropyl, cyclopentyl or cyclohexyl group.

24. The compound according to claim 3, or a pharmaceutically acceptable salt, hydrate or solvate thereof, wherein $R_2$ is H or $C_{1-6}$ alkyl; and $R_3$ is H, $C_{2-6}$ alkenyl, $C_{1-6}$ alkyl, halogen or phenyl; wherein said $C_{1-6}$ alkyl is optionally substituted with substituents selected from the group consisting of $C_{1-6}$ alkoxy, hydroxyl, phenoxy and phenyl.

25. The compound according to claim 3, or a pharmaceutically acceptable salt, hydrate or solvate thereof, wherein $R_2$ is H or $CH_3$; and $R_3$ is H, $CH_3$ or benzyl.

26. The compound according to claim 3, or a pharmaceutically acceptable salt, hydrate or solvate thereof, wherein $R_2$ is H or $CH_3$; and $R_3$ is H, methyl, ethyl, n-propyl, isopropyl, isobutyl, n-butyl, n-pentyl, vinyl, hydroxymethyl, methoxymethyl, benzyl, phenyl or phenoxymethyl.

27. The compound according to claim 1, or a pharmaceutically acceptable salt, hydrate or solvate thereof, wherein $R_2$ is H or $CH_3$; and $R_3$ is H, methyl, ethyl, n-propyl, isopropyl, isobutyl, n-butyl, n-pentyl, vinyl, hydroxymethyl, methoxymethyl, benzyl, phenyl, phenoxymethyl, methylsulfanylmethyl, ethoxymethyl, cyclopropyl, 1-but-2-enyl, or allyl; or $R_2$ and $R_3$ together with the carbon to which they are both bonded form a cyclopropyl, cyclopentyl or cyclohexyl group.

28. The compound according to claim 3, wherein:

X is N, Z is $CR_7$, wherein $R_7$ is carboxyl, —$CO_2Et$ or tetrazol-5-yl; or

X is $CR_7$, wherein $R_7$ is carboxyl, —$O_2Et$ or tetrazolyl, and Z is N;

$R_1$, $R_4$, $R_5$ and $R_6$ are each H;

$R_2$ is H or $CH_3$; and $R_3$ is H, methyl, ethyl, n-propyl, isopropyl, isobutyl, n-butyl, n-pentyl, vinyl, hydroxymethyl, methoxymethyl, benzyl, phenyl or phenoxymethyl; or a pharmaceutically acceptable salt, hydrate or solvate thereof.

29. The compound according to claim 3, wherein:

X is N, Z is $CR_7$, and $R_7$ is carboxyl, —$CO_2Et$ or tetrazol-5-yl;

$R_1$, $R_4$, $R_5$ and $R_6$ are each H;

$R_2$ is H or $CH_3$; and $R_3$ is H, methyl, ethyl, n-propyl, isopropyl, isobutyl, n-butyl, n-pentyl, vinyl, hydroxymethyl, methoxymethyl, benzyl, phenyl or phenoxymethyl; or a pharmaceutically acceptable salt, hydrate or solvate thereof.

30. The compound according to claim 3, wherein:

X is N, Z is $CR_7$, and $R_7$ is carboxyl; or

X is $CR_7$, $R_7$ is carboxyl or tetrazol-5-yl, and Z is N;

$R_1$, $R_4$, $R_5$ and $R_6$ are each H;

$R_2$ is H or $CH_3$; and $R_3$ is H, $CH_3$ or benzyl; or a pharmaceutically acceptable salt, hydrate or solvate thereof.

31. The compound according to claim 3, having the structure:

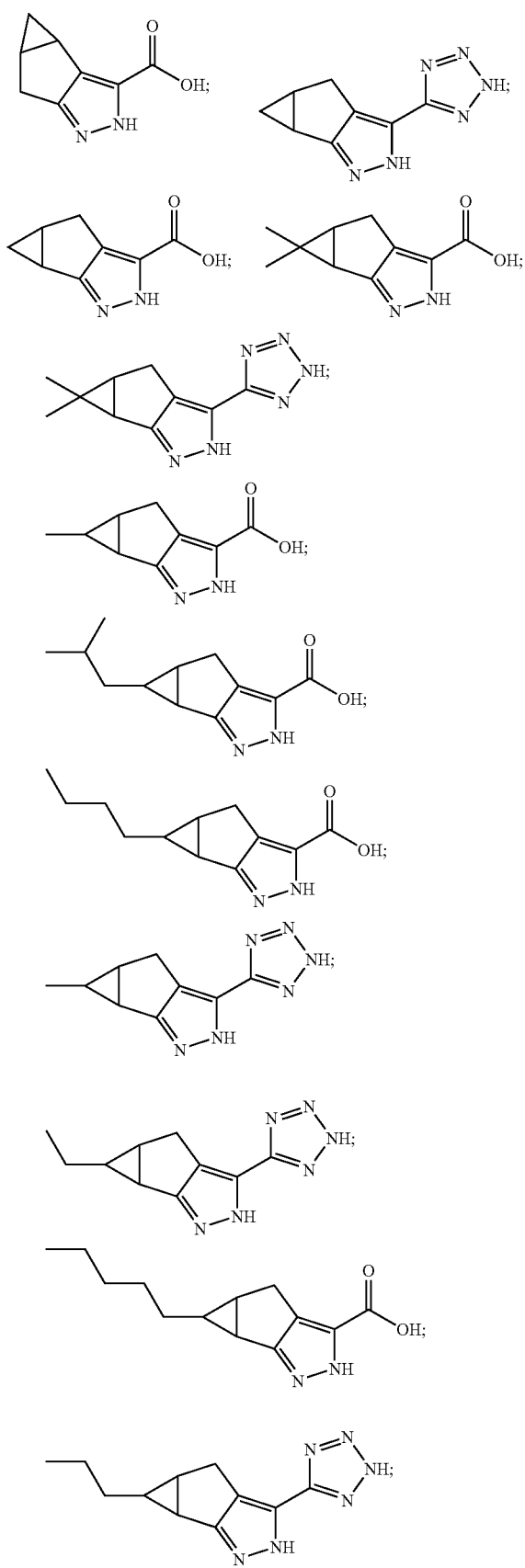
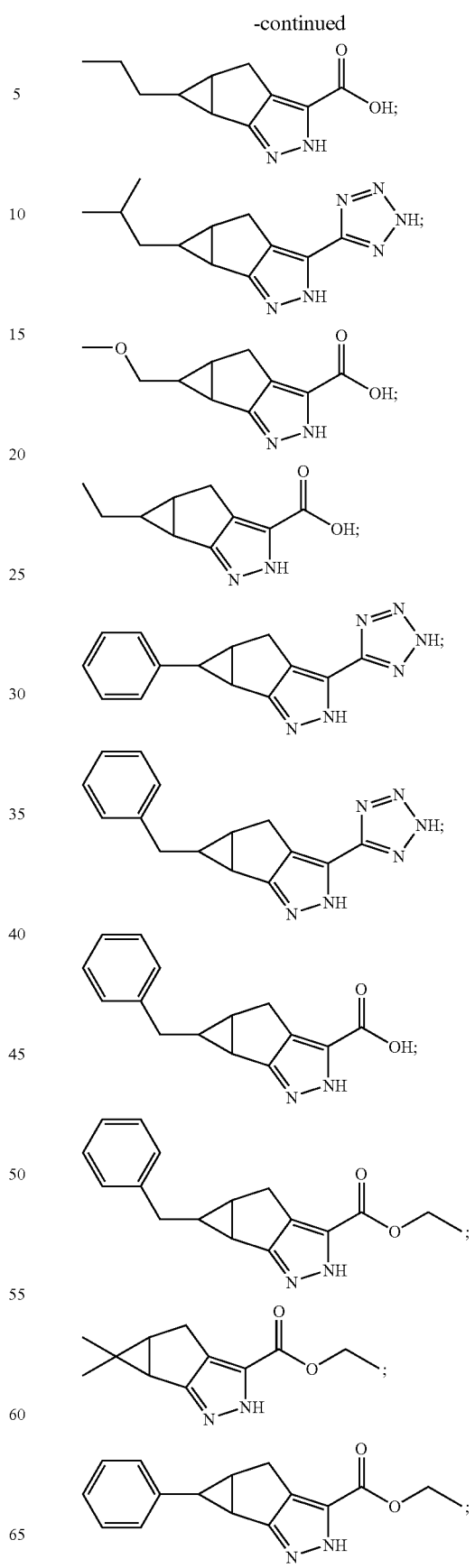

-continued
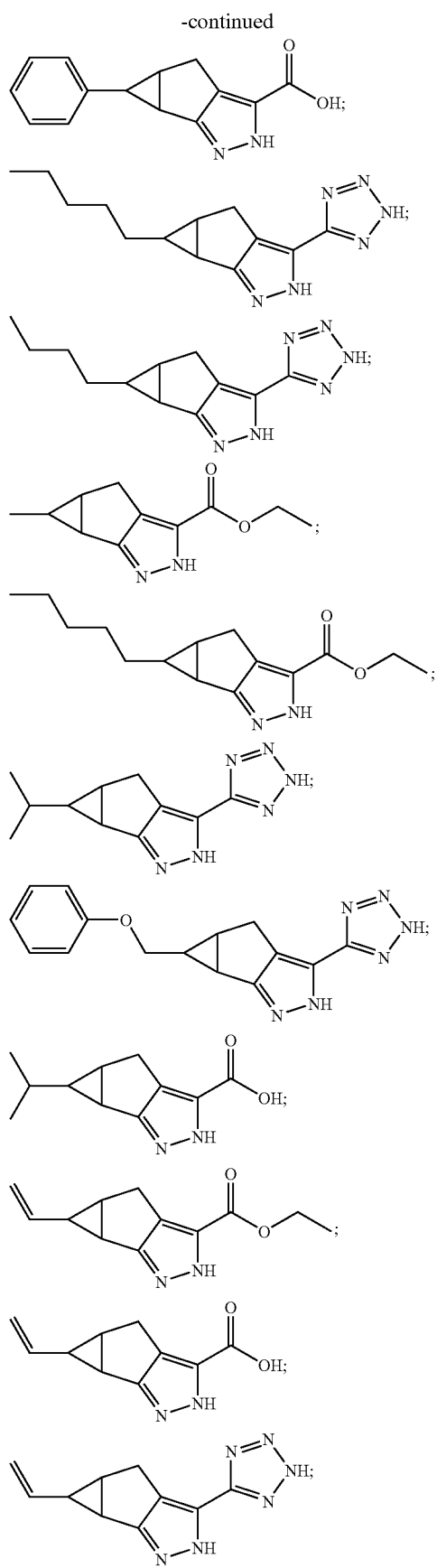
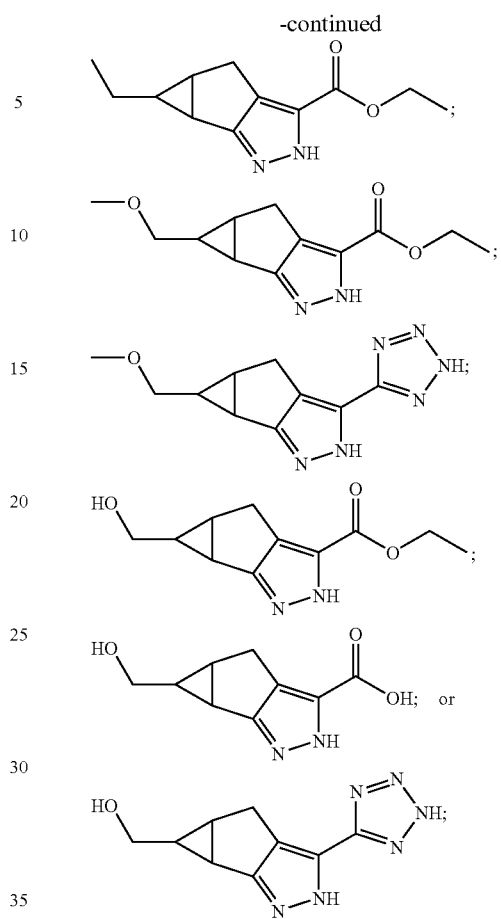
or a pharmaceutically acceptable salt, solvate or hydrate thereof.
32. The compound according to claim 1, having the structure:
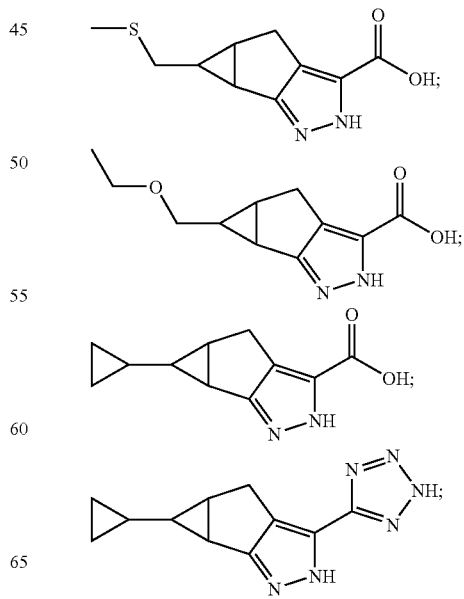

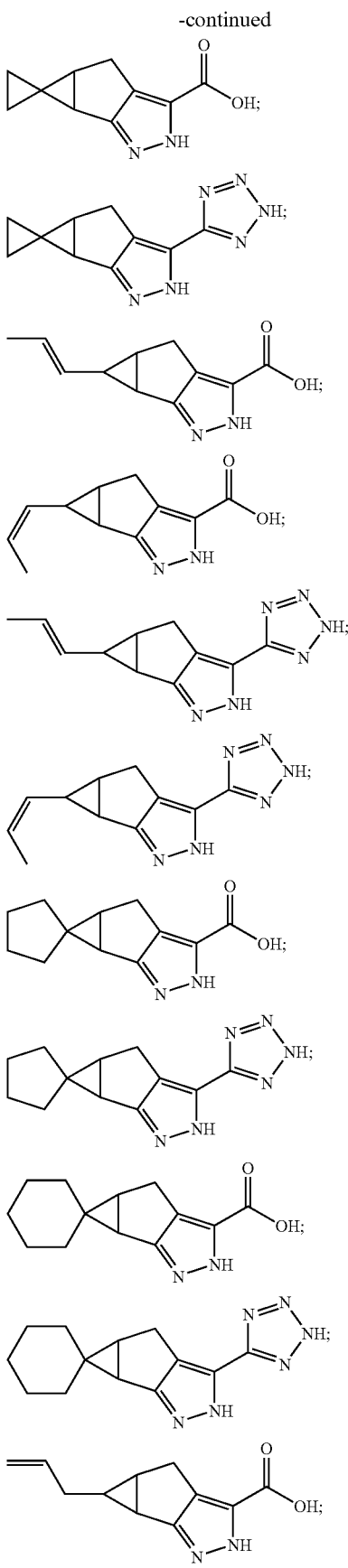

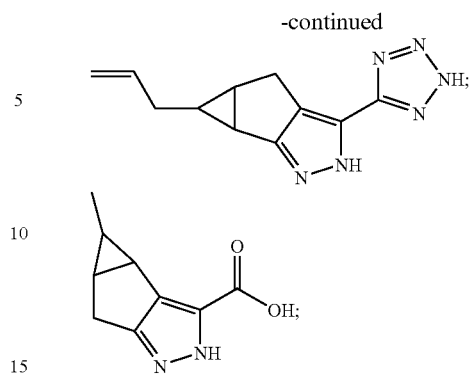

or a pharmaceutically acceptable salt, solvate or hydrate thereof.

33. The compound according to claim 3, selected from the group consisting of:
    3b,4,4a,5-Tetrahydro-2H-cyclopropa[3,4]cyclopenta[1,2-c]pyrazole-3-carboxylic acid;
    1a,3,5,5a-Tetrahydro-1H-2,3-diaza-cyclopropa[a]pentalene-4-carboxylic acid; and
    4-(2H-Tetrazol-5-yl)-1a,3,5,5a-tetrahydro-1H-2,3-diaza-cyclopropa[a]pentalene; or
    a pharmaceutically acceptable salt, hydrate or solvate thereof.

34. The compound according to claim 33, or a pharmaceutically acceptable salt, hydrate or solvate thereof, wherein the stereochemistry for the two carbons assigned as 3b and 4a, or 1a and 5a are both R.

35. The compound according to claim 3, selected from the group consisting of:
    1-Benzyl-1a,3,5,5a-tetrahydro-1H-2,3-diaza-cyclopropa[a]pentalene-4-carboxylic acid;
    1,1-Dimethyl-1a,3,5,5a-tetrahydro-1H-2,3-diaza-cyclopropa[a]pentalene-4-carboxylic acid;
    1,1-Dimethyl-4-(2H-tetrazol-5-yl)-1a,3,5,5a-tetrahydro-1H-2,3-diaza-cyclopropa[a]pentalene; and
    1-Benzyl-4-(2H-tetrazol-5-yl)-1a,3,5,5a-tetrahydro-1H-2,3diaza-cyclopropa[a]pentalene; or
    a pharmaceutically acceptable salt, hydrate or solvate thereof.

36. The compound according to claim 3, selected from the group consisting of:
    1-Methyl-1a,3,5,5a-tetrahydro-1H-2,3-diaza-cyclopropa[a]pentalene-4-carboxylic acid;
    1-Isobutyl-1a,3,5,5a-tetrahydro-1H-2,3-diaza-cyclopropa[a]pentalene-4-carboxylic acid;
    1-Butyl-1a,3,5,5a-tetrahydro-1H-2,3-diaza-cyclopropa[a]pentalene-4-carboxylic acid;
    1-Pentyl-1a,3,5,5a-tetrahydro-1H-2,3-diaza-cyclopropa[a]pentalene-4-carboxylic acid;
    1-Propyl-1a,3,5,5a-tetrahydro-1H-2,3-diaza-cyclopropa[a]pentalene-4-carboxylic acid;
    1-Methoxymethyl-1a,3,5,5a-tetrahydro-1H-2,3-diaza-cyclopropa[a]pentalene-4-carboxylic acid;
    1-Ethyl-1a,3,5,5a-tetrahydro-1H-2,3-diaza-cyclopropa[a]pentalene-4-carboxylic acid;
    1-Benzyl-1a,3,5,5a-tetrahydro-1H-2,3-diaza-cyclopropa[a]pentalene-4-carboxylic acid;
    1-Benzyl-1a,3,5,5a-tetrahydro-1H-2,3-diaza-cyclopropa[a]pentalene-4-carboxylic acid ethyl ester;
    1,1-Dimethyl-1a,3,5,5a-tetrahydro-1H-2,3-diaza-cyclopropa[a]pentalene-4-carboxylic acid ethyl ester;

1-Phenyl-1a,3,5,5a-tetrahydro-1H-2,3-diaza-cyclopropa[a]pentalene-4-carboxylic acid ethyl ester;
1-Phenyl-1a,3,5,5a-tetrahydro-1H-2,3-diaza-cyclopropa[a]pentalene-4-carboxylic acid;
1-Ethyl-1a,3,5,5a-tetrahydro-1H-2,3-diaza-cyclopropa[a]pentalene-4-carboxylic acid ethyl ester;
1-Methyl-1a,3,5,5a-tetrahydro-1H-2,3-diaza-cyclopropa[a]pentalene-4-carboxylic acid ethyl ester;
1-Pentyl-1a,3,5,5a-tetrahydro-1H-2,3-diaza-cyclopropa[a]pentalene-4-carboxylic acid ethyl ester;
1-Isopropyl-1a,3,5,5a-tetrahydro-1H-2,3-diaza-cyclopropa[a]pentalene-4-carboxylic acid;
1-Vinyl-1a,3,5,5a-tetrahydro-1H-2,3-diaza-cyclopropa[a]pentalene-4-carboxylic acid ethyl ester;
1-Vinyl-1a,3,5,5a-tetrahydro-1H-2,3-diaza-cyclopropa[a]pentalene-4-carboxylic acid;
1-Ethyl-1a,3,5,5a-tetrahydro-1H-2,3-diaza-cyclopropa[a]pentalene-4-carboxylic acid ethyl ester;
1-Methoxymethyl-1a,3,5,5a-tetrahydro-1H-2,3-diaza-cyclopropa[a]pentalene-4-carboxylic acid ethyl ester;
1-Hydroxymethyl-1a,3,5,5a-tetrahydro-1H-2,3-diaza-cyclopropa[a]pentalene-4-carboxylic acid ethyl ester; and
1-Hydroxymethyl-1a,3,5,5a-tetrahydro-1H-2,3-diaza-cyclopropa[a]pentalene-4-carboxylic acid; or
a pharmaceutically acceptable salt, hydrate or solvate thereof.

37. The compound according to claim 1, selected from the group consisting of:
1-Methylsulfanylmethyl-1a,3,5,5a-tetrahydro-1H-2,3-diaza-cyclopropa[a]pentalene-4-carboxylic acid;
1-Ethoxymethyl-1a,3,5,5a-tetrahydro-1H-2,3-diaza-cyclopropa[a]pentalene-4-carboxylic acid;
1-Cyclopropyl-1a,3,5,5a-tetrahydro-1H-2,3-diaza-cyclopropa[a]pentalene-4-carboxylic acid;
1-Spirocyclopropyl-1a,3,5,5a-tetrahydro-1H-2,3-diaza-cyclopropa[a]pentalene-4-carboxylic acid;
(E)-1-Propenyl-1a,3,5,5a-tetrahydro-1H-2,3-diaza-cyclopropa[a]pentalene-4-carboxylic acid;
(Z)-1-Propenyl-1a,3,5,5a-tetrahydro-1H-2,3-diaza-cyclopropa[a]pentalene-4-carboxylic acid;
1-Phenoxymethyl-1a,3,5,5a-tetrahydro-1H-2,3-diaza-cyclopropa[a]pentalene-4-carboxylic acid;
Spiro[1a,3,5,5a-tetrahydro-1H-2,3diaza-cyclopropa[a]pentalene-1,1'-cyclopentan]4-carboxylic acid;
Spiro[1a,3,5,5a-tetrahydro-1H-2,3-diaza-cyclopropa[a]pentalene-1,1'-cyclohexan]-4-carboxylic acid;
1-Allyl-1a,3,5,5a-tetrahydro-1H-2,3-diaza-cyclopropa[a]pentalene-4-carboxylic acid; and
4-Methyl-3b,4,4a,5-tetrahydro-2H-cyclopropa[3,4]cyclopenta[1,2-c]pyrazole-3-carboxylic acid;
1-Cyclopropylmethyl-1a,3,5,5a-tetrahydro-1H-2,3-diaza-cyclopropa[a]pentalene-4-carboxylic acid; or
a pharmaceutically acceptable salt, hydrate or solvate thereof.

38. The compound according to claim 3, selected from the group consisting of:
1-Methyl-4-(2H-tetrazol-5-yl)-1a,3,5,5a-tetrahydro-1H-2,3-diaza-cyclopropa[a]pentalene;
1-Ethyl-4-(2H-tetrazol-5-yl)-1a,3,5,5a-tetrahydro-1H-2,3-diaza-cyclopropa[a]pentalene;
1-Propyl-4-(2H-tetrazol-5-yl)-1a,3,5,5a-tetrahydro-1H-2,3-diaza-cyclopropa[a]pentalene;
1-Isobutyl-4-(2H-tetrazol-5-yl)-1a,3,5,5a-tetrahydro-1H-2,3-diaza-cyclopropa[a]pentalene;
1-Phenyl-4-(2H-tetrazol-5-yl)-1a,3,5,5a-tetrahydro-1H-2,3-diaza-cyclopropa[a]pentalene;
1-Benzyl-4-(2H-tetrazol-5-yl)-1a,3,5,5a-tetrahydro-1H-2,3-diaza-cyclopropa[a]pentalene;
1-Pentyl-4-(2H-tetrazol-5-yl)-1a,3,5,5a-tetrahydro-1H-2,3-diaza-cyclopropa[a]pentalene;
1-Butyl-4-(2H-tetrazol-5-yl)-1a,3,5,5a-tetrahydro-1H-2,3-diaza-cyclopropa[a]pentalene;
1-Isopropyl-4-(2H-tetrazol-5-yl)-1a,3,5,5a-tetrahydro-1H-2,3-diaza-cyclopropa[a]pentalene;
1-Phenoxymethyl-4-(2H-tetrazol-5-yl)-1a,3,5,5a-tetrahydro-1H-2,3-diaza-cyclopropa[a]pentalene;
4-(2H-Tetrazol-5-yl)-1-vinyl-1a,3,5,5a-tetrahydro-1H-2,3-diaza-cyclopropa[a]pentalene;
1-Methoxymethyl-4-(2H-tetrazol-5-yl)-1a,3,5,5a-tetrahydro-1H-2,3-diaza-cyclopropa[a]pentalene; and
[4-(2H-Tetrazol-5-yl)-1a,3,5,5a-tetrahydro-1H-2,3-diaza-cyclopropa[a]pentalen-1-yl]-methanol; or
a pharmaceutically acceptable salt, hydrate or solvate thereof.

39. The compound according to claim 1, selected from the group consisting of:
1-Cyclopropyl-4-(2H-tetrazol-5-yl)-1a,3,5,5a-tetrahydro-1H-2,3-diaza-cyclopropa[a]pentalene;
1-Spirocyclopropyl-4-(2H-tetrazol-5-yl)-1a,3,5,5a-tetrahydro-1H-2,3diaza-cyclopropa[a]pentalene;
(E)-1-Propenyl-4-(2H-tetrazol-5-yl)-1a,3,5,5a-tetrahydro-1H-2,3-diaza-cyclopropa[a]pentalene;
(Z)-1-Propenyl-4-(2H-tetrazol-5-yl)-1a,3,5,5a-tetrahydro-1H-2,3-diaza-cyclopropa[a]pentalene;
5-(Spiro-[1a,3,5,5a-tetrahydro-1H-2,3-diaza-cyclopropa[a]pentalene-1,1'-cyclopentan]-4-yl)-1H-tetrazole;
5-(Spiro-[1a,3,5,5a-tetrahydro-1H-2,3-diaza-cyclopropa[a]pentalene-1,1'-cyclohexan]-4-yl)-1H-tetrazole; and
1-Allyl-4-(2H-tetrazol-5-yl)-1a,3,5,5a-tetrahydro-1H-2,3-diaza-cyclopropa[a]pentalene; or
a pharmaceutically acceptable salt, hydrate or solvate thereof.

40. A pharmaceutical composition comprising a compound according to claim 1, or a pharmaceutically acceptable salt, hydrate or solvate thereof, combination with a pharmaceutically acceptable carrier.

41. A pharmaceutical composition comprising a compound according to claim 3, or a pharmaceutically acceptable salt, hydrate or solvate thereof, combination with a pharmaceutically acceptable carrier.

42. A pharmaceutical composition according to claim 40 or 41 further comprising an agent selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer, thiazolidinedione and DP receptor antagonist.

43. A compound according to claim 1 that is:

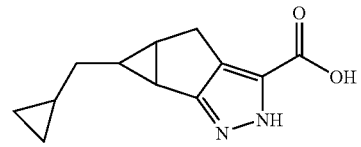

1-cyclopropylmethyl-1a,3,5,5a-tetrahydro-1H-2,3-diaza-cycloproypa[a]pentalene-4-carboxylic acid,
or a pharmaceutically acceptable salt, hydrate or solvate thereof.

44. A compound according to claim 1 that is:

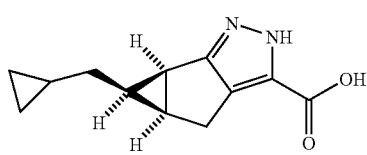

endo-(1aR, 5aS)-1-cyclopropylmethyl-1a,3,5,5a-tetrahydro-1H-2,3-diaza-cyclopropa[a]pentalene-4-carboxylic acid, or a pharmaceutically acceptable salt, hydrate or solvate thereof.

45. A compound according to claim 1 that is:

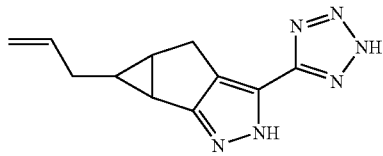

1-allyl-4-(2H-tetrazol-5-yl)-1a,3,5,5a-tetrahydro-1H-2,3-diaza-cyclopropa[a]pentalene, or a pharmaceutically acceptable salt, hydrate or solvate thereof.

46. A compound according to claim 1 that is:

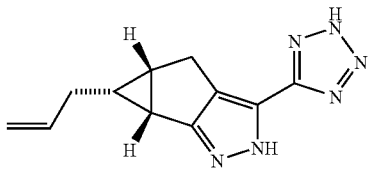

endo-(1aR, 5aS)-1-allyl-4-(2H-tetrazol-5-yl)-1a,3,5,5a-tetrahydro-1H-2,3-diaza-cyclopropa[a]pentalene, or a pharmaceutically acceptable salt, hydrate or solvate thereof.

47. A compound according to claim 1 that is:

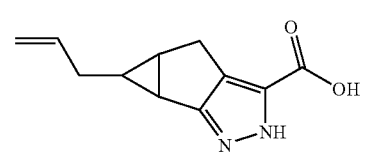

1-allyl-1a,3,5,5a-tetrahydro-1H-2,3-diaza-cyclopropa[a]pentalene-4-carboxylic acid, or a pharmaceutically acceptable salt, hydrate or solvate thereof.

48. A compound according to claim 1 that is:

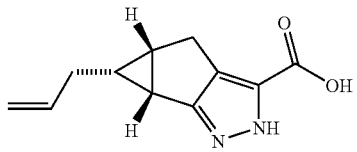

endo-(1aR, 5aS)-1-allyl-1a,3,5,5a-tetrahydro-1H-2,3-diaza-cyclopropa[a]pentalene-4-carboxylic acid, or a pharmaceutically acceptable salt, hydrate or solvate thereof.

49. A compound according to claim 1 that is:

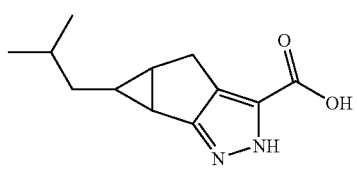

1-isobutyl-1a,3,5,5a-tetrahydro-1H-2,3-diaza-cyclopropa[a]pentalene-4-carboxylic acid, or a pharmaceutically acceptable salt, hydrate or solvate thereof.

50. A compound according to claim 1 that is:

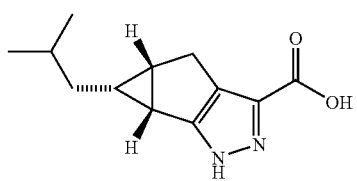

endo-(1aR, 5aS)-1-isobutyl-1a,3,5,5a-tetrahydro-1H-2,3-diaza-cyclopropa[a]pentalene-4-carboxylic acid, or a pharmaceutically acceptable salt, hydrate or solvate thereof.

51. A compound according to claim 1 that is:

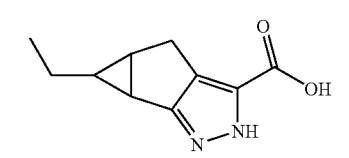

1-ethyl-1a,3,5,5a-tetrahydro-1H-2,3-diaza-cyclopropa[a]pentalene-4-carboxylic acid, or a pharmaceutically acceptable salt, hydrate or solvate thereof.

52. A compound according to claim 1 that is:

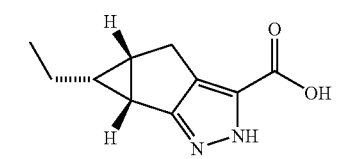

endo-(1aR, 5aS)-1-ethyl-1a,3,5,5a-tetrahydro-1H-2,3-diaza-cyclopropa[a]pentalene-4-carboxylic acid, or a pharmaceutically acceptable salt, hydrate or solvate thereof.

53. A compound according to claim 1 that is:

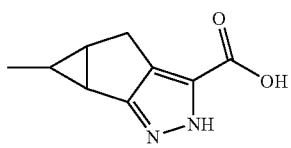

1-methyl-1a,3,5,5a-tetrahydro-1H-2,3-diaza-cyclopropa[a]pentalene-4-carboxylic acid, or a pharmaceutically acceptable salt, hydrate or solvate thereof.

54. A compound according to claim 1 that is:

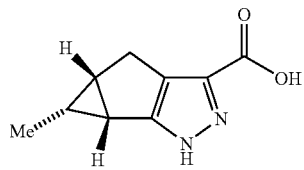

endo-(1aR, 5aS)-1-methyl-1a,3,5,5a-tetrahydro-1H-2,3-diaza-cyclopropa[a]pentalene-4-carboxylic acid, or a pharmaceutically acceptable salt, hydrate or solvate thereof.

55. A compound according to claim 1 that is:

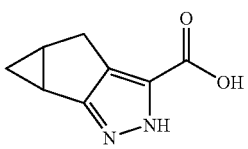

1a,3,5,5a-tetrahydro-1H-2,3-diaza-cyclopropa[a]pentalene-4-carboxylic acid, or a pharmaceutically acceptable salt, hydrate or solvate thereof.

56. A compound according to claim 1 that is:

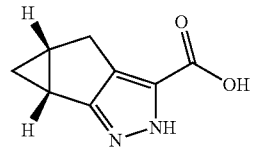

(1aR, 5aR)-1a,3,5,5a-tetrahydro-1H-2,3-diaza-cyclopropa[a]pentalene-4-carboxylic acid, or a pharmaceutically acceptable salt, hydrate or solvate thereof.

57. A compound according to claim 1 that is:

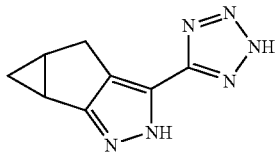

4-(2H-tetrazol-5-yl)-1a,3,5,5a-tetrahydro-1H-2,3-diaza-cyclopropa[a]pentalene, or a pharmaceutically acceptable salt, hydrate or solvate thereof.

58. A compound according to claim 1 that is:

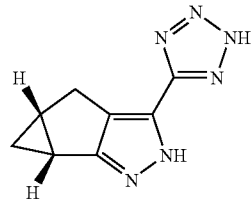

(1aR,5aR)-4-(2H-tetrazol-5-yl)-1a,3,5,5a-tetrahydro-1H-2,3-diaza-cyclopropa[a]pentalene, or a pharmaceutically acceptable salt, hydrate or solvate thereof.

59. A pharmaceutical composition comprising a compound according to any one of claims 43 to 58, or a pharmaceutically acceptable salt, hydrate or solvate thereof, in combination with a pharmaceutically acceptable carrier.

60. A pharmaceutical composition according to claim 59 further comprising an agent selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer, thiazolidinedione and DP receptor antagonist.

61. A pharmaceutical composition according to claim 42 wherein said DP receptor antagonist is selected from the group consisting of:

Compound A

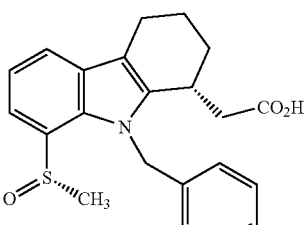

Compound B

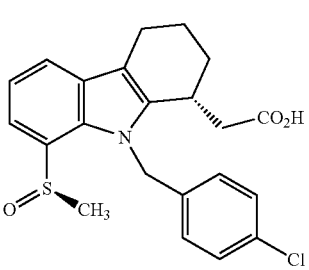

-continued
Compound C
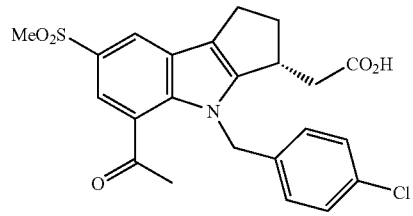
Compound D
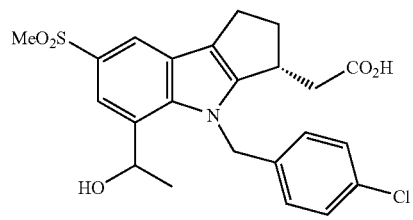
Compound E
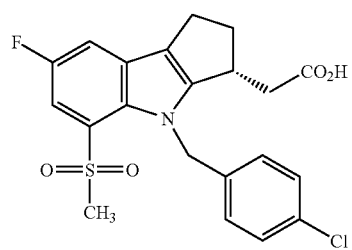
Compound F
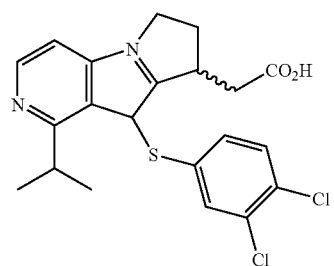
Compound G
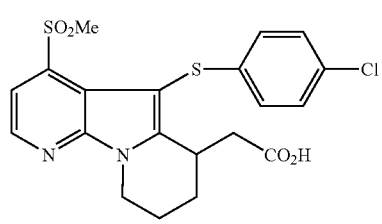
Compound H
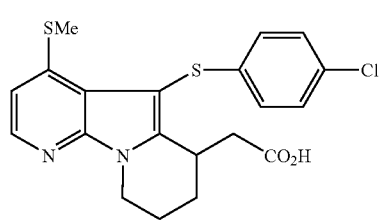
-continued
Compound I
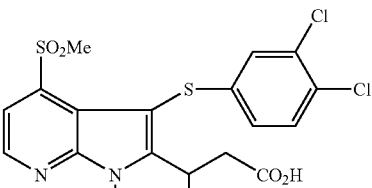
Compound J
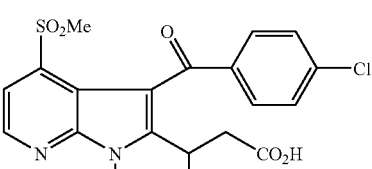
Compound K
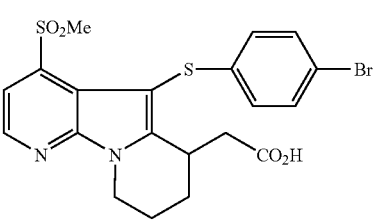
Compound L
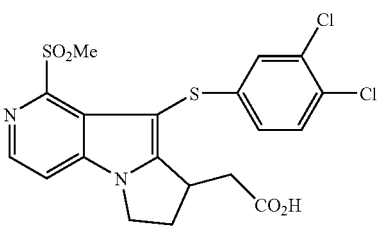
Compound M
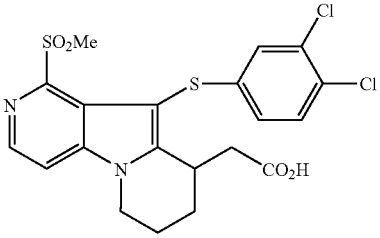
Compound N
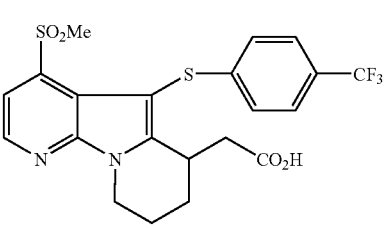
Compound O
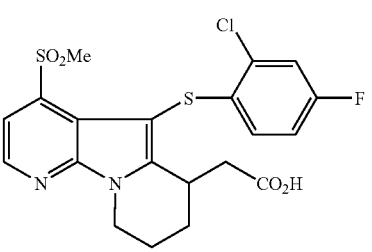

-continued
Compound P
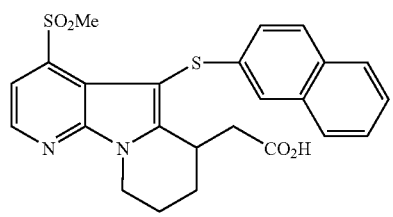
Compound Q
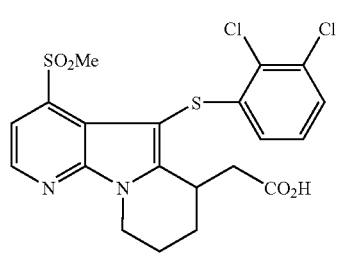
Compound R
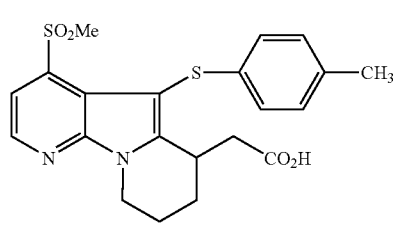
Compound S
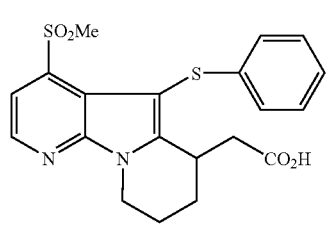
Compound T
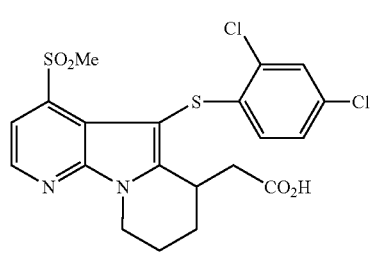
Compound U
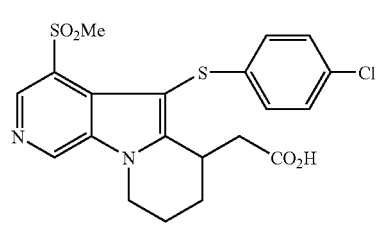
Compound V
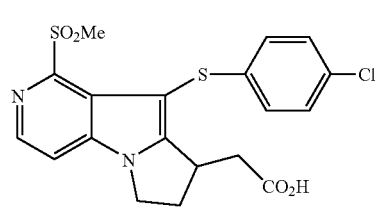
-continued
Compound W
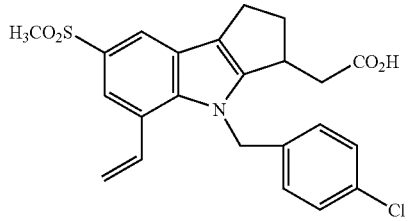
Compound X
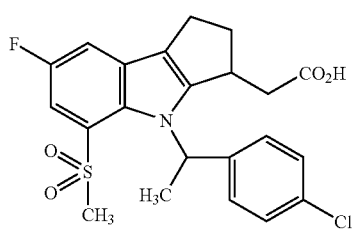
Compound X
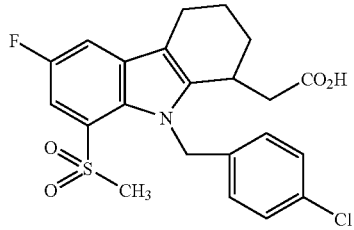
Compound Z
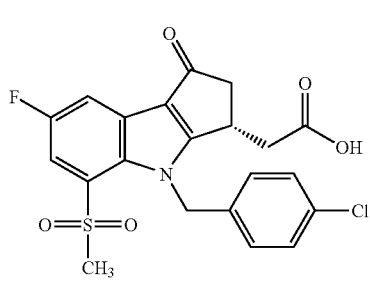
Compound AA
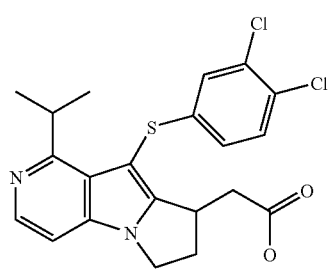
Compound AB
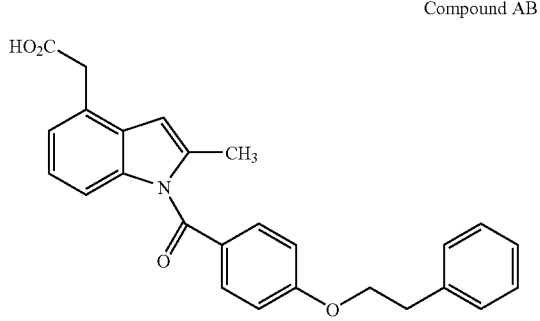

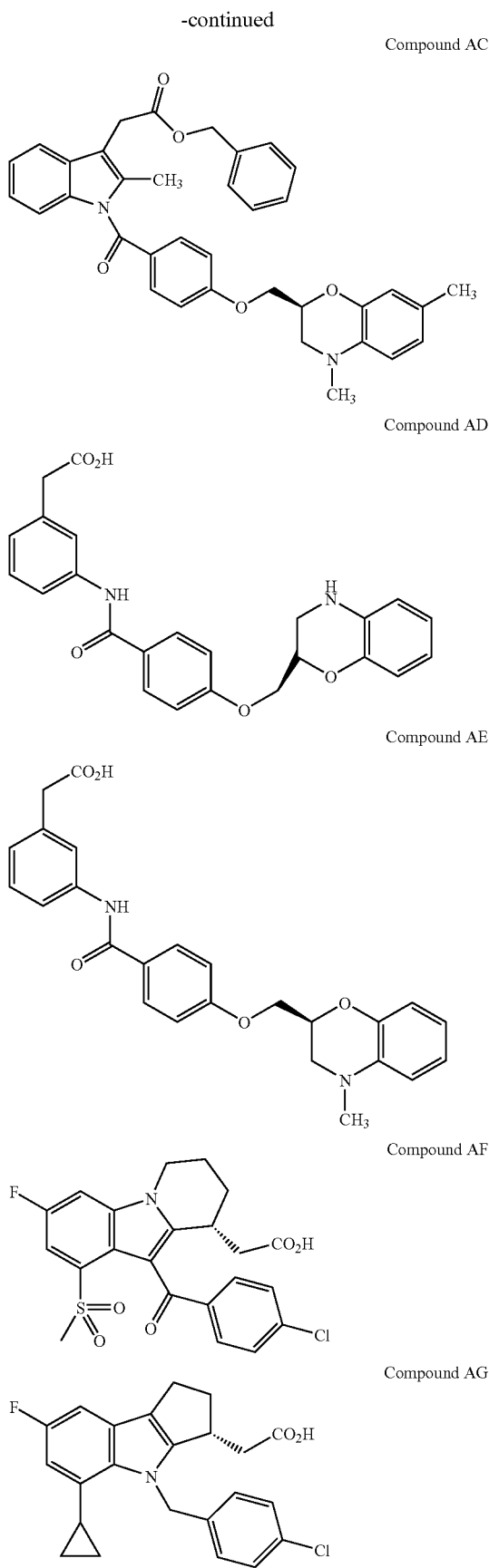
or a pharmaceutically acceptable salt, solvate or hydrate thereof.
62. A pharmaceutical composition according to claim 60 wherein said DP receptor antagonist is selected from the group consisting of:

-continued
Compound D
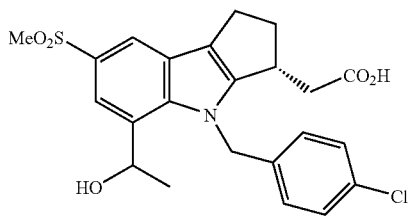
Compound E
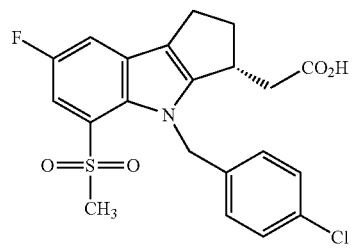
Compound F
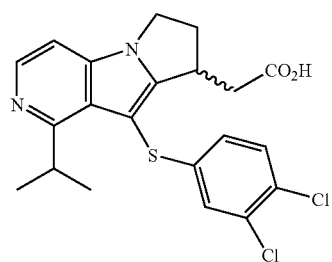
Compound G
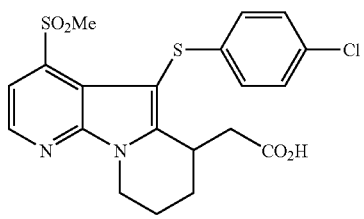
Compound H
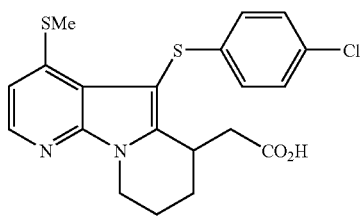
Compound I
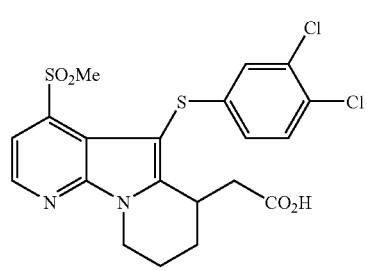
-continued
Compound J
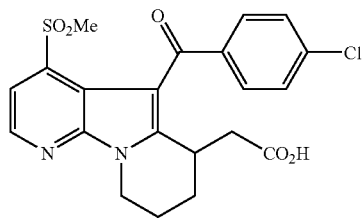
Compound K
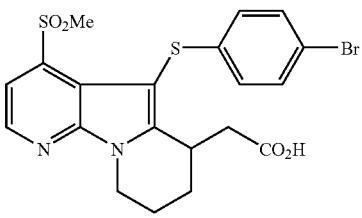
Compound L
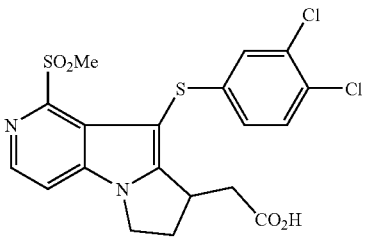
Compound M
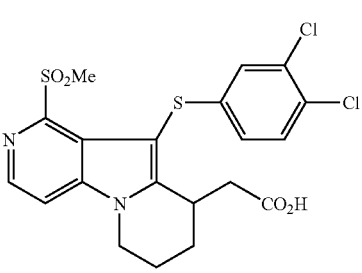
Compound N
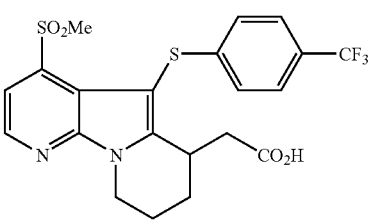
Compound O
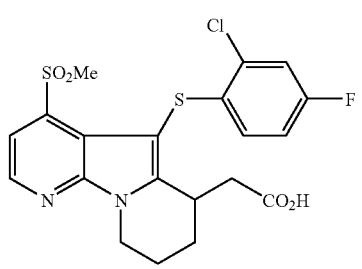

Compound P
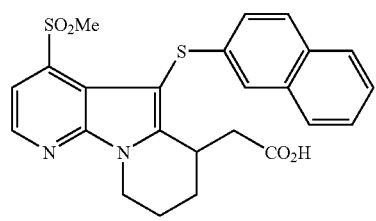
Compound Q
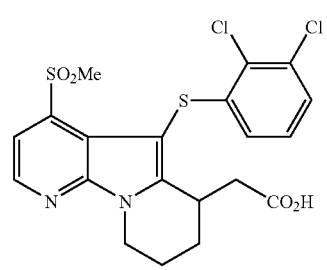
Compound R
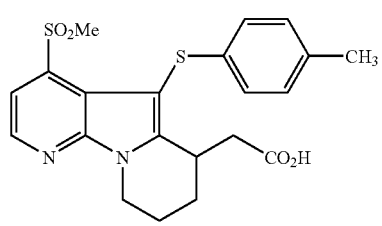
Compound S
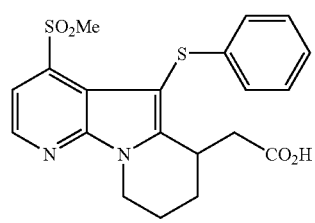
Compound T
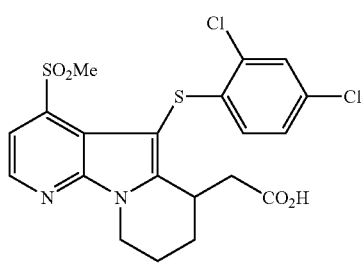
Compound U
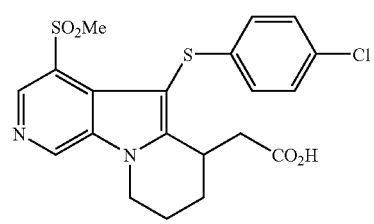
Compound V
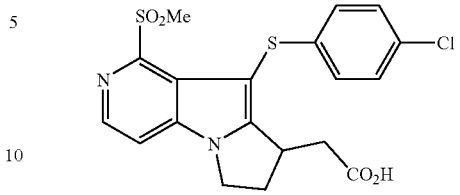
Compound W
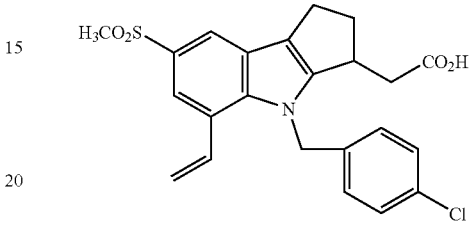
Compound X
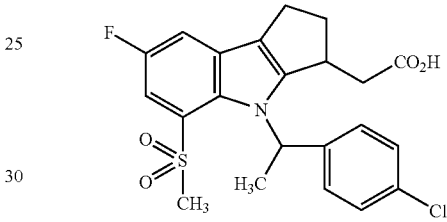
Compound X
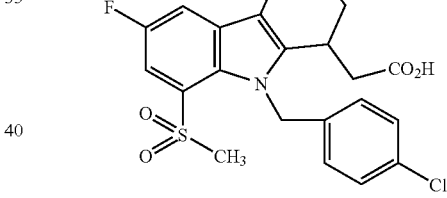
Compound Z
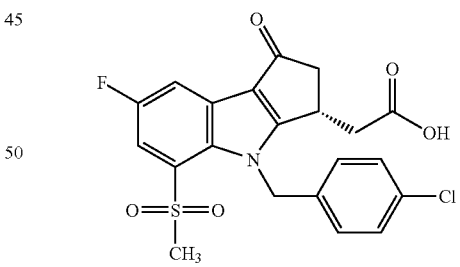
Compound AA
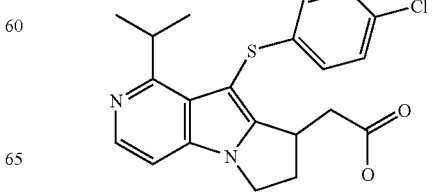

-continued
Compound AB
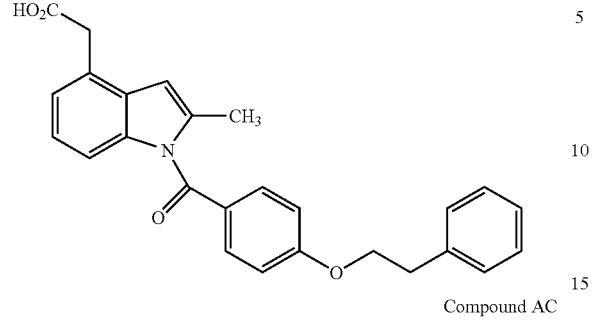
Compound AC
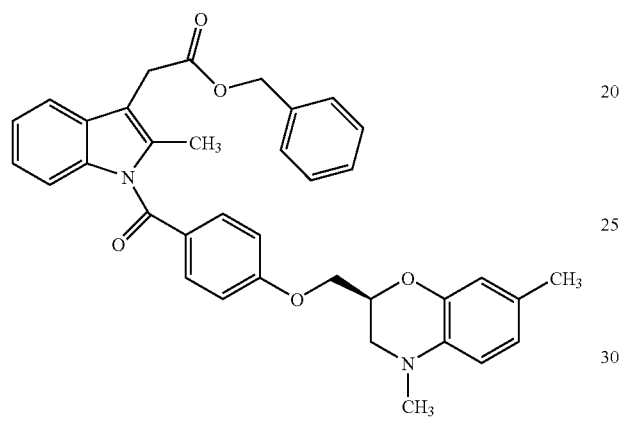
Compound AD
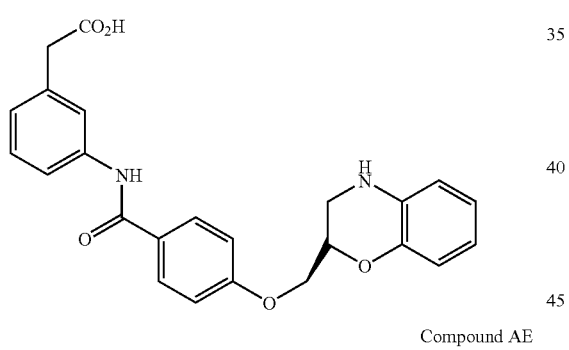
Compound AE
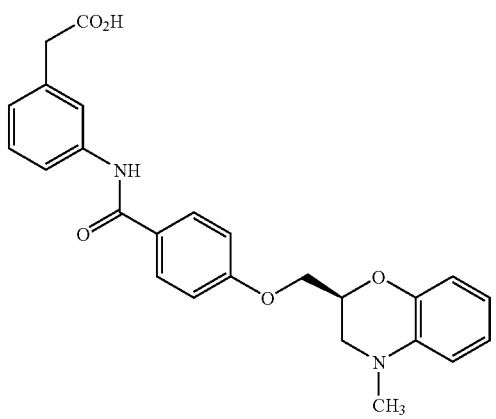
-continued
Compound AF
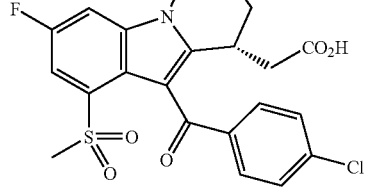
Compound AG
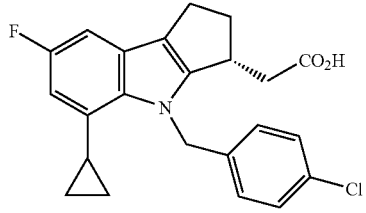
Compound AH
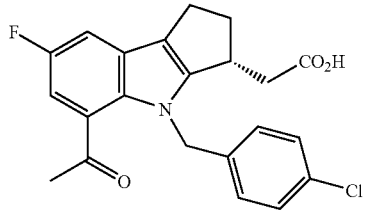
Compound AI
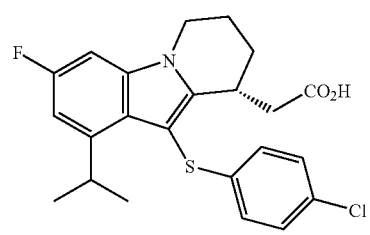
Compound AJ
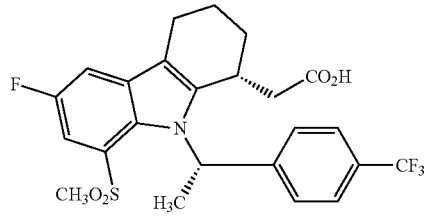
or a pharmaceutically acceptable salt, solvate or hydrate thereof.
* * * * *

UNITED STATES PATENT AND TRADEMARK OFFICE
CERTIFICATE OF CORRECTION

PATENT NO.       : 7,241,792 B2
APPLICATION NO.  : 11/315753
DATED            : July 10, 2007
INVENTOR(S)      : P. Douglas Boatman et al.

It is certified that error appears in the above-identified patent and that said Letters Patent is hereby corrected as shown below:

In Col. 17, line 16, replace "sulfmyl" with --sulfinyl--

In Col. 42, line 62, replace "1aR, 5a)" with --(1aR, 5aS)--

In Col. 64, line 49, replace "SR1441716" with --SR141716--

In Col. 73, line 53, replace "ccrivastatin" with --cerivastatin--

In Col. 81, line 31, replace "Md." with --MD.--

In Col. 84, line 4, replace "PimiI" with --PimII--

In Col. 92, line 67, replace "[M-$N_2$+H]+" --[M-$N_2$+H]$^+$--

In Col. 94, line 43, replace "n/z" with --m/z--

In Col. 110, line 25, in the text for Example 9.21, replace "1-methyl" with
--l-methyl-4- --

In Col. 111, line 25, in the text for Example 9.22, replace "pentalene-l-carboxylic" with
-- pentalene-4-carboxylic --

In Col. 112, line 7, in the text for Example 9.24, Step A, replace
"pentalene-l-carboxylic" with -- pentalene-4-carboxylic --

In Col. 112, line 27, in the text for Example 9.24, Step B, replace
"pentalene-l-carbonitrile" with -- pentalene-4-carbonitrile --

In Col. 112, line 66, replace "(dd, 1H, $J_1$=32 Hz)" with --(dd, 1H, $J_1$=4.2 Hz,
$J_2$=3.2 Hz)--

In Col. 113, line 27, replace "pentalene-carboxylic acid" with -- pentalene-4-carboxylic
acid--

In Col. 116, line 23, replace "[M+Na]+" with --[M+Na]$^+$--

In Col. 116, line 24, replace "[M+H]+" with --[M+H]$^+$--

In Col. 116, line 50, replace "[M+H]hu+" with --[M+H]$^+$--

UNITED STATES PATENT AND TRADEMARK OFFICE
CERTIFICATE OF CORRECTION

PATENT NO. : 7,241,792 B2
APPLICATION NO. : 11/315753
DATED : July 10, 2007
INVENTOR(S) : P. Douglas Boatman et al.

It is certified that error appears in the above-identified patent and that said Letters Patent is hereby corrected as shown below:

In Col. 118, line 24, insert after (m, 1H), --0.90-0.80 (m, 3H),--

In Col. 128, line 30, replace "pentalene-l-carboxylic" with -- pentalene-4-carboxylic--

In Col. 154, line 20, replace "l h" with --1H--

In Col. 162, line 66, replace "ThA" with -- TFA--

In Col. 167, line 51, replace "mmol" with --µmol--

In the claims:

In Col. 184, line 36, replace "O$_2$Et" with --CO$_2$Et--

In Col. 187, line 20, insert the missing compound with structure:

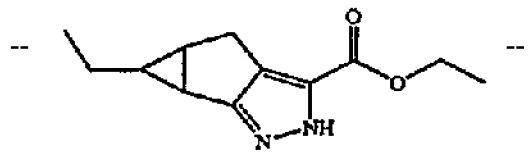

In Col. 192, line 40, after thereof, insert --in--

In Col. 192, line 44, after thereof, insert --in--

Signed and Sealed this

Twentieth Day of November, 2007

JON W. DUDAS
*Director of the United States Patent and Trademark Office*